United States Patent
Shelton, IV et al.

(10) Patent No.: US 11,051,836 B2
(45) Date of Patent: Jul. 6, 2021

(54) SURGICAL CLIP APPLIER COMPRISING AN EMPTY CLIP CARTRIDGE LOCKOUT

(71) Applicant: Ethicon LLC, Guaynabo, PR (US)

(72) Inventors: Frederick E. Shelton, IV, Hillsboro, OH (US); Andrew C. Deck, Blue Ash, OH (US); Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 77 days.

(21) Appl. No.: 16/112,245

(22) Filed: Aug. 24, 2018

(65) Prior Publication Data

US 2019/0125352 A1  May 2, 2019

Related U.S. Application Data

(60) Provisional application No. 62/578,793, filed on Oct. 30, 2017, provisional application No. 62/578,804, (Continued)

(51) Int. Cl.
*A61B 17/29* (2006.01)
*A61B 18/14* (2006.01)
(Continued)

(52) U.S. Cl.
CPC .......... *A61B 17/2909* (2013.01); *A61B 17/00* (2013.01); *A61B 17/0469* (2013.01); *A61B 17/0482* (2013.01); *A61B 17/0483* (2013.01); *A61B 17/0491* (2013.01); *A61B 17/062* (2013.01); *A61B 17/06004* (2013.01); *A61B 17/068* (2013.01); *A61B 17/0625* (2013.01); *A61B 17/06066* (2013.01); *A61B 17/06114* (2013.01); *A61B 17/06133* (2013.01); *A61B 17/105* (2013.01); *A61B 17/128* (2013.01);
(Continued)

(58) Field of Classification Search
CPC ..... A61B 17/10; A61B 17/068; A61B 17/128; A61B 17/34; A61B 34/30; A61B 17/00; A61B 17/0469; A61B 17/0482; A61B 17/0483; A61B 17/0491; A61B 17/06004; A61B 17/06066; A61B 17/06144; A61B 17/06133; A61B 17/062; A61B 17/0625; A61B 17/105; A61B 17/1285
See application file for complete search history.

(56) References Cited

U.S. PATENT DOCUMENTS

| 1,853,416 A | 4/1932 | Hall |
| 3,082,426 A | 3/1963 | Miles |

(Continued)

FOREIGN PATENT DOCUMENTS

| AU | 2015201140 A1 | 3/2015 |
| CA | 2795323 A1 | 5/2014 |

(Continued)

OTHER PUBLICATIONS

US 10,504,709, 8/2018, Karancsi et al. (withdrawn).
(Continued)

*Primary Examiner* — George J Ulsh

(57) ABSTRACT

A surgical clip applier comprising a rotatable clip cartridge is disclosed. The surgical clip applier comprises a lockout that at least locks out the crimping drive of the surgical clip applier when the rotatable clip cartridge is empty.

20 Claims, 68 Drawing Sheets

Related U.S. Application Data filed on Oct. 30, 2017, provisional application No. 62/578,817, filed on Oct. 30, 2017, provisional application No. 62/578,835, filed on Oct. 30, 2017, provisional application No. 62/578,844, filed on Oct. 30, 2017, provisional application No. 62/578,855, filed on Oct. 30, 2017, provisional application No. 62/665,129, filed on May 1, 2018, provisional application No. 62/665,139, filed on May 1, 2018, provisional application No. 62/665,177, filed on May 1, 2018, provisional application No. 62/665,128, filed on May 1, 2018, provisional application No. 62/665,192, filed on May 1, 2018, provisional application No. 62/665,134, filed on May 1, 2018.

(51) Int. Cl.

| | | |
|---|---|---|
| *A61B 17/04* | (2006.01) | |
| *A61B 17/06* | (2006.01) | |
| *A61B 18/12* | (2006.01) | |
| *A61B 34/30* | (2016.01) | |
| *A61B 17/00* | (2006.01) | |
| *A61B 17/128* | (2006.01) | |
| *A61B 90/98* | (2016.01) | |
| *A61B 17/062* | (2006.01) | |
| *A61B 17/068* | (2006.01) | |
| *A61B 17/28* | (2006.01) | |
| *A61B 17/285* | (2006.01) | |
| *A61B 17/295* | (2006.01) | |
| *A61B 90/00* | (2016.01) | |
| *A61B 17/10* | (2006.01) | |
| *A61B 17/34* | (2006.01) | |
| *G06F 3/147* | (2006.01) | |
| *A61B 34/00* | (2016.01) | |
| *A61B 18/00* | (2006.01) | |
| *A61B 17/32* | (2006.01) | |
| *B33Y 80/00* | (2015.01) | |
| *A61B 17/3201* | (2006.01) | |
| *F16D 27/108* | (2006.01) | |
| *F16D 27/12* | (2006.01) | |
| *G09G 3/34* | (2006.01) | |
| *G09G 3/36* | (2006.01) | |
| *G09G 3/38* | (2006.01) | |
| *F16D 27/00* | (2006.01) | |

(52) U.S. Cl.
CPC ........ *A61B 17/1285* (2013.01); *A61B 17/282* (2013.01); *A61B 17/285* (2013.01); *A61B 17/2841* (2013.01); *A61B 17/29* (2013.01); *A61B 17/295* (2013.01); *A61B 17/3421* (2013.01); *A61B 17/3468* (2013.01); *A61B 18/1206* (2013.01); *A61B 18/1445* (2013.01); *A61B 34/30* (2016.02); *A61B 34/76* (2016.02); *A61B 90/03* (2016.02); *A61B 90/98* (2016.02); *G06F 3/147* (2013.01); *A61B 17/2833* (2013.01); *A61B 17/3201* (2013.01); *A61B 2017/0003* (2013.01); *A61B 2017/00017* (2013.01); *A61B 2017/00026* (2013.01); *A61B 2017/00039* (2013.01); *A61B 2017/0046* (2013.01); *A61B 2017/00057* (2013.01); *A61B 2017/00061* (2013.01); *A61B 2017/00075* (2013.01); *A61B 2017/00115* (2013.01); *A61B 2017/00119* (2013.01); *A61B 2017/00128* (2013.01); *A61B 2017/00212* (2013.01); *A61B 2017/00221* (2013.01); *A61B 2017/00327* (2013.01); *A61B 2017/00367* (2013.01); *A61B 2017/00393* (2013.01); *A61B 2017/00398* (2013.01); *A61B 2017/00407* (2013.01); *A61B 2017/00424* (2013.01); *A61B 2017/00438* (2013.01); *A61B 2017/00464* (2013.01); *A61B 2017/00473* (2013.01); *A61B 2017/00477* (2013.01); *A61B 2017/00526* (2013.01); *A61B 2017/00734* (2013.01); *A61B 2017/06052* (2013.01); *A61B 2017/06076* (2013.01); *A61B 2017/2825* (2013.01); *A61B 2017/2845* (2013.01); *A61B 2017/2902* (2013.01); *A61B 2017/2903* (2013.01); *A61B 2017/2911* (2013.01); *A61B 2017/2923* (2013.01); *A61B 2017/2925* (2013.01); *A61B 2017/2926* (2013.01); *A61B 2017/2927* (2013.01); *A61B 2017/2929* (2013.01); *A61B 2017/2931* (2013.01); *A61B 2017/2943* (2013.01); *A61B 2017/2945* (2013.01); *A61B 2017/320044* (2013.01); *A61B 2018/0063* (2013.01); *A61B 2018/0072* (2013.01); *A61B 2018/00077* (2013.01); *A61B 2018/00083* (2013.01); *A61B 2018/00136* (2013.01); *A61B 2018/00178* (2013.01); *A61B 2018/00208* (2013.01); *A61B 2018/00404* (2013.01); *A61B 2018/00577* (2013.01); *A61B 2018/00595* (2013.01); *A61B 2018/00601* (2013.01); *A61B 2018/00642* (2013.01); *A61B 2018/00672* (2013.01); *A61B 2018/00678* (2013.01); *A61B 2018/00696* (2013.01); *A61B 2018/00702* (2013.01); *A61B 2018/00708* (2013.01); *A61B 2018/00767* (2013.01); *A61B 2018/00827* (2013.01); *A61B 2018/00875* (2013.01); *A61B 2018/00892* (2013.01); *A61B 2018/126* (2013.01); *A61B 2018/1253* (2013.01); *A61B 2018/1266* (2013.01); *A61B 2018/146* (2013.01); *A61B 2018/1452* (2013.01); *A61B 2018/1457* (2013.01); *A61B 2090/035* (2016.02); *A61B 2090/0811* (2016.02); *B33Y 80/00* (2014.12); *F16D 27/004* (2013.01); *F16D 27/108* (2013.01); *F16D 27/12* (2013.01); *G09G 3/344* (2013.01); *G09G 3/3648* (2013.01); *G09G 3/38* (2013.01); *G09G 2380/08* (2013.01)

(56) References Cited

U.S. PATENT DOCUMENTS

| | | |
|---|---|---|
| 3,503,396 A | 3/1970 | Pierie et al. |
| 3,584,628 A | 6/1971 | Green |
| 3,633,584 A | 1/1972 | Farrell |
| 3,759,017 A | 9/1973 | Young |
| 4,412,539 A | 11/1983 | Jarvik |
| 4,448,193 A | 5/1984 | Ivanov |
| 4,523,695 A | 6/1985 | Braun et al. |
| 4,608,160 A | 8/1986 | Zoch |
| 4,614,366 A | 9/1986 | North et al. |
| 4,701,193 A | 10/1987 | Robertson et al. |
| 4,735,603 A | 4/1988 | Goodson et al. |
| 4,788,977 A | 12/1988 | Farin et al. |
| 4,892,244 A | 1/1990 | Fox et al. |
| 5,035,692 A | 7/1991 | Lyon et al. |
| 5,042,460 A | 8/1991 | Sakurai et al. |
| 5,084,057 A | 1/1992 | Green et al. |
| 5,100,402 A | 3/1992 | Fan |
| 5,129,570 A | 7/1992 | Schulze et al. |
| 5,151,102 A | 9/1992 | Kamiyama et al. |
| 5,156,315 A | 10/1992 | Green et al. |
| 5,158,585 A | 10/1992 | Saho et al. |
| 5,197,962 A | 3/1993 | Sansom et al. |
| 5,242,474 A | 9/1993 | Herbst et al. |
| 5,253,793 A | 10/1993 | Green et al. |

(56) References Cited

U.S. PATENT DOCUMENTS

| | | |
|---|---|---|
| 5,271,543 A | 12/1993 | Grant et al. |
| RE34,519 E | 1/1994 | Fox et al. |
| 5,318,516 A | 6/1994 | Cosmescu |
| 5,322,055 A | 6/1994 | Davison et al. |
| 5,342,349 A | 8/1994 | Kaufman |
| 5,383,880 A | 1/1995 | Hooven |
| 5,396,900 A | 3/1995 | Slater et al. |
| 5,397,046 A | 3/1995 | Savage et al. |
| 5,403,312 A | 4/1995 | Yates et al. |
| 5,403,327 A | 4/1995 | Thornton et al. |
| 5,413,267 A | 5/1995 | Solyntjes et al. |
| 5,415,335 A | 5/1995 | Knodell, Jr. |
| 5,417,699 A | 5/1995 | Klein et al. |
| 5,439,468 A | 8/1995 | Schulze et al. |
| 5,445,304 A | 8/1995 | Plyley et al. |
| 5,465,895 A | 11/1995 | Knodel et al. |
| 5,467,911 A | 11/1995 | Tsuruta et al. |
| 5,474,566 A | 12/1995 | Alesi et al. |
| 5,485,947 A | 1/1996 | Olson et al. |
| 5,496,315 A | 3/1996 | Weaver et al. |
| 5,503,320 A | 4/1996 | Webster et al. |
| 5,531,743 A | 7/1996 | Nettekoven et al. |
| 5,545,148 A | 8/1996 | Wurster |
| 5,584,425 A | 12/1996 | Savage et al. |
| 5,610,379 A | 3/1997 | Muz et al. |
| 5,613,966 A | 3/1997 | Makower et al. |
| 5,624,452 A | 4/1997 | Yates |
| 5,626,587 A | 5/1997 | Bishop et al. |
| 5,643,291 A | 7/1997 | Pier et al. |
| 5,654,750 A | 8/1997 | Weil et al. |
| 5,673,841 A | 10/1997 | Schulze et al. |
| 5,673,842 A | 10/1997 | Bittner et al. |
| 5,675,227 A | 10/1997 | Roos et al. |
| 5,693,052 A | 12/1997 | Weaver |
| 5,695,502 A * | 12/1997 | Pier .................... A61B 17/1285 606/143 |
| 5,697,926 A | 12/1997 | Weaver |
| 5,706,998 A | 1/1998 | Plyley et al. |
| 5,718,359 A | 2/1998 | Palmer et al. |
| 5,725,536 A | 3/1998 | Oberlin et al. |
| 5,725,542 A | 3/1998 | Yoon |
| 5,735,445 A | 4/1998 | Vidal et al. |
| 5,735,848 A | 4/1998 | Yates et al. |
| 5,746,209 A | 5/1998 | Yost et al. |
| 5,749,362 A | 5/1998 | Funda et al. |
| 5,749,893 A | 5/1998 | Vidal et al. |
| 5,752,644 A | 5/1998 | Bolanos et al. |
| 5,762,255 A | 6/1998 | Chrisman et al. |
| 5,766,186 A | 6/1998 | Faraz et al. |
| 5,769,791 A | 6/1998 | Benaron et al. |
| 5,797,537 A | 8/1998 | Oberlin et al. |
| D399,561 S | 10/1998 | Ellingson |
| 5,817,093 A | 10/1998 | Williamson, IV et al. |
| 5,820,009 A | 10/1998 | Melling et al. |
| 5,836,849 A | 11/1998 | Mathiak et al. |
| 5,836,909 A | 11/1998 | Cosmescu |
| 5,843,080 A | 12/1998 | Fleenor et al. |
| 5,846,237 A | 12/1998 | Nettekoven |
| 5,849,022 A | 12/1998 | Sakashita et al. |
| 5,873,873 A | 2/1999 | Smith et al. |
| 5,878,938 A | 3/1999 | Bittner et al. |
| 5,893,849 A | 4/1999 | Weaver |
| 5,906,625 A | 5/1999 | Bito et al. |
| 5,942,333 A | 8/1999 | Arnett et al. |
| 5,947,996 A | 9/1999 | Logeman |
| 5,968,032 A | 10/1999 | Sleister |
| 5,980,510 A | 11/1999 | Tsonton et al. |
| 5,997,528 A | 12/1999 | Bisch et al. |
| 6,010,054 A | 1/2000 | Johnson et al. |
| 6,030,437 A | 2/2000 | Gourrier et al. |
| 6,036,637 A | 3/2000 | Kudo |
| 6,039,734 A | 3/2000 | Goble |
| 6,039,735 A | 3/2000 | Greep |
| 6,059,799 A | 5/2000 | Aranyi et al. |
| 6,066,137 A | 5/2000 | Greep |
| 6,079,606 A | 6/2000 | Milliman et al. |
| 6,090,107 A | 7/2000 | Borgmeier et al. |
| 6,099,537 A | 8/2000 | Sugai et al. |
| 6,109,500 A | 8/2000 | Alli et al. |
| 6,155,473 A | 12/2000 | Tompkins et al. |
| 6,214,000 B1 | 4/2001 | Fleenor et al. |
| 6,258,105 B1 | 7/2001 | Hart et al. |
| 6,273,887 B1 | 8/2001 | Yamauchi et al. |
| 6,301,495 B1 | 10/2001 | Gueziec et al. |
| 6,302,881 B1 | 10/2001 | Farin |
| 6,308,089 B1 | 10/2001 | von der Ruhr et al. |
| 6,325,808 B1 | 12/2001 | Bernard et al. |
| 6,325,811 B1 | 12/2001 | Messerly |
| 6,341,164 B1 | 1/2002 | Dilkie et al. |
| 6,391,102 B1 | 5/2002 | Bodden et al. |
| 6,434,416 B1 | 8/2002 | Mizoguchi et al. |
| 6,443,973 B1 | 9/2002 | Whitman |
| 6,454,781 B1 | 9/2002 | Witt et al. |
| 6,457,625 B1 | 10/2002 | Tormala et al. |
| 6,461,352 B2 | 10/2002 | Morgan et al. |
| 6,530,933 B1 | 3/2003 | Yeung et al. |
| 6,551,243 B2 | 4/2003 | Bocionek et al. |
| 6,569,109 B2 | 5/2003 | Sakurai et al. |
| 6,582,424 B2 | 6/2003 | Fleenor et al. |
| 6,585,791 B1 | 7/2003 | Garito et al. |
| 6,618,626 B2 | 9/2003 | West, Jr. et al. |
| 6,648,223 B2 | 11/2003 | Boukhny et al. |
| 6,685,704 B2 | 2/2004 | Greep |
| 6,699,187 B2 | 3/2004 | Webb et al. |
| 6,742,895 B2 | 6/2004 | Robin |
| 6,752,816 B2 | 6/2004 | Culp et al. |
| 6,773,444 B2 | 8/2004 | Messerly |
| 6,775,575 B2 | 8/2004 | Bommannan et al. |
| 6,778,846 B1 | 8/2004 | Martinez et al. |
| 6,781,683 B2 | 8/2004 | Kacyra et al. |
| 6,783,524 B2 | 8/2004 | Anderson et al. |
| 6,783,525 B2 | 8/2004 | Greep et al. |
| 6,793,663 B2 | 9/2004 | Kneifel et al. |
| 6,846,308 B2 | 1/2005 | Whitman et al. |
| 6,852,219 B2 | 2/2005 | Hammond |
| 6,863,650 B1 | 3/2005 | Irion |
| 6,869,430 B2 | 3/2005 | Balbierz et al. |
| 6,869,435 B2 | 3/2005 | Blake, III |
| 6,911,033 B2 | 6/2005 | de Guillebon et al. |
| 6,937,892 B2 | 8/2005 | Leyde et al. |
| 6,945,981 B2 | 9/2005 | Donofrio et al. |
| 6,951,559 B1 | 10/2005 | Greep |
| 6,978,921 B2 | 12/2005 | Shelton, IV et al. |
| 6,988,649 B2 | 1/2006 | Shelton, IV et al. |
| 7,000,818 B2 | 2/2006 | Shelton, IV et al. |
| 7,030,146 B2 | 4/2006 | Baynes et al. |
| 7,032,798 B2 | 4/2006 | Whitman et al. |
| 7,041,941 B2 | 5/2006 | Faries, Jr. et al. |
| 7,044,352 B2 | 5/2006 | Shelton, IV et al. |
| 7,044,911 B2 | 5/2006 | Drinan et al. |
| 7,048,775 B2 | 5/2006 | Jornitz et al. |
| 7,053,752 B2 | 5/2006 | Wang et al. |
| 7,055,730 B2 | 6/2006 | Ehrenfels et al. |
| 7,077,853 B2 | 7/2006 | Kramer et al. |
| 7,077,856 B2 | 7/2006 | Whitman |
| 7,081,096 B2 | 7/2006 | Brister et al. |
| 7,097,640 B2 | 8/2006 | Wang et al. |
| 7,103,688 B2 | 9/2006 | Strong |
| 7,118,564 B2 | 10/2006 | Ritchie et al. |
| 7,121,460 B1 | 10/2006 | Parsons et al. |
| 7,137,980 B2 | 11/2006 | Buysse et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,147,139 B2 | 12/2006 | Schwemberger et al. |
| 7,155,316 B2 | 12/2006 | Sutherland et al. |
| 7,169,145 B2 | 1/2007 | Isaacson et al. |
| 7,177,533 B2 | 2/2007 | McFarlin et al. |
| 7,182,775 B2 | 2/2007 | De Guillebon et al. |
| 7,208,005 B2 | 4/2007 | Frecker et al. |
| 7,230,529 B2 | 6/2007 | Ketcherside, Jr. et al. |
| 7,232,447 B2 | 6/2007 | Gellman et al. |
| 7,236,817 B2 | 6/2007 | Papas et al. |
| 7,246,734 B2 | 7/2007 | Shelton, IV |

(56) References Cited

U.S. PATENT DOCUMENTS

| | | |
|---|---|---|
| 7,278,563 B1 | 10/2007 | Green |
| 7,294,106 B2 | 11/2007 | Birkenbach et al. |
| 7,294,116 B1 | 11/2007 | Ellman et al. |
| 7,296,724 B2 | 11/2007 | Green et al. |
| 7,317,955 B2 | 1/2008 | McGreevy |
| 7,328,828 B2 | 2/2008 | Ortiz et al. |
| 7,334,717 B2 | 2/2008 | Rethy et al. |
| 7,343,565 B2 | 3/2008 | Ying et al. |
| 7,362,228 B2 | 4/2008 | Nycz et al. |
| 7,371,227 B2 | 5/2008 | Zeiner |
| 7,380,695 B2 | 6/2008 | Doll et al. |
| 7,383,088 B2 | 6/2008 | Spinelli et al. |
| 7,391,173 B2 | 6/2008 | Schena |
| 7,407,074 B2 | 8/2008 | Ortiz et al. |
| 7,422,139 B2 | 9/2008 | Shelton, IV et al. |
| 7,423,972 B2 | 9/2008 | Shaham et al. |
| 7,457,804 B2 | 11/2008 | Uber, III et al. |
| 7,464,847 B2 | 12/2008 | Viola et al. |
| 7,464,849 B2 | 12/2008 | Shelton, IV et al. |
| 7,515,961 B2 | 4/2009 | Germanson et al. |
| 7,575,144 B2 | 8/2009 | Ortiz et al. |
| 7,617,137 B2 | 11/2009 | Kreiner et al. |
| 7,621,192 B2 | 11/2009 | Conti et al. |
| 7,621,898 B2 | 11/2009 | Lalomia et al. |
| 7,637,410 B2 | 12/2009 | Marczyk |
| 7,641,092 B2 | 1/2010 | Kruszynski et al. |
| 7,644,848 B2 | 1/2010 | Swayze et al. |
| 7,667,839 B2 | 2/2010 | Bates |
| 7,670,334 B2 | 3/2010 | Hueil et al. |
| 7,694,865 B2 | 4/2010 | Scirica |
| 7,699,860 B2 | 4/2010 | Huitema et al. |
| 7,720,306 B2 | 5/2010 | Gardiner et al. |
| 7,721,934 B2 | 5/2010 | Shelton, IV et al. |
| 7,721,936 B2 | 5/2010 | Shalton, IV et al. |
| 7,736,357 B2 | 6/2010 | Lee, Jr. et al. |
| 7,742,176 B2 | 6/2010 | Braunecker et al. |
| 7,743,960 B2 | 6/2010 | Whitman et al. |
| 7,753,245 B2 | 7/2010 | Boudreaux et al. |
| 7,766,207 B2 | 8/2010 | Mather et al. |
| 7,766,905 B2 | 8/2010 | Paterson et al. |
| 7,770,773 B2 | 8/2010 | Whitman et al. |
| 7,776,037 B2 | 8/2010 | Odom |
| 7,782,789 B2 | 8/2010 | Stultz et al. |
| 7,784,663 B2 | 8/2010 | Shelton, IV |
| 7,803,151 B2 | 9/2010 | Whitman |
| 7,810,692 B2 | 10/2010 | Hall et al. |
| 7,818,041 B2 | 10/2010 | Kim et al. |
| 7,819,298 B2 | 10/2010 | Hall et al. |
| 7,832,612 B2 | 11/2010 | Baxter, III et al. |
| 7,836,085 B2 | 11/2010 | Petakov et al. |
| 7,837,079 B2 | 11/2010 | Holsten et al. |
| 7,837,680 B2 | 11/2010 | Isaacson et al. |
| 7,841,980 B2 | 11/2010 | Minosawa et al. |
| 7,845,537 B2 | 12/2010 | Shelton, IV et al. |
| 7,857,185 B2 | 12/2010 | Swayze et al. |
| 7,862,560 B2 | 1/2011 | Marion |
| 7,862,579 B2 | 1/2011 | Ortiz et al. |
| 7,865,236 B2 | 1/2011 | Cory et al. |
| 7,887,530 B2 | 2/2011 | Zemlok et al. |
| 7,892,337 B2 | 2/2011 | Palmerton et al. |
| 7,907,166 B2 | 3/2011 | Lamprecht et al. |
| 7,913,891 B2 | 3/2011 | Doll et al. |
| 7,918,230 B2 | 4/2011 | Whitman et al. |
| 7,918,377 B2 | 4/2011 | Measamer et al. |
| 7,920,706 B2 | 4/2011 | Asokan et al. |
| 7,927,014 B2 | 4/2011 | Dehler |
| 7,942,300 B2 | 5/2011 | Rethy et al. |
| 7,954,682 B2 | 6/2011 | Giordano et al. |
| 7,955,322 B2 | 6/2011 | Devengenzo et al. |
| 7,956,620 B2 | 6/2011 | Gilbert |
| 7,963,433 B2 | 6/2011 | Whitman et al. |
| 7,966,269 B2 | 6/2011 | Bauer et al. |
| 7,967,180 B2 | 6/2011 | Scirica |
| 7,976,553 B2 | 7/2011 | Shelton, IV et al. |
| 7,979,157 B2 | 7/2011 | Anvari |
| 7,980,443 B2 | 7/2011 | Scheib et al. |
| 7,982,776 B2 | 7/2011 | Dunki-Jacobs et al. |
| 7,988,028 B2 | 8/2011 | Farascioni et al. |
| 7,993,140 B2 | 8/2011 | Sakezles |
| 7,995,045 B2 | 8/2011 | Dunki-Jacobs |
| 8,005,947 B2 | 8/2011 | Morris et al. |
| 8,007,494 B1 | 8/2011 | Taylor et al. |
| 8,007,513 B2 | 8/2011 | Nalagatla et al. |
| 8,010,180 B2 | 8/2011 | Quaid et al. |
| 8,012,170 B2 | 9/2011 | Whitman et al. |
| 8,015,976 B2 | 9/2011 | Shah |
| 8,016,855 B2 | 9/2011 | Whitman et al. |
| 8,025,199 B2 | 9/2011 | Whitman et al. |
| 8,027,710 B1 | 9/2011 | Dannan |
| 8,035,685 B2 | 10/2011 | Jensen |
| 8,038,686 B2 | 10/2011 | Huitema et al. |
| 8,038,693 B2 | 10/2011 | Allen |
| 8,043,560 B2 | 10/2011 | Okumoto et al. |
| 8,054,184 B2 | 11/2011 | Cline et al. |
| 8,054,752 B2 | 11/2011 | Druke et al. |
| 8,062,306 B2 | 11/2011 | Nobis et al. |
| 8,062,330 B2 | 11/2011 | Prommersberger et al. |
| 8,066,721 B2 | 11/2011 | Kortenbach et al. |
| 8,075,571 B2 | 12/2011 | Vitali et al. |
| 8,096,459 B2 | 1/2012 | Ortiz et al. |
| 8,118,206 B2 | 2/2012 | Zand et al. |
| 8,120,301 B2 | 2/2012 | Goldberg et al. |
| 8,123,764 B2 | 2/2012 | Meade et al. |
| 8,131,565 B2 | 3/2012 | Dicks et al. |
| 8,136,712 B2 | 3/2012 | Zingman |
| 8,147,486 B2 | 4/2012 | Honour et al. |
| 8,155,479 B2 | 4/2012 | Hoffman et al. |
| 8,157,145 B2 | 4/2012 | Shelton, IV et al. |
| 8,157,150 B2 | 4/2012 | Viola et al. |
| 8,160,098 B1 | 4/2012 | Yan et al. |
| 8,161,977 B2 | 4/2012 | Shelton, IV et al. |
| 8,170,396 B2 | 5/2012 | Kuspa et al. |
| 8,172,836 B2 | 5/2012 | Ward |
| 8,181,839 B2 | 5/2012 | Beetel |
| 8,185,409 B2 | 5/2012 | Putnam et al. |
| 8,206,345 B2 | 6/2012 | Abboud et al. |
| 8,210,411 B2 | 7/2012 | Yates et al. |
| 8,214,007 B2 | 7/2012 | Baker et al. |
| 8,216,849 B2 | 7/2012 | Petty |
| 8,220,688 B2 | 7/2012 | Laurent et al. |
| 8,225,643 B2 | 7/2012 | Abboud et al. |
| 8,225,979 B2 | 7/2012 | Farascioni et al. |
| 8,229,549 B2 | 7/2012 | Whitman et al. |
| 8,257,387 B2 | 9/2012 | Cunningham |
| 8,260,016 B2 | 9/2012 | Maeda et al. |
| 8,262,560 B2 | 9/2012 | Whitman |
| 8,292,888 B2 | 10/2012 | Whitman |
| 8,295,902 B2 | 10/2012 | Salahieh et al. |
| 8,308,040 B2 | 11/2012 | Huang et al. |
| 8,321,581 B2 | 11/2012 | Katis et al. |
| 8,328,065 B2 | 12/2012 | Shah |
| 8,335,590 B2 | 12/2012 | Costa et al. |
| 8,343,065 B2 | 1/2013 | Bartol et al. |
| 8,346,392 B2 | 1/2013 | Walser et al. |
| 8,360,299 B2 | 1/2013 | Zemlok et al. |
| 8,364,222 B2 | 1/2013 | Cook et al. |
| 8,365,975 B1 | 2/2013 | Manoux et al. |
| 8,388,652 B2 | 3/2013 | Viola |
| 8,393,514 B2 | 3/2013 | Shelton, IV et al. |
| 8,397,972 B2 | 3/2013 | Kostrzewski |
| 8,398,541 B2 | 3/2013 | DiMaio et al. |
| 8,403,944 B2 | 3/2013 | Pain et al. |
| 8,403,945 B2 | 3/2013 | Whitfield et al. |
| 8,403,946 B2 | 3/2013 | Whitfield et al. |
| 8,406,859 B2 | 3/2013 | Zuzak et al. |
| 8,422,035 B2 | 4/2013 | Hinderling et al. |
| 8,423,182 B2 | 4/2013 | Robinson et al. |
| 8,428,722 B2 | 4/2013 | Verhoef et al. |
| 8,439,910 B2 | 5/2013 | Greep et al. |
| 8,444,663 B2 | 5/2013 | Houser et al. |
| 8,452,615 B2 | 5/2013 | Abri |
| 8,454,506 B2 | 6/2013 | Rothman et al. |
| 8,461,744 B2 | 6/2013 | Wiener et al. |
| 8,468,030 B2 | 6/2013 | Stroup et al. |

(56) References Cited

U.S. PATENT DOCUMENTS

| | | |
|---|---|---|
| 8,469,973 B2 | 6/2013 | Meade et al. |
| 8,472,630 B2 | 6/2013 | Konrad et al. |
| 8,476,227 B2 | 7/2013 | Kaplan et al. |
| 8,489,235 B2 | 7/2013 | Moll et al. |
| 8,499,992 B2 | 8/2013 | Whitman et al. |
| 8,500,756 B2 | 8/2013 | Papa et al. |
| 8,503,759 B2 | 8/2013 | Greer et al. |
| 8,505,801 B2 | 8/2013 | Ehrenfels et al. |
| 8,506,478 B2 | 8/2013 | Mizuyoshi |
| 8,512,325 B2 | 8/2013 | Mathonnet |
| 8,512,365 B2 | 8/2013 | Wiener et al. |
| 8,521,331 B2 | 8/2013 | Itkowitz |
| 8,523,043 B2 | 9/2013 | Ullrich et al. |
| 8,546,996 B2 | 10/2013 | Messerly et al. |
| 8,554,697 B2 | 10/2013 | Claus et al. |
| 8,560,047 B2 | 10/2013 | Haider et al. |
| 8,561,870 B2 | 10/2013 | Baxter, III et al. |
| 8,562,598 B2 | 10/2013 | Falkenstein et al. |
| 8,566,115 B2 | 10/2013 | Moore |
| 8,571,598 B2 | 10/2013 | Valavi |
| 8,573,459 B2 | 11/2013 | Smith et al. |
| 8,573,465 B2 | 11/2013 | Shelton, IV |
| 8,590,762 B2 | 11/2013 | Hess et al. |
| 8,591,536 B2 | 11/2013 | Robertson |
| 8,595,607 B2 | 11/2013 | Nekoomaram et al. |
| 8,596,513 B2 | 12/2013 | Olson et al. |
| 8,596,515 B2 | 12/2013 | Okoniewski |
| 8,608,044 B2 | 12/2013 | Hueil et al. |
| 8,608,045 B2 | 12/2013 | Smith et al. |
| 8,616,431 B2 | 12/2013 | Timm et al. |
| 8,620,055 B2 | 12/2013 | Barratt et al. |
| 8,620,473 B2 | 12/2013 | Diolaiti et al. |
| 8,623,027 B2 | 1/2014 | Price et al. |
| 8,627,483 B2 | 1/2014 | Rachlin et al. |
| 8,627,995 B2 | 1/2014 | Smith et al. |
| 8,628,518 B2 | 1/2014 | Blumenkranz et al. |
| 8,628,545 B2 | 1/2014 | Cabrera et al. |
| 8,631,987 B2 | 1/2014 | Shelton, IV et al. |
| 8,632,525 B2 | 1/2014 | Kerr et al. |
| 8,636,190 B2 | 1/2014 | Zemlok et al. |
| 8,652,086 B2 | 2/2014 | Gerg et al. |
| 8,652,121 B2 | 2/2014 | Quick et al. |
| 8,652,128 B2 | 2/2014 | Ward |
| 8,657,176 B2 | 2/2014 | Shelton, IV et al. |
| 8,657,177 B2 | 2/2014 | Scirica et al. |
| 8,663,220 B2 | 3/2014 | Wiener et al. |
| 8,666,544 B2 | 3/2014 | Moll et al. |
| 8,682,049 B2 | 3/2014 | Zhao et al. |
| 8,682,489 B2 | 3/2014 | Itkowitz et al. |
| 8,685,056 B2 | 4/2014 | Evans et al. |
| 8,688,188 B2 | 4/2014 | Heller et al. |
| 8,701,962 B2 | 4/2014 | Kostrzewski |
| 8,719,061 B2 | 5/2014 | Birchall |
| 8,720,766 B2 | 5/2014 | Hess et al. |
| 8,733,613 B2 | 5/2014 | Huitema et al. |
| 8,740,840 B2 | 6/2014 | Foley et al. |
| 8,740,866 B2 | 6/2014 | Reasoner et al. |
| 8,747,238 B2 | 6/2014 | Shelton, IV et al. |
| 8,752,749 B2 | 6/2014 | Moore et al. |
| 8,757,465 B2 | 6/2014 | Woodard, Jr. et al. |
| 8,761,717 B1 | 6/2014 | Buchheit |
| 8,763,879 B2 | 7/2014 | Shelton, IV et al. |
| 8,768,251 B2 | 7/2014 | Claus et al. |
| 8,771,270 B2 | 7/2014 | Burbank |
| 8,775,196 B2 | 7/2014 | Simpson et al. |
| 8,779,648 B2 | 7/2014 | Giordano et al. |
| 8,790,253 B2 | 7/2014 | Sunagawa et al. |
| 8,794,497 B2 | 8/2014 | Zingman |
| 8,799,008 B2 | 8/2014 | Johnson et al. |
| 8,799,009 B2 | 8/2014 | Mellin et al. |
| 8,800,838 B2 | 8/2014 | Shelton, IV |
| 8,801,703 B2 | 8/2014 | Gregg et al. |
| 8,814,996 B2 | 8/2014 | Giurgiutiu et al. |
| 8,818,556 B2 | 8/2014 | Sanchez et al. |
| 8,820,603 B2 | 9/2014 | Shelton, IV et al. |
| 8,820,608 B2 | 9/2014 | Miyamoto |
| 8,827,134 B2 | 9/2014 | Viola et al. |
| 8,840,003 B2 | 9/2014 | Morgan et al. |
| 8,851,354 B2 | 10/2014 | Swensgard et al. |
| 8,852,174 B2 | 10/2014 | Burbank |
| 8,875,973 B2 | 11/2014 | Whitman |
| 8,882,662 B2 | 11/2014 | Charles |
| 8,893,949 B2 | 11/2014 | Shelton, IV et al. |
| 8,899,479 B2 | 12/2014 | Cappuzzo et al. |
| 8,905,977 B2 | 12/2014 | Shelton et al. |
| 8,912,746 B2 | 12/2014 | Reid et al. |
| 8,914,098 B2 | 12/2014 | Brennan et al. |
| 8,918,207 B2 | 12/2014 | Frisco |
| 8,920,414 B2 | 12/2014 | Stone et al. |
| 8,920,433 B2 | 12/2014 | Barrier et al. |
| 8,930,203 B2 | 1/2015 | Kiaie et al. |
| 8,930,214 B2 | 1/2015 | Woolford |
| 8,931,679 B2 | 1/2015 | Kostrzewski |
| 8,945,095 B2 | 2/2015 | Blumenkranz et al. |
| 8,945,163 B2 | 2/2015 | Voegele et al. |
| 8,955,732 B2 | 2/2015 | Zemlok et al. |
| 8,956,581 B2 | 2/2015 | Rosenbaum et al. |
| 8,960,519 B2 | 2/2015 | Whitman et al. |
| 8,960,520 B2 | 2/2015 | McCuen |
| 8,962,062 B2 | 2/2015 | Podhajsky et al. |
| 8,967,443 B2 | 3/2015 | McCuen |
| 8,967,455 B2 | 3/2015 | Zhou |
| 8,968,276 B2 | 3/2015 | Zemlok et al. |
| 8,968,309 B2 | 3/2015 | Roy et al. |
| 8,968,337 B2 | 3/2015 | Whitfield et al. |
| 8,968,358 B2 | 3/2015 | Reschke |
| 8,974,429 B2 | 3/2015 | Gordon et al. |
| 8,979,890 B2 | 3/2015 | Boudreaux |
| 8,986,302 B2 | 3/2015 | Aldridge et al. |
| 8,989,903 B2 | 3/2015 | Weir et al. |
| 8,991,678 B2 | 3/2015 | Wellman et al. |
| 8,992,565 B2 | 3/2015 | Brisson et al. |
| 8,998,797 B2 | 4/2015 | Omori |
| 9,002,518 B2 | 4/2015 | Manzo et al. |
| 9,010,611 B2 | 4/2015 | Ross et al. |
| 9,011,366 B2 | 4/2015 | Dean et al. |
| 9,011,427 B2 | 4/2015 | Price et al. |
| 9,016,539 B2 | 4/2015 | Kostrzewski et al. |
| 9,017,326 B2 | 4/2015 | DiNardo et al. |
| 9,020,240 B2 | 4/2015 | Pettersson et al. |
| 9,023,071 B2 | 5/2015 | Miller et al. |
| 9,027,431 B2 | 5/2015 | Tang et al. |
| 9,028,494 B2 | 5/2015 | Shelton, IV et al. |
| 9,035,568 B2 | 5/2015 | Ganton et al. |
| 9,038,882 B2 | 5/2015 | Racenet et al. |
| 9,043,027 B2 | 5/2015 | Durant et al. |
| 9,044,227 B2 | 6/2015 | Shelton, IV et al. |
| 9,044,244 B2 | 6/2015 | Ludwin et al. |
| 9,044,261 B2 | 6/2015 | Houser |
| 9,050,063 B2 | 6/2015 | Roe et al. |
| 9,050,083 B2 | 6/2015 | Yates et al. |
| 9,050,120 B2 | 6/2015 | Swarup et al. |
| 9,052,809 B2 | 6/2015 | Vesto |
| 9,055,035 B2 | 6/2015 | Porsch et al. |
| 9,060,770 B2 | 6/2015 | Shelton, IV et al. |
| 9,060,775 B2 | 6/2015 | Wiener et al. |
| 9,066,650 B2 | 6/2015 | Sekiguchi |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,078,727 B2 | 7/2015 | Miller |
| 9,084,606 B2 | 7/2015 | Greep |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,099,863 B2 | 8/2015 | Smith et al. |
| 9,101,358 B2 | 8/2015 | Kerr et al. |
| 9,101,359 B2 | 8/2015 | Smith et al. |
| 9,101,374 B1 | 8/2015 | Hoch et al. |
| 9,106,270 B2 | 8/2015 | Puterbaugh et al. |
| 9,107,573 B2 | 8/2015 | Birnkrant |
| 9,107,662 B2 | 8/2015 | Kostrzewski |
| 9,107,684 B2 | 8/2015 | Ma |

(56) References Cited

U.S. PATENT DOCUMENTS

| | | |
|---|---|---|
| 9,107,688 B2 | 8/2015 | Kimball et al. |
| 9,107,689 B2 | 8/2015 | Robertson et al. |
| 9,107,694 B2 | 8/2015 | Hendriks et al. |
| 9,111,548 B2 | 8/2015 | Nandy et al. |
| 9,113,880 B2 | 8/2015 | Zemlok et al. |
| 9,114,494 B1 | 8/2015 | Mah |
| 9,116,597 B1 | 8/2015 | Gulasky |
| 9,119,617 B2 | 9/2015 | Souls et al. |
| 9,119,655 B2 | 9/2015 | Bowling et al. |
| 9,119,657 B2 | 9/2015 | Shelton, IV et al. |
| 9,123,155 B2 | 9/2015 | Cunningham et al. |
| 9,125,644 B2 | 9/2015 | Lane et al. |
| 9,129,054 B2 | 9/2015 | Nawana et al. |
| 9,137,254 B2 | 9/2015 | Bilbrey et al. |
| 9,138,129 B2 | 9/2015 | Diolaiti |
| 9,138,225 B2 | 9/2015 | Huang et al. |
| 9,149,322 B2 | 10/2015 | Knowlton |
| 9,161,803 B2 | 10/2015 | Yates et al. |
| 9,168,054 B2 | 10/2015 | Turner et al. |
| 9,179,912 B2 | 11/2015 | Yates et al. |
| 9,183,723 B2 | 11/2015 | Sherman et al. |
| 9,186,143 B2 | 11/2015 | Timm et al. |
| 9,192,375 B2 | 11/2015 | Skinlo et al. |
| 9,192,447 B2 | 11/2015 | Choi et al. |
| 9,192,707 B2 | 11/2015 | Gerber et al. |
| 9,202,078 B2 | 12/2015 | Abuelsaad et al. |
| 9,204,879 B2 | 12/2015 | Shelton, IV |
| 9,204,995 B2 | 12/2015 | Scheller et al. |
| 9,216,062 B2 | 12/2015 | Duque et al. |
| 9,218,053 B2 | 12/2015 | Komuro et al. |
| 9,226,689 B2 | 1/2016 | Jacobsen et al. |
| 9,226,766 B2 | 1/2016 | Aldridge et al. |
| 9,226,767 B2 | 1/2016 | Stulen et al. |
| 9,232,883 B2 | 1/2016 | Ozawa et al. |
| 9,237,891 B2 | 1/2016 | Shelton, IV |
| 9,237,921 B2 | 1/2016 | Messerly et al. |
| 9,241,728 B2 | 1/2016 | Price et al. |
| 9,241,731 B2 | 1/2016 | Boudreaux et al. |
| 9,247,996 B1 | 2/2016 | Merana et al. |
| 9,250,172 B2 | 2/2016 | Harris et al. |
| 9,255,907 B2 | 2/2016 | Heanue et al. |
| 9,265,585 B2 | 2/2016 | Wingardner et al. |
| 9,272,406 B2 | 3/2016 | Aronhalt et al. |
| 9,277,956 B2 | 3/2016 | Zhang |
| 9,280,884 B1 | 3/2016 | Schultz et al. |
| 9,282,974 B2 | 3/2016 | Shelton, IV |
| 9,283,054 B2 | 3/2016 | Morgan et al. |
| 9,289,211 B2 | 3/2016 | Williams et al. |
| 9,289,212 B2 | 3/2016 | Shelton, IV et al. |
| 9,295,514 B2 | 3/2016 | Shelton, IV et al. |
| 9,301,691 B2 | 4/2016 | Hufnagel et al. |
| 9,301,753 B2 | 4/2016 | Aldridge et al. |
| 9,301,759 B2 | 4/2016 | Spivey et al. |
| 9,301,810 B2 | 4/2016 | Amiri et al. |
| 9,302,213 B2 | 4/2016 | Manahan et al. |
| 9,307,894 B2 | 4/2016 | von Grunberg et al. |
| 9,307,914 B2 | 4/2016 | Fahey |
| 9,307,986 B2 | 4/2016 | Hall et al. |
| 9,314,246 B2 | 4/2016 | Shelton, IV et al. |
| 9,314,308 B2 | 4/2016 | Parihar et al. |
| 9,325,732 B1 | 4/2016 | Stickle et al. |
| 9,326,767 B2 | 5/2016 | Koch et al. |
| 9,331,422 B2 | 5/2016 | Nazzaro et al. |
| 9,332,987 B2 | 5/2016 | Leimbach et al. |
| 9,333,042 B2 | 5/2016 | Diolaiti et al. |
| 9,336,385 B1 | 5/2016 | Spencer et al. |
| 9,341,704 B2 | 5/2016 | Picard et al. |
| 9,345,481 B2 | 5/2016 | Hall et al. |
| 9,345,490 B2 | 5/2016 | Ippisch |
| 9,345,546 B2 | 5/2016 | Toth et al. |
| 9,351,726 B2 | 5/2016 | Leimbach et al. |
| 9,351,727 B2 | 5/2016 | Leimbach et al. |
| 9,358,003 B2 | 6/2016 | Hall et al. |
| 9,358,685 B2 | 6/2016 | Meier et al. |
| 9,360,449 B2 | 6/2016 | Duric |
| 9,364,231 B2 | 6/2016 | Wenchell |
| 9,364,249 B2 | 6/2016 | Kimball et al. |
| 9,364,294 B2 | 6/2016 | Razzaque et al. |
| 9,370,400 B2 | 6/2016 | Parihar |
| 9,375,282 B2 | 6/2016 | Nau, Jr. et al. |
| 9,375,539 B2 | 6/2016 | Stearns et al. |
| 9,381,003 B2 | 7/2016 | Todor et al. |
| 9,381,058 B2 | 7/2016 | Houser et al. |
| 9,386,984 B2 | 7/2016 | Aronhalt et al. |
| 9,386,988 B2 | 7/2016 | Baxter, III et al. |
| 9,387,295 B1 | 7/2016 | Mastri et al. |
| 9,393,017 B2 | 7/2016 | Flanagan et al. |
| 9,393,037 B2 | 7/2016 | Olson et al. |
| 9,398,905 B2 | 7/2016 | Martin |
| 9,398,911 B2 | 7/2016 | Auld |
| 9,402,629 B2 | 8/2016 | Ehrenfels et al. |
| 9,414,776 B2 | 8/2016 | Sillay et al. |
| 9,419,018 B2 | 8/2016 | Sasagawa et al. |
| 9,421,014 B2 | 8/2016 | Ingmanson et al. |
| 9,433,470 B2 | 9/2016 | Choi |
| 9,439,622 B2 | 9/2016 | Case et al. |
| 9,439,668 B2 | 9/2016 | Timm et al. |
| 9,439,736 B2 | 9/2016 | Olson |
| 9,445,764 B2 | 9/2016 | Gross et al. |
| 9,445,813 B2 | 9/2016 | Shelton, IV et al. |
| 9,450,701 B2 | 9/2016 | Do et al. |
| 9,451,949 B2 | 9/2016 | Gorek et al. |
| 9,451,958 B2 | 9/2016 | Shelton, IV et al. |
| 9,463,022 B2 | 10/2016 | Swayze et al. |
| 9,468,438 B2 | 10/2016 | Baber et al. |
| 9,480,492 B2 | 11/2016 | Aranyi et al. |
| 9,485,475 B2 | 11/2016 | Speier et al. |
| 9,492,146 B2 | 11/2016 | Kostrzewski et al. |
| 9,492,237 B2 | 11/2016 | Kang et al. |
| 9,498,215 B2 | 11/2016 | Duque et al. |
| 9,498,231 B2 | 11/2016 | Haider et al. |
| 9,516,239 B2 | 12/2016 | Blanquart et al. |
| 9,519,753 B1 | 12/2016 | Gerdeman et al. |
| 9,522,003 B2 | 12/2016 | Weir et al. |
| 9,526,407 B2 | 12/2016 | Hoeg et al. |
| 9,526,499 B2 | 12/2016 | Kostrzewski et al. |
| 9,526,587 B2 | 12/2016 | Zhao et al. |
| 9,539,007 B2 | 1/2017 | Dhakad et al. |
| 9,539,020 B2 | 1/2017 | Conlon et al. |
| 9,542,481 B2 | 1/2017 | Halter et al. |
| 9,546,662 B2 | 1/2017 | Shener-Irmakoglu et al. |
| 9,554,794 B2 | 1/2017 | Baber et al. |
| 9,554,854 B2 | 1/2017 | Yates et al. |
| 9,561,038 B2 | 2/2017 | Shelton, IV et al. |
| 9,561,045 B2 | 2/2017 | Hinman et al. |
| 9,566,708 B2 | 2/2017 | Kurnianto |
| 9,572,592 B2 | 2/2017 | Price et al. |
| 9,579,503 B2 | 2/2017 | McKinney et al. |
| 9,585,657 B2 | 3/2017 | Shelton, IV et al. |
| 9,592,095 B2 | 3/2017 | Panescu et al. |
| 9,597,081 B2 | 3/2017 | Swayze et al. |
| 9,600,138 B2 | 3/2017 | Thomas et al. |
| 9,603,024 B2 | 3/2017 | Wang et al. |
| 9,610,114 B2 | 4/2017 | Baxter, III et al. |
| 9,622,808 B2 | 4/2017 | Beller et al. |
| 9,628,501 B2 | 4/2017 | Datta Ray et al. |
| 9,629,560 B2 | 4/2017 | Joseph |
| 9,629,623 B2 | 4/2017 | Lytle, IV et al. |
| 9,629,628 B2 | 4/2017 | Aranyi |
| 9,629,629 B2 | 4/2017 | Leimbach et al. |
| 9,630,318 B2 | 4/2017 | Ibarz Gabardos et al. |
| 9,636,188 B2 | 5/2017 | Gattani et al. |
| 9,636,825 B2 | 5/2017 | Penn et al. |
| 9,641,596 B2 | 5/2017 | Unagami et al. |
| 9,641,815 B2 | 5/2017 | Richardson et al. |
| 9,642,620 B2 | 5/2017 | Baxter, III et al. |
| 9,649,110 B2 | 5/2017 | Parihar et al. |
| 9,649,111 B2 | 5/2017 | Shelton, IV et al. |
| 9,649,126 B2 | 5/2017 | Robertson et al. |
| 9,649,169 B2 | 5/2017 | Cinquin et al. |
| 9,652,655 B2 | 5/2017 | Satish et al. |
| 9,655,616 B2 | 5/2017 | Aranyi |
| 9,656,092 B2 | 5/2017 | Golden |
| 9,662,116 B2 | 5/2017 | Smith et al. |

(56) References Cited

U.S. PATENT DOCUMENTS

| | | |
|---|---|---|
| 9,662,177 B2 | 5/2017 | Weir et al. |
| 9,668,729 B2 | 6/2017 | Williams et al. |
| 9,668,732 B2 | 6/2017 | Patel et al. |
| 9,668,765 B2 | 6/2017 | Grace et al. |
| 9,671,860 B2 | 6/2017 | Ogawa et al. |
| 9,675,264 B2 | 6/2017 | Acquista et al. |
| 9,675,354 B2 | 6/2017 | Weir et al. |
| 9,681,870 B2 | 6/2017 | Baxter, III et al. |
| 9,686,306 B2 | 6/2017 | Chizeck et al. |
| 9,687,230 B2 | 6/2017 | Leimbach et al. |
| 9,690,362 B2 | 6/2017 | Leimbach et al. |
| 9,700,292 B2 | 7/2017 | Nawana et al. |
| 9,700,309 B2 | 7/2017 | Jaworek et al. |
| 9,700,312 B2 | 7/2017 | Kostrzewski et al. |
| 9,706,993 B2 | 7/2017 | Hessler et al. |
| 9,710,214 B2 | 7/2017 | Lin et al. |
| 9,710,644 B2 | 7/2017 | Reybok et al. |
| 9,713,424 B2 | 7/2017 | Spaide |
| 9,717,141 B1 | 7/2017 | Tegg |
| 9,717,498 B2 | 8/2017 | Aranyi et al. |
| 9,717,525 B2 | 8/2017 | Ahluwalia et al. |
| 9,717,548 B2 | 8/2017 | Couture |
| 9,724,094 B2 | 8/2017 | Baber et al. |
| 9,724,118 B2 | 8/2017 | Schulte et al. |
| 9,733,663 B2 | 8/2017 | Leimbach et al. |
| 9,737,301 B2 | 8/2017 | Baber et al. |
| 9,737,310 B2 | 8/2017 | Whitfield et al. |
| 9,737,335 B2 | 8/2017 | Butler et al. |
| 9,737,355 B2 | 8/2017 | Yates et al. |
| 9,740,826 B2 | 8/2017 | Raghavan et al. |
| 9,743,016 B2 | 8/2017 | Nestares et al. |
| 9,743,929 B2 | 8/2017 | Leimbach et al. |
| 9,743,946 B2 | 8/2017 | Faller et al. |
| 9,743,947 B2 | 8/2017 | Price et al. |
| 9,750,499 B2 | 9/2017 | Leimbach et al. |
| 9,750,500 B2 | 9/2017 | Malkowski |
| 9,750,522 B2 | 9/2017 | Scheib et al. |
| 9,750,523 B2 | 9/2017 | Tsubuku |
| 9,753,135 B2 | 9/2017 | Bosch |
| 9,753,568 B2 | 9/2017 | McMillen |
| 9,757,126 B2 | 9/2017 | Cappola |
| 9,757,128 B2 | 9/2017 | Baber et al. |
| 9,757,142 B2 | 9/2017 | Shimizu |
| 9,757,152 B2 | 9/2017 | Ogilvie et al. |
| 9,763,741 B2 | 9/2017 | Alvarez et al. |
| 9,764,164 B2 | 9/2017 | Wiener et al. |
| 9,770,541 B2 | 9/2017 | Carr et al. |
| 9,777,913 B2 | 10/2017 | Talbert et al. |
| 9,782,164 B2 | 10/2017 | Mumaw et al. |
| 9,782,169 B2 | 10/2017 | Kimsey et al. |
| 9,782,212 B2 | 10/2017 | Wham et al. |
| 9,782,214 B2 | 10/2017 | Houser et al. |
| 9,788,836 B2 | 10/2017 | Overmyer et al. |
| 9,788,851 B2 | 10/2017 | Dannaher et al. |
| 9,788,902 B2 | 10/2017 | Inoue et al. |
| 9,788,907 B1 | 10/2017 | Alvi et al. |
| 9,795,436 B2 | 10/2017 | Yates et al. |
| 9,797,486 B2 | 10/2017 | Zergiebel et al. |
| 9,801,531 B2 | 10/2017 | Morita et al. |
| 9,801,626 B2 | 10/2017 | Parihar et al. |
| 9,801,627 B2 | 10/2017 | Harris et al. |
| 9,801,679 B2 | 10/2017 | Trees et al. |
| 9,802,033 B2 | 10/2017 | Hibner et al. |
| 9,804,618 B2 | 10/2017 | Leimbach et al. |
| 9,805,472 B2 | 10/2017 | Chou et al. |
| 9,808,244 B2 | 11/2017 | Leimbach et al. |
| 9,808,245 B2 | 11/2017 | Richard et al. |
| 9,808,246 B2 | 11/2017 | Shelton, IV et al. |
| 9,808,248 B2 | 11/2017 | Hoffman |
| 9,808,249 B2 | 11/2017 | Shelton, IV |
| 9,814,457 B2 | 11/2017 | Martin et al. |
| 9,814,460 B2 | 11/2017 | Kimsey et al. |
| 9,814,462 B2 | 11/2017 | Woodard, Jr. et al. |
| 9,814,463 B2 | 11/2017 | Williams et al. |
| 9,820,699 B2 | 11/2017 | Bingley et al. |
| 9,820,738 B2 | 11/2017 | Lytle, IV et al. |
| 9,820,741 B2 | 11/2017 | Kostrzewski |
| 9,826,976 B2 | 11/2017 | Parihar et al. |
| 9,826,977 B2 | 11/2017 | Leimbach et al. |
| 9,827,054 B2 | 11/2017 | Richmond et al. |
| 9,827,059 B2 | 11/2017 | Robinson et al. |
| 9,830,424 B2 | 11/2017 | Dixon et al. |
| 9,833,241 B2 | 12/2017 | Huitema et al. |
| 9,839,419 B2 | 12/2017 | Deck et al. |
| 9,839,424 B2 | 12/2017 | Zergiebel et al. |
| 9,839,428 B2 | 12/2017 | Baxter, III et al. |
| 9,839,470 B2 | 12/2017 | Gilbert et al. |
| 9,839,487 B2 | 12/2017 | Dachs, II |
| 9,844,368 B2 | 12/2017 | Boudreaux et al. |
| 9,844,369 B2 | 12/2017 | Huitema et al. |
| 9,844,374 B2 | 12/2017 | Lytle, IV et al. |
| 9,844,375 B2 | 12/2017 | Overmyer et al. |
| 9,844,379 B2 | 12/2017 | Shelton, IV et al. |
| 9,848,058 B2 | 12/2017 | Johnson et al. |
| 9,848,877 B2 | 12/2017 | Shelton, IV et al. |
| 9,861,354 B2 | 1/2018 | Saliman et al. |
| 9,861,363 B2 | 1/2018 | Chen et al. |
| 9,861,428 B2 | 1/2018 | Trees et al. |
| 9,867,612 B2 | 1/2018 | Parihar et al. |
| 9,867,651 B2 | 1/2018 | Wham |
| 9,867,914 B2 | 1/2018 | Bonano et al. |
| 9,872,609 B2 | 1/2018 | Levy |
| 9,872,683 B2 | 1/2018 | Hopkins et al. |
| 9,877,718 B2 | 1/2018 | Weir et al. |
| 9,877,721 B2 | 1/2018 | Schellin et al. |
| 9,883,860 B2 | 2/2018 | Leimbach |
| 9,888,914 B2 | 2/2018 | Martin et al. |
| 9,888,919 B2 | 2/2018 | Leimbach et al. |
| 9,888,921 B2 | 2/2018 | Williams et al. |
| 9,888,975 B2 | 2/2018 | Auld |
| 9,895,148 B2 | 2/2018 | Shelton, IV et al. |
| 9,900,787 B2 | 2/2018 | Ou |
| 9,901,342 B2 | 2/2018 | Shelton, IV et al. |
| 9,901,406 B2 | 2/2018 | State et al. |
| 9,905,000 B2 | 2/2018 | Chou et al. |
| 9,907,550 B2 | 3/2018 | Sniffin et al. |
| 9,913,642 B2 | 3/2018 | Leimbach et al. |
| 9,913,645 B2 | 3/2018 | Zerkle et al. |
| 9,918,730 B2 | 3/2018 | Trees et al. |
| 9,918,778 B2 | 3/2018 | Walberg et al. |
| 9,918,788 B2 | 3/2018 | Paul et al. |
| 9,922,304 B2 | 3/2018 | DeBusk et al. |
| 9,924,941 B2 | 3/2018 | Burbank |
| 9,924,944 B2 | 3/2018 | Shelton, IV et al. |
| 9,924,961 B2 | 3/2018 | Shelton, IV et al. |
| 9,931,040 B2 | 4/2018 | Homyk et al. |
| 9,931,118 B2 | 4/2018 | Shelton, IV et al. |
| 9,931,124 B2 | 4/2018 | Gokharu |
| 9,936,942 B2 | 4/2018 | Chin et al. |
| 9,936,955 B2 | 4/2018 | Miller et al. |
| 9,936,961 B2 | 4/2018 | Chien et al. |
| 9,937,012 B2 | 4/2018 | Hares et al. |
| 9,937,014 B2 | 4/2018 | Bowling et al. |
| 9,937,626 B2 | 4/2018 | Rockrohr |
| 9,938,972 B2 | 4/2018 | Walley |
| 9,943,230 B2 | 4/2018 | Kaku et al. |
| 9,943,309 B2 | 4/2018 | Shelton, IV et al. |
| 9,943,312 B2 | 4/2018 | Posada et al. |
| 9,943,377 B2 | 4/2018 | Yates et al. |
| 9,943,379 B2 | 4/2018 | Gregg, II et al. |
| 9,943,918 B2 | 4/2018 | Grogan et al. |
| 9,949,785 B2 | 4/2018 | Price et al. |
| 9,962,157 B2 | 5/2018 | Sapre |
| 9,968,355 B2 | 5/2018 | Shelton, IV et al. |
| 9,980,769 B2 | 5/2018 | Trees et al. |
| 9,980,778 B2 | 5/2018 | Ohline et al. |
| 9,987,000 B2 | 6/2018 | Shelton, IV et al. |
| 9,990,856 B2 | 6/2018 | Kuchenbecker et al. |
| 9,993,248 B2 | 6/2018 | Shelton, IV et al. |
| 9,993,258 B2 | 6/2018 | Shelton, IV et al. |
| 9,993,305 B2 | 6/2018 | Andersson |
| 10,004,491 B2 | 6/2018 | Martin et al. |
| 10,004,497 B2 | 6/2018 | Overmyer et al. |
| 10,004,500 B2 | 6/2018 | Shelton, IV et al. |

(56) References Cited

U.S. PATENT DOCUMENTS

| | | |
|---|---|---|
| 10,004,501 B2 | 6/2018 | Shelton, IV et al. |
| 10,004,527 B2 | 6/2018 | Gee et al. |
| 10,004,557 B2 | 6/2018 | Gross |
| D822,206 S | 7/2018 | Shelton, IV et al. |
| 10,010,322 B2 | 7/2018 | Shelton, IV et al. |
| 10,010,324 B2 | 7/2018 | Huitema et al. |
| 10,013,049 B2 | 7/2018 | Leimbach et al. |
| 10,016,199 B2 | 7/2018 | Baber et al. |
| 10,021,318 B2 | 7/2018 | Hugosson et al. |
| 10,022,120 B2 | 7/2018 | Martin et al. |
| 10,022,391 B2 | 7/2018 | Ruderman Chen et al. |
| 10,022,568 B2 | 7/2018 | Messerly et al. |
| 10,028,744 B2 | 7/2018 | Shelton, IV et al. |
| 10,028,761 B2 | 7/2018 | Leimbach et al. |
| 10,028,788 B2 | 7/2018 | Kang |
| 10,034,704 B2 | 7/2018 | Asher et al. |
| 10,037,641 B2 | 7/2018 | Hyde et al. |
| D826,405 S | 8/2018 | Shelton, IV et al. |
| 10,039,564 B2 | 8/2018 | Hibner et al. |
| 10,039,565 B2 | 8/2018 | Vezzu |
| 10,041,822 B2 | 8/2018 | Zemlok |
| 10,044,791 B2 | 8/2018 | Kamen et al. |
| 10,045,776 B2 | 8/2018 | Shelton, IV et al. |
| 10,045,779 B2 | 8/2018 | Savage et al. |
| 10,045,781 B2 | 8/2018 | Cropper et al. |
| 10,045,813 B2 | 8/2018 | Mueller |
| 10,048,379 B2 | 8/2018 | Markendorf et al. |
| 10,052,044 B2 | 8/2018 | Shelton, IV et al. |
| 10,052,102 B2 | 8/2018 | Baxter, III et al. |
| 10,052,104 B2 | 8/2018 | Shelton, IV et al. |
| 10,054,441 B2 | 8/2018 | Schorr et al. |
| 10,069,633 B2 | 9/2018 | Gulati et al. |
| 10,076,326 B2 | 9/2018 | Yates et al. |
| 10,080,618 B2 | 9/2018 | Marshall et al. |
| D831,209 S | 10/2018 | Huitema et al. |
| 10,085,748 B2 | 10/2018 | Morgan et al. |
| 10,085,749 B2 | 10/2018 | Cappola et al. |
| 10,095,942 B2 | 10/2018 | Mentese et al. |
| 10,097,578 B2 | 10/2018 | Baldonado et al. |
| 10,098,527 B2 | 10/2018 | Weisenburgh, II et al. |
| 10,098,635 B2 | 10/2018 | Burbank |
| 10,098,642 B2 | 10/2018 | Baxter, III et al. |
| 10,098,705 B2 | 10/2018 | Brisson et al. |
| 10,105,140 B2 | 10/2018 | Malinouskas et al. |
| 10,105,142 B2 | 10/2018 | Baxter, III et al. |
| 10,111,658 B2 | 10/2018 | Chowaniec et al. |
| 10,111,665 B2 | 10/2018 | Aranyi et al. |
| 10,111,679 B2 | 10/2018 | Baber et al. |
| 10,117,649 B2 | 11/2018 | Baxter et al. |
| 10,117,651 B2 | 11/2018 | Whitman et al. |
| 10,117,702 B2 | 11/2018 | Danziger et al. |
| 10,118,119 B2 | 11/2018 | Sappok et al. |
| 10,130,359 B2 | 11/2018 | Hess et al. |
| 10,130,360 B2 | 11/2018 | Olson et al. |
| 10,130,361 B2 | 11/2018 | Yates et al. |
| 10,130,367 B2 | 11/2018 | Cappola et al. |
| 10,133,248 B2 | 11/2018 | Fitzsimmons et al. |
| 10,135,242 B2 | 11/2018 | Baber et al. |
| 10,136,887 B2 | 11/2018 | Shelton, IV et al. |
| 10,136,949 B2 | 11/2018 | Felder et al. |
| 10,143,526 B2 | 12/2018 | Walker et al. |
| 10,143,948 B2 | 12/2018 | Bonifas et al. |
| 10,149,680 B2 | 12/2018 | Parihar et al. |
| 10,152,789 B2 | 12/2018 | Carnes et al. |
| 10,154,841 B2 | 12/2018 | Weaner et al. |
| 10,159,044 B2 | 12/2018 | Hrabak |
| 10,159,481 B2 | 12/2018 | Whitman et al. |
| 10,159,483 B2 | 12/2018 | Beckman et al. |
| 10,164,466 B2 | 12/2018 | Calderoni |
| 10,166,025 B2 | 1/2019 | Leimbach et al. |
| 10,169,862 B2 | 1/2019 | Andre et al. |
| 10,172,687 B2 | 1/2019 | Garbus et al. |
| 10,175,096 B2 | 1/2019 | Dickerson |
| 10,175,127 B2 | 1/2019 | Collins et al. |
| 10,178,992 B2 | 1/2019 | Wise et al. |
| 10,179,413 B2 | 1/2019 | Rockrohr |
| 10,180,463 B2 | 1/2019 | Beckman et al. |
| 10,182,814 B2 | 1/2019 | Okoniewski |
| 10,182,816 B2 | 1/2019 | Shelton, IV et al. |
| 10,182,818 B2 | 1/2019 | Hensel et al. |
| 10,188,385 B2 | 1/2019 | Kerr et al. |
| 10,189,157 B2 | 1/2019 | Schlegel et al. |
| 10,194,907 B2 | 2/2019 | Marczyk et al. |
| 10,194,913 B2 | 2/2019 | Nalagatla et al. |
| 10,197,803 B2 | 2/2019 | Badiali et al. |
| 10,198,965 B2 | 2/2019 | Hart |
| 10,201,311 B2 | 2/2019 | Chou et al. |
| 10,201,349 B2 | 2/2019 | Leimbach et al. |
| 10,201,364 B2 | 2/2019 | Leimbach et al. |
| 10,201,365 B2 | 2/2019 | Boudreaux et al. |
| 10,205,708 B1 | 2/2019 | Fletcher et al. |
| 10,206,605 B2 | 2/2019 | Shelton, IV et al. |
| 10,206,752 B2 | 2/2019 | Hares et al. |
| 10,213,201 B2 | 2/2019 | Shelton, IV et al. |
| 10,213,203 B2 | 2/2019 | Swayze et al. |
| 10,213,266 B2 | 2/2019 | Zemlok et al. |
| 10,213,268 B2 | 2/2019 | Dachs, II |
| 10,219,491 B2 | 3/2019 | Stiles, Jr. et al. |
| 10,220,522 B2 | 3/2019 | Rockrohr |
| 10,222,750 B2 | 3/2019 | Bang et al. |
| 10,226,249 B2 | 3/2019 | Jaworek et al. |
| 10,226,250 B2 | 3/2019 | Beckman et al. |
| 10,226,302 B2 | 3/2019 | Lacal et al. |
| 10,231,634 B2 | 3/2019 | Zand et al. |
| 10,231,733 B2 | 3/2019 | Ehrenfels et al. |
| 10,231,775 B2 | 3/2019 | Shelton, IV et al. |
| 10,238,413 B2 | 3/2019 | Hibner et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,033 B2 | 4/2019 | Overmyer et al. |
| 10,245,037 B2 | 4/2019 | Conklin et al. |
| 10,245,038 B2 | 4/2019 | Hopkins et al. |
| 10,251,661 B2 | 4/2019 | Collings et al. |
| 10,251,725 B2 | 4/2019 | Valentine et al. |
| 10,258,331 B2 | 4/2019 | Shelton, IV et al. |
| 10,258,359 B2 | 4/2019 | Kapadia |
| 10,258,362 B2 | 4/2019 | Conlon |
| 10,258,363 B2 | 4/2019 | Worrell et al. |
| 10,258,415 B2 | 4/2019 | Harrah et al. |
| 10,258,418 B2 | 4/2019 | Shelton, IV et al. |
| 10,258,425 B2 | 4/2019 | Mustufa et al. |
| 10,263,171 B2 | 4/2019 | Wiener et al. |
| 10,265,035 B2 | 4/2019 | Fehre et al. |
| 10,265,068 B2 | 4/2019 | Harris et al. |
| 10,265,072 B2 | 4/2019 | Shelton, IV et al. |
| 10,265,090 B2 | 4/2019 | Ingmanson et al. |
| 10,265,130 B2 | 4/2019 | Hess et al. |
| 10,271,840 B2 | 4/2019 | Sapre |
| 10,271,844 B2 | 4/2019 | Valentine et al. |
| 10,271,850 B2 | 4/2019 | Williams |
| 10,271,851 B2 | 4/2019 | Shelton, IV et al. |
| D847,989 S | 5/2019 | Shelton, IV et al. |
| 10,278,698 B2 | 5/2019 | Racenet |
| 10,278,778 B2 | 5/2019 | State et al. |
| 10,283,220 B2 | 5/2019 | Azizian et al. |
| 10,285,694 B2 | 5/2019 | Viola et al. |
| 10,285,698 B2 | 5/2019 | Cappola et al. |
| 10,285,700 B2 | 5/2019 | Scheib |
| 10,285,705 B2 | 5/2019 | Shelton, IV et al. |
| 10,292,704 B2 | 5/2019 | Harris et al. |
| 10,292,707 B2 | 5/2019 | Shelton, IV et al. |
| 10,292,758 B2 | 5/2019 | Boudreaux et al. |
| 10,292,771 B2 | 5/2019 | Wood et al. |
| 10,299,792 B2 | 5/2019 | Huitema et al. |
| 10,299,870 B2 | 5/2019 | Connolly et al. |
| 10,305,926 B2 | 5/2019 | Mihan et al. |
| D850,617 S | 6/2019 | Shelton, IV et al. |
| 10,307,159 B2 | 6/2019 | Harris et al. |
| 10,307,170 B2 | 6/2019 | Parfett et al. |
| 10,307,199 B2 | 6/2019 | Farritor et al. |
| 10,311,036 B1 | 6/2019 | Hussam et al. |
| 10,313,137 B2 | 6/2019 | Aarnio et al. |

(56) References Cited

U.S. PATENT DOCUMENTS

| | | | |
|---|---|---|---|
| 10,314,577 | B2 | 6/2019 | Laurent et al. |
| 10,314,582 | B2 | 6/2019 | Shelton, IV et al. |
| 10,321,907 | B2 | 6/2019 | Shelton, IV et al. |
| 10,321,964 | B2 | 6/2019 | Grover et al. |
| 10,327,764 | B2 | 6/2019 | Harris et al. |
| 10,335,147 | B2 | 7/2019 | Rector et al. |
| 10,335,149 | B2 | 7/2019 | Baxter, III et al. |
| 10,335,180 | B2 | 7/2019 | Johnson et al. |
| 10,335,227 | B2 | 7/2019 | Heard |
| 10,342,543 | B2 | 7/2019 | Shelton, IV et al. |
| 10,342,602 | B2 | 7/2019 | Strobl et al. |
| 10,342,623 | B2 | 7/2019 | Huelman et al. |
| 10,343,102 | B2 | 7/2019 | Reasoner et al. |
| 10,357,246 | B2 | 7/2019 | Shelton, IV et al. |
| 10,357,247 | B2 | 7/2019 | Shelton, IV et al. |
| 10,362,179 | B2 | 7/2019 | Harris |
| 10,363,032 | B2 | 7/2019 | Scheib et al. |
| 10,363,037 | B2 | 7/2019 | Aronhalt et al. |
| 10,368,861 | B2 | 8/2019 | Baxter, III et al. |
| 10,368,865 | B2 | 8/2019 | Harris et al. |
| 10,368,867 | B2 | 8/2019 | Harris et al. |
| 10,368,876 | B2 | 8/2019 | Bhatnagar et al. |
| 10,368,894 | B2 | 8/2019 | Madan et al. |
| 10,368,903 | B2 | 8/2019 | Morales et al. |
| 10,376,263 | B2 | 8/2019 | Morgan et al. |
| 10,376,305 | B2 | 8/2019 | Yates et al. |
| 10,376,337 | B2 | 8/2019 | Kilroy et al. |
| 10,376,338 | B2 | 8/2019 | Taylor et al. |
| 10,378,893 | B2 | 8/2019 | Mankovskii |
| 10,383,518 | B2 | 8/2019 | Abu-Tarif et al. |
| 10,383,699 | B2 | 8/2019 | Kilroy et al. |
| 10,390,718 | B2 | 8/2019 | Chen et al. |
| 10,390,794 | B2 | 8/2019 | Kuroiwa et al. |
| 10,390,825 | B2 | 8/2019 | Shelton, IV et al. |
| 10,390,831 | B2 | 8/2019 | Holsten et al. |
| 10,390,895 | B2 | 8/2019 | Henderson et al. |
| 10,398,434 | B2 | 9/2019 | Shelton, IV et al. |
| 10,398,517 | B2 | 9/2019 | Eckert et al. |
| 10,398,521 | B2 | 9/2019 | Itkowitz et al. |
| 10,404,521 | B2 | 9/2019 | McChord et al. |
| 10,404,801 | B2 | 9/2019 | Martch |
| 10,405,857 | B2 | 9/2019 | Shelton, IV et al. |
| 10,405,863 | B2 | 9/2019 | Wise et al. |
| 10,413,291 | B2 | 9/2019 | Worthington et al. |
| 10,413,293 | B2 | 9/2019 | Shelton, IV et al. |
| 10,413,297 | B2 | 9/2019 | Harris et al. |
| 10,417,446 | B2 | 9/2019 | Takeyama |
| 10,420,552 | B2 | 9/2019 | Shelton, IV et al. |
| 10,420,558 | B2 | 9/2019 | Nalagatla et al. |
| 10,420,559 | B2 | 9/2019 | Marczyk et al. |
| 10,420,620 | B2 | 9/2019 | Rockrohr |
| 10,420,865 | B2 | 9/2019 | Reasoner et al. |
| 10,422,727 | B2 | 9/2019 | Pliskin |
| 10,426,466 | B2 | 10/2019 | Contini et al. |
| 10,426,467 | B2 | 10/2019 | Miller et al. |
| 10,426,468 | B2 | 10/2019 | Contini et al. |
| 10,426,471 | B2 | 10/2019 | Shelton, IV et al. |
| 10,433,837 | B2 | 10/2019 | Worthington et al. |
| 10,433,844 | B2 | 10/2019 | Shelton, IV et al. |
| 10,433,849 | B2 | 10/2019 | Shelton, IV et al. |
| 10,433,918 | B2 | 10/2019 | Shelton, IV et al. |
| 10,441,279 | B2 | 10/2019 | Shelton, IV et al. |
| 10,441,345 | B2 | 10/2019 | Aldridge et al. |
| 10,448,948 | B2 | 10/2019 | Shelton, IV et al. |
| 10,448,950 | B2 | 10/2019 | Shelton, IV et al. |
| 10,456,137 | B2 | 10/2019 | Vendely et al. |
| 10,456,140 | B2 | 10/2019 | Shelton, IV et al. |
| 10,456,193 | B2 | 10/2019 | Yates et al. |
| 10,463,365 | B2 | 11/2019 | Williams |
| 10,463,367 | B2 | 11/2019 | Kostrzewski et al. |
| 10,463,371 | B2 | 11/2019 | Kostrzewski |
| 10,463,436 | B2 | 11/2019 | Jackson et al. |
| 10,470,762 | B2 | 11/2019 | Leimbach et al. |
| 10,470,764 | B2 | 11/2019 | Baxter, III et al. |
| 10,470,768 | B2 | 11/2019 | Harris et al. |
| 10,470,791 | B2 | 11/2019 | Houser |
| 10,471,254 | B2 | 11/2019 | Sano et al. |
| 10,478,181 | B2 | 11/2019 | Shelton, IV et al. |
| 10,478,189 | B2 | 11/2019 | Bear et al. |
| 10,478,190 | B2 | 11/2019 | Miller et al. |
| 10,478,544 | B2 | 11/2019 | Friederichs et al. |
| 10,485,450 | B2 | 11/2019 | Gupta et al. |
| 10,485,542 | B2 | 11/2019 | Shelton, IV et al. |
| 10,485,543 | B2 | 11/2019 | Shelton, IV et al. |
| 10,492,783 | B2 | 12/2019 | Shelton, IV et al. |
| 10,492,785 | B2 | 12/2019 | Overmyer et al. |
| 10,496,788 | B2 | 12/2019 | Amarasingham et al. |
| 10,498,269 | B2 | 12/2019 | Zemlok et al. |
| 10,499,891 | B2 | 12/2019 | Chaplin et al. |
| 10,499,914 | B2 | 12/2019 | Huang et al. |
| 10,499,915 | B2 | 12/2019 | Aranyi |
| 10,499,994 | B2 | 12/2019 | Luks et al. |
| 10,507,068 | B2 | 12/2019 | Kopp et al. |
| 10,512,461 | B2 | 12/2019 | Gupta et al. |
| 10,512,499 | B2 | 12/2019 | McHenry et al. |
| 10,512,514 | B2 | 12/2019 | Nowlin et al. |
| 10,517,588 | B2 | 12/2019 | Gupta et al. |
| 10,517,595 | B2 | 12/2019 | Hunter et al. |
| 10,517,596 | B2 | 12/2019 | Hunter et al. |
| 10,517,686 | B2 | 12/2019 | Vokrot et al. |
| 10,524,789 | B2 | 1/2020 | Swayze et al. |
| 10,531,874 | B2 | 1/2020 | Morgan et al. |
| 10,531,929 | B2 | 1/2020 | Widenhouse et al. |
| 10,532,330 | B2 | 1/2020 | Diallo et al. |
| 10,536,617 | B2 | 1/2020 | Liang et al. |
| 10,537,324 | B2 | 1/2020 | Shelton, IV et al. |
| 10,537,325 | B2 | 1/2020 | Bakos et al. |
| 10,537,351 | B2 | 1/2020 | Shelton, IV et al. |
| 10,542,978 | B2 | 1/2020 | Chowaniec et al. |
| 10,542,979 | B2 | 1/2020 | Shelton, IV et al. |
| 10,542,982 | B2 | 1/2020 | Beckman et al. |
| 10,542,991 | B2 | 1/2020 | Shelton, IV et al. |
| 10,548,504 | B2 | 2/2020 | Shelton, IV et al. |
| 10,548,612 | B2 | 2/2020 | Martinez et al. |
| 10,548,673 | B2 | 2/2020 | Harris et al. |
| 10,552,574 | B2 | 2/2020 | Sweeney |
| 10,555,675 | B2 | 2/2020 | Satish et al. |
| 10,555,748 | B2 | 2/2020 | Yates et al. |
| 10,555,750 | B2 | 2/2020 | Conlon et al. |
| 10,555,769 | B2 | 2/2020 | Worrell et al. |
| 10,561,422 | B2 | 2/2020 | Schellin et al. |
| 10,561,471 | B2 | 2/2020 | Nichogi |
| 10,568,625 | B2 | 2/2020 | Harris et al. |
| 10,568,626 | B2 | 2/2020 | Shelton, IV et al. |
| 10,568,632 | B2 | 2/2020 | Miller et al. |
| 10,568,704 | B2 | 2/2020 | Savall et al. |
| 10,575,868 | B2 | 3/2020 | Hall et al. |
| 10,582,928 | B2 | 3/2020 | Hunter et al. |
| 10,582,931 | B2 | 3/2020 | Mujawar |
| 10,586,074 | B2 | 3/2020 | Rose et al. |
| 10,588,625 | B2 | 3/2020 | Weaner et al. |
| 10,588,629 | B2 | 3/2020 | Malinouskas et al. |
| 10,588,630 | B2 | 3/2020 | Shelton, IV et al. |
| 10,588,631 | B2 | 3/2020 | Shelton, IV et al. |
| 10,588,632 | B2 | 3/2020 | Shelton, IV et al. |
| 10,588,711 | B2 | 3/2020 | DiCarlo et al. |
| 10,592,067 | B2 | 3/2020 | Merdan et al. |
| 10,595,882 | B2 | 3/2020 | Parfett et al. |
| 10,595,887 | B2 | 3/2020 | Shelton, IV et al. |
| 10,595,930 | B2 | 3/2020 | Scheib et al. |
| 10,595,952 | B2 | 3/2020 | Forrest et al. |
| 10,602,848 | B2 | 3/2020 | Magana |
| 10,603,036 | B2 | 3/2020 | Hunter et al. |
| 10,603,128 | B2 | 3/2020 | Zergiebel et al. |
| 10,610,223 | B2 | 4/2020 | Wellman et al. |
| 10,610,224 | B2 | 4/2020 | Shelton, IV et al. |
| 10,610,286 | B2 | 4/2020 | Wiener et al. |
| 10,610,313 | B2 | 4/2020 | Bailey et al. |
| 10,617,412 | B2 | 4/2020 | Shelton, IV et al. |
| 10,617,414 | B2 | 4/2020 | Shelton, IV et al. |
| 10,617,482 | B2 | 4/2020 | Houser et al. |
| 10,617,484 | B2 | 4/2020 | Kilroy et al. |
| 10,624,635 | B2 | 4/2020 | Harris et al. |
| 10,624,691 | B2 | 4/2020 | Wiener et al. |

(56) References Cited

U.S. PATENT DOCUMENTS

| | | |
|---|---|---|
| 10,631,423 B2 | 4/2020 | Collins et al. |
| 10,631,912 B2 | 4/2020 | McFarlin et al. |
| 10,631,916 B2 | 4/2020 | Horner et al. |
| 10,631,917 B2 | 4/2020 | Ineson |
| 10,631,939 B2 | 4/2020 | Dachs, II et al. |
| 10,639,027 B2 | 5/2020 | Shelton, IV et al. |
| 10,639,034 B2 | 5/2020 | Harris et al. |
| 10,639,035 B2 | 5/2020 | Shelton, IV et al. |
| 10,639,036 B2 | 5/2020 | Yates et al. |
| 10,639,037 B2 | 5/2020 | Shelton, IV et al. |
| 10,639,039 B2 | 5/2020 | Vendely et al. |
| 10,639,098 B2 | 5/2020 | Cosman et al. |
| 10,639,111 B2 | 5/2020 | Kopp |
| 10,639,185 B2 | 5/2020 | Agrawal et al. |
| 10,653,413 B2 | 5/2020 | Worthington et al. |
| 10,653,476 B2 | 5/2020 | Ross |
| 10,653,489 B2 | 5/2020 | Kopp |
| 10,656,720 B1 | 5/2020 | Holz |
| 10,660,705 B2 | 5/2020 | Piron et al. |
| 10,667,809 B2 | 6/2020 | Bakos et al. |
| 10,667,810 B2 | 6/2020 | Shelton, IV et al. |
| 10,667,811 B2 | 6/2020 | Harris et al. |
| 10,667,877 B2 | 6/2020 | Kapadia |
| 10,674,897 B2 | 6/2020 | Levy |
| 10,675,035 B2 | 6/2020 | Zingman |
| 10,695,134 B2 | 6/2020 | Barral et al. |
| D893,717 S | 8/2020 | Messerly et al. |
| 10,729,458 B2 | 8/2020 | Stoddard et al. |
| 10,751,052 B2 | 8/2020 | Stokes et al. |
| D896,379 S | 9/2020 | Shelton, IV et al. |
| 10,786,317 B2 | 9/2020 | Zhou et al. |
| 10,786,327 B2 | 9/2020 | Anderson et al. |
| 10,792,118 B2 | 10/2020 | Prpa et al. |
| 10,842,897 B2 | 11/2020 | Schwartz et al. |
| 10,864,050 B2 | 12/2020 | Tabandeh et al. |
| 10,881,446 B2 | 1/2021 | Strobl |
| 10,905,418 B2 | 2/2021 | Shelton, IV et al. |
| 10,905,420 B2 | 2/2021 | Jasemian et al. |
| 2002/0049551 A1 | 4/2002 | Friedman et al. |
| 2003/0093503 A1 | 5/2003 | Yamaki et al. |
| 2003/0114851 A1 | 6/2003 | Truckai et al. |
| 2003/0210812 A1 | 11/2003 | Khamene et al. |
| 2003/0223877 A1 | 12/2003 | Anstine et al. |
| 2004/0078236 A1 | 4/2004 | Stoodley et al. |
| 2004/0199180 A1 | 10/2004 | Knodel et al. |
| 2004/0199659 A1 | 10/2004 | Ishikawa et al. |
| 2004/0206365 A1 | 10/2004 | Knowlton |
| 2004/0243148 A1 | 12/2004 | Wasielewski |
| 2004/0243435 A1 | 12/2004 | Williams |
| 2005/0020909 A1 | 1/2005 | Moctezuma De La Barrera et al. |
| 2005/0063575 A1 | 3/2005 | Ma et al. |
| 2005/0065438 A1 | 3/2005 | Miller |
| 2005/0131390 A1 | 6/2005 | Heinrich et al. |
| 2005/0143759 A1 | 6/2005 | Kelly |
| 2005/0149001 A1 | 7/2005 | Uchikubo et al. |
| 2005/0149356 A1 | 7/2005 | Cyr et al. |
| 2005/0192633 A1 | 9/2005 | Montpetit |
| 2005/0222631 A1 | 10/2005 | Dalal et al. |
| 2005/0236474 A1 | 10/2005 | Onuma et al. |
| 2005/0277913 A1 | 12/2005 | McCary |
| 2006/0020272 A1 | 1/2006 | Gildenberg |
| 2006/0059018 A1 | 3/2006 | Shiobara et al. |
| 2006/0116908 A1 | 6/2006 | Dew et al. |
| 2006/0241399 A1 | 10/2006 | Fabian |
| 2007/0010838 A1 | 1/2007 | Shelton et al. |
| 2007/0016235 A1 | 1/2007 | Tanaka et al. |
| 2007/0027459 A1 | 2/2007 | Horvath et al. |
| 2007/0049947 A1 | 3/2007 | Menn et al. |
| 2007/0078678 A1 | 4/2007 | DiSilvestro et al. |
| 2007/0167702 A1 | 7/2007 | Hasser et al. |
| 2007/0168461 A1 | 7/2007 | Moore |
| 2007/0173803 A1 | 7/2007 | Wham et al. |
| 2007/0175955 A1 | 8/2007 | Shelton et al. |
| 2007/0225556 A1 | 9/2007 | Ortiz et al. |
| 2007/0244478 A1 | 10/2007 | Bahney |
| 2007/0249990 A1 | 10/2007 | Cosmescu |
| 2007/0270660 A1 | 11/2007 | Caylor et al. |
| 2007/0293218 A1 | 12/2007 | Meylan et al. |
| 2008/0013460 A1 | 1/2008 | Allen et al. |
| 2008/0015664 A1 | 1/2008 | Podhajsky |
| 2008/0015912 A1 | 1/2008 | Rosenthal et al. |
| 2008/0033404 A1 | 2/2008 | Romoda et al. |
| 2008/0040151 A1 | 2/2008 | Moore |
| 2008/0059658 A1 | 3/2008 | Williams |
| 2008/0077158 A1 | 3/2008 | Haider et al. |
| 2008/0083414 A1 | 4/2008 | Messerges |
| 2008/0177362 A1 | 7/2008 | Phillips et al. |
| 2008/0255413 A1 | 10/2008 | Zemlok et al. |
| 2008/0262654 A1 | 10/2008 | Omori et al. |
| 2008/0281301 A1 | 11/2008 | DeBoer et al. |
| 2008/0281678 A1 | 11/2008 | Keuls et al. |
| 2008/0296346 A1 | 12/2008 | Shelton, IV et al. |
| 2009/0036750 A1 | 2/2009 | Weinstein et al. |
| 2009/0036794 A1 | 2/2009 | Stubhaug et al. |
| 2009/0043253 A1 | 2/2009 | Podaima |
| 2009/0046146 A1 | 2/2009 | Hoyt |
| 2009/0048589 A1 | 2/2009 | Takashino et al. |
| 2009/0076409 A1 | 3/2009 | Wu et al. |
| 2009/0090763 A1 | 4/2009 | Zemlok et al. |
| 2009/0099866 A1 | 4/2009 | Newman |
| 2009/0182577 A1 | 7/2009 | Squilla et al. |
| 2009/0206131 A1 | 8/2009 | Weisenburgh, II et al. |
| 2009/0217932 A1 | 9/2009 | Voegele |
| 2009/0234352 A1 | 9/2009 | Behnke et al. |
| 2009/0259149 A1 | 10/2009 | Tahara et al. |
| 2009/0259221 A1 | 10/2009 | Tahara et al. |
| 2009/0307681 A1 | 12/2009 | Armado et al. |
| 2009/0326321 A1 | 12/2009 | Jacobsen et al. |
| 2009/0326336 A1 | 12/2009 | Lemke et al. |
| 2010/0065604 A1 | 3/2010 | Weng |
| 2010/0069942 A1 | 3/2010 | Shelton, IV |
| 2010/0070417 A1 | 3/2010 | Flynn et al. |
| 2010/0132334 A1 | 6/2010 | Duclos et al. |
| 2010/0137845 A1 | 6/2010 | Ramstein et al. |
| 2010/0179831 A1 | 7/2010 | Brown et al. |
| 2010/0191100 A1 | 7/2010 | Anderson et al. |
| 2010/0198248 A1 | 8/2010 | Vakharia |
| 2010/0217991 A1 | 8/2010 | Choi |
| 2010/0235689 A1 | 9/2010 | Tian et al. |
| 2010/0250571 A1 | 9/2010 | Pierce et al. |
| 2010/0292535 A1 | 11/2010 | Paskar |
| 2011/0022032 A1 | 1/2011 | Zemlok et al. |
| 2011/0077512 A1 | 3/2011 | Boswell |
| 2011/0087238 A1 | 4/2011 | Wang et al. |
| 2011/0105895 A1 | 5/2011 | Kornblau et al. |
| 2011/0118708 A1 | 5/2011 | Burbank et al. |
| 2011/0119075 A1 | 5/2011 | Dhoble |
| 2011/0125149 A1 | 5/2011 | El-Galley et al. |
| 2011/0237883 A1 | 9/2011 | Chun |
| 2011/0306840 A1 | 12/2011 | Allen et al. |
| 2012/0022519 A1 | 1/2012 | Huang et al. |
| 2012/0059684 A1 | 3/2012 | Hampapur et al. |
| 2012/0116381 A1 | 5/2012 | Houser et al. |
| 2012/0130217 A1 | 5/2012 | Kauphusman et al. |
| 2012/0172696 A1 | 7/2012 | Kallback et al. |
| 2012/0191091 A1 | 7/2012 | Allen |
| 2012/0203785 A1 | 8/2012 | Awada |
| 2012/0211542 A1 | 8/2012 | Racenet |
| 2012/0245958 A1 | 9/2012 | Lawrence et al. |
| 2012/0265555 A1 | 10/2012 | Cappuzzo et al. |
| 2012/0292367 A1 | 11/2012 | Morgan et al. |
| 2012/0319859 A1 | 12/2012 | Taub et al. |
| 2013/0024213 A1 | 1/2013 | Poon |
| 2013/0046182 A1 | 2/2013 | Hegg et al. |
| 2013/0046279 A1 | 2/2013 | Niklewski et al. |
| 2013/0066647 A1 | 3/2013 | Andrie et al. |
| 2013/0090526 A1 | 4/2013 | Suzuki et al. |
| 2013/0093829 A1 | 4/2013 | Rosenblatt et al. |
| 2013/0105552 A1 | 5/2013 | Weir et al. |
| 2013/0116218 A1 | 5/2013 | Kaplan et al. |
| 2013/0165776 A1 | 6/2013 | Blomqvist |
| 2013/0178853 A1 | 7/2013 | Hyink et al. |
| 2013/0206813 A1 | 8/2013 | Nalagatla |
| 2013/0214025 A1 | 8/2013 | Zemlok et al. |

(56) References Cited

U.S. PATENT DOCUMENTS

| | | |
|---|---|---|
| 2013/0253480 A1 | 9/2013 | Kimball et al. |
| 2013/0256373 A1 | 10/2013 | Schmid et al. |
| 2013/0277410 A1 | 10/2013 | Fernandez et al. |
| 2013/0317837 A1 | 11/2013 | Ballantyne et al. |
| 2013/0321425 A1 | 12/2013 | Greene et al. |
| 2013/0325809 A1 | 12/2013 | Kim et al. |
| 2013/0331874 A1 | 12/2013 | Ross et al. |
| 2013/0331875 A1 | 12/2013 | Ross et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0006132 A1 | 1/2014 | Barker |
| 2014/0006943 A1 | 1/2014 | Robbins et al. |
| 2014/0029411 A1 | 1/2014 | Nayak et al. |
| 2014/0035762 A1 | 2/2014 | Shelton, IV et al. |
| 2014/0066700 A1 | 3/2014 | Wilson et al. |
| 2014/0081255 A1 | 3/2014 | Johnson et al. |
| 2014/0081659 A1 | 3/2014 | Nawana et al. |
| 2014/0087999 A1 | 3/2014 | Kaplan et al. |
| 2014/0092089 A1 | 4/2014 | Kasuya et al. |
| 2014/0107697 A1 | 4/2014 | Patani et al. |
| 2014/0108035 A1 | 4/2014 | Akbay et al. |
| 2014/0108983 A1 | 4/2014 | William et al. |
| 2014/0148729 A1 | 5/2014 | Schmitz et al. |
| 2014/0166724 A1 | 6/2014 | Schellin et al. |
| 2014/0171923 A1 | 6/2014 | Aranyi |
| 2014/0187856 A1 | 7/2014 | Holoien et al. |
| 2014/0204190 A1 | 7/2014 | Rosenblatt, III et al. |
| 2014/0243799 A1 | 8/2014 | Parihar |
| 2014/0243809 A1 | 8/2014 | Gelfand et al. |
| 2014/0246475 A1 | 9/2014 | Hall et al. |
| 2014/0249557 A1 | 9/2014 | Koch et al. |
| 2014/0252064 A1 | 9/2014 | Mozdzierz et al. |
| 2014/0263541 A1 | 9/2014 | Leimbach et al. |
| 2014/0263552 A1 | 9/2014 | Hall et al. |
| 2014/0303660 A1 | 10/2014 | Boyden et al. |
| 2015/0006201 A1 | 1/2015 | Pait et al. |
| 2015/0025549 A1 | 1/2015 | Kilroy et al. |
| 2015/0032150 A1 | 1/2015 | Ishida et al. |
| 2015/0051617 A1 | 2/2015 | Takemura et al. |
| 2015/0053737 A1 | 2/2015 | Leimbach et al. |
| 2015/0066000 A1 | 3/2015 | An et al. |
| 2015/0070187 A1 | 3/2015 | Wiesner et al. |
| 2015/0108198 A1 | 4/2015 | Estrella et al. |
| 2015/0122870 A1 | 5/2015 | Zemlok et al. |
| 2015/0133945 A1 | 5/2015 | Dushyant et al. |
| 2015/0196295 A1 | 7/2015 | Shelton, IV et al. |
| 2015/0199109 A1 | 7/2015 | Lee |
| 2015/0238355 A1 | 8/2015 | Vezzu et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0297200 A1 | 10/2015 | Fitzsimmons et al. |
| 2015/0297222 A1 | 10/2015 | Huitema et al. |
| 2015/0297228 A1 | 10/2015 | Huitema et al. |
| 2015/0297233 A1 | 10/2015 | Huitema et al. |
| 2015/0297311 A1 | 10/2015 | Tesar |
| 2015/0302157 A1 | 10/2015 | Collar et al. |
| 2015/0310174 A1 | 10/2015 | Coudert et al. |
| 2015/0313538 A1 | 11/2015 | Bechtel et al. |
| 2015/0317899 A1 | 11/2015 | Dumbauld et al. |
| 2015/0332003 A1 | 11/2015 | Stamm et al. |
| 2015/0332196 A1 | 11/2015 | Stiller et al. |
| 2015/0374369 A1 | 12/2015 | Yates et al. |
| 2016/0000437 A1 | 1/2016 | Giordano et al. |
| 2016/0015471 A1 | 1/2016 | Piron et al. |
| 2016/0034648 A1 | 2/2016 | Mohlenbrock et al. |
| 2016/0038253 A1 | 2/2016 | Piron et al. |
| 2016/0066913 A1 | 3/2016 | Swayze et al. |
| 2016/0078190 A1 | 3/2016 | Greene et al. |
| 2016/0106516 A1 | 4/2016 | Mesallum |
| 2016/0106934 A1 | 4/2016 | Hiraga et al. |
| 2016/0166256 A1 | 6/2016 | Baxter, III et al. |
| 2016/0180045 A1 | 6/2016 | Syed |
| 2016/0192960 A1 | 7/2016 | Bueno et al. |
| 2016/0199125 A1 | 7/2016 | Jones |
| 2016/0206202 A1 | 7/2016 | Frangioni |
| 2016/0235303 A1 | 8/2016 | Fleming et al. |
| 2016/0249910 A1 | 9/2016 | Shelton, IV et al. |
| 2016/0253472 A1 | 9/2016 | Pedersen et al. |
| 2016/0256154 A1 | 9/2016 | Shelton, IV et al. |
| 2016/0287912 A1 | 10/2016 | Warnking |
| 2016/0296246 A1 | 10/2016 | Schaller |
| 2016/0302210 A1 | 10/2016 | Thornton et al. |
| 2016/0310055 A1 | 10/2016 | Zand et al. |
| 2016/0310203 A1 | 10/2016 | Gaspredes et al. |
| 2016/0321400 A1 | 11/2016 | Durrant et al. |
| 2016/0323283 A1 | 11/2016 | Kang et al. |
| 2016/0324537 A1 | 11/2016 | Green et al. |
| 2016/0342916 A1 | 11/2016 | Arceneaux et al. |
| 2016/0345857 A1 | 12/2016 | Jensrud et al. |
| 2016/0345976 A1 | 12/2016 | Gonzalez et al. |
| 2016/0350490 A1 | 12/2016 | Martinez et al. |
| 2016/0361070 A1 | 12/2016 | Ardel et al. |
| 2016/0374665 A1 | 12/2016 | DiNardo et al. |
| 2016/0374723 A1 | 12/2016 | Frankhouser et al. |
| 2016/0374762 A1 | 12/2016 | Case et al. |
| 2017/0000516 A1 | 1/2017 | Stulen et al. |
| 2017/0000553 A1 | 1/2017 | Wiener et al. |
| 2017/0000554 A1 | 1/2017 | Yates et al. |
| 2017/0020462 A1 | 1/2017 | Brown, III et al. |
| 2017/0027603 A1 | 2/2017 | Pandey |
| 2017/0035514 A1 | 2/2017 | Fox et al. |
| 2017/0056116 A1 | 3/2017 | Kostrzewski |
| 2017/0061375 A1 | 3/2017 | Laster et al. |
| 2017/0068792 A1 | 3/2017 | Reiner |
| 2017/0079730 A1 | 3/2017 | Azizian et al. |
| 2017/0086829 A1 | 3/2017 | Vendely et al. |
| 2017/0086911 A1 | 3/2017 | Wiener et al. |
| 2017/0086930 A1 | 3/2017 | Thompson et al. |
| 2017/0105754 A1 | 4/2017 | Boudreaux et al. |
| 2017/0116873 A1 | 4/2017 | Lendvay et al. |
| 2017/0132374 A1 | 5/2017 | Lee et al. |
| 2017/0132785 A1 | 5/2017 | Wshah et al. |
| 2017/0143284 A1 | 5/2017 | Sehnert et al. |
| 2017/0143442 A1 | 5/2017 | Tesar et al. |
| 2017/0151026 A1 | 6/2017 | Panescu et al. |
| 2017/0156076 A1 | 6/2017 | Eom et al. |
| 2017/0164997 A1 | 6/2017 | Johnson et al. |
| 2017/0165012 A1 | 6/2017 | Chaplin et al. |
| 2017/0165725 A1 | 6/2017 | Hersey et al. |
| 2017/0171231 A1 | 6/2017 | Reybok, Jr. et al. |
| 2017/0172565 A1 | 6/2017 | Heneveld |
| 2017/0172614 A1 | 6/2017 | Scheib et al. |
| 2017/0177807 A1 | 6/2017 | Fabian |
| 2017/0181745 A1 | 6/2017 | Penna et al. |
| 2017/0196637 A1 | 7/2017 | Shelton, IV et al. |
| 2017/0202591 A1 | 7/2017 | Shelton, IV et al. |
| 2017/0202605 A1 | 7/2017 | Shelton, IV et al. |
| 2017/0202607 A1 | 7/2017 | Shelton, IV et al. |
| 2017/0202609 A1 | 7/2017 | Shelton, IV et al. |
| 2017/0224332 A1 | 8/2017 | Hunter et al. |
| 2017/0224334 A1 | 8/2017 | Worthington et al. |
| 2017/0224428 A1 | 8/2017 | Kopp |
| 2017/0231627 A1 | 8/2017 | Shelton, IV et al. |
| 2017/0231628 A1 | 8/2017 | Shelton, IV et al. |
| 2017/0245809 A1 | 8/2017 | Ma et al. |
| 2017/0249432 A1 | 8/2017 | Grantcharov |
| 2017/0252095 A1 | 9/2017 | Johnson |
| 2017/0255751 A1 | 9/2017 | Sanmugalingham |
| 2017/0262604 A1 | 9/2017 | Francois |
| 2017/0265864 A1 | 9/2017 | Hessler et al. |
| 2017/0273715 A1 | 9/2017 | Piron et al. |
| 2017/0281164 A1 | 10/2017 | Harris et al. |
| 2017/0281169 A1 | 10/2017 | Harris et al. |
| 2017/0281171 A1 | 10/2017 | Shelton, IV et al. |
| 2017/0281173 A1 | 10/2017 | Shelton, IV et al. |
| 2017/0281174 A1 | 10/2017 | Harris et al. |
| 2017/0281186 A1 | 10/2017 | Shelton, IV et al. |
| 2017/0281187 A1 | 10/2017 | Shelton, IV et al. |
| 2017/0281189 A1 | 10/2017 | Nalagatla et al. |
| 2017/0290585 A1 | 10/2017 | Shelton, IV et al. |
| 2017/0290586 A1 | 10/2017 | Wellman |

(56) References Cited

U.S. PATENT DOCUMENTS

| | | |
|---|---|---|
| 2017/0296169 A1 | 10/2017 | Yates et al. |
| 2017/0296173 A1 | 10/2017 | Shelton, IV et al. |
| 2017/0296177 A1 | 10/2017 | Harris et al. |
| 2017/0296185 A1 | 10/2017 | Swensgard et al. |
| 2017/0296213 A1 | 10/2017 | Swensgard et al. |
| 2017/0303984 A1 | 10/2017 | Malackowski |
| 2017/0304020 A1 | 10/2017 | Ng et al. |
| 2017/0312456 A1 | 11/2017 | Phillips |
| 2017/0325813 A1 | 11/2017 | Aranyi et al. |
| 2017/0325876 A1 | 11/2017 | Nakadate et al. |
| 2017/0354470 A1 | 12/2017 | Farritor et al. |
| 2017/0360438 A1 | 12/2017 | Cappola |
| 2017/0360439 A1 | 12/2017 | Chen et al. |
| 2017/0360499 A1 | 12/2017 | Greep et al. |
| 2017/0367695 A1 | 12/2017 | Shelton, IV et al. |
| 2017/0367696 A1 | 12/2017 | Shelton, IV et al. |
| 2017/0367697 A1 | 12/2017 | Shelton, IV et al. |
| 2017/0367698 A1 | 12/2017 | Shelton, IV et al. |
| 2017/0367754 A1 | 12/2017 | Narisawa |
| 2017/0367771 A1 | 12/2017 | Tako et al. |
| 2017/0370710 A1 | 12/2017 | Chen et al. |
| 2018/0008260 A1 | 1/2018 | Baxter, III et al. |
| 2018/0008359 A1 | 1/2018 | Randle |
| 2018/0011983 A1 | 1/2018 | Zuhars et al. |
| 2018/0014848 A1 | 1/2018 | Messerly et al. |
| 2018/0049817 A1 | 2/2018 | Swayze et al. |
| 2018/0050196 A1 | 2/2018 | Pawsey et al. |
| 2018/0055529 A1 | 3/2018 | Messerly et al. |
| 2018/0064498 A1 | 3/2018 | Kapadia et al. |
| 2018/0065248 A1 | 3/2018 | Barral et al. |
| 2018/0098816 A1 | 4/2018 | Govari et al. |
| 2018/0110523 A1 | 4/2018 | Shelton, IV |
| 2018/0116662 A1 | 5/2018 | Shelton, IV et al. |
| 2018/0116735 A1 | 5/2018 | Tierney et al. |
| 2018/0122506 A1 | 5/2018 | Grantcharov et al. |
| 2018/0125590 A1 | 5/2018 | Giordano et al. |
| 2018/0132895 A1 | 5/2018 | Silver |
| 2018/0153574 A1 | 6/2018 | Faller et al. |
| 2018/0153628 A1 | 6/2018 | Grover et al. |
| 2018/0153632 A1 | 6/2018 | Tokarchuk et al. |
| 2018/0154297 A1 | 6/2018 | Maletich et al. |
| 2018/0161716 A1 | 6/2018 | Li et al. |
| 2018/0168575 A1 | 6/2018 | Simms et al. |
| 2018/0168577 A1 | 6/2018 | Aronhalt et al. |
| 2018/0168578 A1 | 6/2018 | Aronhalt et al. |
| 2018/0168579 A1 | 6/2018 | Aronhalt et al. |
| 2018/0168584 A1 | 6/2018 | Harris et al. |
| 2018/0168586 A1 | 6/2018 | Shelton, IV et al. |
| 2018/0168589 A1 | 6/2018 | Swayze et al. |
| 2018/0168590 A1 | 6/2018 | Overmyer et al. |
| 2018/0168591 A1 | 6/2018 | Swayze et al. |
| 2018/0168592 A1 | 6/2018 | Overmyer et al. |
| 2018/0168593 A1 | 6/2018 | Overmyer et al. |
| 2018/0168594 A1 | 6/2018 | Shelton, IV et al. |
| 2018/0168597 A1 | 6/2018 | Fanelli et al. |
| 2018/0168598 A1 | 6/2018 | Shelton, IV et al. |
| 2018/0168600 A1 | 6/2018 | Shelton, IV et al. |
| 2018/0168601 A1 | 6/2018 | Bakos et al. |
| 2018/0168603 A1 | 6/2018 | Morgan et al. |
| 2018/0168605 A1 | 6/2018 | Baber et al. |
| 2018/0168606 A1 | 6/2018 | Shelton, IV et al. |
| 2018/0168607 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168614 A1 | 6/2018 | Shelton, IV et al. |
| 2018/0168615 A1 | 6/2018 | Shelton, IV et al. |
| 2018/0168616 A1 | 6/2018 | Shelton, IV et al. |
| 2018/0168617 A1 | 6/2018 | Shelton, IV et al. |
| 2018/0168618 A1 | 6/2018 | Scott et al. |
| 2018/0168619 A1 | 6/2018 | Scott et al. |
| 2018/0168621 A1 | 6/2018 | Shelton, IV et al. |
| 2018/0168623 A1 | 6/2018 | Simms et al. |
| 2018/0168624 A1 | 6/2018 | Shelton, IV et al. |
| 2018/0168625 A1 | 6/2018 | Posada et al. |
| 2018/0168627 A1 | 6/2018 | Weaner et al. |
| 2018/0168628 A1 | 6/2018 | Hunter et al. |
| 2018/0168629 A1 | 6/2018 | Shelton, IV et al. |
| 2018/0168630 A1 | 6/2018 | Shelton, IV et al. |
| 2018/0168632 A1 | 6/2018 | Harris et al. |
| 2018/0168633 A1 | 6/2018 | Shelton, IV et al. |
| 2018/0168637 A1 | 6/2018 | Harris et al. |
| 2018/0168639 A1 | 6/2018 | Shelton, IV et al. |
| 2018/0168643 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168649 A1 | 6/2018 | Shelton, IV et al. |
| 2018/0168650 A1 | 6/2018 | Shelton, IV et al. |
| 2018/0168651 A1 | 6/2018 | Shelton, IV et al. |
| 2018/0168748 A1 | 6/2018 | Kapadia |
| 2018/0168763 A1 | 6/2018 | Scheib et al. |
| 2018/0177557 A1 | 6/2018 | Kapadia et al. |
| 2018/0199995 A1 | 7/2018 | Odermatt et al. |
| 2018/0214025 A1 | 8/2018 | Homyk et al. |
| 2018/0221598 A1 | 8/2018 | Silver |
| 2018/0228557 A1 | 8/2018 | Darisse et al. |
| 2018/0235719 A1 | 8/2018 | Jarc |
| 2018/0242967 A1 | 8/2018 | Meade |
| 2018/0250080 A1 | 9/2018 | Kopp |
| 2018/0250084 A1 | 9/2018 | Kopp et al. |
| 2018/0263710 A1 | 9/2018 | Sakaguchi et al. |
| 2018/0263717 A1 | 9/2018 | Kopp |
| 2018/0268320 A1 | 9/2018 | Shekhar |
| 2018/0271520 A1 | 9/2018 | Shelton, IV et al. |
| 2018/0271603 A1 | 9/2018 | Nir et al. |
| 2018/0296286 A1 | 10/2018 | Peine et al. |
| 2018/0304471 A1 | 10/2018 | Tokuchi |
| 2018/0310935 A1 | 11/2018 | Wixey |
| 2018/0310986 A1 | 11/2018 | Batchelor et al. |
| 2018/0310997 A1 | 11/2018 | Peine et al. |
| 2018/0317826 A1 | 11/2018 | Muhsin et al. |
| 2018/0317915 A1 | 11/2018 | McDonald, II |
| 2018/0338806 A1 | 11/2018 | Grubbs |
| 2018/0351987 A1 | 12/2018 | Patel et al. |
| 2018/0358112 A1 | 12/2018 | Sharifi Sedeh et al. |
| 2018/0360449 A1 | 12/2018 | Shelton, IV et al. |
| 2018/0360452 A1 | 12/2018 | Shelton, IV et al. |
| 2018/0360454 A1 | 12/2018 | Shelton, IV et al. |
| 2018/0360456 A1 | 12/2018 | Shelton, IV et al. |
| 2018/0368930 A1 | 12/2018 | Esterberg et al. |
| 2018/0369511 A1 | 12/2018 | Zergiebel et al. |
| 2019/0000446 A1 | 1/2019 | Shelton, IV et al. |
| 2019/0000448 A1 | 1/2019 | Shelton, IV et al. |
| 2019/0000465 A1 | 1/2019 | Shelton, IV et al. |
| 2019/0000478 A1 | 1/2019 | Messerly et al. |
| 2019/0000530 A1 | 1/2019 | Yates et al. |
| 2019/0000565 A1 | 1/2019 | Shelton, IV et al. |
| 2019/0000569 A1 | 1/2019 | Crawford et al. |
| 2019/0001079 A1 | 1/2019 | Zergiebel et al. |
| 2019/0005641 A1 | 1/2019 | Yamamoto |
| 2019/0006047 A1 | 1/2019 | Gorek et al. |
| 2019/0008600 A1 | 1/2019 | Pedros et al. |
| 2019/0025040 A1 | 1/2019 | Andreason et al. |
| 2019/0029712 A1 | 1/2019 | Stoddard et al. |
| 2019/0038335 A1 | 2/2019 | Mohr et al. |
| 2019/0038364 A1 | 2/2019 | Enoki |
| 2019/0053801 A1 | 2/2019 | Wixey et al. |
| 2019/0053866 A1 | 2/2019 | Seow et al. |
| 2019/0054620 A1 | 2/2019 | Griffiths et al. |
| 2019/0069949 A1 | 3/2019 | Vrba et al. |
| 2019/0069964 A1 | 3/2019 | Hagn |
| 2019/0070550 A1 | 3/2019 | Lalomia et al. |
| 2019/0070731 A1 | 3/2019 | Bowling et al. |
| 2019/0087544 A1 | 3/2019 | Peterson |
| 2019/0090969 A1 | 3/2019 | Jarc et al. |
| 2019/0099180 A1 | 4/2019 | Leimbach et al. |
| 2019/0099227 A1 | 4/2019 | Rockrohr |
| 2019/0104919 A1 | 4/2019 | Shelton, IV et al. |
| 2019/0125320 A1 | 5/2019 | Shelton, IV et al. |
| 2019/0125321 A1 | 5/2019 | Shelton, IV et al. |
| 2019/0125324 A1 | 5/2019 | Scheib et al. |
| 2019/0125335 A1 | 5/2019 | Shelton, IV et al. |
| 2019/0125336 A1 | 5/2019 | Deck et al. |
| 2019/0125337 A1 | 5/2019 | Shelton, IV et al. |

(56) References Cited

U.S. PATENT DOCUMENTS

| | | |
|---|---|---|
| 2019/0125338 A1 | 5/2019 | Shelton, IV et al. |
| 2019/0125339 A1 | 5/2019 | Shelton, IV et al. |
| 2019/0125344 A1 | 5/2019 | DiNardo et al. |
| 2019/0125347 A1 | 5/2019 | Stokes et al. |
| 2019/0125348 A1 | 5/2019 | Shelton, IV et al. |
| 2019/0125353 A1 | 5/2019 | Shelton, IV et al. |
| 2019/0125354 A1 | 5/2019 | Deck et al. |
| 2019/0125355 A1 | 5/2019 | Shelton, IV et al. |
| 2019/0125356 A1 | 5/2019 | Shelton, IV et al. |
| 2019/0125357 A1 | 5/2019 | Shelton, IV et al. |
| 2019/0125358 A1 | 5/2019 | Shelton, IV et al. |
| 2019/0125359 A1 | 5/2019 | Shelton, IV et al. |
| 2019/0125360 A1 | 5/2019 | Shelton, IV et al. |
| 2019/0125361 A1 | 5/2019 | Shelton, IV et al. |
| 2019/0125377 A1 | 5/2019 | Shelton, IV |
| 2019/0125378 A1 | 5/2019 | Shelton, IV et al. |
| 2019/0125379 A1 | 5/2019 | Shelton, IV et al. |
| 2019/0125380 A1 | 5/2019 | Hunter et al. |
| 2019/0125381 A1 | 5/2019 | Scheib et al. |
| 2019/0125382 A1 | 5/2019 | Scheib et al. |
| 2019/0125383 A1 | 5/2019 | Scheib et al. |
| 2019/0125384 A1 | 5/2019 | Scheib et al. |
| 2019/0125385 A1 | 5/2019 | Scheib et al. |
| 2019/0125386 A1 | 5/2019 | Shelton, IV et al. |
| 2019/0125387 A1 | 5/2019 | Parihar et al. |
| 2019/0125388 A1 | 5/2019 | Shelton, IV et al. |
| 2019/0125389 A1 | 5/2019 | Shelton, IV et al. |
| 2019/0125390 A1 | 5/2019 | Shelton, IV et al. |
| 2019/0125430 A1 | 5/2019 | Shelton, IV et al. |
| 2019/0125431 A1 | 5/2019 | Shelton, IV et al. |
| 2019/0125432 A1 | 5/2019 | Shelton, IV et al. |
| 2019/0125454 A1 | 5/2019 | Stokes et al. |
| 2019/0125455 A1 | 5/2019 | Shelton, IV et al. |
| 2019/0125456 A1 | 5/2019 | Shelton, IV et al. |
| 2019/0125457 A1 | 5/2019 | Parihar et al. |
| 2019/0125458 A1 | 5/2019 | Shelton, IV et al. |
| 2019/0125459 A1 | 5/2019 | Shelton, IV et al. |
| 2019/0125476 A1 | 5/2019 | Shelton, IV et al. |
| 2019/0133703 A1 | 5/2019 | Seow et al. |
| 2019/0142449 A1 | 5/2019 | Shelton, IV et al. |
| 2019/0142535 A1 | 5/2019 | Seow et al. |
| 2019/0145942 A1 | 5/2019 | Dutriez et al. |
| 2019/0150975 A1 | 5/2019 | Kawasaki et al. |
| 2019/0159777 A1 | 5/2019 | Ehrenfels et al. |
| 2019/0159778 A1 | 5/2019 | Shelton, IV et al. |
| 2019/0162179 A1 | 5/2019 | O'Shea et al. |
| 2019/0164285 A1 | 5/2019 | Nye et al. |
| 2019/0192157 A1 | 6/2019 | Scott et al. |
| 2019/0192236 A1 | 6/2019 | Shelton, IV et al. |
| 2019/0200844 A1 | 7/2019 | Shelton, IV et al. |
| 2019/0200863 A1 | 7/2019 | Shelton, IV et al. |
| 2019/0200905 A1 | 7/2019 | Shelton, IV et al. |
| 2019/0200906 A1 | 7/2019 | Shelton, IV et al. |
| 2019/0200977 A1 | 7/2019 | Shelton, IV et al. |
| 2019/0200980 A1 | 7/2019 | Shelton, IV et al. |
| 2019/0200981 A1 | 7/2019 | Harris et al. |
| 2019/0200984 A1 | 7/2019 | Shelton, IV et al. |
| 2019/0200985 A1 | 7/2019 | Shelton, IV et al. |
| 2019/0200986 A1 | 7/2019 | Shelton, IV et al. |
| 2019/0200987 A1 | 7/2019 | Shelton, IV et al. |
| 2019/0200988 A1 | 7/2019 | Shelton, IV |
| 2019/0200996 A1 | 7/2019 | Shelton, IV et al. |
| 2019/0200997 A1 | 7/2019 | Shelton, IV et al. |
| 2019/0200998 A1 | 7/2019 | Shelton, IV et al. |
| 2019/0201018 A1 | 7/2019 | Shelton, IV et al. |
| 2019/0201020 A1 | 7/2019 | Shelton, IV et al. |
| 2019/0201021 A1 | 7/2019 | Shelton, IV et al. |
| 2019/0201023 A1 | 7/2019 | Shelton, IV et al. |
| 2019/0201024 A1 | 7/2019 | Shelton, IV et al. |
| 2019/0201025 A1 | 7/2019 | Shelton, IV et al. |
| 2019/0201026 A1 | 7/2019 | Shelton, IV et al. |
| 2019/0201027 A1 | 7/2019 | Shelton, IV et al. |
| 2019/0201028 A1 | 7/2019 | Shelton, IV et al. |
| 2019/0201029 A1 | 7/2019 | Shelton, IV et al. |
| 2019/0201030 A1 | 7/2019 | Shelton, IV et al. |
| 2019/0201033 A1 | 7/2019 | Yates et al. |
| 2019/0201034 A1 | 7/2019 | Shelton, IV et al. |
| 2019/0201036 A1 | 7/2019 | Nott et al. |
| 2019/0201037 A1 | 7/2019 | Houser et al. |
| 2019/0201038 A1 | 7/2019 | Yates et al. |
| 2019/0201039 A1 | 7/2019 | Widenhouse et al. |
| 2019/0201040 A1 | 7/2019 | Messerly et al. |
| 2019/0201041 A1 | 7/2019 | Kimball et al. |
| 2019/0201042 A1 | 7/2019 | Nott et al. |
| 2019/0201043 A1 | 7/2019 | Shelton, IV et al. |
| 2019/0201044 A1 | 7/2019 | Shelton, IV et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201073 A1 | 7/2019 | Nott et al. |
| 2019/0201074 A1 | 7/2019 | Yates et al. |
| 2019/0201075 A1 | 7/2019 | Shelton, IV et al. |
| 2019/0201077 A1 | 7/2019 | Yates et al. |
| 2019/0201079 A1 | 7/2019 | Shelton, IV et al. |
| 2019/0201080 A1 | 7/2019 | Messerly et al. |
| 2019/0201081 A1 | 7/2019 | Shelton, IV et al. |
| 2019/0201082 A1 | 7/2019 | Shelton, IV et al. |
| 2019/0201083 A1 | 7/2019 | Shelton, IV et al. |
| 2019/0201084 A1 | 7/2019 | Shelton, IV et al. |
| 2019/0201085 A1 | 7/2019 | Shelton, IV et al. |
| 2019/0201086 A1 | 7/2019 | Shelton, IV et al. |
| 2019/0201087 A1 | 7/2019 | Shelton, IV et al. |
| 2019/0201088 A1 | 7/2019 | Shelton, IV et al. |
| 2019/0201090 A1 | 7/2019 | Shelton, IV et al. |
| 2019/0201091 A1 | 7/2019 | Yates et al. |
| 2019/0201092 A1 | 7/2019 | Yates et al. |
| 2019/0201102 A1 | 7/2019 | Shelton, IV et al. |
| 2019/0201104 A1 | 7/2019 | Shelton, IV et al. |
| 2019/0201105 A1 | 7/2019 | Shelton, IV et al. |
| 2019/0201111 A1 | 7/2019 | Shelton, IV et al. |
| 2019/0201112 A1 | 7/2019 | Wiener et al. |
| 2019/0201113 A1 | 7/2019 | Shelton, IV et al. |
| 2019/0201114 A1 | 7/2019 | Shelton, IV et al. |
| 2019/0201115 A1 | 7/2019 | Messerly et al. |
| 2019/0201116 A1 | 7/2019 | Shelton, IV et al. |
| 2019/0201117 A1 | 7/2019 | Yates et al. |
| 2019/0201118 A1 | 7/2019 | Shelton, IV et al. |
| 2019/0201119 A1 | 7/2019 | Harris et al. |
| 2019/0201120 A1 | 7/2019 | Shelton, IV et al. |
| 2019/0201122 A1 | 7/2019 | Shelton, IV et al. |
| 2019/0201123 A1 | 7/2019 | Shelton, IV et al. |
| 2019/0201124 A1 | 7/2019 | Shelton, IV et al. |
| 2019/0201125 A1 | 7/2019 | Shelton, IV et al. |
| 2019/0201126 A1 | 7/2019 | Shelton, IV et al. |
| 2019/0201127 A1 | 7/2019 | Shelton, IV et al. |
| 2019/0201128 A1 | 7/2019 | Yates et al. |
| 2019/0201129 A1 | 7/2019 | Shelton, IV et al. |
| 2019/0201130 A1 | 7/2019 | Shelton, IV et al. |
| 2019/0201135 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201138 A1 | 7/2019 | Yates et al. |
| 2019/0201139 A1 | 7/2019 | Shelton, IV et al. |
| 2019/0201140 A1 | 7/2019 | Yates et al. |
| 2019/0201141 A1 | 7/2019 | Shelton, IV et al. |
| 2019/0201142 A1 | 7/2019 | Shelton, IV et al. |
| 2019/0201143 A1 | 7/2019 | Shelton, IV et al. |
| 2019/0201144 A1 | 7/2019 | Shelton, IV et al. |
| 2019/0201145 A1 | 7/2019 | Shelton, IV et al. |
| 2019/0201146 A1 | 7/2019 | Shelton, IV et al. |
| 2019/0201158 A1 | 7/2019 | Shelton, IV et al. |
| 2019/0201159 A1 | 7/2019 | Shelton, IV et al. |
| 2019/0201593 A1 | 7/2019 | Shelton, IV et al. |
| 2019/0201594 A1 | 7/2019 | Shelton, IV et al. |
| 2019/0201597 A1 | 7/2019 | Shelton, IV et al. |
| 2019/0204201 A1 | 7/2019 | Shelton, IV et al. |
| 2019/0205001 A1 | 7/2019 | Messerly et al. |
| 2019/0205441 A1 | 7/2019 | Shelton, IV et al. |
| 2019/0205566 A1 | 7/2019 | Shelton, IV et al. |
| 2019/0205567 A1 | 7/2019 | Shelton, IV et al. |
| 2019/0206003 A1 | 7/2019 | Harris et al. |
| 2019/0206004 A1 | 7/2019 | Shelton, IV et al. |
| 2019/0206050 A1 | 7/2019 | Yates et al. |
| 2019/0206216 A1 | 7/2019 | Shelton, IV et al. |

(56) References Cited

U.S. PATENT DOCUMENTS

| | | |
|---|---|---|
| 2019/0206542 A1 | 7/2019 | Shelton, IV et al. |
| 2019/0206551 A1 | 7/2019 | Yates et al. |
| 2019/0206555 A1 | 7/2019 | Morgan et al. |
| 2019/0206556 A1 | 7/2019 | Shelton, IV et al. |
| 2019/0206561 A1 | 7/2019 | Shelton, IV et al. |
| 2019/0206562 A1 | 7/2019 | Shelton, IV et al. |
| 2019/0206563 A1 | 7/2019 | Shelton, IV et al. |
| 2019/0206564 A1 | 7/2019 | Shelton, IV et al. |
| 2019/0206565 A1 | 7/2019 | Shelton, IV |
| 2019/0206569 A1 | 7/2019 | Shelton, IV et al. |
| 2019/0206576 A1 | 7/2019 | Shelton, IV et al. |
| 2019/0207773 A1 | 7/2019 | Shelton, IV et al. |
| 2019/0207857 A1 | 7/2019 | Shelton, IV et al. |
| 2019/0207911 A1 | 7/2019 | Wiener et al. |
| 2019/0208641 A1 | 7/2019 | Yates et al. |
| 2019/0223291 A1 | 7/2019 | Seow et al. |
| 2019/0254759 A1 | 8/2019 | Azizian |
| 2019/0261984 A1 | 8/2019 | Nelson et al. |
| 2019/0269476 A1 | 9/2019 | Bowling et al. |
| 2019/0274662 A1 | 9/2019 | Rockman et al. |
| 2019/0274705 A1 | 9/2019 | Sawhney et al. |
| 2019/0274706 A1 | 9/2019 | Nott et al. |
| 2019/0274707 A1 | 9/2019 | Sawhney et al. |
| 2019/0274708 A1 | 9/2019 | Boudreaux |
| 2019/0274709 A1 | 9/2019 | Scoggins |
| 2019/0274710 A1 | 9/2019 | Black |
| 2019/0274711 A1 | 9/2019 | Scoggins et al. |
| 2019/0274712 A1 | 9/2019 | Faller et al. |
| 2019/0274713 A1 | 9/2019 | Scoggins et al. |
| 2019/0274714 A1 | 9/2019 | Cuti et al. |
| 2019/0274716 A1 | 9/2019 | Nott et al. |
| 2019/0274717 A1 | 9/2019 | Nott et al. |
| 2019/0274718 A1 | 9/2019 | Denzinger et al. |
| 2019/0274719 A1 | 9/2019 | Stulen |
| 2019/0274720 A1 | 9/2019 | Gee et al. |
| 2019/0274749 A1 | 9/2019 | Brady et al. |
| 2019/0274750 A1 | 9/2019 | Jayme et al. |
| 2019/0274752 A1 | 9/2019 | Denzinger et al. |
| 2019/0290389 A1 | 9/2019 | Kopp |
| 2019/0298340 A1 | 10/2019 | Shelton, IV et al. |
| 2019/0298341 A1 | 10/2019 | Shelton, IV et al. |
| 2019/0298342 A1 | 10/2019 | Shelton, IV et al. |
| 2019/0298343 A1 | 10/2019 | Shelton, IV et al. |
| 2019/0298346 A1 | 10/2019 | Shelton, IV et al. |
| 2019/0298347 A1 | 10/2019 | Shelton, IV et al. |
| 2019/0298350 A1 | 10/2019 | Shelton, IV et al. |
| 2019/0298351 A1 | 10/2019 | Shelton, IV et al. |
| 2019/0298352 A1 | 10/2019 | Shelton, IV et al. |
| 2019/0298353 A1 | 10/2019 | Shelton, IV et al. |
| 2019/0298354 A1 | 10/2019 | Shelton, IV et al. |
| 2019/0298355 A1 | 10/2019 | Shelton, IV et al. |
| 2019/0298356 A1 | 10/2019 | Shelton, IV et al. |
| 2019/0298357 A1 | 10/2019 | Shelton, IV et al. |
| 2019/0298464 A1 | 10/2019 | Abbott |
| 2019/0298481 A1 | 10/2019 | Rosenberg et al. |
| 2019/0307520 A1 | 10/2019 | Peine et al. |
| 2019/0314015 A1 | 10/2019 | Shelton, IV et al. |
| 2019/0314016 A1 | 10/2019 | Huitema et al. |
| 2019/0321117 A1 | 10/2019 | Itkowitz et al. |
| 2019/0333626 A1 | 10/2019 | Mansi et al. |
| 2019/0343594 A1 | 11/2019 | Garcia Kilroy et al. |
| 2019/0374140 A1 | 12/2019 | Tucker et al. |
| 2020/0054317 A1 | 2/2020 | Pisarnwongs et al. |
| 2020/0054320 A1 | 2/2020 | Harris et al. |
| 2020/0054321 A1 | 2/2020 | Harris et al. |
| 2020/0054322 A1 | 2/2020 | Harris et al. |
| 2020/0054323 A1 | 2/2020 | Harris et al. |
| 2020/0054325 A1 | 2/2020 | Harris et al. |
| 2020/0054326 A1 | 2/2020 | Harris et al. |
| 2020/0054327 A1 | 2/2020 | Harris et al. |
| 2020/0054328 A1 | 2/2020 | Harris et al. |
| 2020/0054329 A1 | 2/2020 | Shelton, IV et al. |
| 2020/0054330 A1 | 2/2020 | Harris et al. |
| 2020/0054331 A1 | 2/2020 | Harris et al. |
| 2020/0100830 A1 | 4/2020 | Henderson et al. |
| 2020/0162896 A1 | 5/2020 | Su et al. |
| 2020/0178971 A1 | 6/2020 | Harris et al. |
| 2020/0261075 A1 | 8/2020 | Boudreaux et al. |
| 2020/0261076 A1 | 8/2020 | Boudreaux et al. |
| 2020/0261077 A1 | 8/2020 | Shelton, IV et al. |
| 2020/0261078 A1 | 8/2020 | Bakos et al. |
| 2020/0261080 A1 | 8/2020 | Bakos et al. |
| 2020/0261081 A1 | 8/2020 | Boudreaux et al. |
| 2020/0261082 A1 | 8/2020 | Boudreaux et al. |
| 2020/0261083 A1 | 8/2020 | Bakos et al. |
| 2020/0261084 A1 | 8/2020 | Bakos et al. |
| 2020/0261085 A1 | 8/2020 | Boudreaux et al. |
| 2020/0261086 A1 | 8/2020 | Zeiner et al. |
| 2020/0261087 A1 | 8/2020 | Timm et al. |
| 2020/0261088 A1 | 8/2020 | Harris et al. |
| 2020/0261089 A1 | 8/2020 | Shelton, IV et al. |
| 2020/0275930 A1 | 9/2020 | Harris et al. |
| 2020/0281665 A1 | 9/2020 | Kopp |
| 2020/0405375 A1 | 12/2020 | Shelton, IV et al. |
| 2021/0000555 A1 | 1/2021 | Shelton, IV et al. |
| 2021/0015568 A1 | 1/2021 | Liao et al. |
| 2021/0022738 A1 | 1/2021 | Weir et al. |
| 2021/0022809 A1 | 1/2021 | Crawford et al. |

FOREIGN PATENT DOCUMENTS

| | | |
|---|---|---|
| CN | 101617950 A | 1/2010 |
| CN | 104490448 B | 3/2017 |
| CN | 206097107 U | 4/2017 |
| CN | 108652695 A | 10/2018 |
| DE | 2037167 A1 | 7/1980 |
| DE | 3824913 A1 | 2/1990 |
| DE | 4002843 C1 | 4/1991 |
| DE | 102005051367 A1 | 4/2007 |
| DE | 102016207666 A1 | 11/2017 |
| EP | 0000756 B1 | 10/1981 |
| EP | 2732772 A1 | 5/2014 |
| EP | 2942023 A2 | 11/2015 |
| EP | 3047806 A1 | 7/2016 |
| EP | 3056923 A1 | 8/2016 |
| EP | 3095399 A2 | 11/2016 |
| EP | 3120781 A2 | 1/2017 |
| EP | 3135225 A2 | 3/2017 |
| EP | 3141181 A1 | 3/2017 |
| GB | 2509523 A | 7/2014 |
| JP | S5373315 A | 6/1978 |
| JP | 2017513561 A | 6/2017 |
| KR | 20140104587 A | 8/2014 |
| KR | 101587721 B1 | 1/2016 |
| WO | WO-9734533 A1 | 9/1997 |
| WO | WO-0024322 A1 | 5/2000 |
| WO | WO-0108578 A1 | 2/2001 |
| WO | WO-0112089 A1 | 2/2001 |
| WO | WO-0120892 A3 | 11/2001 |
| WO | WO-03079909 A2 | 10/2003 |
| WO | WO-2007137304 A2 | 11/2007 |
| WO | WO-2008056618 A2 | 5/2008 |
| WO | WO-2008069816 A1 | 6/2008 |
| WO | WO-2008147555 A2 | 12/2008 |
| WO | WO-2011112931 A1 | 9/2011 |
| WO | WO-2013143573 A1 | 10/2013 |
| WO | WO-2014134196 A1 | 9/2014 |
| WO | WO-2015129395 A1 | 9/2015 |
| WO | WO-2016100719 A1 | 6/2016 |
| WO | WO-2016206015 A1 | 12/2016 |
| WO | WO-2017011382 A1 | 1/2017 |
| WO | WO-2017011646 A1 | 1/2017 |
| WO | WO-2017058695 A1 | 4/2017 |
| WO | WO-2017151996 A1 | 9/2017 |
| WO | WO-2017189317 A1 | 11/2017 |
| WO | WO-2017205308 A1 | 11/2017 |
| WO | WO-2017210499 A1 | 12/2017 |

(56) References Cited

FOREIGN PATENT DOCUMENTS

| WO | WO-2017210501 A1 | 12/2017 |
|----|------------------|---------|
| WO | WO-2018152141 A1 | 8/2018  |

OTHER PUBLICATIONS

Flores et al., "Large-scale Offloading in the Internet of Things," 2017 IEEE International Conference on Pervasive Computing and Communications Workshops (PERCOM Workshops), IEEE, pp. 479-484, Mar. 13, 2017.

Kalantarian et al., "Computation Offloading for Real-Time Health-Monitoring Devices," 2016 38th Annual International Conference of the IEEE Engineering in Medicine and Biology Society (EBMC), IEEE, pp. 4971-4974, Aug. 16, 2016.

Yuyi Mao et al., "A Survey on Mobile Edge Computing: The Communication Perspective," IEEE Communications Surveys & Tutorials, pp. 2322-2358, Jun. 13, 2017.

Khazaei et al., "Health Informatics for Neonatal Intensive Care Units: An Analytical Modeling Perspective," IEEE Journal of Translational Engineering in Health and Medicine, vol. 3, pp. 1-9, Oct. 21, 2015.

Benkmann et al., "Concept of iterative optimization of minimally invasive surgery," 2017 22nd International Conference on Methods and Models in Automation and Robotics (MMAR), IEEE pp. 443-446, Aug. 28, 2017.

Trautman, Peter, "Breaking the Human-Robot Deadlock: Surpassing Shared Control Performance Limits with Sparse Human-Robot Interaction," Robotics: Science and Systems XIIII, pp. 1-10, Jul. 12, 2017.

Yang et al., "A dynamic stategy for packet scheduling and bandwidth allocation based on channel quality in IEEE 802.16e OFDMA system," Journal of Network and Computer Applications, vol. 39, pp. 52-60, May 2, 2013.

Takahashi et al., "Automatic smoke evacuation in laparoscopic surgery: a simplified method for objective evaluation," Surgical Endoscopy, vol. 27, No. 8, pp. 2980-2987, Feb. 23, 2013.

Miksch et al., "Utilizing temporal data abstraction for data validation and therapy planning for artificially ventilated newborn infants," Artificial Intelligence in Medicine, vol. 8, No. 6, pp. 543-576 (1996).

Horn et al., "Effective data validation of high-frequency data: Time-point-time-interval-, and trend-based methods," Computers in Biology and Medic, New York, NY, vol. 27, No. 5, pp. 389-409 (1997).

Stacey et al., "Temporal abstraction in intelligent clinical data analysis: A survey, " Artificial Intelligence in Medicine, vol. 39, No. 1, pp. 1-24 (2006).

Zoccali, Bruno, "A Method for Approximating Component Temperatures at Altitude Conditions Based on CFD Analysis at Sea Level Conditions," (white paper), www.tdmginc.com, Dec. 6, 2018 (9 pages).

Slocinski et al., "Distance measure for impedance spectra for quantified evaluations," Lecture Notes on Impedance Spectroscopy, vol. 3, Taylor and Francis Group (Jul. 2012)—Book Not Attached.

Engel et al. "A safe robot system for craniofacial surgery", 2013 IEEE International Conference on Robotics and Automation (ICRA); May 6-10, 2013; Karlsruhe, Germany, vol. 2, Jan. 1, 2001, pp. 2020-2024.

Bonaci et al., "To Make a Robot Secure: An Experimental Analysis of Cyber Security Threats Against Teleoperated Surgical Robots," May 13, 2015. Retrieved from the Internet: URL:https://arxiv.org/pdf/1504.04339v2.pdf [retrieved on Aug. 24, 2019].

Homa Alemzadeh et al., "Targeted Attacks on Teleoperated Surgical Robots: Dynamic Model-Based Detection and Mitigation," 2016 46th Annual IEEE/IFIP International Conference on Dependable Systems and Networks (DSN), IEEE, Jun. 28, 2016, pp. 395-406.

Phumzile Malindi, "5. QoS in Telemedicine," "Telemedicine," Jun. 20, 2011, IntechOpen, pp. 119-138.

Staub et al., "Contour-based Surgical Instrument Tracking Supported by Kinematic Prediction," Proceedings of the 2010 3rd IEEE RAS & EMBS International Conference on Biomedical Robotics and Biomechatronics, Sep. 1, 2010, pp. 746-752.

Allan et al., "3-D Pose Estimation of Articulated Instruments in Robotic Minimally Invasive Surgery," IEEE Transactions on Medical Imaging, vol. 37, No. 5, May 1, 2018, pp. 1204-1213.

Kassahun et al., "Surgical Robotics Beyond Enhanced Dexterity Instrumentation: A Survey of the Machine Learning Techniques and their Role in Intelligent and Autonomous Surgical Actions." International Journal of Computer Assisted Radiology and Surgery, vol. 11, No. 4, Oct. 8, 2015, pp. 553-568.

Weede et al. "An Intelligent and Autonomous Endoscopic Guidance System for Minimally Invasive Surgery," 2013 IEEE International Conference on Robotics ad Automation (ICRA), May 6-10, 2013. Karlsruhe, Germany, May 1, 2011, pp. 5762-5768.

Altenberg et al., "Genes of Glycolysis are Ubiquitously Overexpressed in 24 Cancer Classes," Genomics, vol. 84, pp. 1014-1020 (2004).

Harold I. Brandon and V. Leroy Young, Mar. 1997, Surgical Services Management vol. 3 No. 3. retrieved from the internet <https://www.surgimedics.com/Research%20Articles/Electrosurgical%20Plume/Characterization%20And%20Removal%20Of%20Electrosurgical%20Smoke.pdf> (Year: 1997).

Marshall Brain, How Microcontrollers Work, 2006, retrieved from the internet <https://web.archive.org/web/20060221235221/http://electronics.howstuffworks.com/microcontroller.htm/printable> (Year: 2006).

CRC Press, "The Measurement, Instrumentation and Sensors Handbook," 1999, Section VII, Chapter 41, Peter O'Shea, "Phase Measurement," pp. 1303-1321, ISBN 0-8493-2145-X.

Jiang, "'Sound of Silence': a secure indoor wireless ultrasonic communication system," Article, 2014, pp. 46-50, Snapshots of Doctoral Research at University College Cork, School of Engineering—Electrical & Electronic Engineering, UCC, Cork, Ireland.

Li, et al., "Short-range ultrasonic communications in air using quadrature modulation," Journal, Oct. 30, 2009, pp. 2060-2072, IEEE Transactions on Ultrasonics, Ferroelectrics, and Frequency Control, vol. 56, No. 10, IEEE.

Salamon, "AI Detects Polyps Better Than Colonoscopists" Online Article, Jun. 3, 2018, Medscape Medical News, Digestive Disease Week (DDW) 2018: Presentation 133.

Misawa, et al. "Artificial Intelligence-Assisted Polyp Detection for Colonoscopy: Initial Experience," Article, Jun. 2018, pp. 2027-2029, vol. 154, Issue 8, American Gastroenterolgy Association.

Dottorato, "Analysis and Design of the Rectangular Microstrip Patch Antennas for TM0n0 operating mode,"Article, Oct. 8, 2010, pp. 1-9, Microwave Journal.

Miller, et al., "Impact of Powered and Tissue-Specific Endoscopic Stapling Technology on Clinical and Economic Outcomes of Video-Assisted Thoracic Surgery Lobectomy Procedures: A Retrospective, Observational Study," Article, Apr. 2018, pp. 707-723, vol. 35 (Issue 5), Advances in Therapy.

Hsiao-Wei Tang, "ARCM", Video, Sep. 2012, YouTube, 5 screenshots, Retrieved from internet: <https://www.youtube.com/watch?v=UldQaxb3fRw&feature=youtu.be>.

Giannios, et al., "Visible to near-infrared refractive properties of freshly-excised human-liver tissues: marking hepatic malignancies," Article, Jun. 14, 2016, pp. 1-10, Scientific Reports 6, Article No. 27910, Nature.

Vander Heiden, et al., "Understanding the Warburg effect: the metabolic requirements of cell proliferation," Article, 22 May 2009, pp. 1-12, vol. 324, Issue 5930, Science.

Hirayama et al., "Quantitative Metabolome Profiling of Colon and Stomach Cancer Microenvironment by Capillary Electrophoresis Time-of-Flight Mass Spectrometry," Article, Jun. 2009, pp. 4918-4925, vol. 69, Issue 11, Cancer Research.

Cengiz, et al., "A Tale of Two Compartments: Interstitial Versus Blood Glucose Monitoring," Article, Jun. 2009, pp. S11-S16, vol. 11, Supplement 1, Diabetes Technology & Therapeutics.

Shen, et al., "An iridium nanoparticles dispersed carbon based thick film electrochemical biosensor and its application for a single use,

(56) References Cited

OTHER PUBLICATIONS disposable glucose biosensor," Article, Feb. 3, 2007, pp. 106-113, vol. 125, Issue 1, Sensors and Actuators B: Chemical, Science Direct.
"ATM-MPLS Network Interworking Version 2.0, af-aic-0178.001" ATM Standard, The ATM Forum Technical Committee, published Aug. 2003.
IEEE Std 802.3-2012 (Revision of IEEE Std 802.3-2008, published Dec. 28, 2012.
IEEE Std No. 177, "Standard Definitions and Methods of Measurement for Piezoelectric Vibrators," published May 1966, The Institute of Electrical and Electronics Engineers, Inc., New York, N.Y.
"Surgical instrumentation: the true cost of instrument trays and a potential strategy for optimization"; Mhlaba et al.; Sep. 23, 2015 (Year: 2015).
Anonymous, "Internet of Things Powers Connected Surgical Device Infrastructure Case Study", Dec. 31, 2016 (Dec. 31, 2016), Retrieved from the Internet: URL:https://www.cognizant.com/services-resources/150110_IoT_connected_surgical_devices.pdf.
Anonymous: "Titanium Key Chain Tool 1.1, Ultralight Multipurpose Key Chain Tool, Forward Cutting Can Opener—Vargo Titanium," vargooutdoors.com, Jul. 5, 2014 (Jul. 5, 2014), retrieved from the internet: https://vargooutdoors.com/titanium-key-chain-tool-1-1.html.
Choi et al., A haptic augmented reality surgeon console for a laparoscopic surgery robot system, 2013, IEEE, pp. 355-357 (Year: 2013).
Draijer, Matthijs et al., "Review of laser pseckle contrast techniques for visualizing tissue perfusion," Lasers in Medical Science, Springer-Verlag, LO, vol. 24, No. 4, Dec. 3, 2008, pp. 639-651.
Nabil Simaan et al, "Intelligent Surgical Robots with Situational Awareness: From Good to Great Surgeons", DOI: 10.1115/1.2015-Sep-6 external link, Sep. 2015 (Sep. 2015), p. 3-6, Retrieved from the Internet: URL:http://memagazineselect.asmedigitalcollection.asme.org/data/journals/meena/936888/me-2015-sep6.pdf XP055530863.
Roy D Cullum, "Handbook of Engineering Design", ISBN: 9780408005586, Jan. 1, 1988 (Jan. 1, 1988), XP055578597, ISBN: 9780408005586, 10-20, Chapter 6, p. 138, right-hand column, paragraph 3.
Shi et al., An intuitive control console for robotic syrgery system, 2014, IEEE, p. 404-407 (Year: 2014).
Sun et al., Innovative effector design for simulation training in robotic surgery, 2010, IEEE, p. 1735-1759 (Year: 2010).
Xie et al., Development of stereo vision and master-slave controller for a compact surgical robot system, 2015, IEEE, p. 403-407 (Year: 2015).

\* cited by examiner

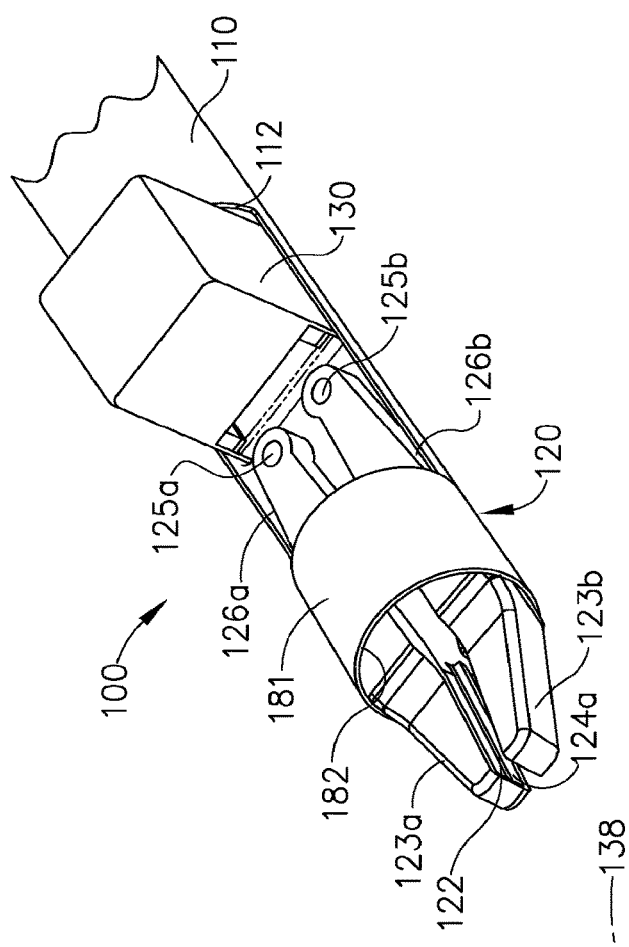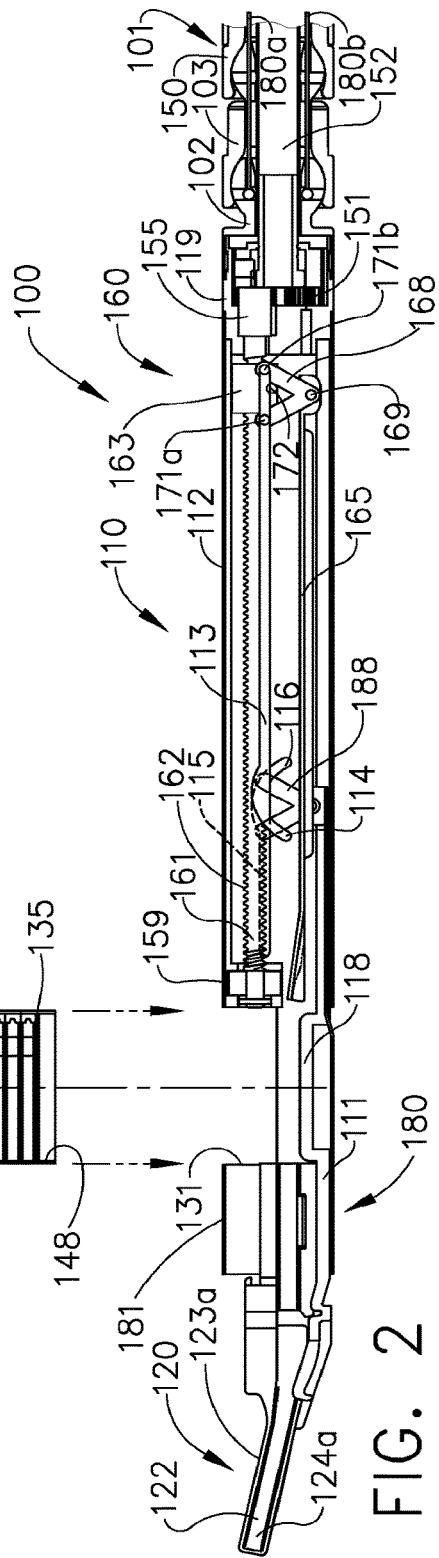

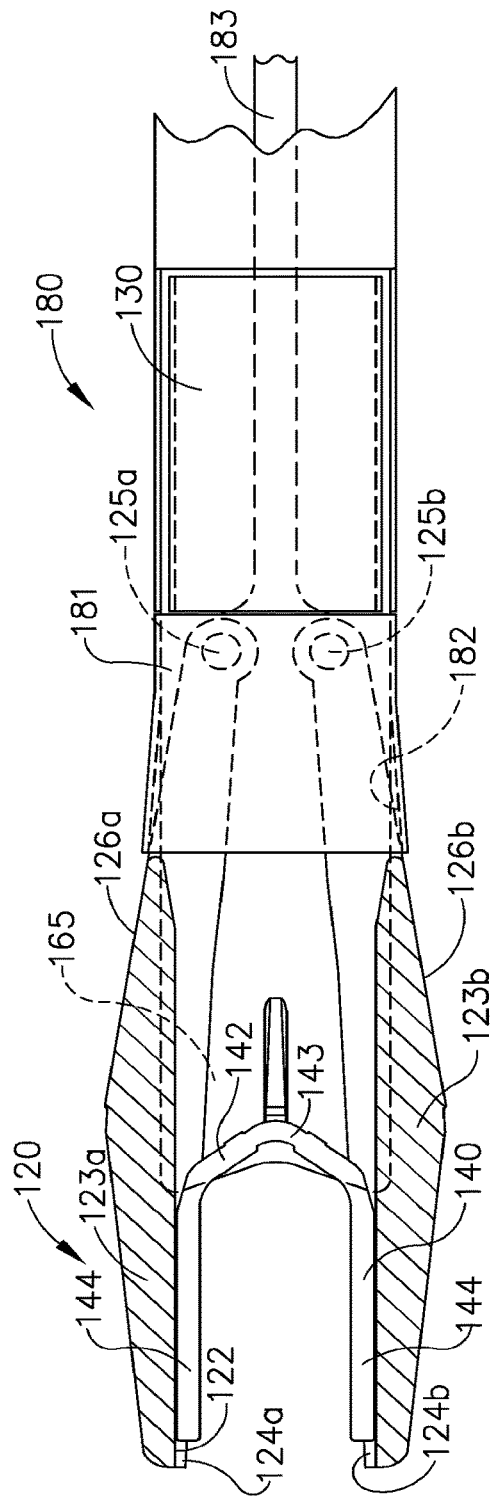
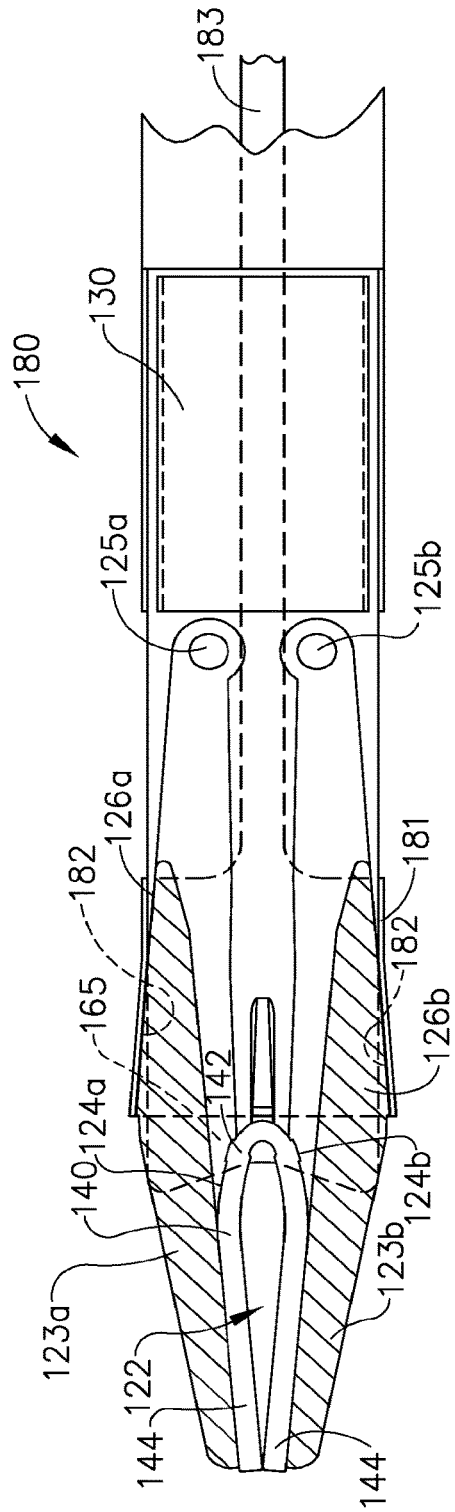
FIG. 3
FIG. 4

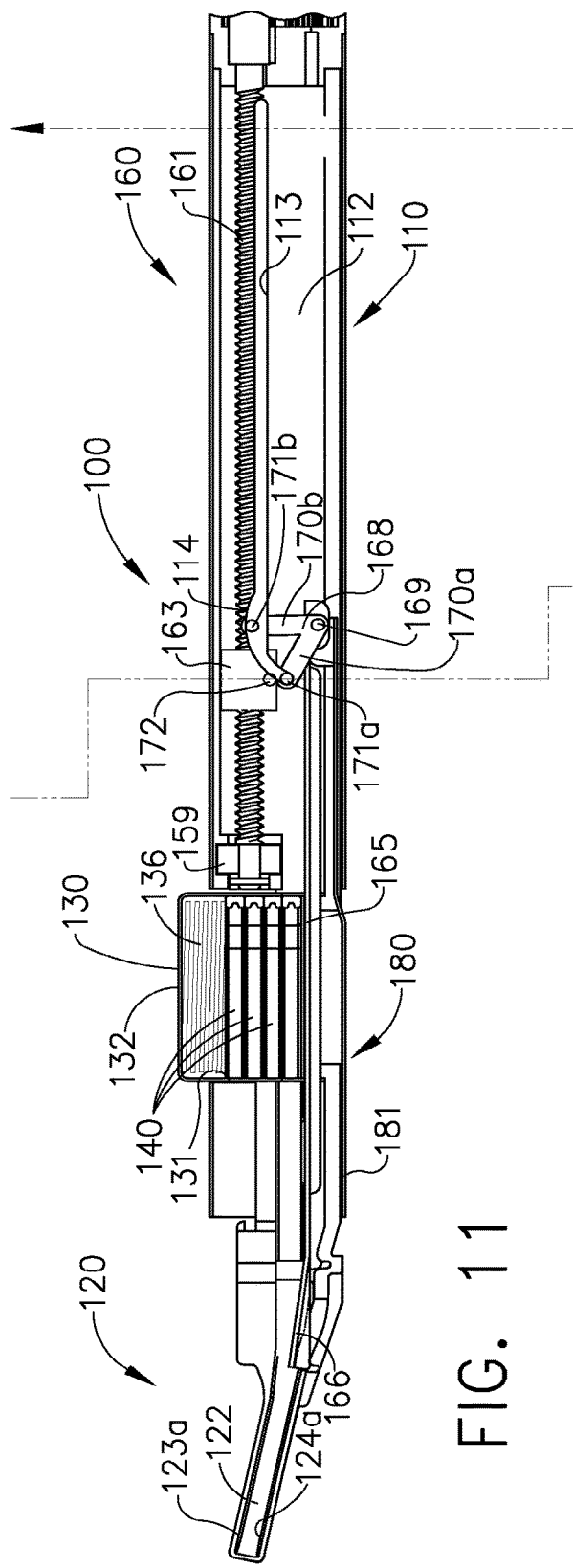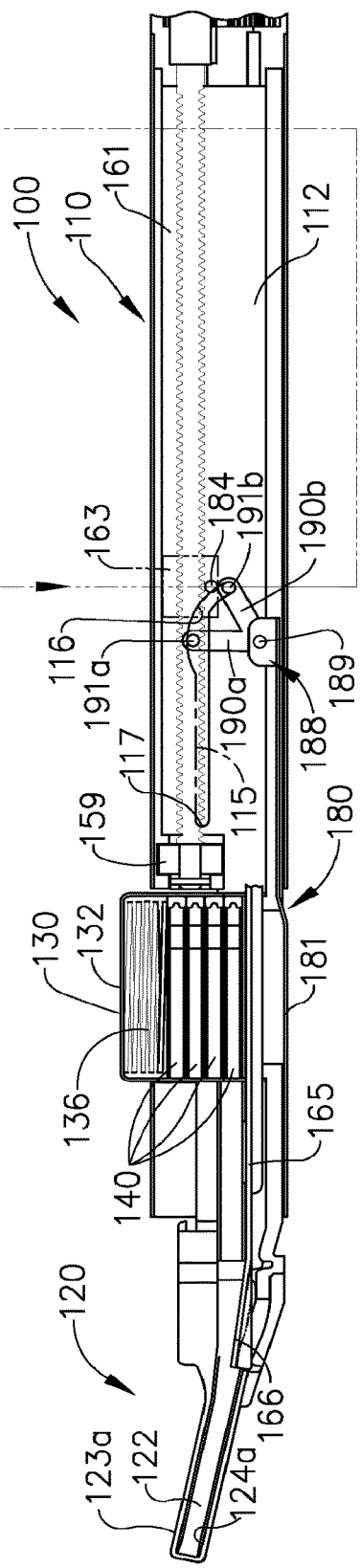
FIG. 11
FIG. 12

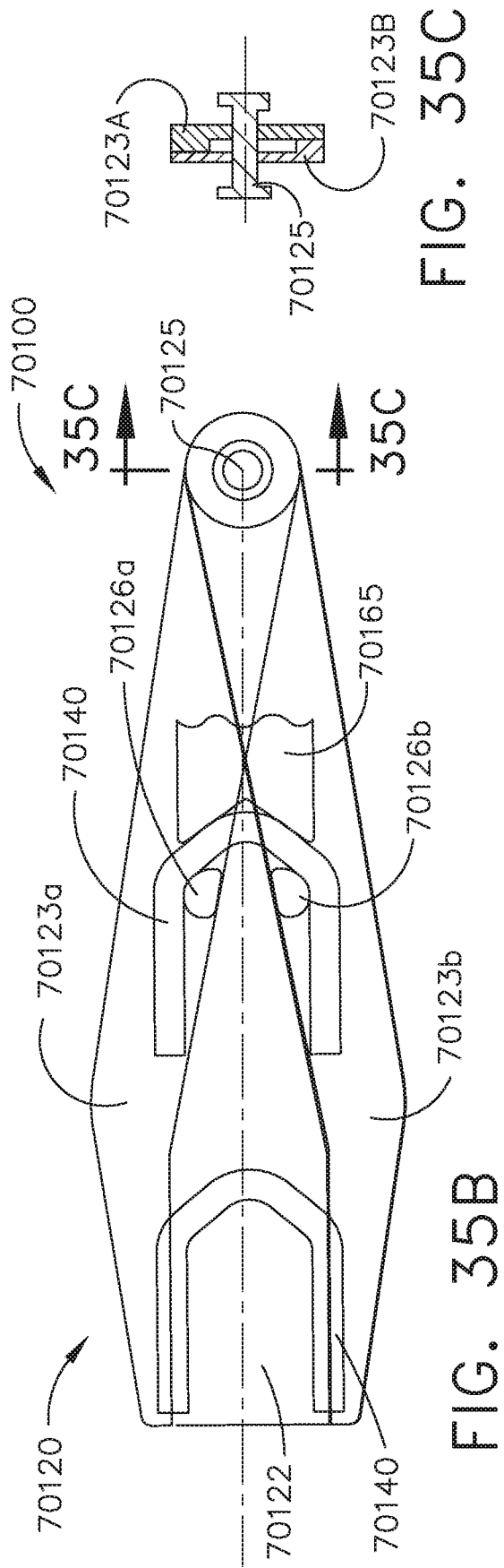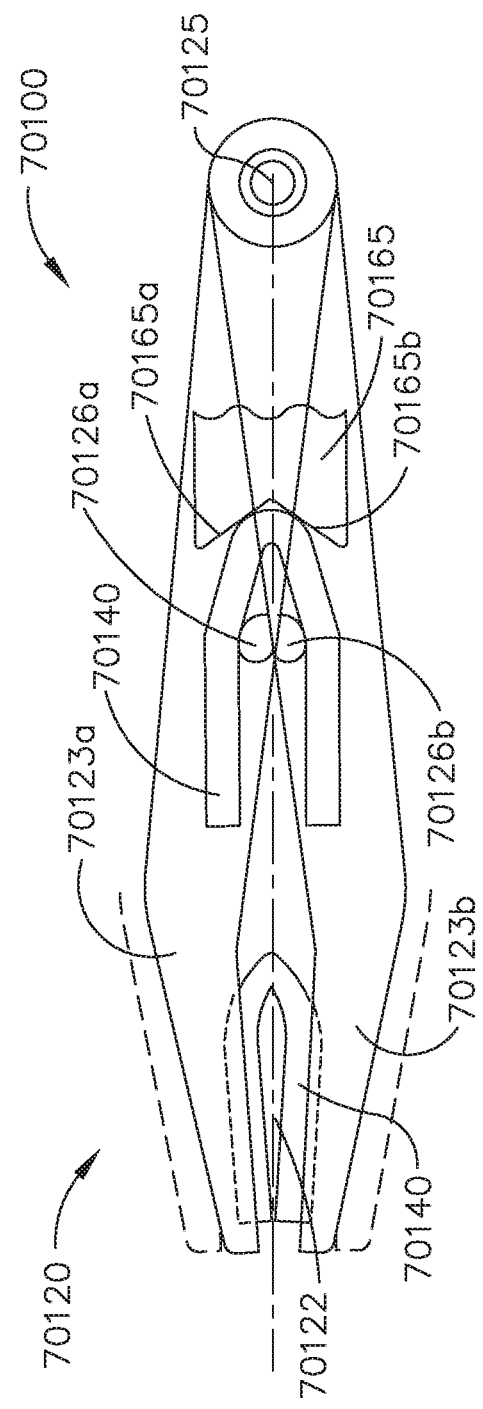

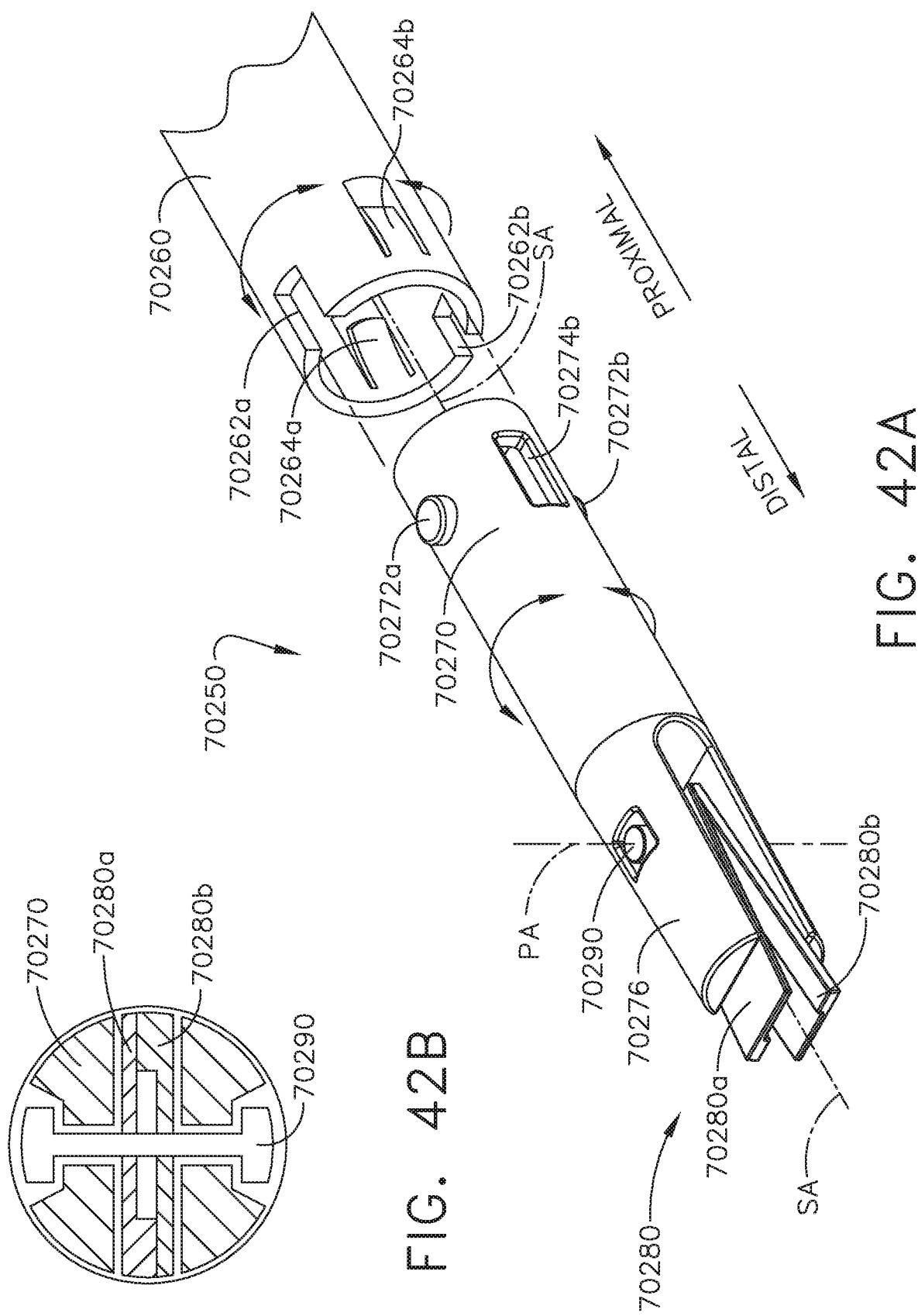

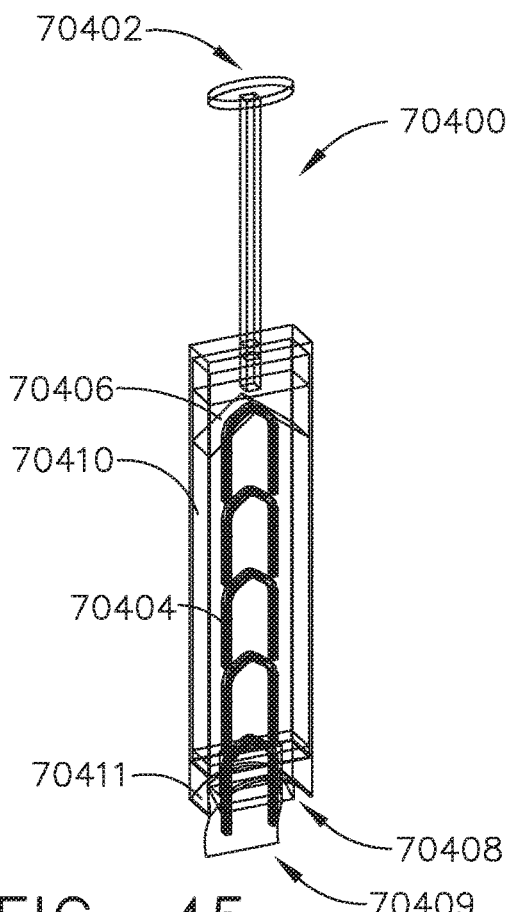
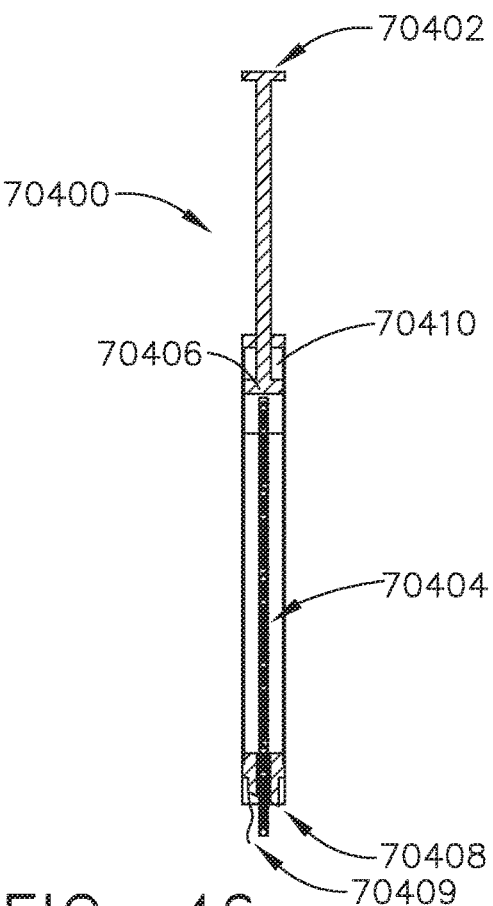
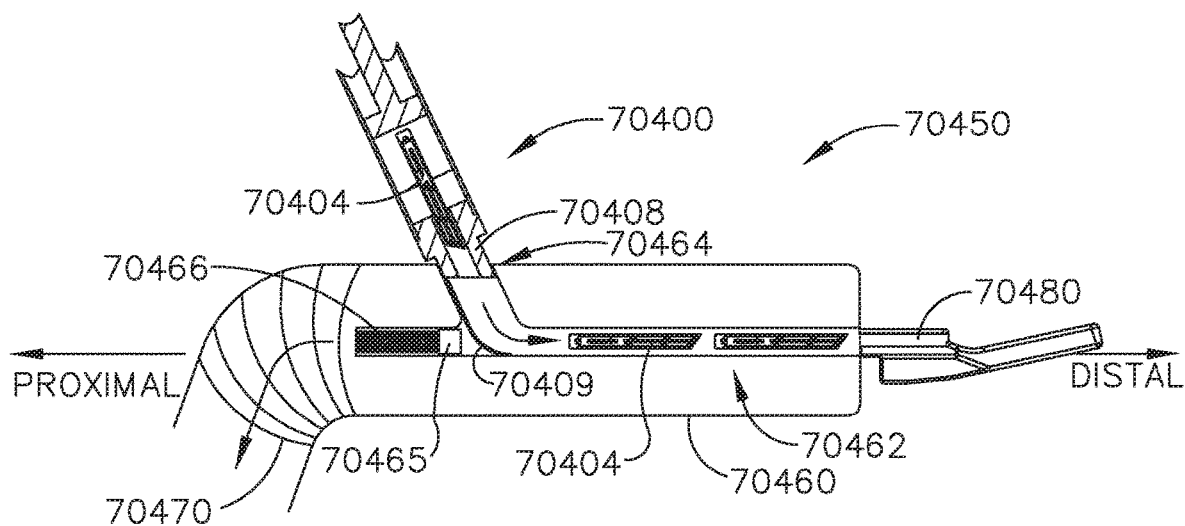
FIG. 45
FIG. 46
FIG. 47

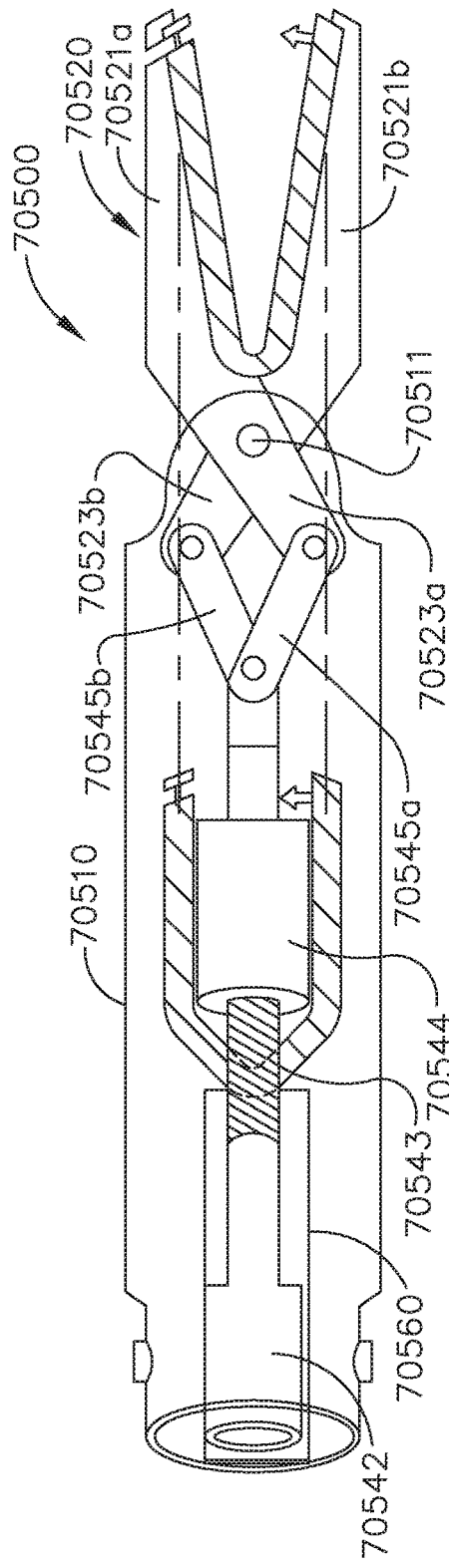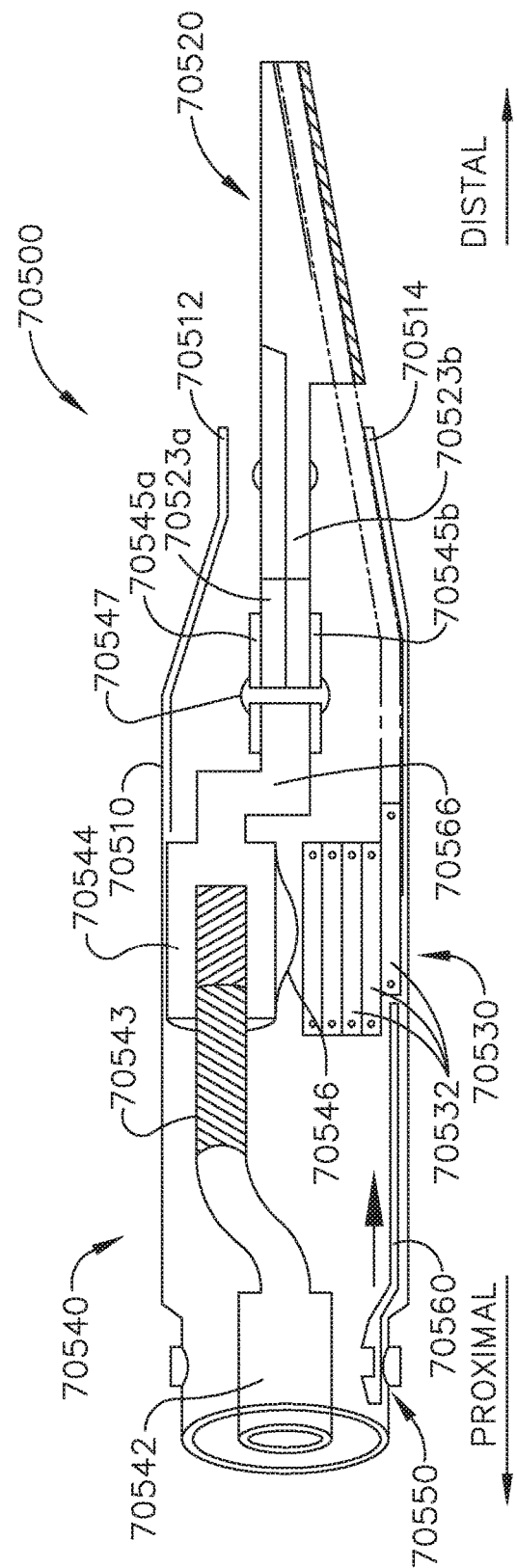

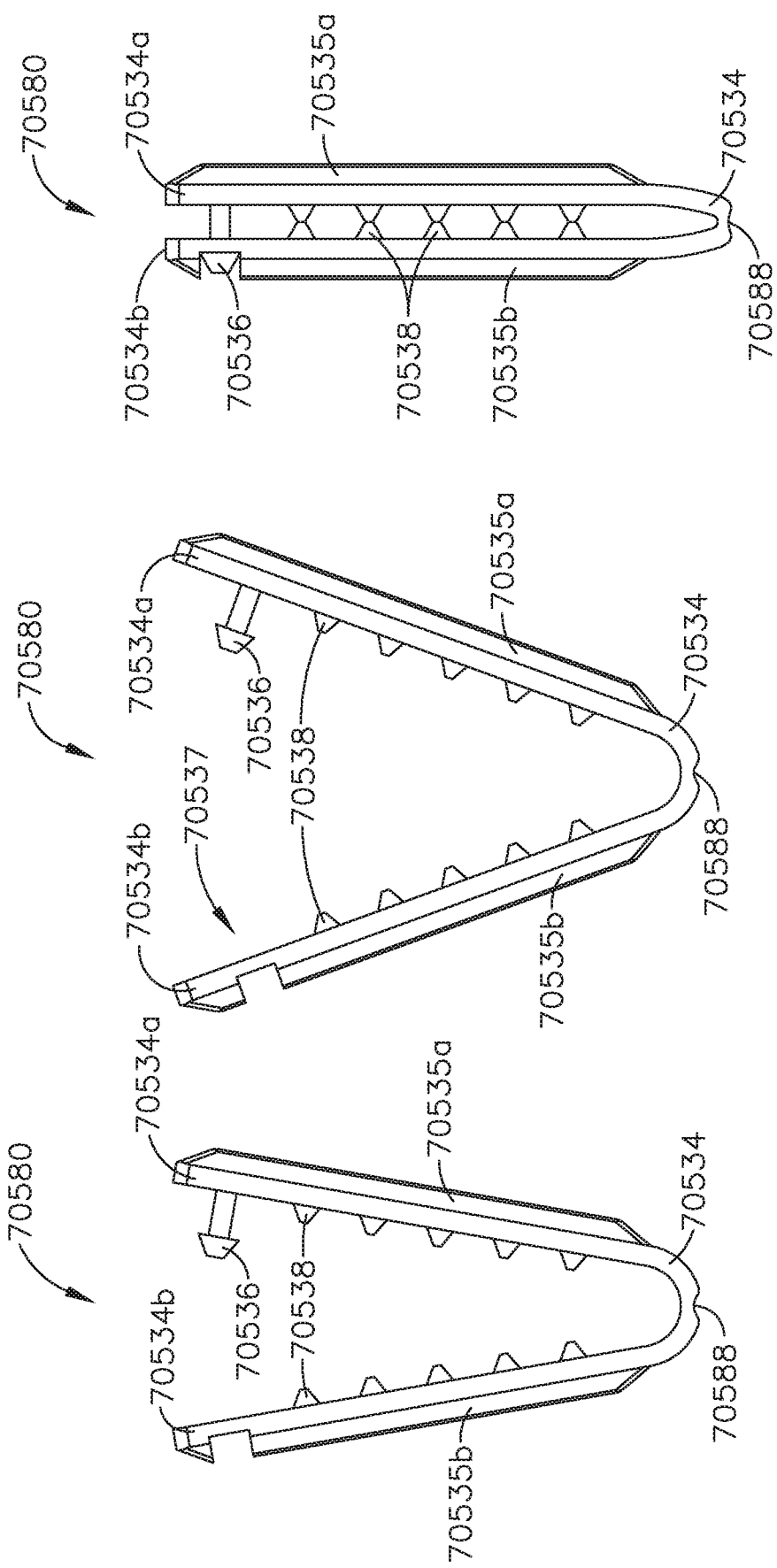

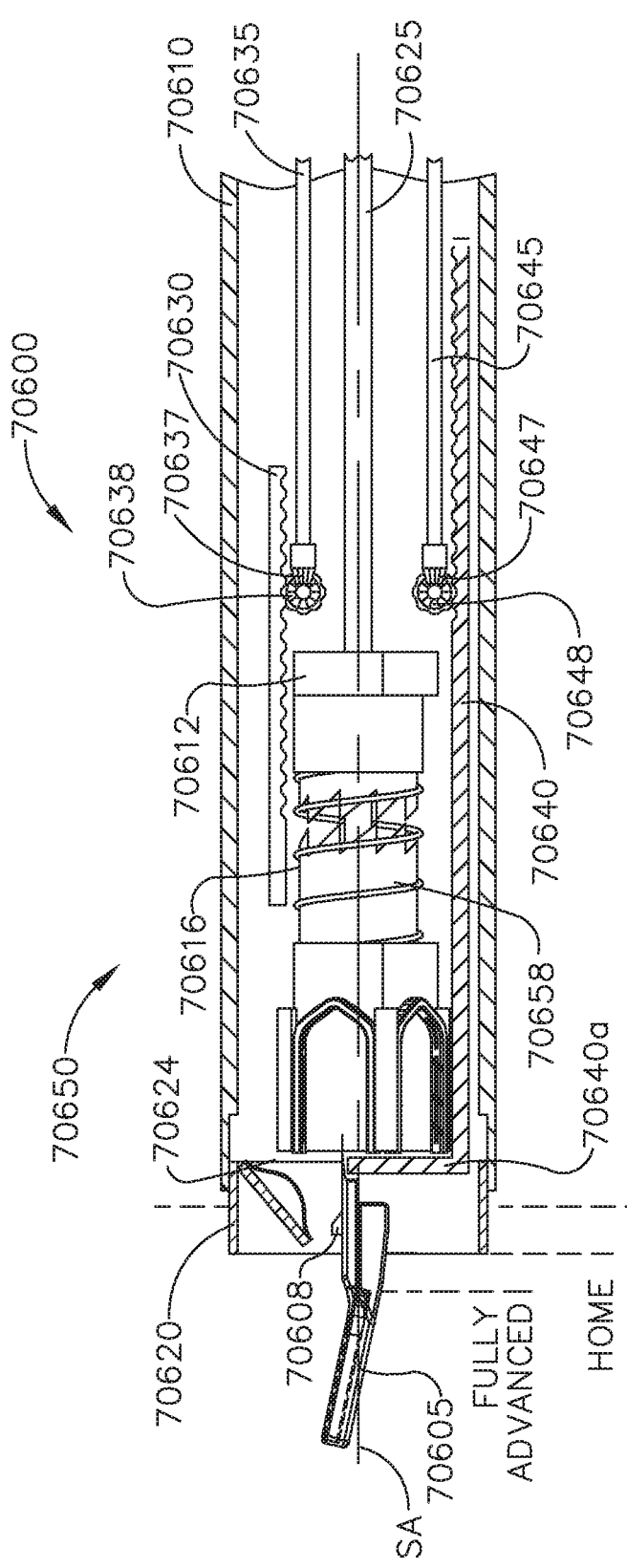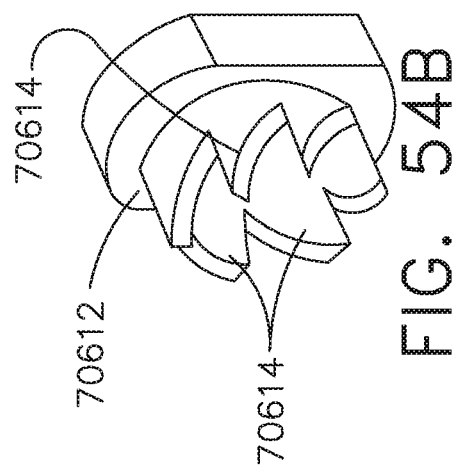

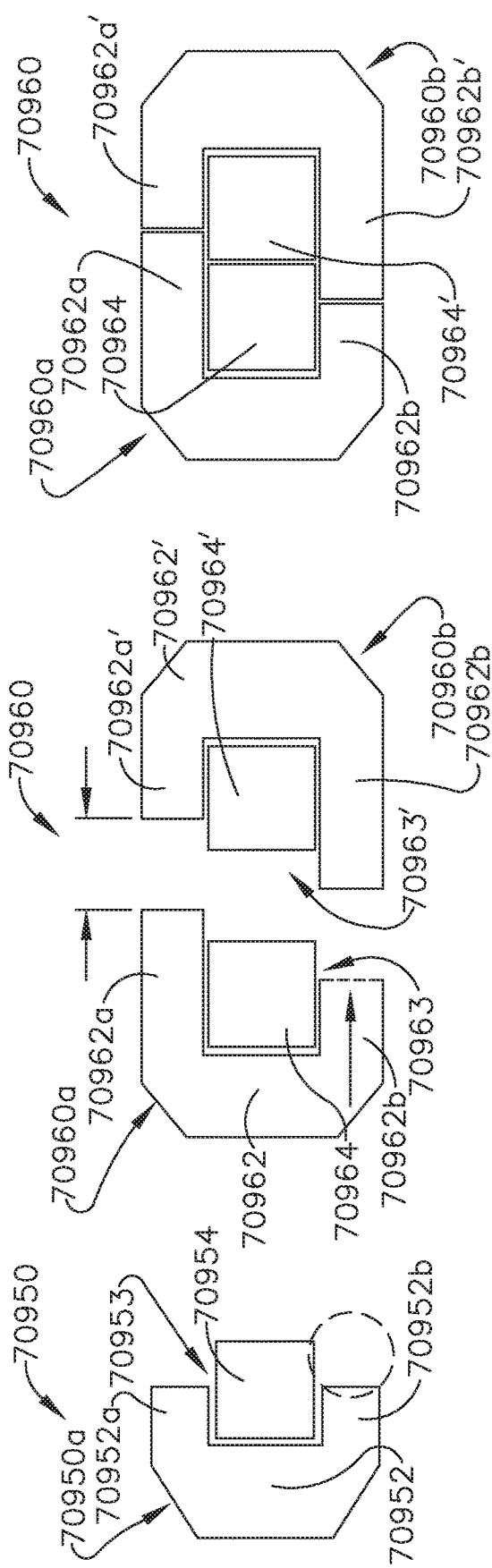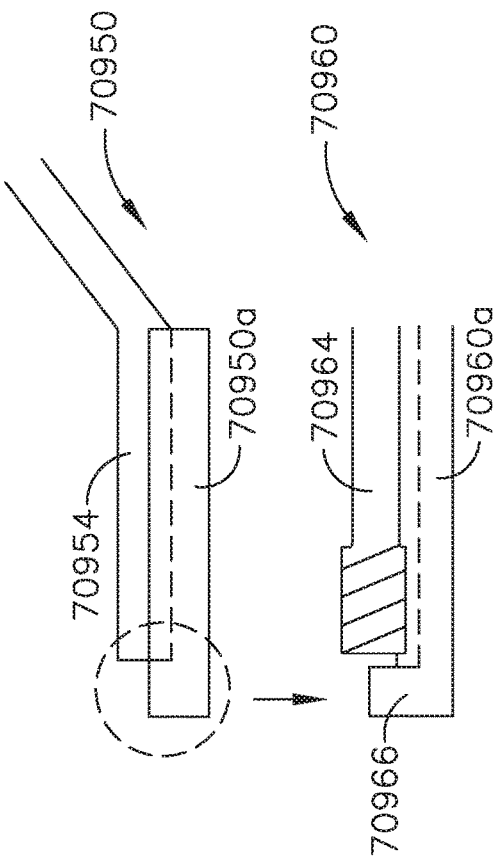
FIG. 65
FIG. 66A
FIG. 66B
FIG. 67
FIG. 68

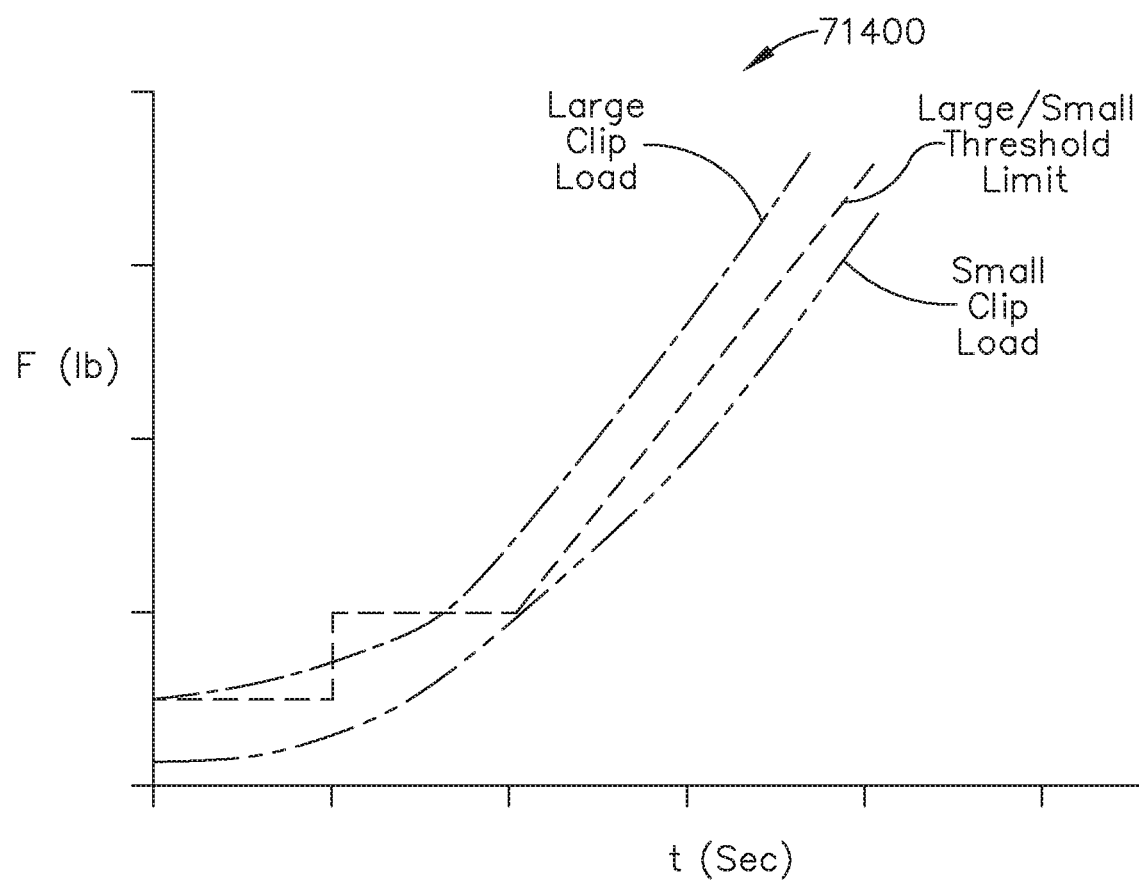
FIG. 72
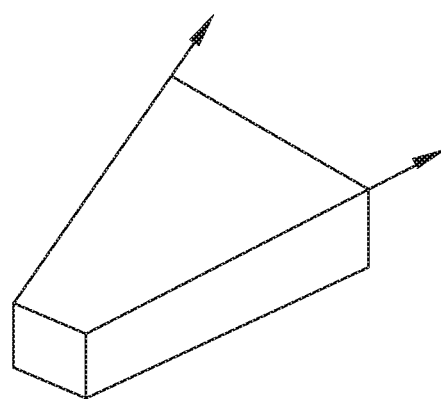
FIG. 73
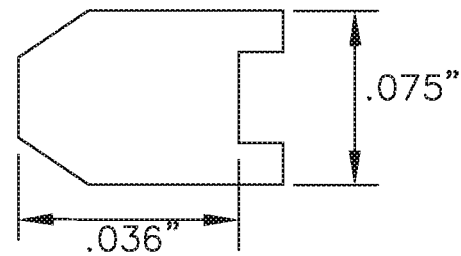
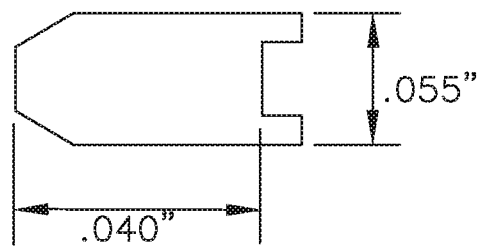
FIG. 74

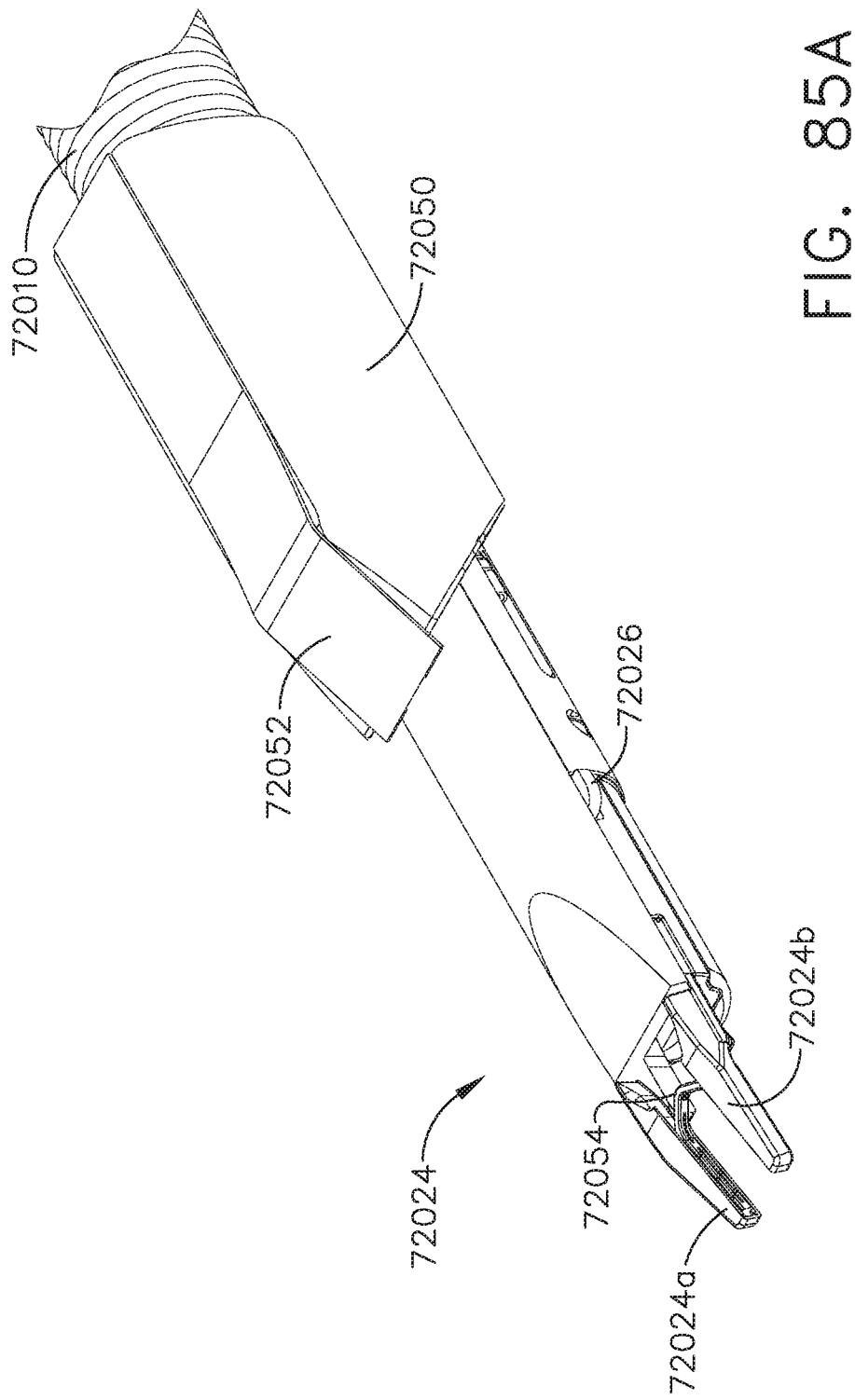

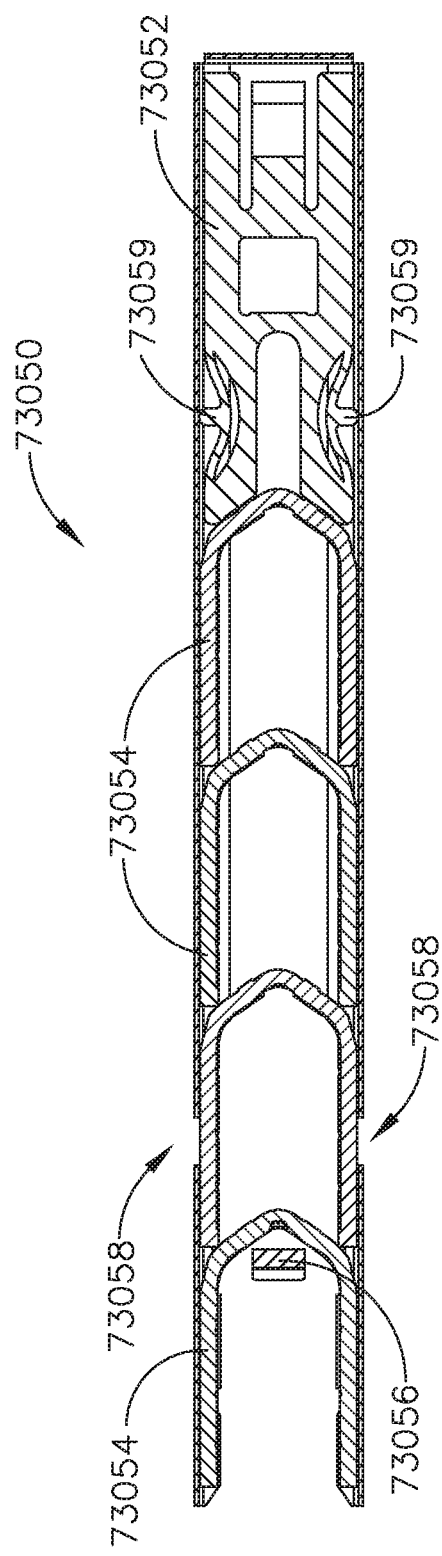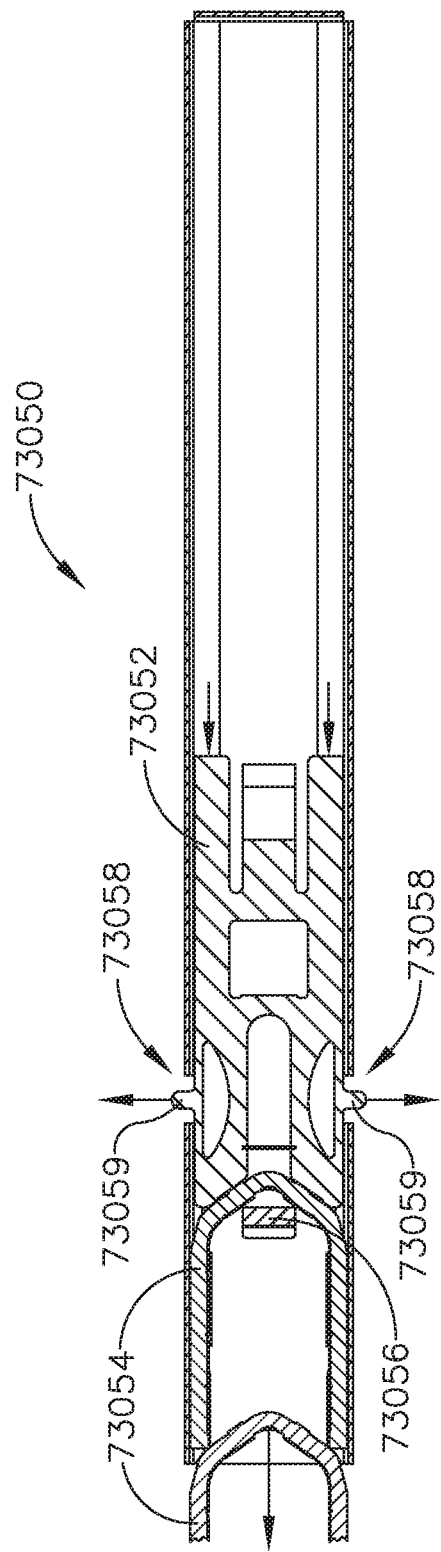

SURGICAL CLIP APPLIER COMPRISING AN EMPTY CLIP CARTRIDGE LOCKOUT

CROSS-REFERENCE TO RELATED APPLICATIONS

This non-provisional application claims the benefit under 35 U.S.C. § 119(e) of U.S. Provisional Patent Application Ser. No. 62/578,793, entitled SURGICAL INSTRUMENT WITH REMOTE RELEASE, filed Oct. 30, 2017, of U.S. Provisional Patent Application Ser. No. 62/578,804, entitled SURGICAL INSTRUMENT HAVING DUAL ROTATABLE MEMBERS TO EFFECT DIFFERENT TYPES OF END EFFECTOR MOVEMENT, filed Oct. 30, 2017, of U.S. Provisional Patent Application Ser. No. 62/578,817, entitled SURGICAL INSTRUMENT WITH ROTARY DRIVE SELECTIVELY ACTUATING MULTIPLE END EFFECTOR FUNCTIONS, filed Oct. 30, 2017, of U.S. Provisional Patent Application Ser. No. 62/578,835, entitled SURGICAL INSTRUMENT WITH ROTARY DRIVE SELECTIVELY ACTUATING MULTIPLE END EFFECTOR FUNCTIONS, filed Oct. 30, 2017, of U.S. Provisional Patent Application Ser. No. 62/578,844, entitled SURGICAL INSTRUMENT WITH MODULAR POWER SOURCES, filed Oct. 30, 2017, and of U.S. Provisional Patent Application Ser. No. 62/578,855, entitled SURGICAL INSTRUMENT WITH SENSOR AND/OR CONTROL SYSTEMS, filed Oct. 30, 2017, the disclosures of which are incorporated by reference herein in their entirety. This non-provisional application claims the benefit under 35 U.S.C. § 119(e) of U.S. Provisional Patent Application Ser. No. 62/665,129, entitled SURGICAL SUTURING SYSTEMS, filed May 1, 2018, of U.S. Provisional Patent Application Ser. No. 62/665,139, entitled SURGICAL INSTRUMENTS COMPRISING CONTROL SYSTEMS, filed May 1, 2018, of U.S. Provisional Patent Application Ser. No. 62/665,177, entitled SURGICAL INSTRUMENTS COMPRISING HANDLE ARRANGEMENTS, filed May 1, 2018, of U.S. Provisional Patent Application Ser. No. 62/665,128, entitled MODULAR SURGICAL INSTRUMENTS, filed May 1, 2018, of U.S. Provisional Patent Application Ser. No. 62/665,192, entitled SURGICAL DISSECTORS, filed May 1, 2018, and of U.S. Provisional Patent Application Ser. No. 62/665,134, entitled SURGICAL CLIP APPLIER, filed May 1, 2018, the disclosures of which are incorporated by reference herein in their entirety.

BACKGROUND

A variety of fasteners can be utilized to treat, clamp, fasten, secure, and/or hold tissue. Clips can be positioned relative to tissue located within a surgical site in a patient and then deformed to apply a clamping force, for example, to the tissue.

BRIEF DESCRIPTION OF THE DRAWINGS

The features and advantages of this invention, and the manner of attaining them, will become more apparent and the invention itself will be better understood by reference to the following description of exemplary embodiments of the invention taken in conjunction with the accompanying drawings, wherein:

FIG. 1 is a partial perspective view of a clip applier;

FIG. 2 is a cross-sectional view of an end effector of the clip applier of FIG. 1 comprising a removable clip cartridge, a reciprocating firing drive for sequentially advancing the clips, a receiver for receiving the clips, and a crimping drive for deforming the clips;

FIG. 3 is a partial cross-sectional view of the clip applier of FIG. 1 in an open configuration;

FIG. 4 is a partial cross-sectional view of the clip applier of FIG. 1 in a closed configuration;

FIG. 11 is a cross-sectional view of the firing drive of the end effector of FIG. 2 in a partially retracted position in which the firing drive is being re-engaged with the firing member;

FIG. 12 is a cross-sectional view of the firing drive of the end effector of FIG. 2 being disengaged from the crimping drive;

FIG. 35A is a partial cross-sectional view of an end effector of a clip applier in a closed configuration;

FIG. 35B is a partial cross-sectional view of the end effector of FIG. 35A in an open configuration;

FIG. 35C is a cross-sectional view of the end effector of FIG. 35A in an open configuration;

FIG. 42A is a perspective view of a clip applier comprising an attachment mechanism;

FIG. 42B is a cross-sectional view of the clip applier of FIG. 42A;

FIG. 45 is a perspective view of a clip reloader;

FIG. 46 is a cross-sectional view of the clip reloader of FIG. 45;

FIG. 47 is a cross-sectional view of the clip reloader of FIG. 45 and an end effector of a clip applier;

FIG. 48 is a partial cross-sectional plan view of a clip applier;

FIG. 49 is a partial cross-sectional side view of the clip applier of FIG. 48;

FIG. 51D is a side view of the clip of FIG. 51C in a storage configuration;

FIG. 51E is a side view of the clip of FIG. 51C in a pre-firing configuration;

FIG. 51F is a side view of the clip of FIG. 51C in a post-firing configuration;

FIG. 54A is a partial cross-sectional view of the clip applier of FIG. 52 illustrating the closure tube in a home position;

FIG. 54B is a perspective view of a ground portion including a clocking portion of the clip applier of FIG. 52;

FIG. 65 is a partial cross-sectional view of a clip applier jaw assembly;

FIG. 66A is a partial cross-sectional view of clip applier jaw assembly including offset support legs;

FIG. 66B is a partial cross-sectional view of the clip applier jaw assembly of FIG. 66A;

FIG. 67 is a partial cross sectional plan view of the clip applier jaw assembly of FIG. 65;

FIG. 68 is a partial cross sectional plan view of the clip applier jaw assembly of FIG. 66A;

FIG. 72 depicts a graph of the force applied to a pair of jaws of a clip applier versus time;

FIG. 73 is directed to an alternative embodiment;

FIG. 74 is directed to an alternative embodiment;

FIG. 85A is a partial perspective view of the clip applier system of FIG. 82;

FIG. 88C is a cross-sectional plan view of the clip applier and the clip magazine of FIG. 87A;

FIG. 88D is a cross-sectional plan view of the clip applier and the clip magazine of FIG. 87A in a nearly spent configuration.

DETAILED DESCRIPTION

Figure 5:
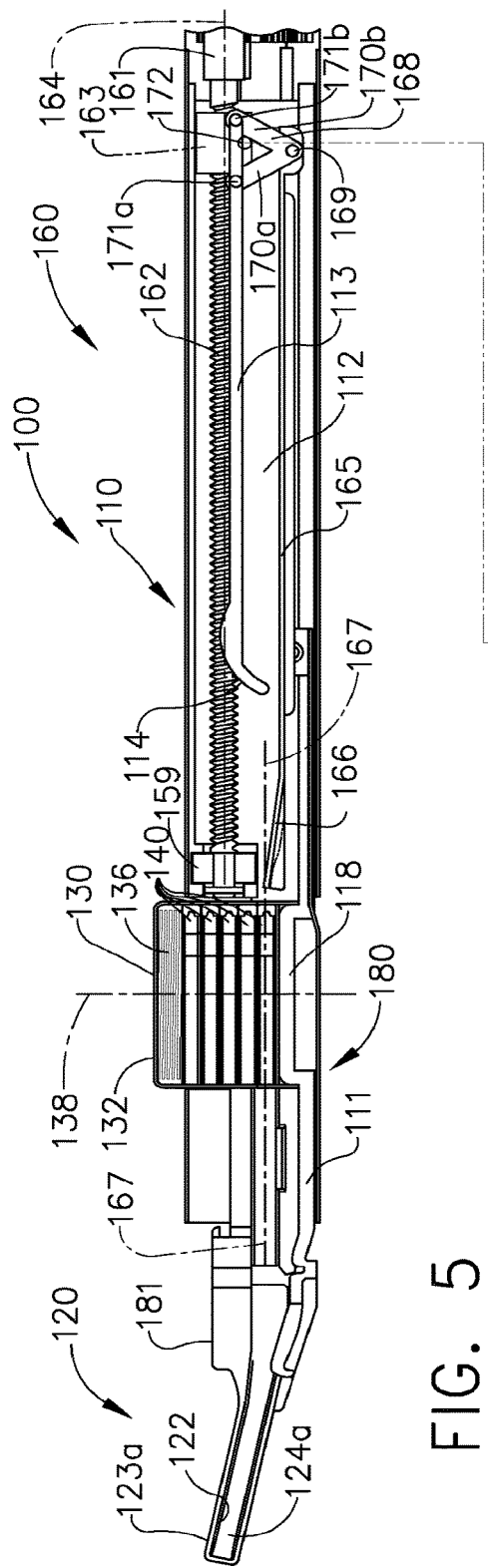
FIG. 5 is a cross-sectional view of the end effector of FIG. 2 in an unfired condition.

Applicant of the present application owns the following U.S. Patent Applications that were filed on Aug. 24, 2018 and which are each herein incorporated by reference in their respective entireties:

U.S. patent application Ser. No. 16/112,129, entitled SURGICAL SUTURING INSTRUMENT CONFIGURED TO MANIPULATE TISSUE USING MECHANICAL AND ELECTRICAL POWER; now U.S. Patent Application Publication No. 2019/0125431;

U.S. patent application Ser. No. 16/112,155, entitled SURGICAL SUTURING INSTRUMENT COMPRISING A CAPTURE WIDTH WHICH IS LARGER THAN TROCAR DIAMETER; now U.S. Patent Application Publication No. 2019/0125335;

U.S. patent application Ser. No. 16/112,168, entitled SURGICAL SUTURING INSTRUMENT COMPRISING A NON-CIRCULAR NEEDLE; now U.S. Patent Application Publication No. 2019/0125336;

U.S. patent application Ser. No. 16/112,180, entitled ELECTRICAL POWER OUTPUT CONTROL BASED ON MECHANICAL FORCES; now U.S. Patent Application Publication No. 2019/0125432;

U.S. patent application Ser. No. 16/112,193, entitled REACTIVE ALGORITHM FOR SURGICAL SYSTEM; now U.S. Pat. No. 10,932,806;

U.S. patent application Ser. No. 16/112,099, entitled SURGICAL INSTRUMENT COMPRISING AN ADAPTIVE ELECTRICAL SYSTEM; now U.S. Patent Application Publication No. 2019/0125378;

U.S. patent application Ser. No. 16/112,112, entitled CONTROL SYSTEM ARRANGEMENTS FOR A MODULAR SURGICAL INSTRUMENT; now U.S. Patent Application Publication No. 2019/0125320;

U.S. patent application Ser. No. 16/112,119, entitled ADAPTIVE CONTROL PROGRAMS FOR A SURGICAL SYSTEM COMPRISING MORE THAN ONE TYPE OF CARTRIDGE; now U.S. Patent Application Publication No. 2019/0125338;

U.S. patent application Ser. No. 16/112,097, entitled SURGICAL INSTRUMENT SYSTEMS COMPRISING BATTERY ARRANGEMENTS; now U.S. Patent Application Publication No. 2019/0125377;

U.S. patent application Ser. No. 16/112,109, entitled SURGICAL INSTRUMENT SYSTEMS COMPRISING HANDLE ARRANGEMENTS; now U.S. Patent Application Publication No. 2019/0125388;

U.S. patent application Ser. No. 16/112,114, entitled SURGICAL INSTRUMENT SYSTEMS COMPRISING FEEDBACK MECHANISMS; now U.S. Patent Application Publication No. 2019/0142449;

U.S. patent application Ser. No. 16/112,117, entitled SURGICAL INSTRUMENT SYSTEMS COMPRISING LOCKOUT MECHANISMS; now U.S. Patent Application Publication No. 2019/0125476;

U.S. patent application Ser. No. 16/112,095, entitled SURGICAL INSTRUMENTS COMPRISING A LOCKABLE END EFFECTOR SOCKET; now U.S. Patent Application Publication No. 2019/0125387;

U.S. patent application Ser. No. 16/112,121, entitled SURGICAL INSTRUMENTS COMPRISING A SHIFTING MECHANISM; now U.S. Patent Application Publication No. 2019/0125389;

U.S. patent application Ser. No. 16/112,151, entitled SURGICAL INSTRUMENTS COMPRISING A SYSTEM FOR ARTICULATION AND ROTATION COMPENSATION; now U.S. Pat. No. 10,772,651;

U.S. patent application Ser. No. 16/112,154, entitled SURGICAL INSTRUMENTS COMPRISING A BIASED SHIFTING MECHANISM; now U.S. Patent Application Publication No. 2019/0125321;

U.S. patent application Ser. No. 16/112,226, entitled SURGICAL INSTRUMENTS COMPRISING AN ARTICULATION DRIVE THAT PROVIDES FOR HIGH ARTICULATION ANGLES; now U.S. Patent Application Publication No. 2019/0125379;

U.S. patent application Ser. No. 16/112,062, entitled SURGICAL DISSECTORS AND MANUFACTURING TECHNIQUES; now U.S. Patent Application Publication No. 2019/0125386;

U.S. patent application Ser. No. 16/112,098, entitled SURGICAL DISSECTORS CONFIGURED TO APPLY MECHANICAL AND ELECTRICAL ENERGY; now U.S. Patent Application Publication No. 2019/0125430;

U.S. patent application Ser. No. 16/112,237, entitled SURGICAL CLIP APPLIER CONFIGURED TO STORE CLIPS IN A STORED STATE; now U.S. Patent Application Publication No. 2019/0125347;

U.S. patent application Ser. No. 16/112,249, entitled SURGICAL CLIP APPLIER COMPRISING AN AUTOMATIC CLIP FEEDING SYSTEM; now U.S. Patent Application Publication No. 2019/0125353;

U.S. patent application Ser. No. 16/112,253, entitled SURGICAL CLIP APPLIER COMPRISING ADAPTIVE FIRING CONTROL; now U.S. Patent Application Publication No. 2019/0125348; and U.S. patent application Ser. No. 16/112,257, entitled SURGICAL CLIP APPLIER COMPRISING ADAPTIVE CONTROL IN RESPONSE TO A STRAIN GAUGE CIRCUIT; now U.S. Patent Application Publication No. 2019/0125354.

Applicant of the present application owns the following U.S. Patent Applications that were filed on May 1, 2018 and which are each herein incorporated by reference in their respective entireties:

U.S. Provisional Patent Application Ser. No. 62/665,129, entitled SURGICAL SUTURING SYSTEMS;

U.S. Provisional Patent Application Ser. No. 62/665,139, entitled SURGICAL INSTRUMENTS COMPRISING CONTROL SYSTEMS;

U.S. Provisional Patent Application Ser. No. 62/665,177, entitled SURGICAL INSTRUMENTS COMPRISING HANDLE ARRANGEMENTS;

U.S. Provisional Patent Application Ser. No. 62/665,128, entitled MODULAR SURGICAL INSTRUMENTS;

U.S. Provisional Patent Application Ser. No. 62/665,192, entitled SURGICAL DISSECTORS; and U.S. Provisional Patent Application Ser. No. 62/665,134, entitled SURGICAL CLIP APPLIER.

Applicant of the present application owns the following U.S. Patent Applications that were filed on Feb. 28, 2018 and which are each herein incorporated by reference in their respective entireties:

U.S. patent application Ser. No. 15/908,021, entitled SURGICAL INSTRUMENT WITH REMOTE RELEASE;

U.S. patent application Ser. No. 15/908,012, entitled SURGICAL INSTRUMENT HAVING DUAL ROTATABLE MEMBERS TO EFFECT DIFFERENT TYPES OF END EFFECTOR MOVEMENT;

U.S. patent application Ser. No. 15/908,040, entitled SURGICAL INSTRUMENT WITH ROTARY DRIVE SELECTIVELY ACTUATING MULTIPLE END EFFECTOR FUNCTIONS;

U.S. patent application Ser. No. 15/908,057, entitled SURGICAL INSTRUMENT WITH ROTARY DRIVE SELECTIVELY ACTUATING MULTIPLE END EFFECTOR FUNCTIONS;

U.S. patent application Ser. No. 15/908,058, entitled SURGICAL INSTRUMENT WITH MODULAR POWER SOURCES; and U.S. patent application Ser. No. 15/908,143, entitled SURGICAL INSTRUMENT WITH SENSOR AND/OR CONTROL SYSTEMS.

Applicant of the present application owns the following U.S. Patent Applications that were filed on Oct. 30, 2017 and which are each herein incorporated by reference in their respective entireties:

U.S. Provisional Patent Application Ser. No. 62/578,793, entitled SURGICAL INSTRUMENT WITH REMOTE RELEASE;

U.S. Provisional Patent Application Ser. No. 62/578,804, entitled SURGICAL INSTRUMENT HAVING DUAL ROTATABLE MEMBERS TO EFFECT DIFFERENT TYPES OF END EFFECTOR MOVEMENT;

U.S. Provisional Patent Application Ser. No. 62/578,817, entitled SURGICAL INSTRUMENT WITH ROTARY DRIVE SELECTIVELY ACTUATING MULTIPLE END EFFECTOR FUNCTIONS;

U.S. Provisional Patent Application Ser. No. 62/578,835, entitled SURGICAL INSTRUMENT WITH ROTARY DRIVE SELECTIVELY ACTUATING MULTIPLE END EFFECTOR FUNCTIONS;

U.S. Provisional Patent Application Ser. No. 62/578,844, entitled SURGICAL INSTRUMENT WITH MODULAR POWER SOURCES; and U.S. Provisional Patent Application Ser. No. 62/578,855, entitled SURGICAL INSTRUMENT WITH SENSOR AND/OR CONTROL SYSTEMS.

Applicant of the present application owns the following U.S. Provisional Patent Applications, filed on Dec. 28, 2017, the disclosure of each of which is herein incorporated by reference in its entirety:
- U.S. Provisional Patent Application Ser. No. 62/611,341, entitled INTERACTIVE SURGICAL PLATFORM;
- U.S. Provisional Patent Application Ser. No. 62/611,340, entitled CLOUD-BASED MEDICAL ANALYTICS; and
- U.S. Provisional Patent Application Ser. No. 62/611,339, entitled ROBOT ASSISTED SURGICAL PLATFORM.

Applicant of the present application owns the following U.S. Provisional Patent Applications, filed on Mar. 28, 2018, each of which is herein incorporated by reference in its entirety:
- U.S. Provisional Patent Application Ser. No. 62/649,302, entitled INTERACTIVE SURGICAL SYSTEMS WITH ENCRYPTED COMMUNICATION CAPABILITIES;
- U.S. Provisional Patent Application Ser. No. 62/649,294, entitled DATA STRIPPING METHOD TO INTERROGATE PATIENT RECORDS AND CREATE ANONYMIZED RECORD;
- U.S. Provisional Patent Application Ser. No. 62/649,300, entitled SURGICAL HUB SITUATIONAL AWARENESS;
- U.S. Provisional Patent Application Ser. No. 62/649,309, entitled SURGICAL HUB SPATIAL AWARENESS TO DETERMINE DEVICES IN OPERATING THEATER;
- U.S. Provisional Patent Application Ser. No. 62/649,310, entitled COMPUTER IMPLEMENTED INTERACTIVE SURGICAL SYSTEMS;
- U.S. Provisional Patent Application Ser. No. 62/649,291, entitled USE OF LASER LIGHT AND RED-GREEN-BLUE COLORATION TO DETERMINE PROPERTIES OF BACK SCATTERED LIGHT;
- U.S. Provisional Patent Application Ser. No. 62/649,296, entitled ADAPTIVE CONTROL PROGRAM UPDATES FOR SURGICAL DEVICES;
- U.S. Provisional Patent Application Ser. No. 62/649,333, entitled CLOUD-BASED MEDICAL ANALYTICS FOR CUSTOMIZATION AND RECOMMENDATIONS TO A USER;
- U.S. Provisional Patent Application Ser. No. 62/649,327, entitled CLOUD-BASED MEDICAL ANALYTICS FOR SECURITY AND AUTHENTICATION TRENDS AND REACTIVE MEASURES;
- U.S. Provisional Patent Application Ser. No. 62/649,315, entitled DATA HANDLING AND PRIORITIZATION IN A CLOUD ANALYTICS NETWORK;
- U.S. Provisional Patent Application Ser. No. 62/649,313, entitled CLOUD INTERFACE FOR COUPLED SURGICAL DEVICES;
- U.S. Provisional Patent Application Ser. No. 62/649,320, entitled DRIVE ARRANGEMENTS FOR ROBOT-ASSISTED SURGICAL PLATFORMS;
- U.S. Provisional Patent Application Ser. No. 62/649,307, entitled AUTOMATIC TOOL ADJUSTMENTS FOR ROBOT-ASSISTED SURGICAL PLATFORMS; and
- U.S. Provisional Patent Application Ser. No. 62/649,323, entitled SENSING ARRANGEMENTS FOR ROBOT-ASSISTED SURGICAL PLATFORMS.

Applicant of the present application owns the following U.S. Patent Applications, filed on Mar. 29, 2018, each of which is herein incorporated by reference in its entirety:
- U.S. patent application Ser. No. 15/940,641, entitled INTERACTIVE SURGICAL SYSTEMS WITH ENCRYPTED COMMUNICATION CAPABILITIES;
- U.S. patent application Ser. No. 15/940,648, entitled INTERACTIVE SURGICAL SYSTEMS WITH CONDITION HANDLING OF DEVICES AND DATA CAPABILITIES;
- U.S. patent application Ser. No. 15/940,656, entitled SURGICAL HUB COORDINATION OF CONTROL AND COMMUNICATION OF OPERATING ROOM DEVICES;
- U.S. patent application Ser. No. 15/940,666, entitled SPATIAL AWARENESS OF SURGICAL HUBS IN OPERATING ROOMS;
- U.S. patent application Ser. No. 15/940,670, entitled COOPERATIVE UTILIZATION OF DATA DERIVED FROM SECONDARY SOURCES BY INTELLIGENT SURGICAL HUBS;
- U.S. patent application Ser. No. 15/940,677, entitled SURGICAL HUB CONTROL ARRANGEMENTS;
- U.S. patent application Ser. No. 15/940,632, entitled DATA STRIPPING METHOD TO INTERROGATE PATIENT RECORDS AND CREATE ANONYMIZED RECORD;
- U.S. patent application Ser. No. 15/940,640, entitled COMMUNICATION HUB AND STORAGE DEVICE FOR STORING PARAMETERS AND STATUS OF A SURGICAL DEVICE TO BE SHARED WITH CLOUD BASED ANALYTICS SYSTEMS;
- U.S. patent application Ser. No. 15/940,645, entitled SELF DESCRIBING DATA PACKETS GENERATED AT AN ISSUING INSTRUMENT;
- U.S. patent application Ser. No. 15/940,649, entitled DATA PAIRING TO INTERCONNECT A DEVICE MEASURED PARAMETER WITH AN OUTCOME;
- U.S. patent application Ser. No. 15/940,654, entitled SURGICAL HUB SITUATIONAL AWARENESS;
- U.S. patent application Ser. No. 15/940,663, entitled SURGICAL SYSTEM DISTRIBUTED PROCESSING;
- U.S. patent application Ser. No. 15/940,668, entitled AGGREGATION AND REPORTING OF SURGICAL HUB DATA;
- U.S. patent application Ser. No. 15/940,671, entitled SURGICAL HUB SPATIAL AWARENESS TO DETERMINE DEVICES IN OPERATING THEATER;
- U.S. patent application Ser. No. 15/940,686, entitled DISPLAY OF ALIGNMENT OF STAPLE CARTRIDGE TO PRIOR LINEAR STAPLE LINE;
- U.S. patent application Ser. No. 15/940,700, entitled STERILE FIELD INTERACTIVE CONTROL DISPLAYS;
- U.S. patent application Ser. No. 15/940,629, entitled COMPUTER IMPLEMENTED INTERACTIVE SURGICAL SYSTEMS;
- U.S. patent application Ser. No. 15/940,704, entitled USE OF LASER LIGHT AND RED-GREEN-BLUE COLORATION TO DETERMINE PROPERTIES OF BACK SCATTERED LIGHT;
- U.S. patent application Ser. No. 15/940,722, entitled CHARACTERIZATION OF TISSUE IRREGULARITIES THROUGH THE USE OF MONO-CHROMATIC LIGHT REFRACTIVITY; and U.S. patent application Ser. No. 15/940,742, entitled DUAL CMOS ARRAY IMAGING.

Applicant of the present application owns the following U.S. Patent Applications, filed on Mar. 29, 2018, each of which is herein incorporated by reference in its entirety:

U.S. patent application Ser. No. 15/940,636, entitled ADAPTIVE CONTROL PROGRAM UPDATES FOR SURGICAL DEVICES;

U.S. patent application Ser. No. 15/940,653, entitled ADAPTIVE CONTROL PROGRAM UPDATES FOR SURGICAL HUBS;

U.S. patent application Ser. No. 15/940,660, entitled CLOUD-BASED MEDICAL ANALYTICS FOR CUSTOMIZATION AND RECOMMENDATIONS TO A USER;

U.S. patent application Ser. No. 15/940,679, entitled CLOUD-BASED MEDICAL ANALYTICS FOR LINKING OF LOCAL USAGE TRENDS WITH THE RESOURCE ACQUISITION BEHAVIORS OF LARGER DATA SET;

U.S. patent application Ser. No. 15/940,694, entitled CLOUD-BASED MEDICAL ANALYTICS FOR MEDICAL FACILITY SEGMENTED INDIVIDUALIZATION OF INSTRUMENT FUNCTION;

U.S. patent application Ser. No. 15/940,634, entitled CLOUD-BASED MEDICAL ANALYTICS FOR SECURITY AND AUTHENTICATION TRENDS AND REACTIVE MEASURES;

U.S. patent application Ser. No. 15/940,706, entitled DATA HANDLING AND PRIORITIZATION IN A CLOUD ANALYTICS NETWORK; and U.S. patent application Ser. No. 15/940,675, entitled CLOUD INTERFACE FOR COUPLED SURGICAL DEVICES.

Applicant of the present application owns the following U.S. Patent Applications, filed on Mar. 29, 2018, each of which is herein incorporated by reference in its entirety:

U.S. patent application Ser. No. 15/940,627, entitled DRIVE ARRANGEMENTS FOR ROBOT-ASSISTED SURGICAL PLATFORMS;

U.S. patent application Ser. No. 15/940,637, entitled COMMUNICATION ARRANGEMENTS FOR ROBOT-ASSISTED SURGICAL PLATFORMS;

U.S. patent application Ser. No. 15/940,642, entitled CONTROLS FOR ROBOT-ASSISTED SURGICAL PLATFORMS;

U.S. patent application Ser. No. 15/940,676, entitled AUTOMATIC TOOL ADJUSTMENTS FOR ROBOT-ASSISTED SURGICAL PLATFORMS;

U.S. patent application Ser. No. 15/940,680, entitled CONTROLLERS FOR ROBOT-ASSISTED SURGICAL PLATFORMS;

U.S. patent application Ser. No. 15/940,683, entitled COOPERATIVE SURGICAL ACTIONS FOR ROBOT-ASSISTED SURGICAL PLATFORMS;

U.S. patent application Ser. No. 15/940,690, entitled DISPLAY ARRANGEMENTS FOR ROBOT-ASSISTED SURGICAL PLATFORMS; and U.S. patent application Ser. No. 15/940,711, entitled SENSING ARRANGEMENTS FOR ROBOT-ASSISTED SURGICAL PLATFORMS.

Applicant of the present application owns the following U.S. Provisional Patent Applications, filed on Mar. 30, 2018, each of which is herein incorporated by reference in its entirety:

U.S. Provisional Patent Application Ser. No. 62/650,887, entitled SURGICAL SYSTEMS WITH OPTIMIZED SENSING CAPABILITIES;

U.S. Provisional Patent Application Ser. No. 62/650,877, entitled SURGICAL SMOKE EVACUATION SENSING AND CONTROLS;

U.S. Provisional Patent Application Ser. No. 62/650,882, entitled SMOKE EVACUATION MODULE FOR INTERACTIVE SURGICAL PLATFORM; and U.S. Provisional Patent Application Ser. No. 62/650,898, entitled CAPACITIVE COUPLED RETURN PATH PAD WITH SEPARABLE ARRAY ELEMENTS.

Applicant of the present application owns the following U.S. Provisional Patent Application, filed on Apr. 19, 2018, which is herein incorporated by reference in its entirety:

U.S. Provisional Patent Application Ser. No. 62/659,900, entitled METHOD OF HUB COMMUNICATION.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, a surgical system, device, or apparatus that "comprises," "has," "includes", or "contains" one or more elements possesses those one or more elements, but is not limited to possessing only those one or more elements. Likewise, an element of a system, device, or apparatus that "comprises," "has," "includes", or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

Figure 13:
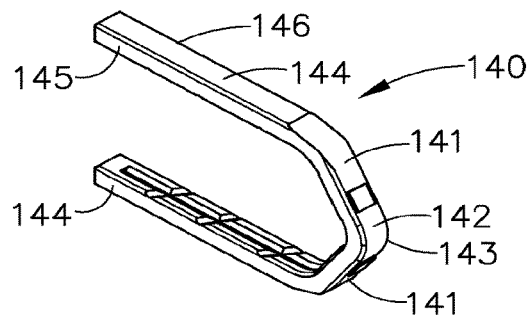
FIG. 13 is a perspective view of a clip illustrated in FIGS. 2-12.

During various surgical procedures, a surgeon, or other clinician, may apply a clip to a patient's tissue in order to achieve various effects and/or therapeutic results. Referring to FIG. 1, a surgical instrument, such as a clip applier 100, for example, can be configured to apply one or more clips to tissue located within a surgical site in the patient. Generally, referring now to FIG. 13, the clip applier 100 can be structured and arranged to position a clip 140 relative to the tissue in order to compress the tissue within the clip 140. The clip applier 100 can be configured to deform the clip 140 as illustrated in FIGS. 3 and 4, for example, and as described in greater detail further below. Each clip 140 can comprise a base 142 and opposing legs 144 extending from the base 142. The base 142 and the legs 144 can comprise any suitable shape and can define a substantially U-shaped configuration and/or a substantially V-shaped configuration, for example. The base 142 can comprise angled portions 141 which are connected together by a joint 143. In use, the legs 144 of the clip 140 can be positioned on opposite sides of the tissue wherein the legs 144 can be pushed toward one another to compress the tissue positioned between the legs 144. The joint 143 can be configured to permit the angled portions 141 of the base 142, and the legs 144 extending therefrom, to deform inwardly. In various circumstances, the clip 140 can be configured to yield, or deform plastically, when the clip 140 is sufficiently compressed, although some amount of elastic deformation, or spring-back, may occur within the deformed clip 140.

Figure 14:
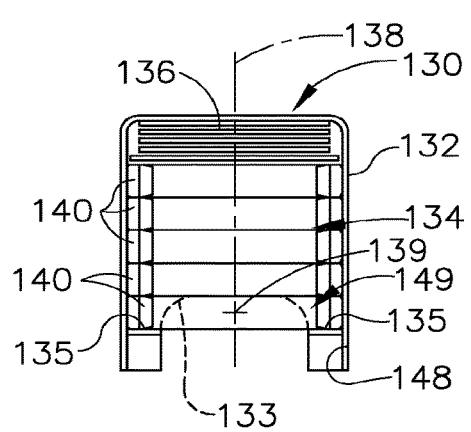
FIG. 14 is a front view of a cartridge illustrated in FIGS. 1-12 comprising a plurality of clips with portions of the cartridge removed to illustrate the clips stored in the cartridge.
Figure 15:
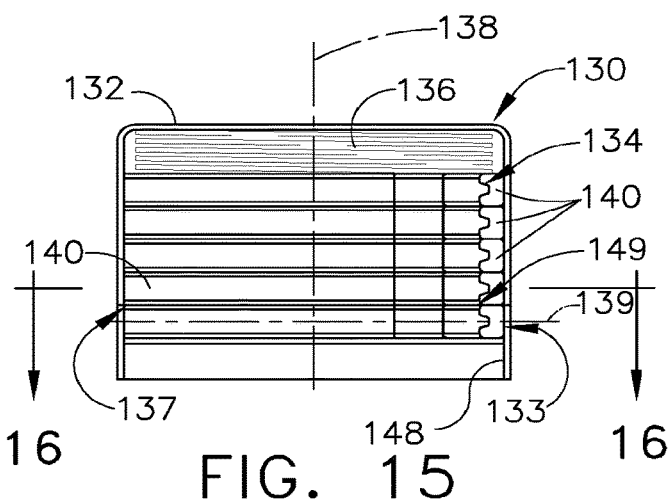
FIG. 15 is a side view of the cartridge of FIG. 14 illustrated with portions removed to illustrate the clips stored in the cartridge.
Figure 16:
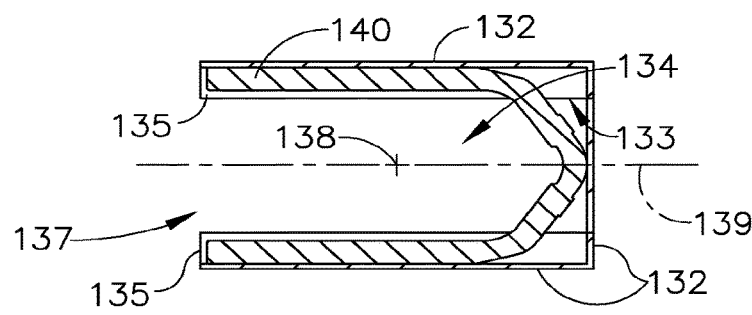
FIG. 16 is a cross-sectional plan view of the cartridge of FIG. 14 taken along line 16-16 in FIG. 15.

Referring now to FIGS. 1 and 2, the clip applier 100 can include a shaft 110, an end effector 120, and a replaceable clip cartridge, or magazine, 130. Referring to FIGS. 14-16, the clip cartridge 130 can comprise a housing 132 and a plurality of clips 140 positioned within the housing 132. The housing 132 can define a storage chamber 134 in which the clips 140 can be stacked. The storage chamber 134 can comprise sidewalls which extend around, or at least substantially around, the perimeter of the clips 140. Referring again to FIG. 13, each clip 140 can comprise opposing faces, such as a top face 145 and a bottom face 146 on opposite sides of the clip 140 wherein, when the clips 140 are stacked in the housing 132, the top face 145 of a clip 140 can be positioned against the bottom face 146 of an adjacent clip 140 and wherein the bottom face 146 of the clip 140 can be positioned against the top face 145 of another adjacent clip 140. In various circumstances, the bottom faces 146 of the clips 140 can face downwardly toward one or more support shelves, or platforms, 135 defined in the housing 132 while the top faces 145 of the clips 140 can face upwardly away from the support shelves 135. The top faces 145 and the bottom faces 146 of the clips 140 may be identical, or at least substantially identical, in some cases, while, in other cases, the top faces 145 and the bottom faces 146 may be different. The stack of clips 140 depicted in FIGS. 14-16 comprises five clips 140, for example; however, other embodiments are envisioned in which the stack of clips 140 can include more than five clips 140 or less than five clips 140. In any event, the clip cartridge 130 can further comprise at least one biasing member, such as biasing member 136, for example, positioned intermediate the housing 132 and the top clip 140 in the stack of clips 140. As described in greater detail below, the biasing member 136 can be configured to bias the bottom clip 140 in the stack of clips 140 or, more particularly, the bottom face 146 of the bottom clip 140, against the support shelves 135 defined in the housing 132. The biasing member 136 can comprise a spring, and/or any suitable compressed elastic element, for example, which can be configured to apply a biasing force to the clips 140, or at least apply a biasing force to the top clip 140 which is transmitted downwardly through the stack of clips 140.

When a clip 140 is positioned against the support shelves 135 as described above, the clip 140 can be supported in a firing position in which the clip 140 can be advanced and ejected from the cartridge 130. In various circumstances, the support shelves 135 can define at least a portion of a firing chamber 149 in which the clips 140 can be sequentially positioned in the firing position. In some cases, the firing chamber 149 can be entirely defined within the cartridge 130 or, in other cases, the firing chamber 149 can be defined within and/or between the shaft 110 and the cartridge 130. In any event, as described in greater detail further below, the clip applier 100 can comprise a firing drive which can advance a firing member into the cartridge 130 and push the clip 140 from its firing position positioned against the support shelves 135 to a fired position in which it is received within the end effector 120 of the clip applier 100. Referring primarily to FIGS. 14-16, the housing 132 of the cartridge 130 can comprise a proximal opening, or window, 133 which can be aligned, or at least substantially aligned, with the support shelves 135 such that the firing member can enter into the cartridge 130 through the proximal opening 133 and advance a clip 140 distally out of the cartridge 130. In at least one such embodiment, the housing 132 can further comprise a distal, or discharge, opening, or window, 137 which is also aligned with the support shelves 135 such that the clip 140 can be advanced, or fired, distally along a firing axis 139 extending through the proximal opening 133, the firing chamber 149, and the distal opening 137, for example.

In order to advance a clip 140 out of the cartridge 130, further to the above, the firing member of the firing drive can be advanced into to the cartridge housing 132 and, in various circumstances, into the firing chamber 149. As disclosed in greater detail further below, the firing member can pass entirely through the cartridge 130 in order to advance the clip 140 into its fired position within the end effector 120. After the clip 140 positioned in the firing chamber 149 has been advanced distally by the firing member, as outlined above, the firing member can be retracted sufficiently such that the biasing member 136 can position another clip 140 against the support shelves 135. In various circumstances, the biasing member 136 can bias a clip 140 against the firing member while the firing member is positioned within the housing 132. Such a clip 140 can be referred to as a queued clip. After the firing member has been sufficiently retracted and slid out from underneath the queued clip 140, the biasing member 136 can then bias the clip 140 against the support shelves 135 where it is staged for the next stroke of the reciprocating firing member. Referring primarily to FIGS. 2 and 14-16, the cartridge 130 can be configured to supply the clips 140 to the firing chamber 149 along a predetermined path, such as supply axis 138, for example. The supply axis 138 can be transverse to the firing axis 139 such that the clips 140 are fed into the firing chamber 149 in a direction which is different than the direction in which the firing member passes through the firing chamber 149. In at least one such embodiment, the supply axis 138 can be perpendicular, or at least substantially perpendicular, to the firing axis 139, for example.

Referring again to FIG. 2, the shaft 110 can comprise a cartridge, or magazine, aperture 131 which can be sized and configured to receive a clip cartridge 130, for example, therein. The cartridge aperture 131 can be sized and configured such that the housing 132 of the cartridge 130 is closely received within the cartridge aperture 131. The sidewalls which define the cartridge aperture 131 can limit, or at least substantially limit, the lateral movement of the cartridge 130 relative to the shaft 110. The shaft 110 and/or the cartridge 130 can further comprise one or more locks which can be configured to releasably hold the cartridge 130 in the cartridge aperture 131. As illustrated in FIG. 2, the cartridge 130 can be loaded into the cartridge aperture 131 along an axis which is, in at least one embodiment, parallel to or collinear with the supply axis 138. As also illustrated in FIG. 2, the shaft 110 can further comprise a pad or seat 118 extending from the sidewall 111 of the shaft 110 wherein the pad 118 can be configured to be received within and/or engaged with the housing 132 of the cartridge 130. The pad 118 can be sized and configured to be closely received within a recess 148 defined in the cartridge housing such that the pad 118 can limit, or at least substantially limit, the lateral movement of the cartridge 130 relative to the shaft 110. The pad 118 can be sized and configured to align the cartridge 130 within the shaft 110 and/or support the cartridge housing 132.

Figure 6:
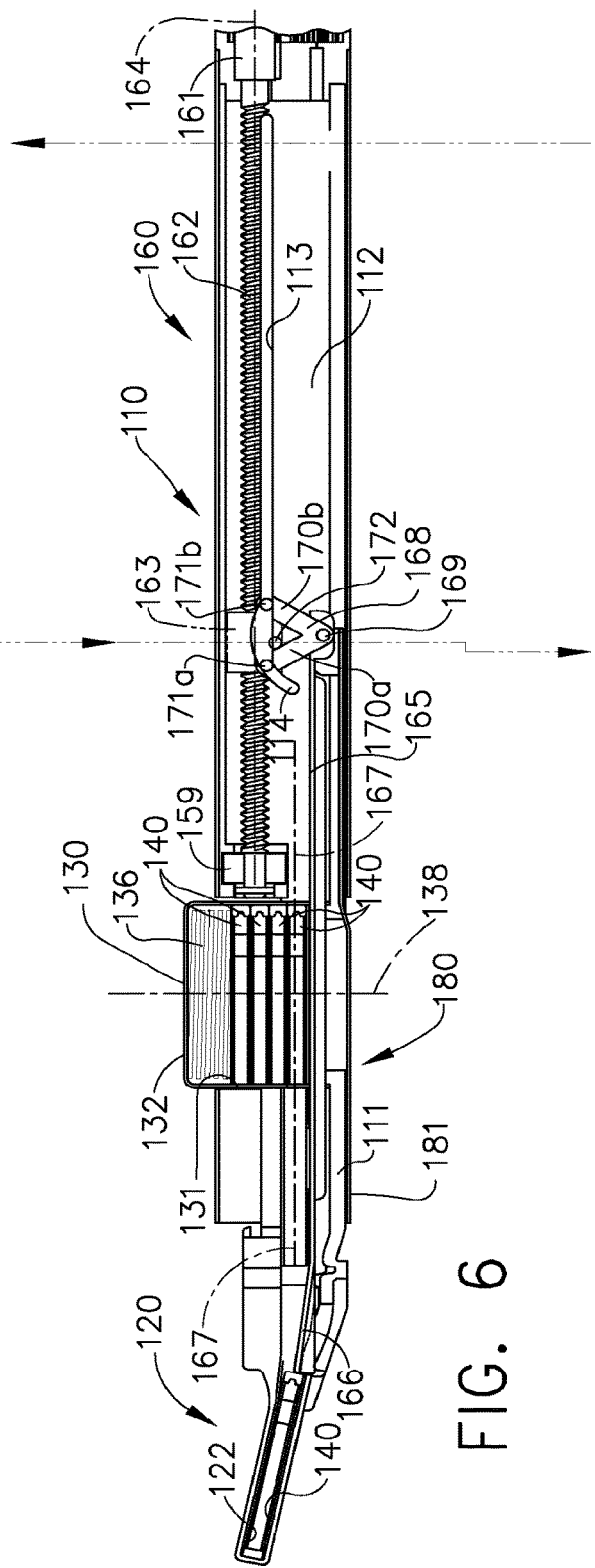
FIG. 6 is a cross-sectional view of the end effector of FIG. 2 illustrating the firing drive in a partially fired condition in which a firing member of the firing drive has advanced a clip into the receiver.

Once the clip cartridge 130 has been positioned and seated within the shaft aperture 131, referring now to FIGS. 5 and 6, a firing drive 160 of the clip applier 100 can be actuated to advance the clips 140 from the clip cartridge 130 as described above. The firing drive 160 can comprise a rotary drive input such as a drive screw 161, for example, and a displaceable firing nut 163 operably engaged with the drive screw 161. The drive screw 161 can comprise at least one drive thread 162 which can be threadably engaged with a threaded aperture extending through the firing nut 163. In various embodiments, the clip applier 100 can further include an electric motor, for example, operably coupled with the drive screw 161. In various instances, the drive screw 161 can be operably coupled with the motor of a surgical instrument system comprising a hand-held instrument or a robotic arm, for example. In any event, the movement of the firing nut 163 within the shaft 110 can be constrained such that the firing nut 163 moves along a longitudinal axis 164 when the drive screw 161 is rotated about the longitudinal axis 164 by the motor. For instance, when the drive screw 161 is rotated in a first direction by the motor, the drive screw 161 can advance the firing nut 163 distally toward the end effector 120, as illustrated in FIG. 6. When the drive screw 161 is rotated in a direction opposite the first direction by the motor, the drive screw 161 can retract the firing nut 163 proximally away from the end effector 120. The shaft 110 can comprise one or more bearings which can be configured to rotatably support the drive screw 161. For instance, a bearing 159 can be configured to rotatably support the distal end of the drive screw 161, for example, as illustrated in FIGS. 5 and 6.

The firing drive 160 can further comprise a firing member 165 extending from the firing nut 163 which can be advanced distally and retracted proximally with the firing nut 163, as described in greater detail further below. Upon comparing FIGS. 5 and 6, the reader will note that the firing nut 163 and the firing member 165 have been advanced from a proximal, unfired position, illustrated in FIG. 5, to a distal, fired position, illustrated in FIG. 6, in which the firing member 165 has advanced a clip 140 from the clip cartridge 130 into the end effector 120. Referring primarily to FIG. 5, the clip cartridge 130 is illustrated as comprising a plurality of clips 140 stored therein wherein one of the clips 140 is positioned in a firing position, as described above. As illustrated in FIGS. 5 and 6, the firing member 165 can include a distal portion 166 which can be advanced into the staple cartridge 130 along a firing axis 167 and engage the clip 140 positioned in the firing position when the firing member 165 and the firing nut 163 are advanced distally. In some cases, the firing member 165 can comprise a linear member while, in other cases, the distal end 166 of the firing member 165 can extend upwardly from the firing member 165, for example. Further to the above, the firing member 165 can advance the clip 140 distally out of the clip cartridge 130 along the firing axis 167 and into a receiving cavity 122 defined in the end effector 120.

In various cases, the firing member 165 can be attached to and extend distally from the firing nut 163 while, in other cases, the firing member 165 and the firing nut 163 can be operably connected to one another by a firing actuator 168. The firing actuator 168 can be pivotably mounted to the firing member 165 at a pivot 169 and can include a distal arm 170a and a proximal arm 170b which can be engaged with a longitudinal slot 113 defined in the housing 112 of the shaft 110. In at least one such embodiment, each of the arms 170a, 170b can include a projection, such as projections 171a and 171b, respectively, extending therefrom which can be configured to slide within the longitudinal slot 113. Further to the above, the firing nut 163 can further include a firing pin 172 extending therefrom which can be configured to engage the distal arm 170a in order to advance the actuator 168 and the firing member 165 distally, as described above. In use, referring again to the progression illustrated in FIGS. 5 and 6, the firing nut 163 can be advanced distally by the drive screw 161 wherein the firing pin 172, which is positioned intermediate the distal arm 170a and the proximal arm 170b, can contact the distal arm 170a and drive the actuator 168 and the firing member 165 distally. As the actuator 168 is advanced distally, the actuator 168 may be prevented from rotating about the pivot pin 169 as one or both of the projections 171a and 171b sliding in the shaft slot 113 can be prevented from being moved laterally relative to the longitudinal shaft slot 113 until the actuator 168 reaches the position illustrated in FIG. 6.

Figure 9:
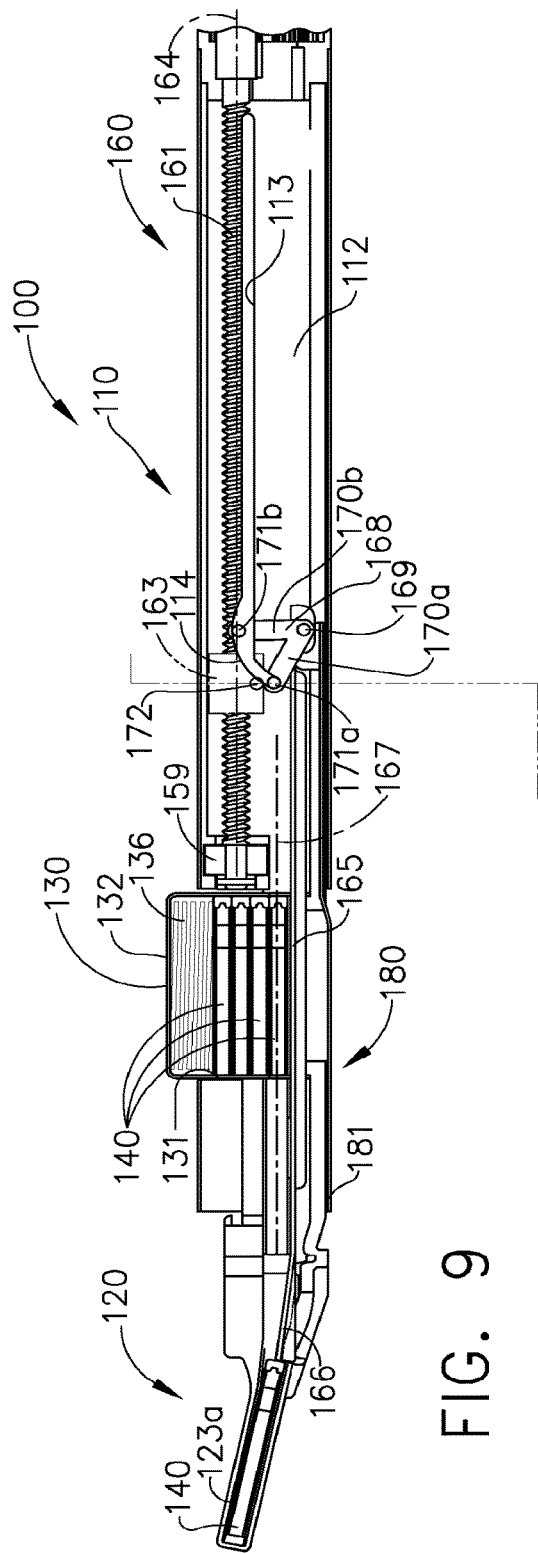
FIG. 9 is a cross-sectional view of the end effector of FIG. 2 illustrating the firing drive becoming disengaged from the firing member.

When the actuator 168 has reached the position illustrated in FIG. 6, the distal projection 171a can enter into a distal slot portion 114 of the longitudinal slot 113 which can be configured to pivot the actuator 168 downwardly, or permit the actuator 168 to be pivoted downwardly, as illustrated in FIG. 9. In at least one such embodiment, the distal projection 171a can come into contact with the sidewall of the distal slot portion 114 which can guide the distal projection 171a downwardly and pivot the actuator 168 about the pivot 169 as the actuator 168 is advanced forward by the firing nut 163. In such a pivoted position, the firing pin 172 extending from the firing nut 163 may no longer be engaged with the distal arm 170a of the actuator 168 wherein, subsequently, the firing nut 163 may move distally independently of the actuator 168 thereby leaving behind the actuator 168 and the firing member 165. Stated another way, the distal end 114 of the longitudinal shaft slot 113 may deactivate the firing member 165 wherein, at such point, the position of the firing member 165 may represent the fully-fired or distal-most position of the firing member 165. In such a position, the clip 140 has been fully advanced into the receiving cavity, or receiver, 122. Furthermore, in such a position, the next clip 140 to be advanced into the receiving cavity 122 may be biased against the top surface of the firing member 165, further to the above.

Once a clip 140 has been positioned within the receiving cavity 122, further to the above, the clip 140 can be deformed by a crimping drive 180, for example. Referring now to FIGS. 3 and 4, the end effector 120 of the clip applier 100 can further comprise a first jaw 123*a* and a second jaw 123*b* wherein the first jaw 123*a* and the second jaw 123*b* can at least partially define the receiving chamber 122. As illustrated in FIGS. 3 and 4, the first jaw 123*a* can comprise a first channel 124*a* and the second jaw 123*b* can comprise a second channel 124*b* which can each be configured to receive and support at least a portion of a clip 140 therein. The first jaw 123*a* can be pivotably coupled to a frame 111 of the shaft 110 by a pin 125*a* and the second jaw 123*b* can be pivotably coupled to the frame 111 by a pin 125*b*. In use, the crimping drive 180 can be configured to rotate the first jaw 123*a* toward the second jaw 123*b* and/or rotate the second jaw 123*b* toward the first jaw 123*a* in order to compress the clip 140 positioned therebetween. In at least one such embodiment, the crimping drive 180 can comprise a cam actuator 181 which can be configured to engage a first cam surface 126*a* defined on the first jaw 123*a* and a second cam surface 126*b* on the second jaw 123*b* in order to pivot the first jaw 123*a* and the second jaw 123*b* toward one another. The cam actuator 181 can comprise a collar which at least partially surrounds the first jaw 123*a* and the second jaw 123*b*. In at least one such embodiment, the collar can comprise an inner cam surface 182 which can be contoured to contact the cam surfaces 126*a*, 126*b* of the jaws 123*a*, 123*b* and drive them inwardly toward one another. In various circumstances, the clip 140 positioned within the receiving chamber 122 defined in the end effector 120 can be positioned relative to tissue before the crimping drive 180 is actuated. In some circumstances, the crimping drive 180 can be at least partially actuated prior to positioning the clip 140 relative to the tissue in order to at least partially compress the clip 140. In certain instances, the clip 140 and the receiving chamber 122 can be sized and configured such that the clip 140 can be biased or flexed inwardly when the end effector 120 is in its unactuated state, as illustrated in FIG. 3. In various instances, the crimping first jaw 123*a* and the second jaw 123*b* can be actuated to elastically crimp and/or permanently crimp the clip 140 positioned therebetween.

Figure 7:
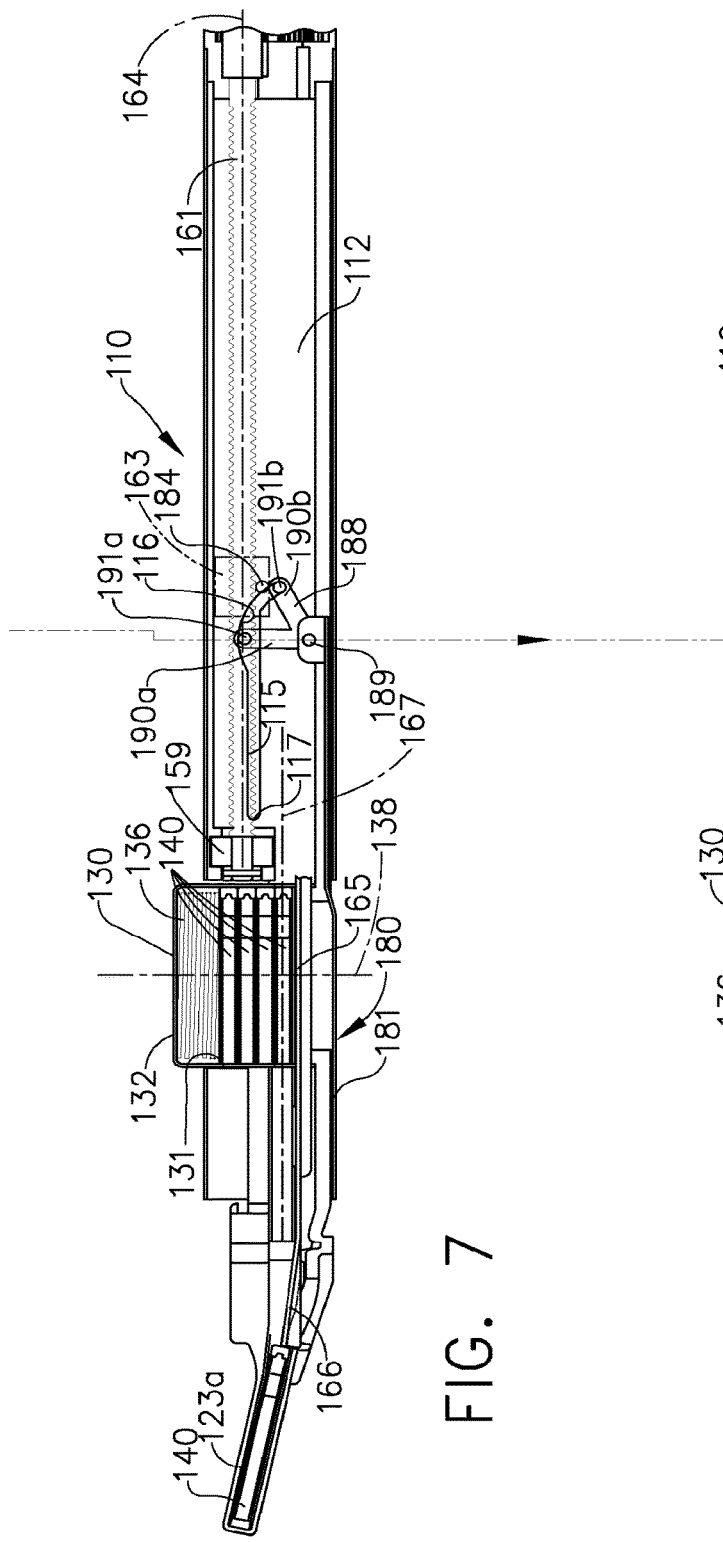
FIG. 7 is a cross-sectional view of the end effector of FIG. 2 illustrating the firing drive coming into engagement with the crimping drive.
Figure 8:
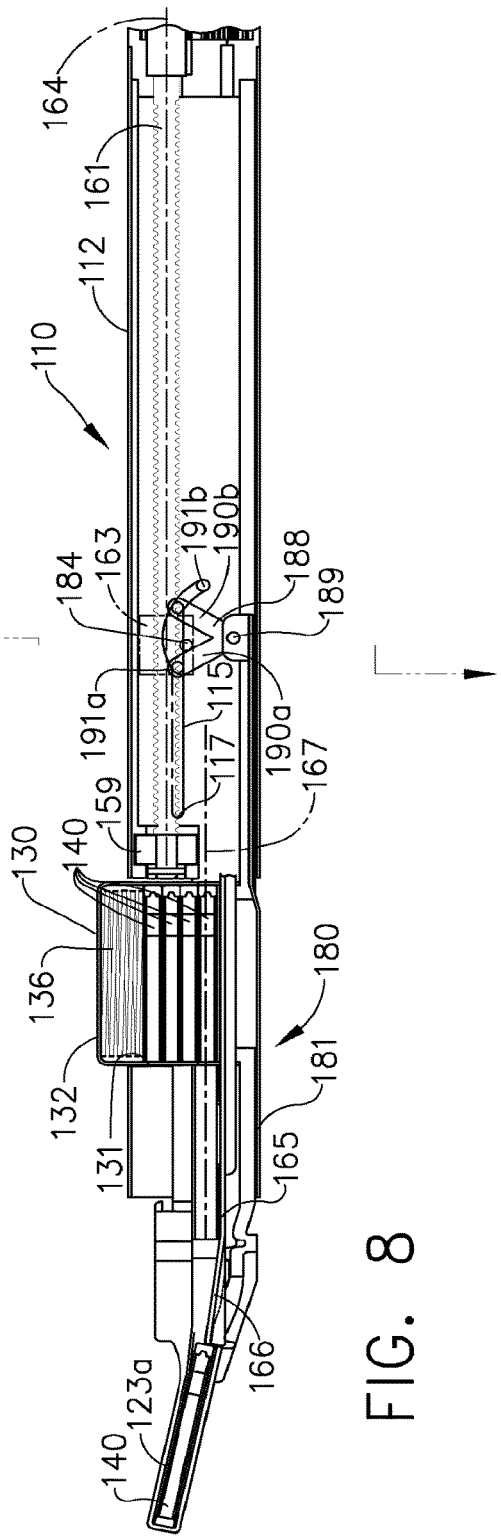
FIG. 8 is a cross-sectional view of the end effector of FIG. 2 illustrating the crimping drive in an at least partially fired condition.

Further to the above, the firing nut 163 can be configured to actuate the crimping drive 180. More particularly, referring now to FIG. 7, the crimping drive 180 can comprise a crimping actuator 188 operably coupled with the cam actuator 181 wherein the crimping actuator 188 can be selectively engaged by the firing nut 163 as the firing nut 163 is advanced distally as described above. In at least one such embodiment, the firing nut 163 can further comprise a second firing pin, such as firing pin 184, for example, extending therefrom which can be configured to engage the crimping actuator 188 as the firing nut 163 is advancing the firing actuator 168. Referring again to FIG. 7, the crimping actuator 188 is positioned in an unactuated position and, when the firing nut 163 is advanced sufficiently to engage a distal arm 190*a* of the crimping actuator 188, the firing nut 163 can rotate the crimping actuator 188 upwardly into an actuated position as illustrated in FIG. 8. As also illustrated in FIG. 8, the distal arm 190*a* and a proximal arm 190*b* can each comprise a projection, such as projections 191*a* and 191*b*, respectively, extending therefrom which can be positioned within a second longitudinal slot defined in shaft 110, such as slot 115, for example. As the crimping actuator 188 is rotated upwardly from its unactuated position about a pivot 189, the projections 191*a* and 191*b* can move from the proximal curved end 116 of the longitudinal slot 115 into a portion of the longitudinal slot 115 which is substantially linear. Similar to the above, the sidewalls of the longitudinal slot 115 can be configured to confine the movement of the crimping actuator 188 along a longitudinal path and can be configured to limit or prevent the rotation of the crimping actuator 188 once the crimping actuator 188 has been rotated upwardly into an at least partially actuated position, as discussed above. As the reader will understand, the firing pin 172 of the firing drive 160 and the firing pin 184 of the crimping drive 180 both extend from the firing nut 163. For the sake of expediency and demonstration, the firing pins 172 and 184 are illustrated as extending from the same side of the firing nut 163; however, it is envisioned that the firing pin 172 can extend from a first lateral side of the firing nut 163 while the firing pin 184 can extend from the other lateral side of the firing nut 163. In such circumstances, the firing actuator 168 can be positioned alongside the first lateral side of the drive screw 161 and the crimping actuator 188 can be positioned alongside the opposite lateral side of the drive screw 161. Correspondingly, the longitudinal slot 113 can be defined in a first lateral side of the shaft housing 112 while the longitudinal slot 115 can be defined in the opposite lateral side of the shaft housing 112.

Figure 10:
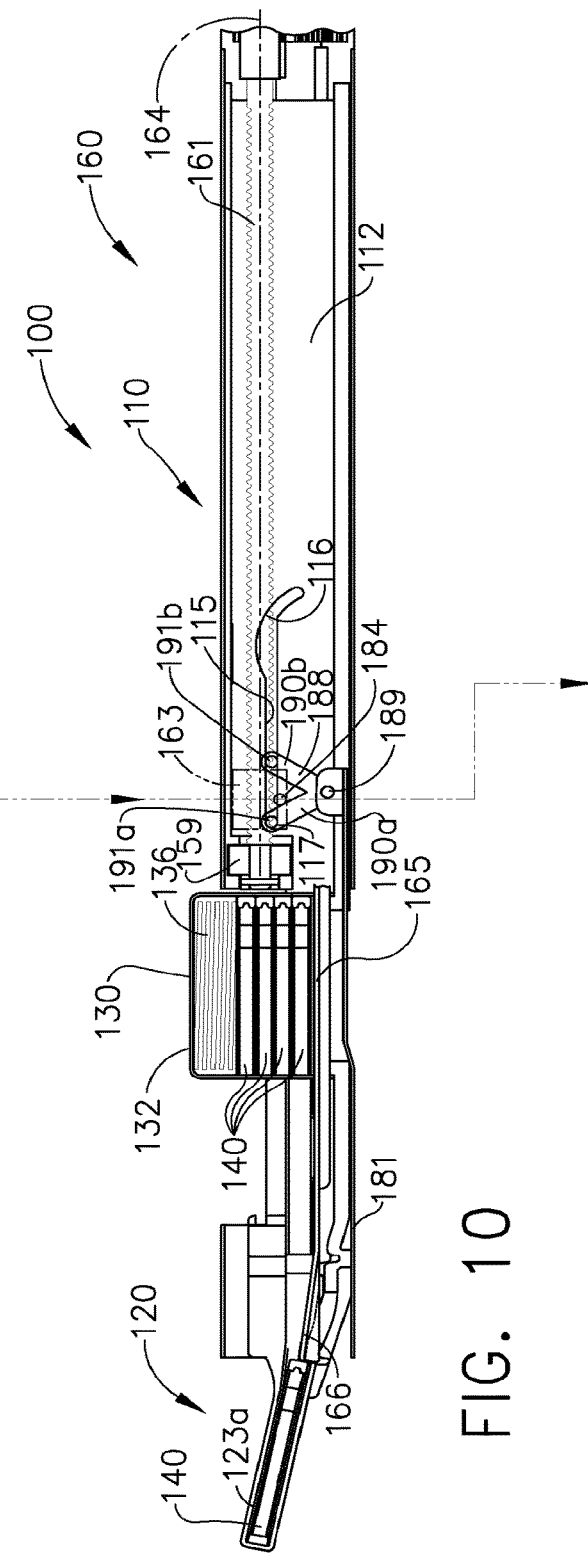
FIG. 10 is a cross-sectional view of the end effector of FIG. 2 illustrating the crimping drive in its fully fired condition.

Further to the above, the cam actuator 181 can be operably coupled with crimping actuator 188 such that, when the crimping actuator 188 is advanced distally by the firing nut 163, the cam actuator 181 can be advanced distally, as illustrated in FIGS. 8 and 10, until the distal projection 191*a* extending from the distal arm 190*a* reaches the distal end 117 of the longitudinal slot 115. In such a distal position, the cam actuator 181 may be in a fully advanced position and the clip 140 positioned within the receiving chamber 122 can be in a fully deformed or crimped configuration. Thereafter, the cam actuator 181 can be retracted and the end effector 120 can be reopened. More particularly, the drive screw 161 can be rotated in an opposite direction in order to move the firing nut 163 proximally and retract the cam actuator 181 wherein, in certain instances, the end effector 120 can further include a biasing member which can be configured to bias the first jaw 123 and the second jaw 123*b* from the closed, or fired, position illustrated in FIG. 4 into the open, or unfired, position illustrated in FIG. 3. As the firing nut 163 is retracted from its position illustrated in FIG. 10, the firing pin 184 extending from the firing nut 163 can engage the proximal arm 190*b* of the crimping actuator 188 and move the crimping actuator 188, and the cam actuator 181 extending therefrom, proximally as illustrated in FIG. 12. Similar to the above, the proximal projection 191*b* extending from the proximal arm 190*b* of the crimping actuator 188 can be configured to contact the sidewall of the curved proximal end 116 wherein the sidewall can guide the crimping actuator 188 downwardly and rotate the crimping actuator 188 about the pivot 189. At such point, the firing pin 184 may no longer be engaged with the crimping actuator 188, the cam actuator 181 may be fully retracted, and the firing nut 163 may continue to be retracted proximally relative to the crimping actuator 188.

Further to the above, referring now to FIG. 11, the firing nut 163 can be configured to re-engage the firing actuator 168 as the firing nut 163 is being retracted proximally. As discussed above, the firing actuator 168 is rotated downwardly when the firing actuator 168 reaches the distal end 114 of the longitudinal slot 113 and, as a result, the firing actuator 168 may still be in its downwardly rotated position when the firing nut 163 is retracted proximally to re-engage the firing actuator 168. As illustrated in FIG. 11, the firing pin 172 extending from the firing nut 163 can engage the proximal arm 170b of the firing actuator 168 and, as the firing nut 163 is further retracted, the firing nut 163 can rotate the firing actuator 168 upwardly such that the projections 171a and 171b extending from the arms 170a and 170b, respectively, can re-enter the longitudinal portion of the longitudinal slot 113. Thereafter, the firing nut 163 and can be retracted until the firing actuator 168 and the firing member 165 extending therefrom have been returned to their starting, or unfired, positions illustrated in FIG. 5. In such circumstances, the firing member 165 can be withdrawn from the clip cartridge 130 as the firing member 165 is retracted proximally by the firing nut 163 such that a new clip 140 can be biased into the firing chamber of the clip cartridge 130 by the biasing member 136. Once the firing member 165 and the firing actuator 168 have been retracted to their starting positions and the next clip 140 has been positioned within the firing chamber, the firing drive 160 can be actuated once again in order to move the firing nut 163 and the firing member 165 distally to advance the next clip 140 into the end effector 120. Likewise, the firing nut 163 can re-actuate the crimping drive 180 as the firing nut 163 is moved distally once again in order to deform the next clip 140. Thereafter, the firing nut 163 can retracted in order to re-set the crimping drive 180 and the firing drive 160 once again. This process can be repeated until a sufficient number of clips 140 have been applied to the targeted tissue and/or until the clips 140 contained within the clip cartridge 130 have been depleted. In the event that additional clips 140 are needed, the expended clip cartridge 130 can be removed from the shaft 110 and a replacement clip cartridge 130 containing additional clips 140 can be inserted into the shaft 110. In some circumstances, an at least partially depleted clip cartridge 130 can be replaced with an identical, or at least nearly identical, replacement clip cartridge 130 while, in other circumstances, the clip cartridge 130 can be replaced with a clip cartridge having more than or less than five clips 140 contained therein and/or a clip cartridge having clips other than clips 140 contained therein, for example.

Referring again to FIGS. 6-9, the firing nut 163 of the illustrated embodiment can be configured to become disengaged from the firing actuator 168 at the same time that the firing nut 163 becomes engaged with the crimping actuator 188. Stated another way, the firing drive 160 can be deactivated at the same time that the crimping drive 180 is activated. In various circumstances, such timing can be achieved when the distal end 114 of the longitudinal slot 113 is aligned, or at least substantially aligned, with the proximal end 116 of the second longitudinal slot 115, for example. In the illustrated embodiment and/or any other suitable embodiment, a lag can exist between the deactivation of the firing drive 160 and the activation of the crimping drive 180. Such a lag between the end of the firing stroke of the firing member 165 and the beginning of the firing stroke of the cam actuator 181 can be created, in some circumstances, to assure that the clip 140 has been positioned in its fully-seated position within the receiving chamber 122 before the clip 140 is deformed by the cam actuator 181. In various circumstances, such a lag can be created when the distal end 114 of the longitudinal slot 113 is positioned proximally with respect to the proximal end 116 of the second longitudinal slot 115, for example. In the illustrated embodiment and/or any other suitable embodiment, the deactivation of the firing drive 160 may occur after the activation of the crimping drive 180. Such an overlap between the end of the firing stroke of the firing member 165 and the beginning of the firing stroke of the cam actuator 181 can be created, in some circumstances, to apply at least some inward pressure on the clip 140 as it is moved into its fully-seated position within the receiving chamber 122 so as to reduce or eliminate relative movement between the clip 140 and the sidewalls of the receiving chamber 122, for example. In various circumstances, such an overlap can be created when the distal end 114 of the longitudinal slot 113 is positioned distally with respect to the proximal end 116 of the second longitudinal slot 115, for example.

Figure 17:
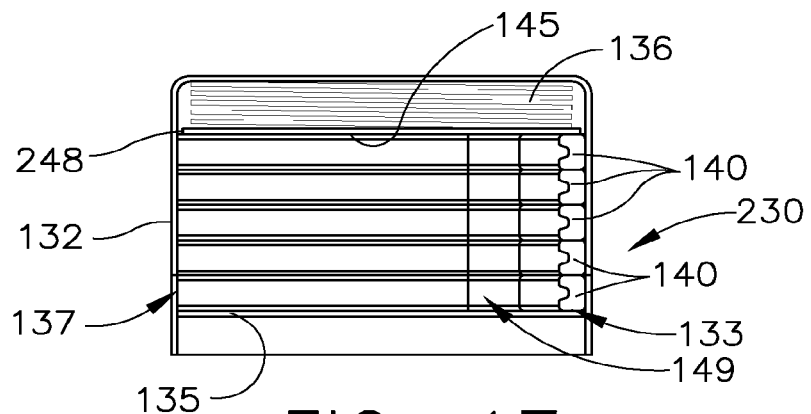
FIG. 17 is a side view of an alternative cartridge usable in connection with the clip applier of FIGS. 1-12 or any other suitable clip applier, wherein the cartridge is illustrated with portions removed to illustrate a biasing member and a pusher plate positioned intermediate the biasing member and the clips contained therein.

In the illustrated embodiment of FIG. 1 and/or any other suitable embodiment, turning now to FIG. 17, a clip cartridge, such as clip cartridge 230, for example, can comprise a pusher plate 248 positioned intermediate the biasing member 136 and the top-most clip 140 stacked within the clip cartridge 230. The pusher plate 248 can be rigid, or at least substantially rigid, and can comprise a first bearing surface against which the biasing member 136 can apply a biasing force. The pusher plate 248 can also comprise a second bearing surface which can transmit the biasing force to the top surface 145 of the top-most clip 140. The pusher plate 248 can be comprised of a sheet of stainless steel material, for example, although the pusher plate 248 can comprise any suitable shape and can be comprised of any suitable material. In certain instances, the pusher plate 248 may not be attached to the biasing member 136 while, in other instances, the pusher plate 248 can be affixed to the biasing member 136 such that the pusher plate 248 does not become dislodged from the cartridge housing 132. In various circumstances, the pusher plate 248 can be sized and configured such that it cannot pass through the proximal opening 133 and/or the distal opening 137 defined in the cartridge housing 132.

Figure 18:
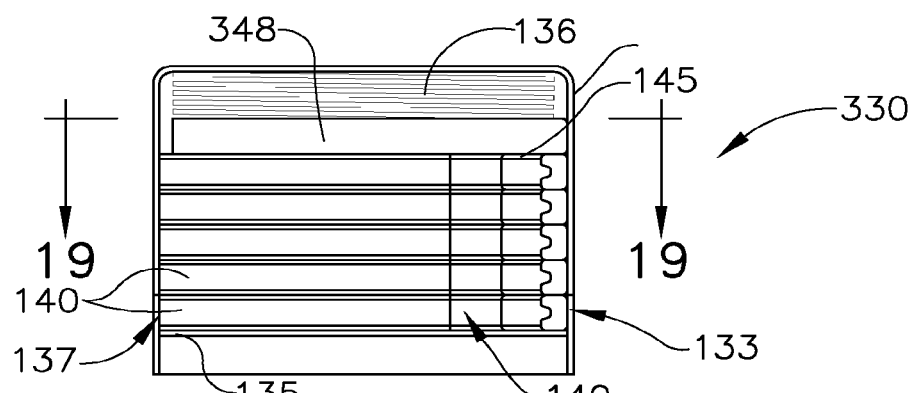
FIG. 18 is a side view of a cartridge in accordance with at least one alternative embodiment illustrated with portions removed to illustrate a biasing member and a lockout plate positioned intermediate the biasing member and the clips contained therein.
Figure 19:
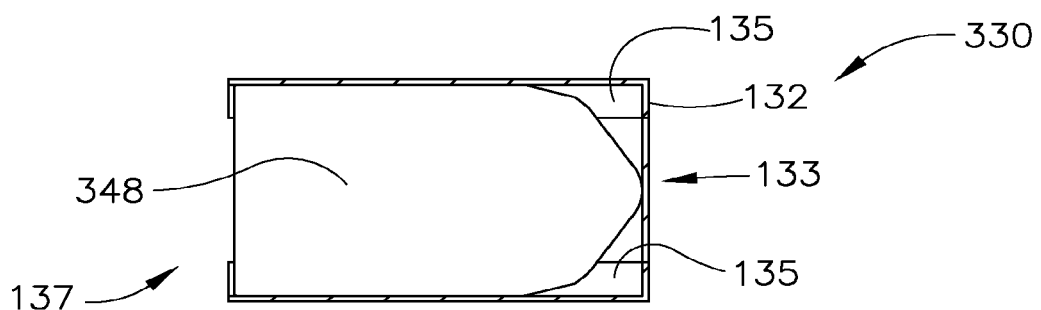
FIG. 19 is a cross-sectional plan view of the cartridge of FIG. 18 taken along line 19-19 in FIG. 18.

In the illustrated embodiment of FIG. 1 and/or any other suitable embodiment, turning now to FIGS. 18 and 19, a clip cartridge, such as clip cartridge 330, for example, can comprise a lockout member which can be positioned within the firing chamber 149 of the clip cartridge 330 after all of the clips 140 contained within the clip cartridge 330 have been ejected from the cartridge 330. The lockout member can comprise a lockout plate 348 which can be positioned intermediate the biasing member 136 and the top surface 145 of the top-most clip 140 contained within the clip cartridge 330. In use, further to the above, the clips 140 can be sequentially positioned in the firing chamber 149 of the clip cartridge 130 and then advanced distally out of the clip housing 132 wherein, after the last clip 140 has been advanced out of the clip housing 132 and the firing member 165 has been withdrawn from the clip cartridge 130, the biasing member 136 can bias the lockout plate 348 against the shelves 135. In such a position, the lockout plate 348 can be aligned with the proximal opening 133 and the distal opening 137 such that the firing member 165 cannot enter, or at least substantially enter, the clip cartridge 130. In such circumstances, the lockout plate 348 can block the firing member 165 from entering into and passing through the housing 132 and, as a result, prevent the inadvertent firing of the clip applier 100 after the clip cartridge 130 has run out of clips. In the event that the operator of the clip applier 100 were to actuate the firing drive 160 and attempt to advance the firing member 165 into the spent clip cartridge 130, the firing member 165 would contact and abut the lockout plate 348 wherein, in such circumstances, a compressive load can be created within the firing member 165. The clip applier 100 can further include a clutch which can be configured to slip and operably disconnect the motor from the drive screw 161 when the compressive load created within the firing member 165 exceeds a certain or predetermined amount. In addition to or in lieu of a clutch, the motor and/or motor controller of the clip applier 100 which operates the firing drive 160, for example, can comprise a load sensor configured to detect the load generated within the firing member 165 and, when the load created within the firing member 165 exceeds a certain or predetermined amount, the voltage and/or current supplied to the motor can be switched off and/or reduced. In any event, the lockout plate 348 can be sized and configured such that the lockout plate 348 cannot be dislodged through the distal opening 137 and/or the proximal opening 133 when the firing member 165 contacts the lockout plate 348. In order to use the clip applier 100 once again, the operator of the clip applier 100 can remove the spent cartridge 330 from the shaft 110 and insert a new clip cartridge 330, for example, into the shaft 110. At such point, a clip 140 may be positioned within the firing chamber 149 of the new clip cartridge 330 and the firing member 165 can be advanced distally into the new clip cartridge 330 to deploy the clip 140 as described above.

Figure 20:
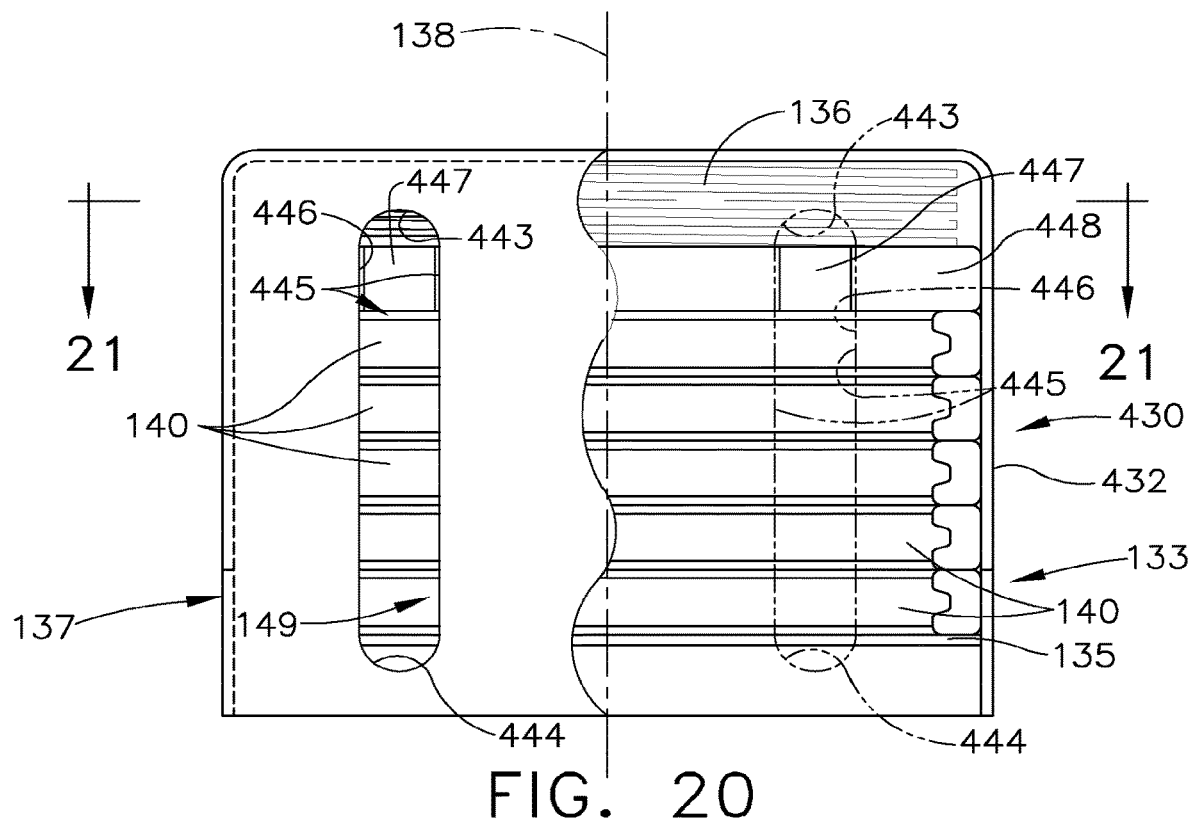
FIG. 20 is a side view of a further alternative cartridge usable in connection with the clip applier of FIGS. 1-12 or any other suitable clip applier, wherein the cartridge can comprise a housing illustrated with portions removed to illustrate a lockout plate comprising guides which are configured to co-operate with guides defined in the cartridge housing.
Figure 21:
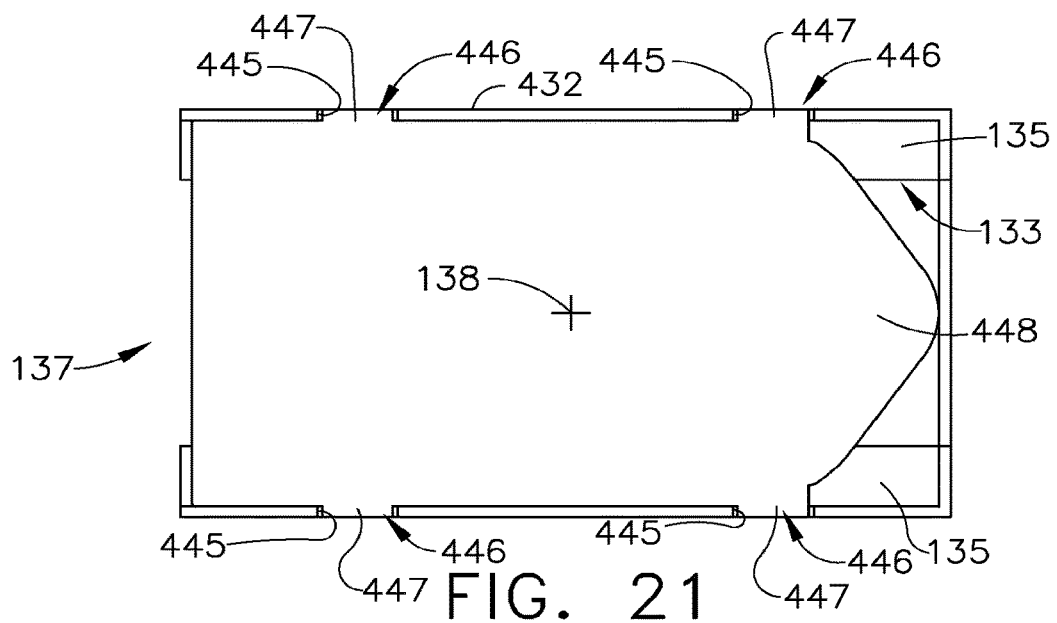
FIG. 21 is a cross-sectional plan view of the cartridge of FIG. 20 taken along line 21-21 in FIG. 20.

In the illustrated embodiment of FIG. 1 and/or any other suitable embodiment, referring now to FIGS. 20 and 21, a clip cartridge, such as clip cartridge 430, for example, can comprise guides which can be configured to limit or confine the movement of a lockout member within the clip cartridge 430. Similar to the above, the lockout member can comprise a lockout plate 448, for example, which can be positioned intermediate the biasing member 136 and the top surface 145 of the top-most clip 140 contained within the housing 432 of the clip cartridge 430. In use, similar to the above, the lockout plate 448 can be progressively pushed downwardly into the firing chamber 149 as the clips 140 are sequentially ejected from the clip cartridge 430. The lockout plate 448 can be sized and configured such that it is closely received within the cartridge housing 432 and such that relative lateral movement between the lockout plate 448 and the housing 432 can be limited in order to reduce, or prevent, the possibility of the lockout plate 448 becoming misaligned within the clip cartridge 430. In the event that the lockout plate 448 were to become misaligned within the clip cartridge 430, the lockout plate 448 may bind within the housing 432 and prevent the biasing member 136 from applying an appropriate biasing force to the stack of clips 140, for example. As illustrated in FIGS. 20 and 21, the lockout plate 438 can further comprise guide members 447 extending therefrom which can be received within guide slots 446 defined in the cartridge housing 432. The guide members 447 and the guide slots 446 can be sized and configured such that the guide members 447 are closely received within the guide slots 446 and such that relative lateral movement between the lockout plate 438 and the cartridge housing 432 can be limited. Each of the guide slots 446 can be defined by opposing sidewalls 445 which can define a distance therebetween which is equal to or slightly larger than the width of the guide member 447 positioned therein such that the guide member 447 can slide between the opposing sidewalls 445 between the top 443 and the bottom 444 of the guide slot 446. Thus, while the guide members 447 and the guide slots 446 can be configured to limit lateral movement therebetween, as outlined above, the guide members 447 and the guide slots 446 can be configured to permit relative movement between the lockout plate 438 and the cartridge housing 432 along a predetermined path parallel to or collinear with the supply axis 138, for example. When the lockout plate 438 is pushed into the firing chamber 149 by the biasing member 136, the lockout plate 438 can inhibit the advancement of the firing member 165 and the operation of the clip applier 100, as outlined above, until the spent clip cartridge 430 is replaced with another suitable clip cartridge.

Figure 22:
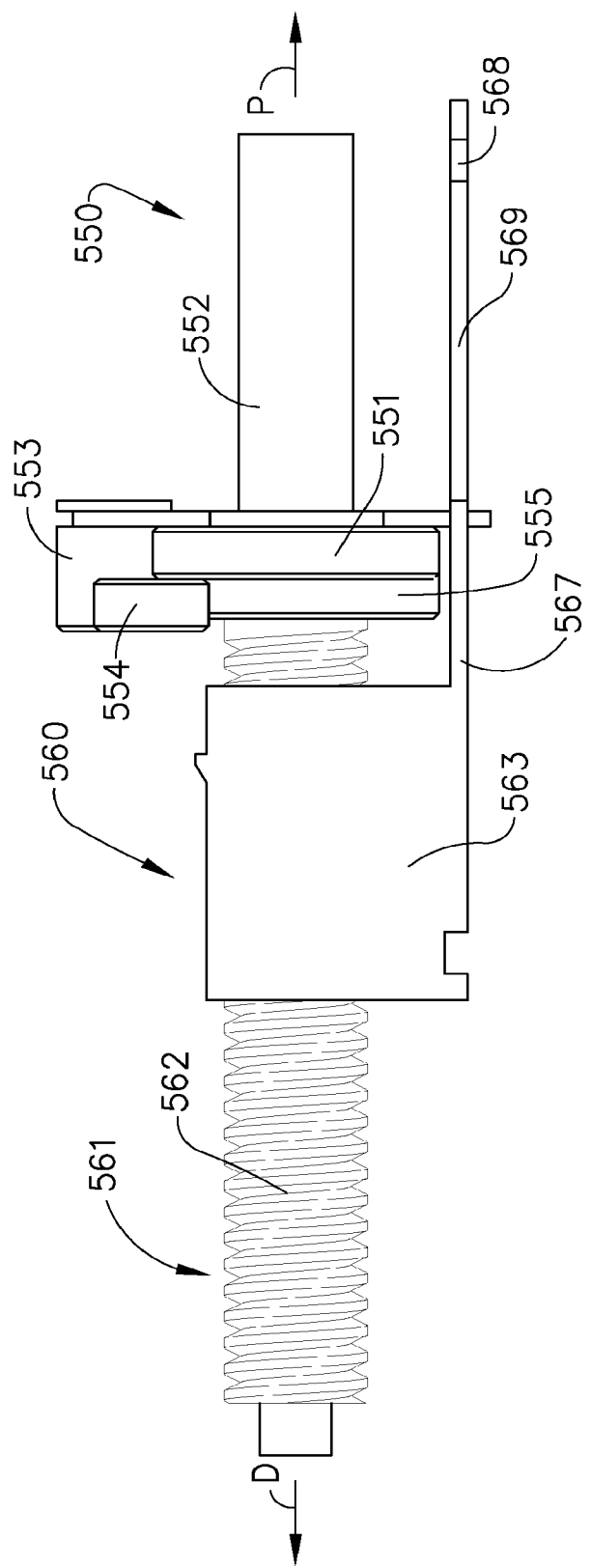
FIG. 22 is an elevational view of a firing drive comprising a rotary input, a rotary output, a firing nut engaged with the rotary output, and a transmission in a firing configuration in accordance with at least one embodiment.
Figure 23:
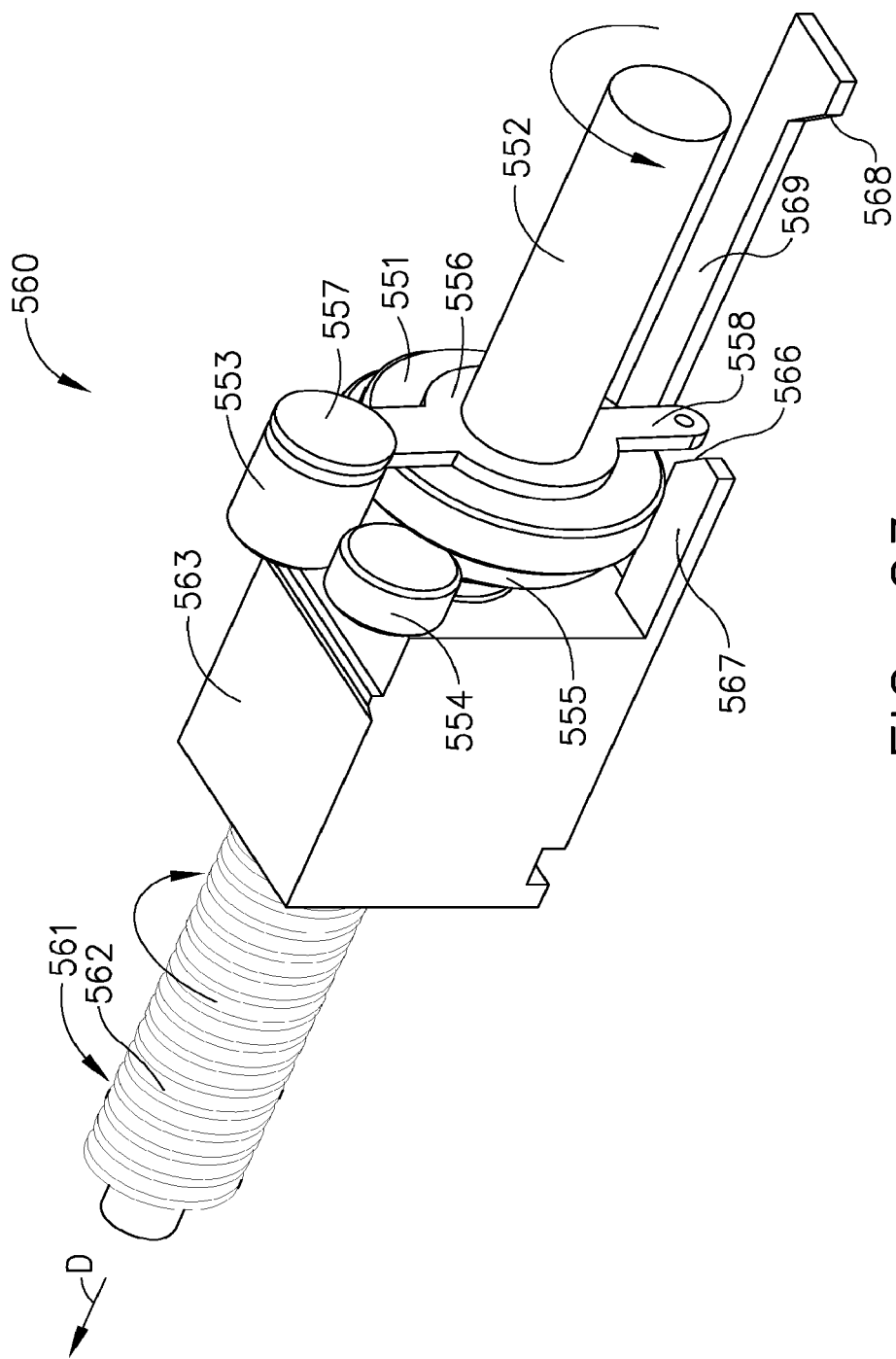
FIG. 23 is a perspective view of the firing drive of FIG. 22 illustrating the firing nut in an unfired position.
Figure 24:
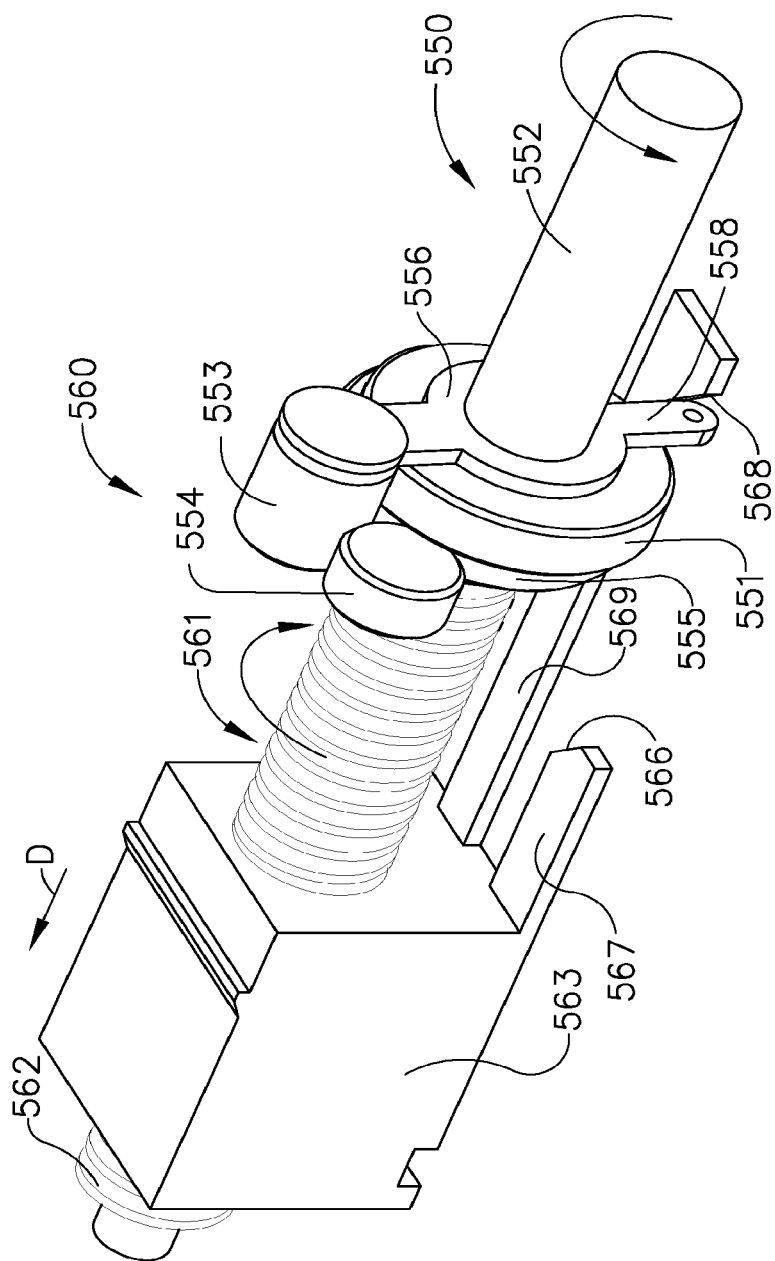
FIG. 24 is a perspective view of the firing drive of FIG. 22 illustrating the firing nut advanced along the rotary output and a cam extending from the firing nut.
Figure 25:
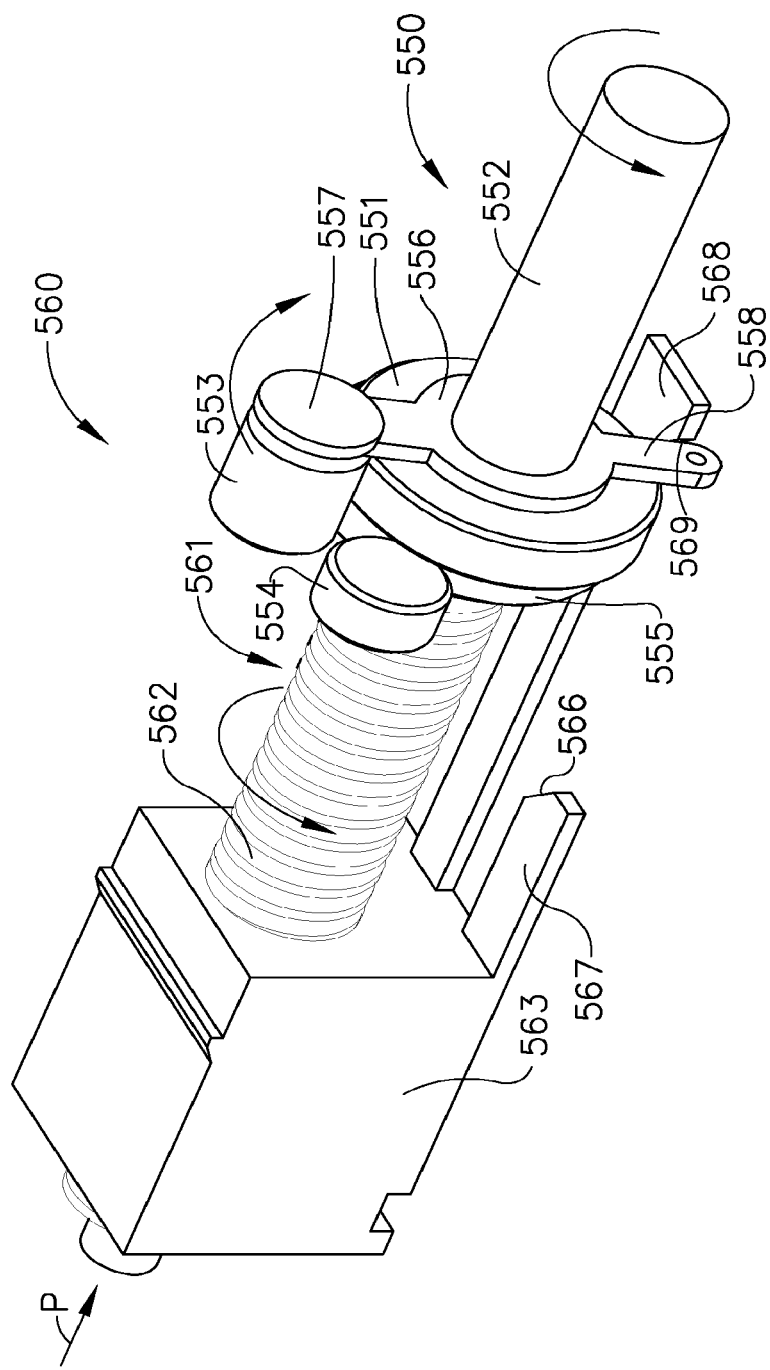
FIG. 25 is a perspective view of the firing drive of FIG. 22 illustrating the cam of the firing nut engaged with the transmission of the firing drive and the transmission in a reverse configuration.
Figure 26:
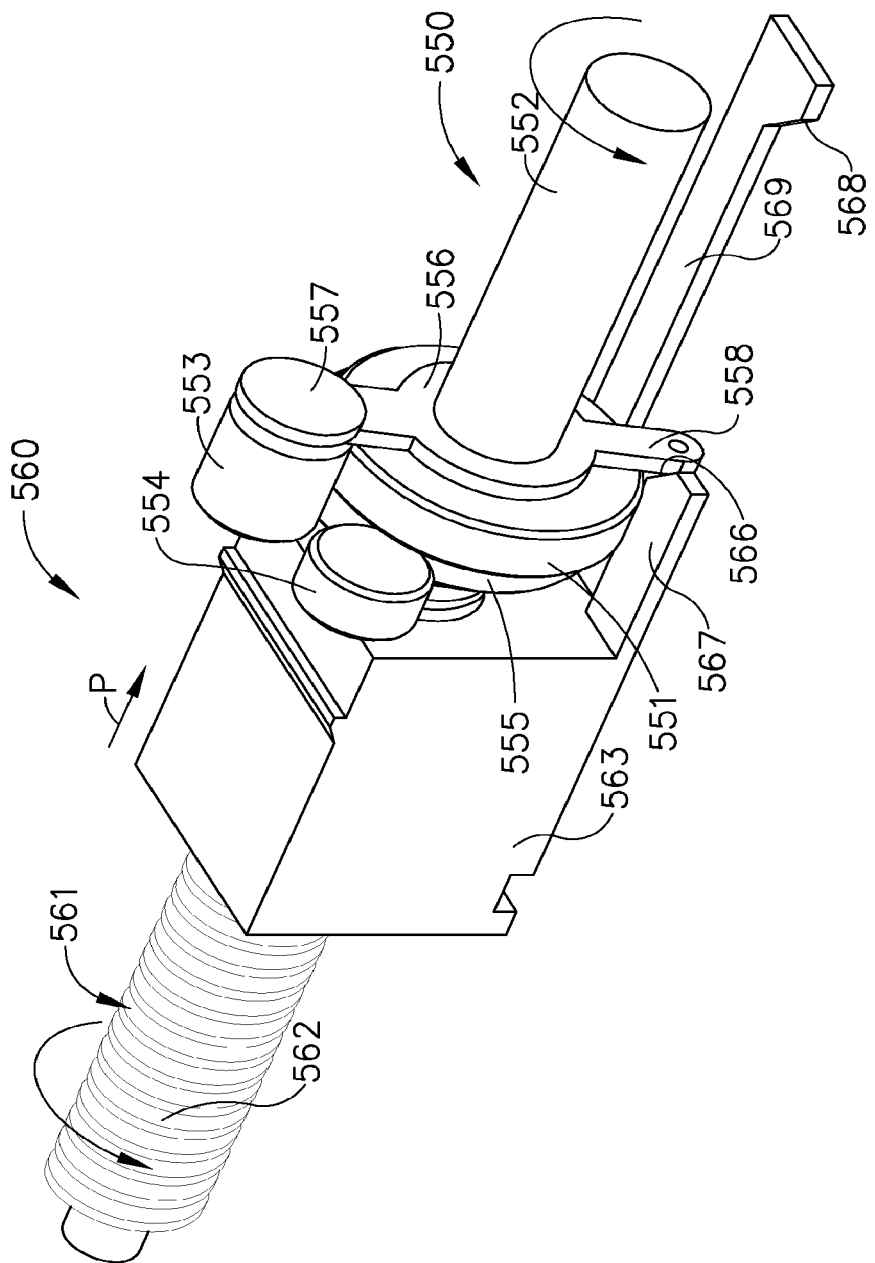
FIG. 26 is a perspective view of the firing drive of FIG. 22 illustrating firing nut in a retracted position and a second cam extending from the firing nut engaged with the transmission to shift the transmission from its reverse configuration to its firing configuration.

In the illustrated embodiment of FIG. 1 and/or any other suitable embodiment, as discussed above, the drive screw 161 can be rotated in a first direction to advance the firing nut 163 distally and rotated in a second, or reverse, direction to retract the firing nut 163 proximally. In order to rotate the drive screw 161 in the first and second directions, the electric motor operably coupled with the drive screw 161 can be operated in corresponding first and second directions. In the illustrated embodiment of FIG. 1 and/or any other suitable embodiment, a clip applier can utilize a motor which is operated in only a first direction wherein the rotation of the motor in such a single direction can be utilized to advance a firing nut distally and retract the firing nut proximally. Turning now to FIGS. 22-26, the output of an electric motor can be transmitted to a drive system 560 via a transmission system 550. The transmission system 550 can comprise an input shaft 552 which is operated in a single direction wherein the transmission system 550 can be switchable or shiftable between a first state, or configuration, in which the transmission system 550 rotates a drive screw 561 of the drive system 560 in a first direction and a second state, of configuration, in which the transmission system 550 rotates the drive screw 561 in a second, or opposite, direction. The first state of the transmission system 550 is depicted in FIGS. 22-24 and the second state of the transmission system 550 is depicted in FIGS. 25 and 26.

Referring again to FIGS. 22-24, the input shaft 552 can comprise an input gear 551 mounted thereto which is operably coupled, or meshingly engaged, with a shifter gear 553 such that the rotation of the input shaft 552 is transmitted to the shifter gear 553. With regard to all of the gears discussed herein, gears which are operably coupled or meshingly engaged with one another can comprise any suitable arrangement of teeth, for example, which can transmit the rotation of one gear to the other. When the input shaft 552 is rotated in the first direction, the shifter gear 553 is rotated in the second, or opposite, direction. In the first state of the transmission system, the shifter gear 553 is in a first position in which the shifter gear 553 is operably coupled with an intermediate gear 554 wherein, when the shifter gear 553 is rotated in the second direction by the input gear 551, as discussed above, the intermediate gear 554 is rotated in the first direction. Although not illustrated, the intermediate gear 554 can be rotatably supported within the shaft 110 of the clip applier 100, for example. The intermediate gear 554 can also be operably coupled with an output gear 555 mounted to the drive screw 561 such that the rotation of the intermediate gear 554 can be transmitted to the output gear 555. When the intermediate gear 554 is driven in the first direction by the shifter gear 553, as described above, the intermediate gear 554 can drive the output gear 555 and the drive screw 561 in the second direction. Similar to the above, the firing nut 563 can be operably coupled with the drive screw 561 and suitably constrained within the shaft 110 such that, when the drive screw 561 is rotated in the second direction, the firing nut 563 is advanced distally as indicated by the arrow D.

Similar to the above, the firing nut 563 can be advanced to its distal-most position, illustrated in FIG. 24, in order to advance a clip 140 from the clip cartridge 130 into the end effector 120 and crimp the clip 140 as described above. As illustrated in FIGS. 23 and 24, the firing nut 563 can further comprise a cam bar 569 extending therefrom which can be configured to shift the transmission system 550 from its first state to its second state. Upon comparing FIG. 24 and FIG.

25, the reader will note that the shifter gear 553 is movable between a first position in which the transmission system 550 is in its first state and a second position in which the transmission system 550 is in its second state. More particularly, the shifter gear 553 is mounted to a shifter 556 which is rotatable about the input shaft 552 such that the shifter gear 553 can be rotated from its first position in which the shifter gear 553 is operably engaged with the input gear 551 and the intermediate gear 554 and its second position in which the shifter gear 553 is operably disengaged from the intermediate gear 554. Although the shifter gear 553 is operably disengaged from the intermediate gear 554 when the shifter gear 553 is in its second position, the shifter gear 553 can be operably coupled with the input gear 551 and the output gear 555 in order to transmit rotary motion from the input shaft 552 to the drive screw 561. As illustrated in FIGS. 24 and 25, the shifter 556 can comprise a central aperture through which the input shaft 552 can extend; however, the shifter 556 may not be operably engaged with the input shaft 552 and, as a result, the rotation of the input shaft 552 may not rotate the shifter 556 and, likewise, the rotation of the shifter 556 may not rotate the input shaft 552. In any event, the shifter 556 can further comprise a cam follower 558 extending therefrom which can be engaged by a cam 568 defined on the cam bar 569 as the firing nut 563 is advanced distally. When the cam 568 engages the cam follower 558, the cam 568 can rotate the shifter 556 and the shifter gear 553 between its first position and its second position as described above.

When the shifter gear 553 is in its second position and the transmission system 550 is in its second state, as described above, the input shaft 552 and the drive screw 561 can both be rotated in the first direction. More particularly, the input shaft 552, when rotated in the first direction, can rotate the input gear 551 in the first direction and, as the shifter gear 553 is directly engaged with the input gear 551, the shifter gear 553 will be rotated in the second direction. The reader will note that the shifter gear 553 rotates in the second direction when the transmission system 550 is in its second state as compared to the first, or opposite, direction when the transmission system 550 is in its first state. Upon comparing FIGS. 24 and 25, further to the above, the reader will appreciate that the intermediate gear 554 is no longer operably positioned intermediate the input gear 551 and the shifter gear 553 when the transmission system 550 is in its second state thereby accounting for the different directions of rotation. As the shifter gear 553 is operably engaged with the input gear 551 and the output gear 555 when the shifter gear 553 is in its second position, the shifter gear 553 can rotate the output gear 555, and the drive screw 561 coupled to the output gear 555, in the first direction. When the drive screw 561 is rotated in the first direction, as illustrated in FIGS. 25 and 26, the firing nut 563 can be retracted proximally to permit the end effector 120 to be reopened and to retract the firing member 165. Referring primarily to FIG. 26, the firing nut 563 can further comprise a second cam bar 567 extending therefrom comprising a cam 566 which can be configured to contact the cam follower 558 of the shifter 556 as the firing nut 563 is retracted proximally into its fully-retracted position. In such circumstances, the cam 566 can push the shifter 556 back into its first position and into operative engagement with the intermediate gear 554 such that the transmission system 550 can be reset into its first state and the clip applier 100 can be actuated once again.

Figure 27:
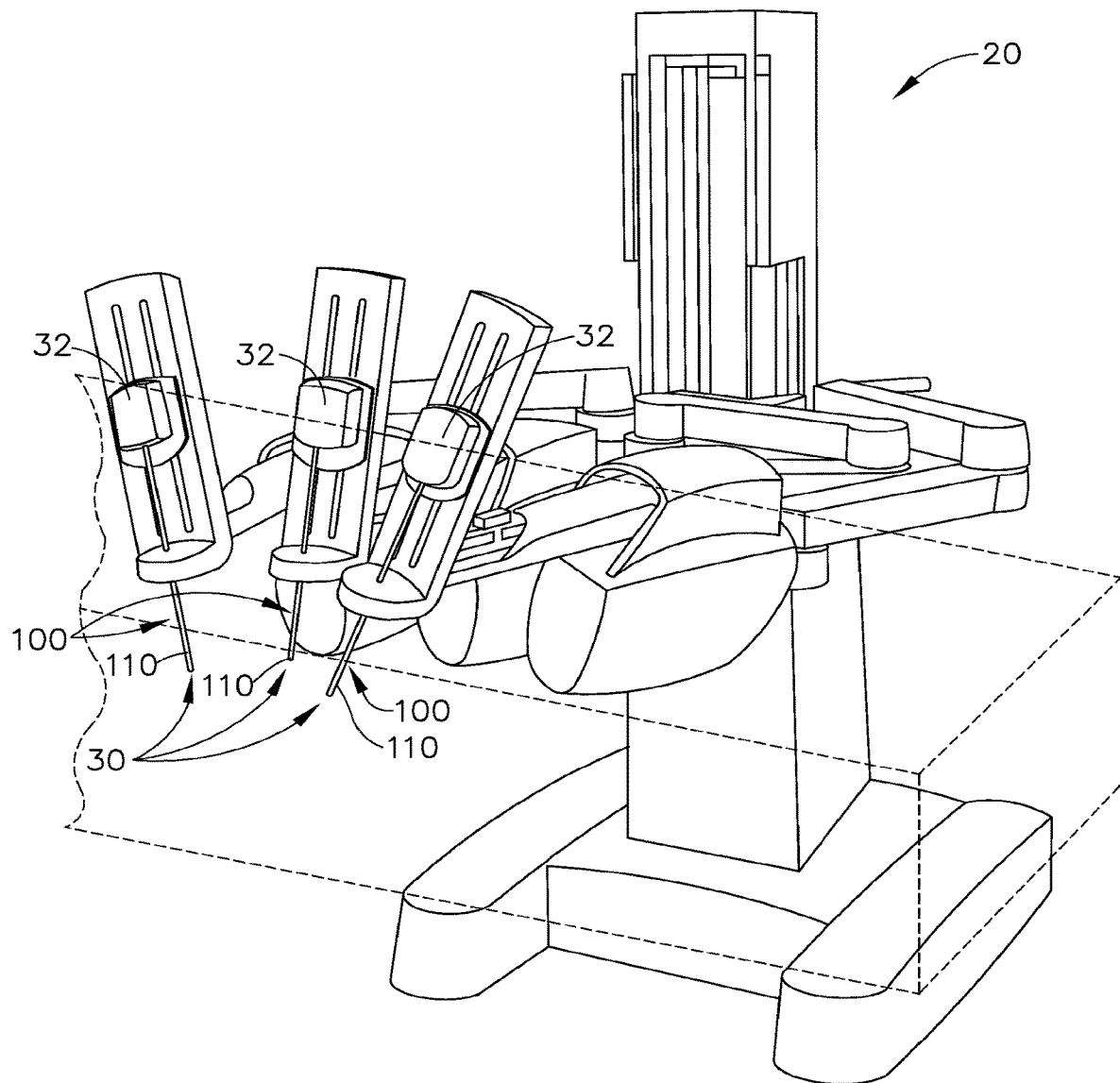
FIG. 27 is a perspective view of a robotic surgical instrument system operably supporting a plurality of surgical tools usable with the clip applier of FIGS. 2-12 or any other suitable clip applier.
Figure 28:
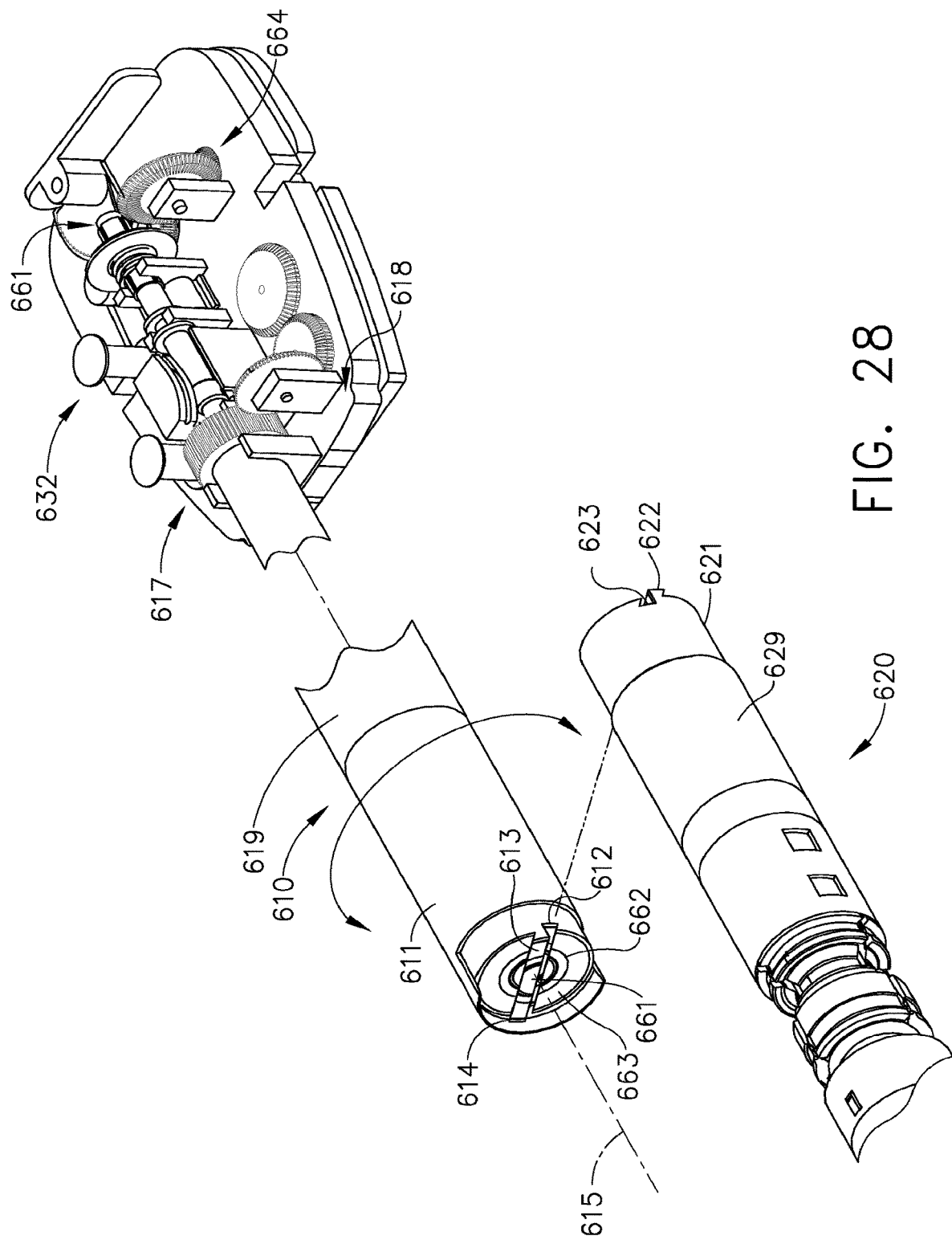
FIG. 28 is a perspective view of a surgical tool including an actuator module, a shaft extending from the actuator module, and a replaceable end effector.

As discussed above, the firing drive of the clip applier 100 can be operated by a surgical instrument system comprising an electric motor. A robotic surgical instrument system 20 is illustrated in FIG. 27 and can comprise a plurality of movable arms 30. Each arm 30 can comprise an actuator module 32 comprising an electric motor configured to supply the rotary motion to the shaft 110 of a clip applier 100, and/or any other suitable surgical instrument. Referring now to FIG. 28, an end effector 620 may be selectively engageable with and disengageable from an actuator shaft 610 of a clip applier wherein the end effector 620 can comprise a proximal end 621 which can be coupled to a distal end 611 of the shaft 610. The proximal end 621 of the end effector 620 can comprise an outer housing 629, a frame extending through the outer housing 629, an outer drive shaft extending through the frame, and an inner drive shaft extending through the outer drive shaft. Similarly, the distal end 611 of the shaft 610 can comprise an outer housing 619, a frame 663 extending through the outer housing 619, an outer drive shaft 662 extending through the frame 663, and an inner drive shaft 661 extending through the outer drive shaft 662. With regard to the distal end 611 of the shaft 610, the frame 663, the outer drive shaft 662, and the inner drive shaft 661 can each comprise a portion of a tongue connector 613 extending therefrom and a portion of a connector groove 612 defined therein, wherein the tongue connector 613 can be configured to be received within a tongue groove 623 defined in the proximal end 621 of the end effector 620, and wherein the tongue groove 612 can be configured to receive a tongue connector 622 extending from the proximal end 621 of the end effector 620. Similar to the tongue connector 613 which extends across the frame 663, the outer drive shaft 662, and the inner drive shaft 661 of the distal shaft end 611, the tongue connector 622 can extend across the frame, the outer drive shaft, and the inner drive shaft of the proximal end 621 of the end effector 620. Also, similar to the tongue groove 612 which extends across the frame 663, the outer drive shaft 662, and the inner drive shaft 661 of the distal shaft end 611, the tongue groove 623 can extend across the frame, the outer drive shaft, and the inner drive shaft of the proximal end 621 of the end effector 620. In the configuration depicted in FIG. 28, the tongue connector 622 of the end effector 620 can be slid laterally into the tongue groove 612 of the shaft 610 at the same time that the tongue connector 613 of the shaft 610 is slid laterally into the tongue groove 623 of the end effector 620. Owing to such assembly, the frame of the end effector 620 can be securely coupled to the frame 663 of the shaft 610, the outer drive shaft of the end effector 620 can be operably coupled to the outer drive shaft 662 of the shaft 110, and the inner drive shaft of the end effector 620 can be operable coupled to the inner drive shaft 661 of the shaft 110. The reader will note that the portions of the tongue connector 612 are aligned with one another, the portions of the tongue groove 613 are aligned with one another, the portions of the tongue groove 622 are aligned with one another, and the portions of the tongue connector 623 are aligned with one another when the end effector 620 is assembled to the shaft 610. Once assembled, the outer drive shaft 662 of the shaft 110 can rotate the outer drive shaft of the end effector 620, and the inner drive shaft 661 of the shaft 610 can rotate the inner drive shaft of the end effector 620. When the outer drive shaft 662 and/or the inner drive shaft 661 are rotated, the portions of the tongue connector 612, the portions of the tongue groove 613, the portions of the tongue groove 622, and the portions of the tongue connector 623 may no longer be aligned. In order to remove the end effector 620 from the shaft 610, the inner drive shaft 661 and/or the outer drive shaft 662 can be rotated into one or more positions in which the tongue connectors 612 and 623 and the tongue grooves 613 and 622 are sufficiently aligned.

Referring again to FIG. 28, the outer housing 619 of the shaft 610 can further comprise a stop 614 which can be configured to limit the lateral movement of the end effector 620 as the end effector 620 is being slid transversely onto the distal end 611 of the shaft 610. The stop 614 can provide a datum from which the inner drive shaft of the end effector 620 and the inner drive shaft 661 of the shaft 610 are aligned along longitudinal axis 615, the outer drive shaft of the end effector 620 and the other drive shaft 662 of the shaft 610 are aligned along longitudinal axis 615, and/or the frame of the end effector 620 and the frame 663 of the shaft 610 are aligned along the longitudinal axis 615. Further to the above, the inner drive shaft 661 can extend into an actuator module 632 which can comprise an electric motor and/or gear train 664 operably coupled with the inner drive shaft 661 configured to rotate the inner drive shaft 661. Furthermore, the actuator module 632 can comprise a second electric motor and gear train operably engaged with the second drive shaft 662 configured to drive the second drive shaft 662. As described in greater detail below, a second electric motor can be utilized to articulate the end effector 620. Also, further to the above, the outer housing 619 and/or the frame 663 of the shaft 610 can further comprise a gear 617 mounted thereto which is operably engaged with an electric motor and gear train 618 which can be configured to rotate the shaft 610 and the end effector 620 about the longitudinal axis 615. For instance, if the electric motor and gear train 618 are operated in a first direction, the shaft 610 and the end effector 620 can be rotated about the axis 615 in a clockwise direction while, if the electric motor and gear train 618 are operated in a second direction, the shaft 610 and the end effector 620 can be rotated about the axis 615 in a counter-clockwise direction in order to position and orient the end effector 620.

Figure 29:
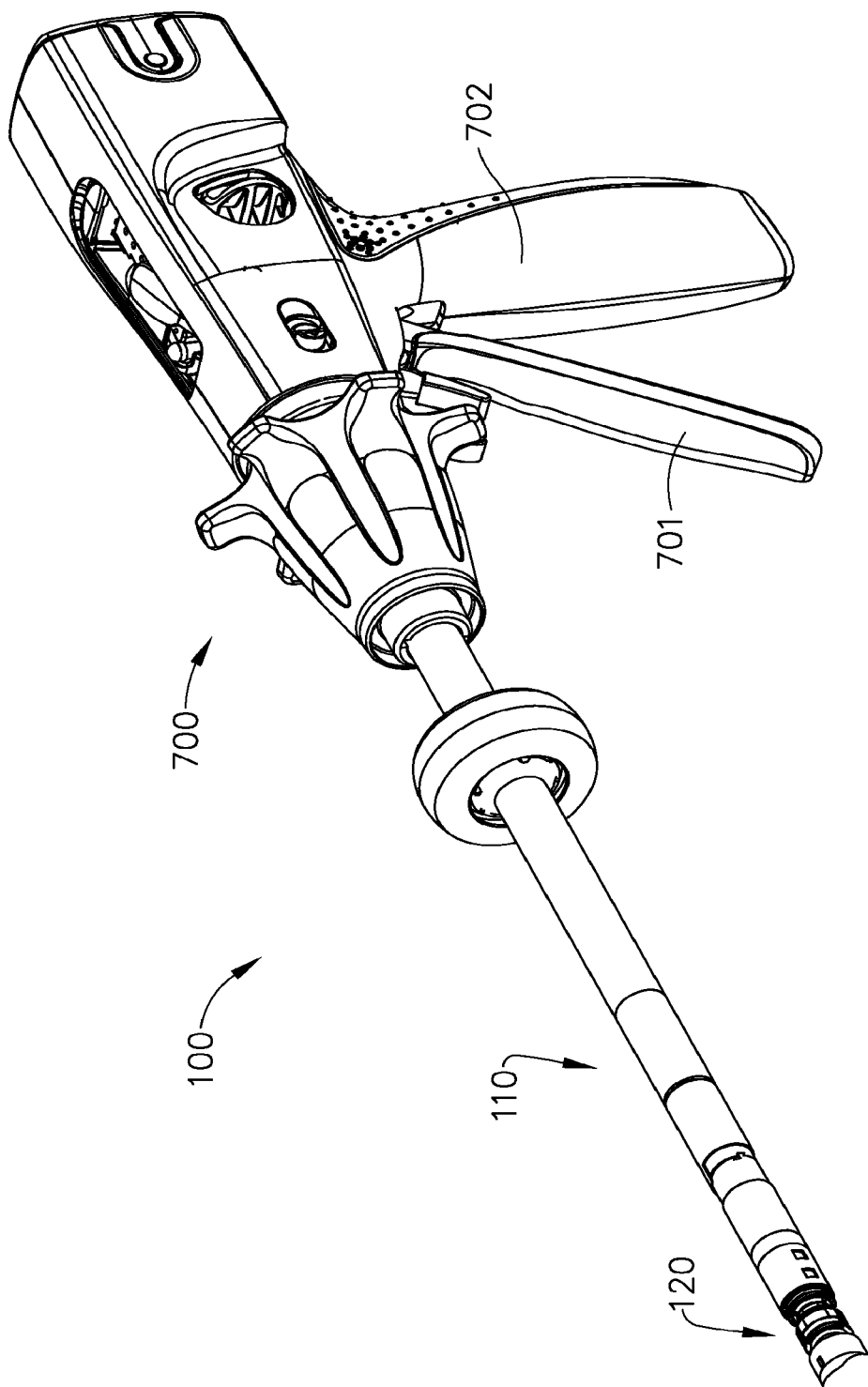
FIG. 29 is a perspective view of a handle actuator usable with the clip applier of FIGS. 2-12 or any other suitable clip applier.

As discussed above, the end effector 620 can be selectively attached to and detached from the shaft 610. The reader will note that the principles discussed in connection with the end effector 620 and shaft 610 can be equally applied to the end effector 120 and the shaft 110 of the embodiment disclosed in FIG. 1, among others. That said, referring again to FIG. 27, one of the robotic arms 30 can be selectively engaged with an end effector 120 of a clip applier or, alternatively, any other suitable end effector, such as the end effector of a surgical stapler, for example. In such circumstances, an end effector 120 can be selectively interchanged with another end effector and, as a result, a single robotic arm 30 can be utilized to perform more than one function. Stated another way, the clip applier 100 can comprise a replaceable loading unit which can be replaced by, or interchanged with, another clip applier loading unit and/or any other suitable replaceable loading unit. Turning now to FIG. 29, the end effector 120 and the shaft 110 of the clip applier 100 can be utilized with a surgical instrument system comprising a handle 700. The handle 700 can comprise an actuator 701 which can be operated, or squeezed toward grip 702, in order to apply a rotary motion to the drive screw 161 as described above. In some cases, the rotation of the actuator 701 can be mechanically transmitted to the drive screw 161 while, in other cases, the actuator 701 can operate a motor operably coupled to the drive screw 161.

Figure 30:
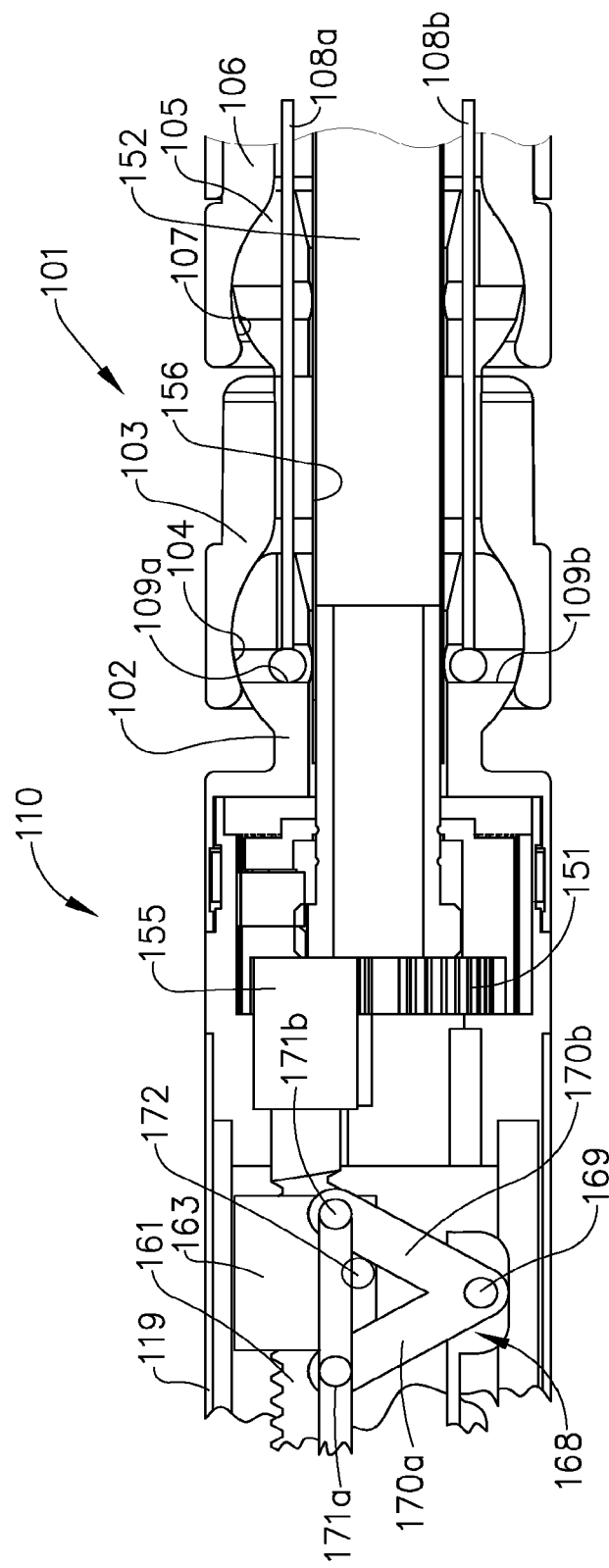
FIG. 30 is a cross-sectional view of the articulation joint illustrated in FIG. 2.

Further to the above, the end effector 120 and the shaft 110 of the clip applier 100 can be aligned along a longitudinal axis of the clip applier 100. Turning now to FIG. 30, the end effector 120 and/or the shaft 110 can further comprise an articulation joint 101 which can be configured to permit the end effector 120 to be articulated relative to the longitudinal axis of the clip applier 100. The shaft 110 can comprise an outer housing, or frame portion, 119 which can comprise a proximal end 102 and can comprise a distal portion of the articulation joint 101. The proximal end 102 can comprise a spherical, or an at least substantially spherical, end 102, for example, which can be received within a spherical, or an at least substantially spherical, cavity 104 defined in an articulation joint member 103. The articulation joint member 103 can also comprise a spherical, or at least substantially spherical, end 105, for example, which can be received within a spherical, or an at least substantially spherical, cavity 107 defined in a shaft frame portion 106. The proximal end 102 of the shaft 110 can be at least partially captured within the cavity 104 such that the proximal end 102 cannot be readily removed from the cavity 104. That said, the proximal end 102 and the cavity 104 can be sized and configured to permit the proximal end 102 to be rotated in any suitable direction within the cavity 104. As also illustrated in FIG. 30, the clip applier 100 can further comprise articulation controls 108a and 108b, for example, which can extend through the articulation joint 101 and can comprise distal ends mounted within mounting apertures 109a and 109b, respectively, defined within the proximal end 102 of the shaft housing 119. In use, the articulation controls 108a and 108b can be pushed and/or pulled in order to move the proximal end 102 within the cavity 104. Further to the above, the end 105 of the articulation joint member 103 can be at least partially captured within the cavity 107 defined in the shaft frame portion 106 such that the end 105 cannot be readily removed from the cavity 107. That said, the end 105 and the cavity 107 can be sized and configured to permit the end 105 to be rotated in any suitable direction within the cavity 107 when the shaft end 102 is pushed and/or pulled by the actuators 108a and 108b as described above.

Further to the above, referring again to FIG. 30, the drive screw 161 can be rotated by an input shaft, such as input shaft 152, for example. The input shaft 152 can extend through an aperture 156 defined within the shaft frame portion 106, the articulation joint member 103, and the proximal end 102 of the shaft housing 119. The input shaft 152 can comprise an input gear 151 mounted to the distal end thereof which can be operably coupled with an output gear 155 mounted to the proximal end of the drive screw 161. In use, the input shaft 152 can be rotated by the electric motor, described above, wherein the input shaft 152 can rotate the drive screw 161. As outlined above, the articulation joint 101 can be configured to permit the end effector 120 and at least a portion of the shaft 110 to be articulated relative to a longitudinal axis defined by the clip applier 100. In order to accommodate such movement, at least the portion of the input shaft 152 extending through the articulation joint 101 can be sufficiently flexible.

Figure 31:
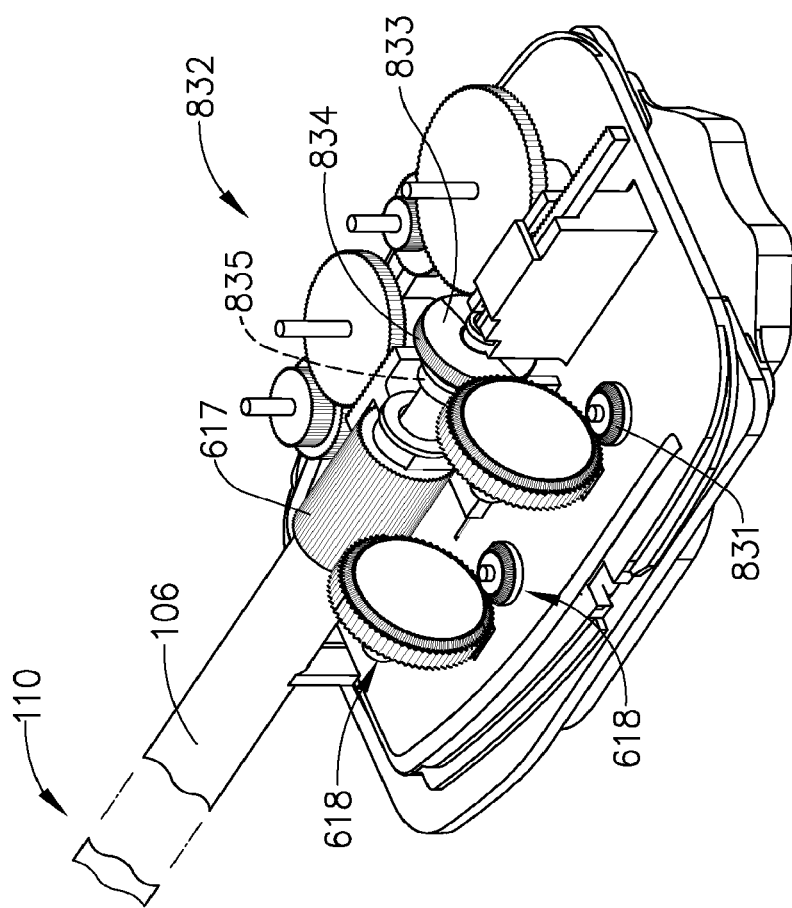
FIG. 31 is a rear perspective view of an alternative actuator module that may be used in place of the actuator module of FIG. 28 with at least a portion of its housing removed.
Figure 32:
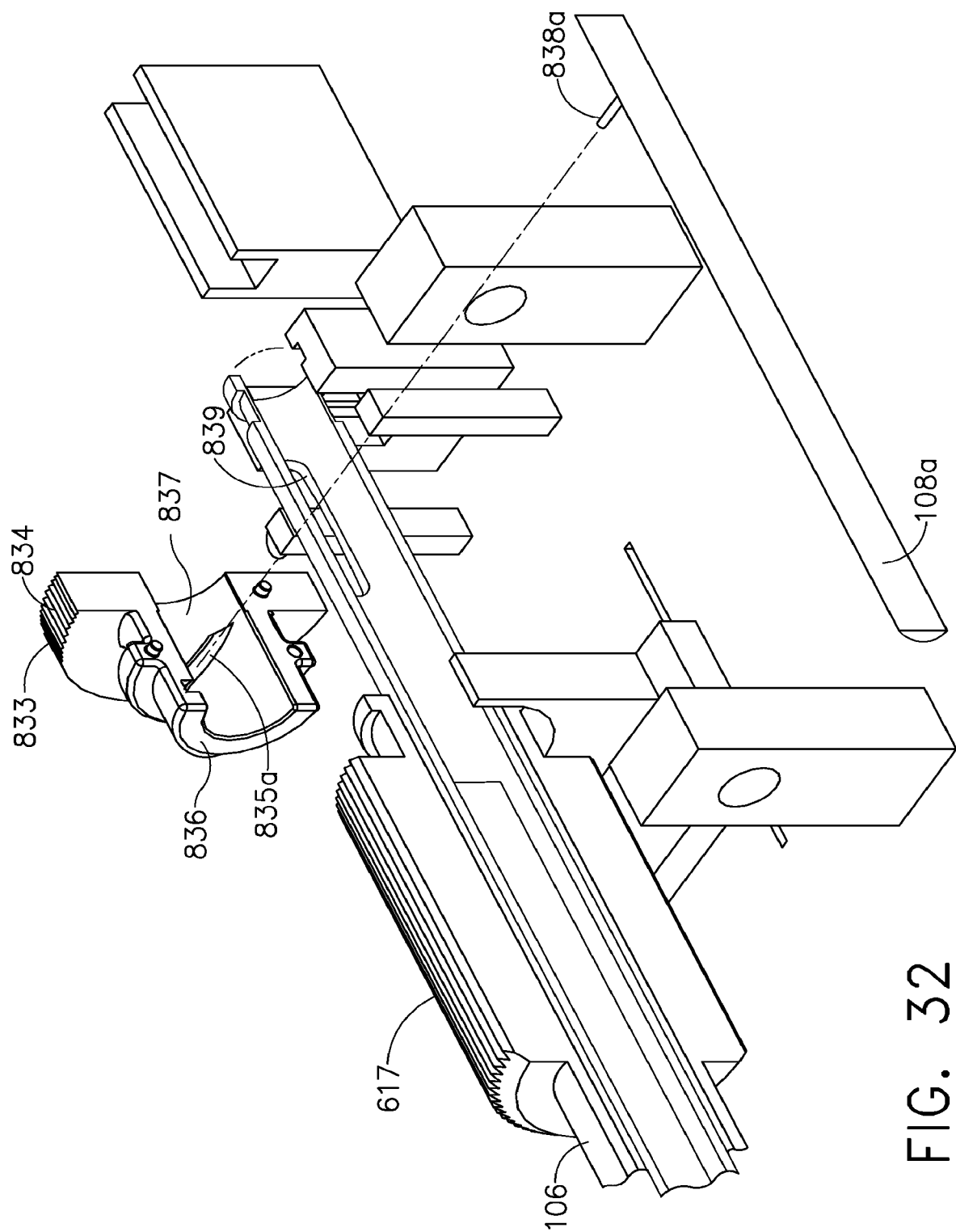
FIG. 32 is an exploded view of a portion of the actuator module of FIG. 31.
Figure 33:
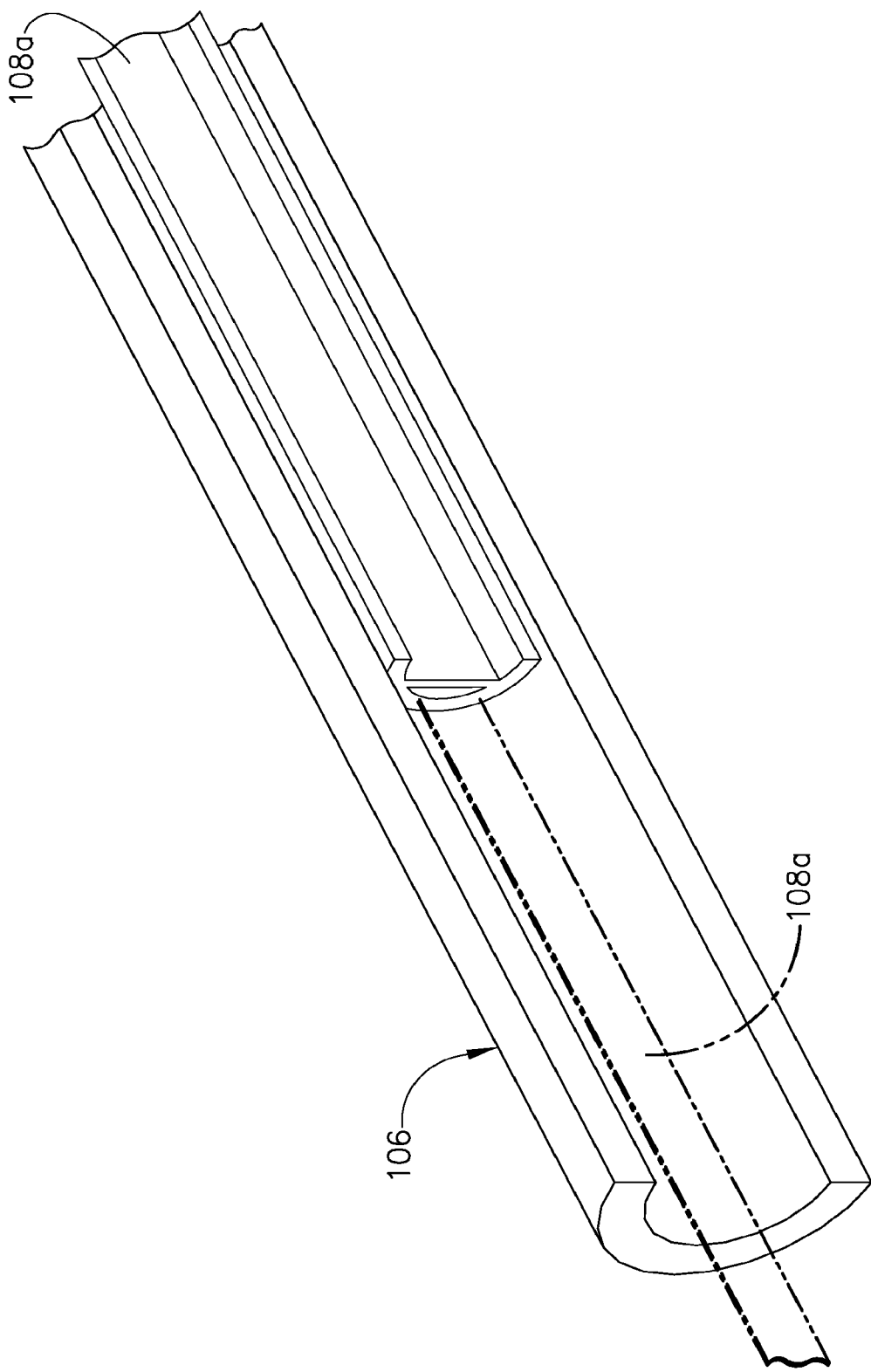
FIG. 33 is a partial sectional view of the actuator module of FIG. 31.
Figure 34:
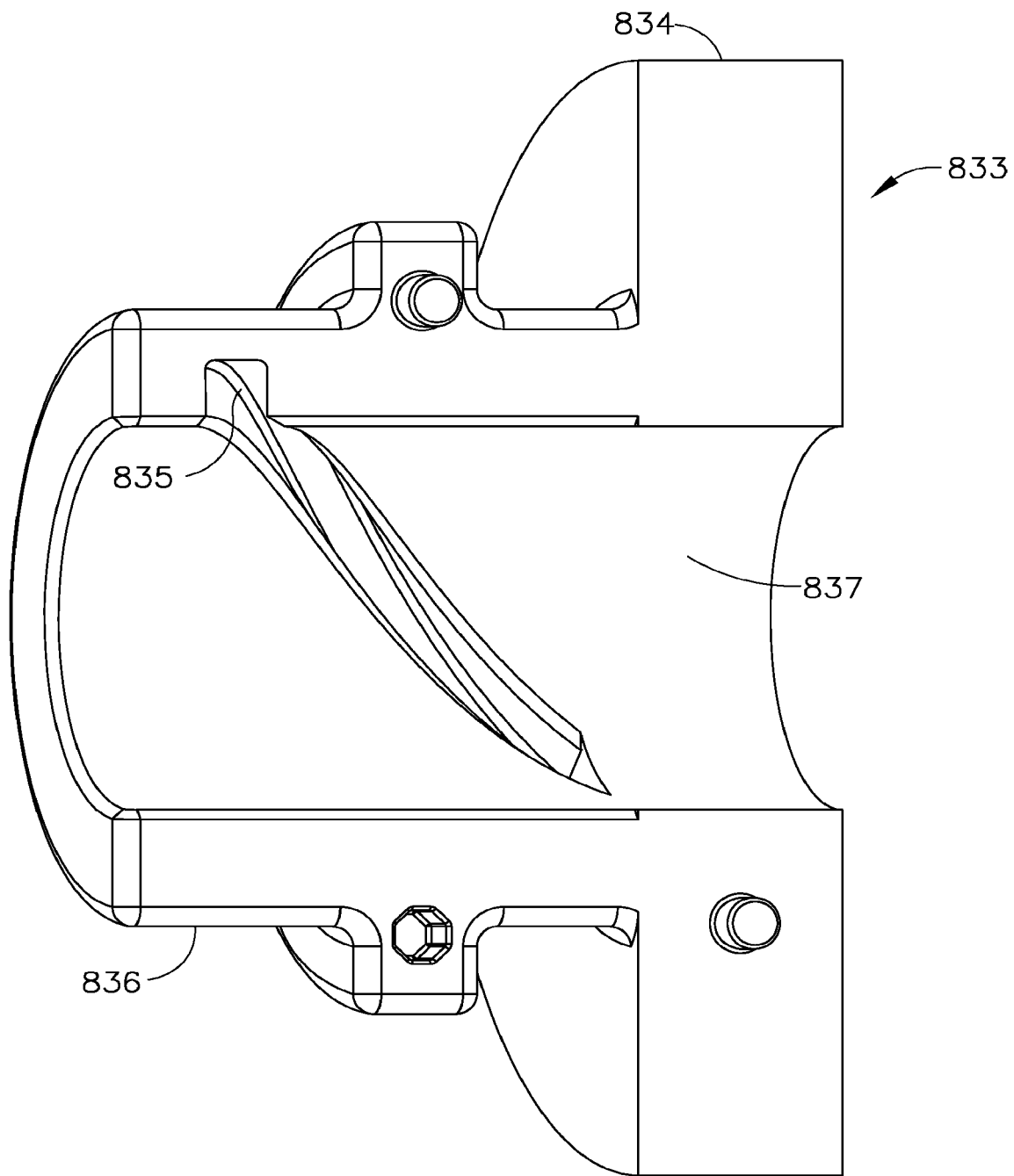
FIG. 34 is a cross-sectional view of an articulation actuator of the actuator module of FIG. 31.

Turning now to FIGS. 31-34, the articulation actuators 108a and 108b can be operated by an actuator module such as module 832, for example. Referring primarily to FIG. 31, the actuator module 832 can comprise a rotatable articulation driver 833 which can be configured to push and pull the articulation actuators 108a and 108b. The articulation driver 833 can comprise a cylindrical, or an at least substantially cylindrical, collar 835 including an aperture 837 which can be configured to receive at least a portion of the shaft frame 106 therein in order to rotatably support the collar 835. The articulation driver 833 can further comprise an input gear portion 834 which can be operably coupled with an electric motor and gear train 831 of the module 832 wherein, when the electric motor and gear train 831 are actuated, the articulation driver 833 can be rotated about the shaft frame 106. Referring primarily to FIGS. 32 and 34, the articulation driver 833 can further comprise two cam slots defined in the sidewall of the collar aperture 837, although the reader will note that only one cam slot 835*a* is illustrated in the provided views. The cam slot 835*a* is configured to receive a cam follower 838*a* extending from the articulation driver 108*a* wherein the cam follower 838*a* is configured to slide within the cam slot 835*a*. When the articulation driver 833 is rotated, the helical contour of the cam slot 835*a*, for example, can be configured to push the cam follower 838*a* distally or pull the cam follower 838*a* proximally, depending on the direction in which the articulation driver 833 is rotated. As a result of the proximal or distal movement of the cam follower 838*a*, the cam actuator 108*a* can be moved proximally or distally, respectively. While not illustrated, the articulation driver 108*b* can comprise a cam follower, similar to the cam follower 838*a*, which can be configured to slide within the other cam slot discussed above. The other cam slot can be configured such that, when the articulation actuator 108*a* is driven distally by the articulation driver 833 when the articulation driver 833 is rotated in a first direction, the articulation actuator 108*b* can be pulled proximally. Similarly, the other cam slot can be configured such that, when the articulation actuator 108*a* is pulled proximally by the articulation driver 833 when the articulation driver 833 is rotated in a second direction, the articulation actuator 108*b* can be driven distally. Referring primarily to FIG. 32, the shaft frame portion 106 can comprise clearance slots 839 defined therein through which the cam followers can extend. Although the above features have been discussed in connection with an actuator module 832, such features could be used in connection with the other actuator modules disclosed herein.

FIGS. 35A, 35B, and 35C depict a clip applier 70100 in accordance with at least one embodiment. The clip applier 70100 is similar to the clip applier 100 in many respects, most of which will not be repeated herein for the sake of brevity. Similar to the clip applier 100, the clip applier 70100 comprises an end effector 70120, a shaft, a clip cartridge, and a firing member 70165. The clip cartridge comprises a plurality of clips 70140 removably stored therein. The end effector 70120 comprise a first jaw 70123*a* and a second jaw 70123*b* wherein the first jaw 70123*a* and the second jaw 70123*b* at least partially define a receiving chamber 70122. Further, the first jaw 70123*a* and the second jaw 70123*b* are pivotally coupled to the shaft by a pin 70125 such that the first jaw 70123*a* and the second jaw 70123*b* are movable relative to each other between an open position (FIG. 35B) and a closed position (FIG. 35A). The first jaw 70123*a* and the second jaw 70123*b* are movable between the open position and the closed position by a crimping drive 70180 (see FIGS. 36-38). Other embodiments are envisioned where the first jaw 70123*a* and the second jaw 70123*b* are pivotally coupled to the shaft utilizing at least one pin similar to the first jaw 125*a* and second jaw 125*b* depicted in FIG. 1. The first jaw 70123*a* and the second jaw 70123*b* include pre-form features, such as protrusions 70126*a* and 70126*b* which are discussed in further detail below.

In use, the firing member 70165 advances a clip 70140 from the clip cartridge onto the protrusions 70126*a* and 70126*b* as depicted in FIG. 35A. In this position, the clip 70140 is in a pre-formed configuration. The width of the clip 70140 in the pre-formed configuration can be 0.080" preferably. When the first jaw 70123*a* and the second jaw 70123*b* are moved from the closed position to the open position, the protrusions 70126*a* and 70126*b* expand the clip 70140 to an expanded configuration as depicted in FIG. 35B. The width of the clip 70140 in the expanded configuration can be 0.210" preferably. During the transition of the clip 70140 from the pre-formed configuration to the expanded configuration, the firing member 70165 supports the backside of the clip 70140. More specifically, the firing member 70165 includes angled surfaces 70165*a* and 70165*b* which provide support for the backside of the clip 70140 as the clip 70140 expands. Further, as the clip 70140 is expanded, the firing member 70165 can be advanced to allow the angled surfaces 70165*a* and 70165*b* to continue to maintain contact against the backside of the clip 70140 as the clip 70140 expands. Once in the expanded configuration, the clip 70140 is advanced into the receiving chamber 70122 by the firing member 70165. The protrusions 70126*a* and 70126*b* include angled portions which allow the clip 70140 to slide over the protrusions 70126*a* and 70126*b* when the clip 70140 is advanced by the firing member 70165. After the clip 70140 has been advanced into the receiving chamber 70122, the firing member 70165 is retracted, and the crimping drive 70180 is actuated to transition the first jaw 70123*a* and the second jaw 70123*b* to the closed position depicted in FIG. 35A to crimp the clip 70140 positioned in the receiving chamber 70122. After the clip 70140 is crimped, another clip 70140 can be advanced onto the protrusions 70126*a* and 70126*b* by the firing member 70165. When the first jaw 70123*a* and the second jaw 70123*b* are moved from the closed position to the open position by the crimping drive 70180, the clip 70140 that has been crimped in the receiving chamber 70122 will be released from the receiving chamber 70122 and the clip 70140 that was advanced onto the protrusions 70126*a* and 70126*b* will be expanded into to the expanded configuration by the protrusions 70126*a* and 70126*b* of the first and second jaws 70123*a* and 70123*b*. Interaction between the crimping drive 70180 and the first and second jaws 70123*a* and 70123*b* is discussed in further detail below.

Figure 36:
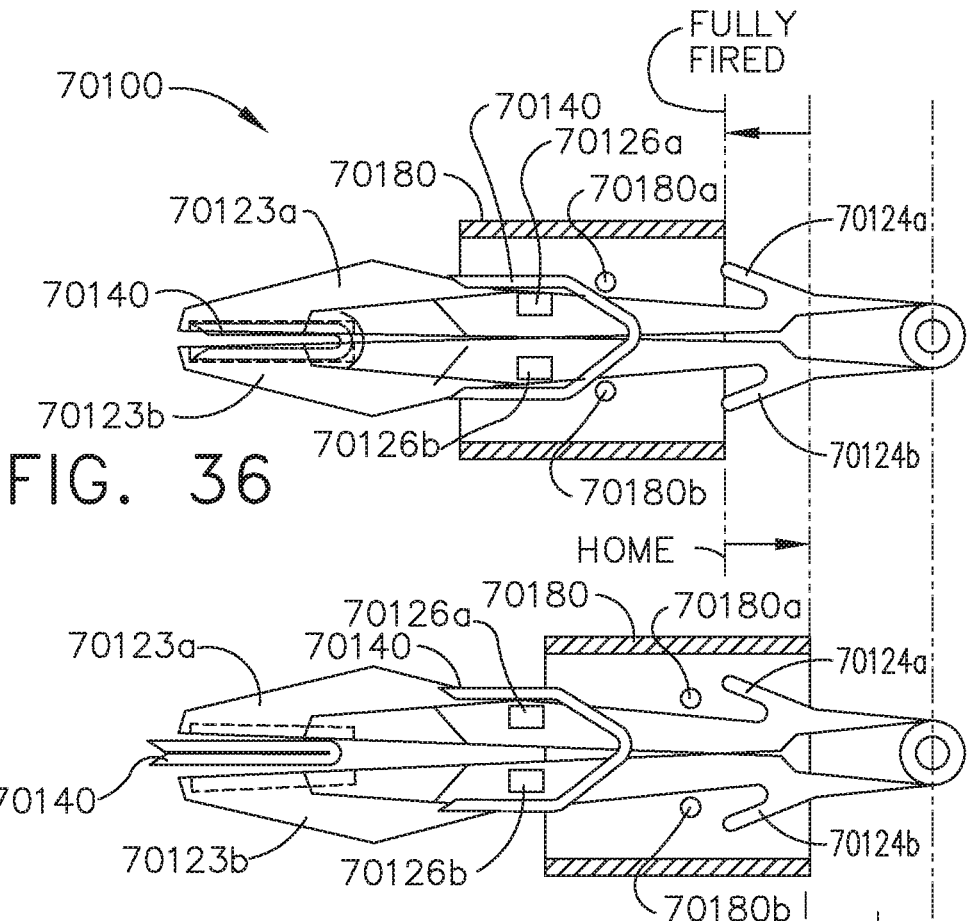
FIG. 36 is a partial cross-sectional view of the end effector of FIG. 35A illustrating the position of a stored clip when a crimping drive of the end effector is in a fully fired position.
Figure 37:
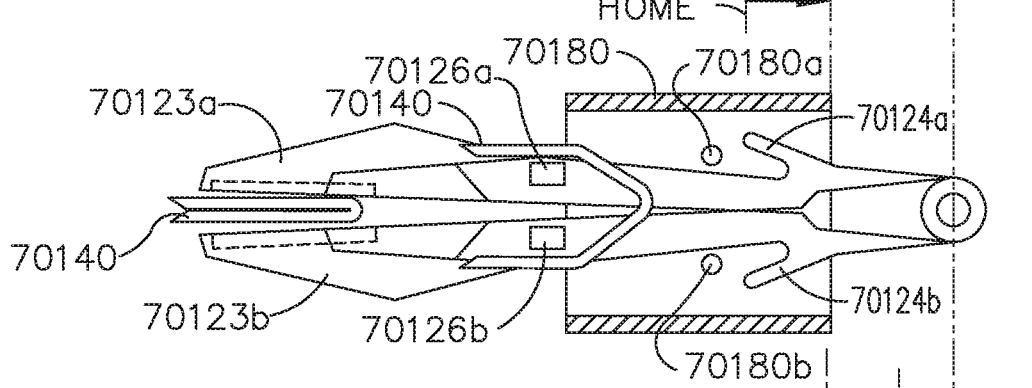
FIG. 37 is a partial cross-sectional view of the end effector of FIG. 35A illustrating the position of the stored clip when the crimping drive is in a home position.
Figure 38:
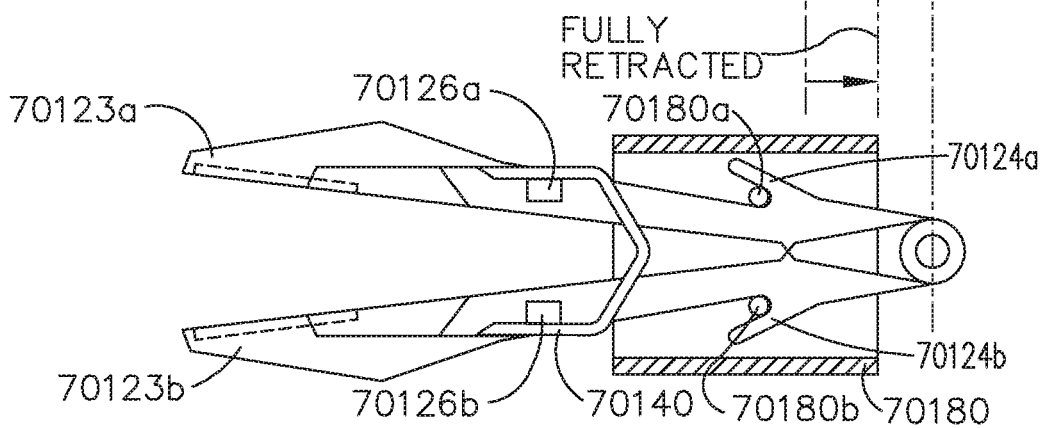
FIG. 38 is a partial cross-sectional view of the end effector of FIG. 35A illustrating the position of the stored clip when the crimping drive is in a fully retracted position.

FIGS. 36-38 depict the clip applier 70100 as described above. In addition, FIGS. 36-38 further depict the interaction between the crimping drive 70180 and the first and second jaws 70123*a* and 70123*b*. The crimping drive 70180 comprises a first crimping drive pin 70180*a* and a second crimping drive pin 70180*b* protruding therefrom. The first jaw 70123*a* comprises a first jaw cam 70124*a* extending therefrom and the second jaw 70123*b* comprises a second jaw cam 70124*b* extending therefrom. In use, the crimping drive 70180 is movable between a fully retracted position (FIG. 38), a home position (FIG. 37), and a fully-fired position (FIG. 36). The fully-fired position can preferably be 0.300" distal to the home position. The fully retracted position can preferably be 0.050" proximal to the home position. Other embodiments are envisioned with different distances between the home position, the fully retracted position, and the fully-fired position. The crimping drive 70180 cammingly engages outer surfaces of the first jaw 70123*a* and the second jaw 70123*b* to transition the first jaw 70123*a* and the second jaw 70123*b* to a closed position when the crimping drive 70180 is moved into the fully-fired position (FIG. 36)—similar to the interaction between the crimping drive 180 and the first and second jaws 123*a* and 123*b* described above. In the home position (FIG. 37), the first and second crimping drive pins 70180*a* and 70180*b* engage the first jaw cam 70124*a* and the second jaw cam 70124*b*, respectively, such that the first jaw 70123*a* and the second jaw 70123*b* are moved toward the open position to release a crimped clip 70140 from the first and second jaws 70123*a* and 70123*b*. When the crimping drive 70180 is in the home position, another clip 70140 can be advanced onto the protrusions 70126a and 70126b as discussed above. Further, as the crimping drive 70180 is moved from the home position (FIG. 37) to the fully retracted position (FIG. 38) the first crimping drive pin 70180a and the second crimping drive pin 70180b transition the first jaw 70123a and the second jaw 70123b towards the open position, and thus, the clip 70140 positioned around the protrusions 70126a and 70126b is expanded into the expanded configuration, as discussed above. Alternative embodiments are envisioned in which a crimped clip 70140 is released from the first and second jaws 70123a and 70123b and, at the same time, another clip 70140 positioned on the protrusions 70126a and 70126b is least partially expanded when the crimping drive is moved from the closed position to the home position.

Figure 39:
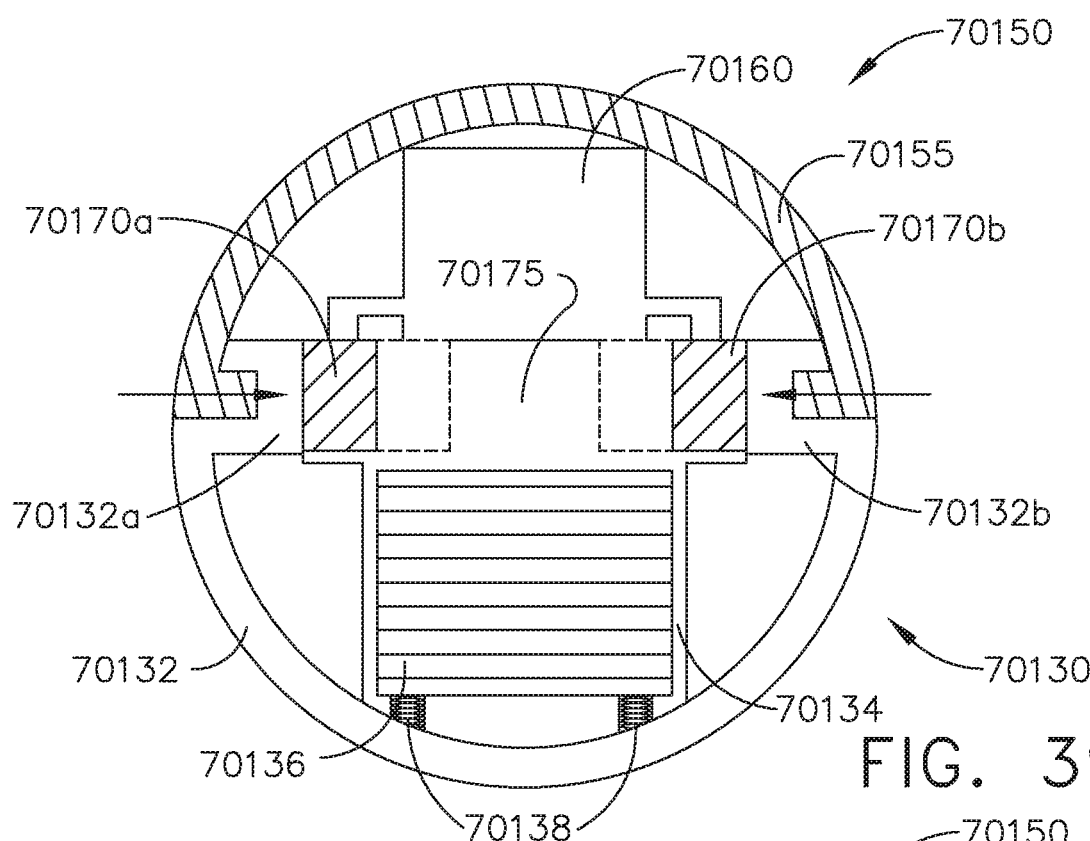
FIG. 39 is a partial cross-sectional view of a clip applier comprising a clip cartridge containing clips having a first size.
Figure 40:
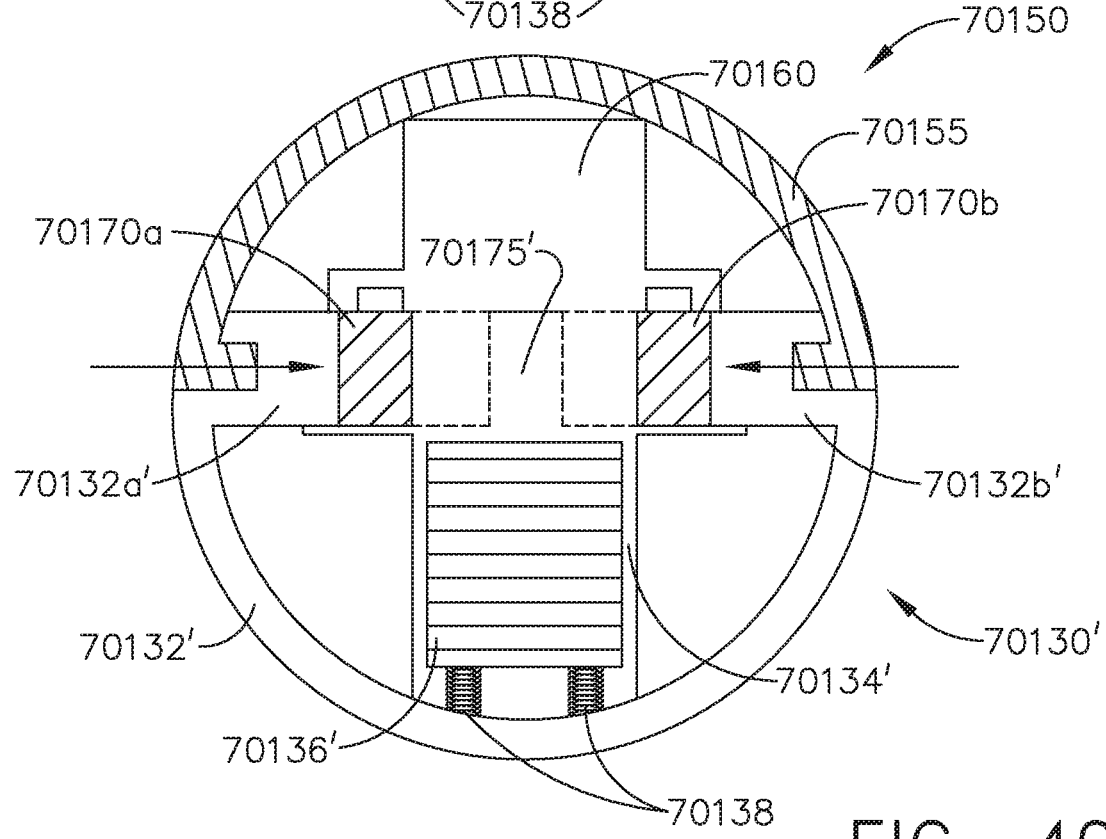
FIG. 40 is a partial cross-sectional view of the clip applier of FIG. 39 comprising a different clip cartridge containing clips having a second size.

FIGS. 39 and 40 depict a clip applier 70150 in accordance with at least one embodiment. The clip applier 70150 comprises a frame 70155, a firing member 70160, a first jaw 70170a, and a second jaw 70170b. The first jaw 70170a and the second jaw 70170b are pivotally coupled to the frame 70155 such that the first jaw 70170a and the second jaw 70170b are movable relative to each other. The clip applier 70150 is configured to receive various types of clip cartridges, such as clip cartridge 70130 depicted in FIG. 39, for example. The clip cartridge 70130 comprises a cartridge body 70132 including a first cartridge jaw 70132a and a second cartridge jaw 70132b that oppose each other. When the clip cartridge 70130 is attached to the frame 70155 of the clip applier 70150, the first cartridge jaw 70132a biases the first jaw 70170a towards the second jaw 70170b, and the second cartridge jaw 70132b biases the second jaw 70170b towards the first jaw 70170a. Thus, when the clip cartridge 70130 is attached to the clip applier 70150, the first and second jaws 70170a and 70170b are approximated to form a receiving chamber 70175. The clip cartridge 70130 further comprises a plurality of clips 70136 removably stored in a clip housing 70134. The clip cartridge 70130 further includes biasing members, such as springs 70138 for example, configured to bias the clips 70136 out of the clip housing 70134 into the receiving chamber 70175. Once in the receiving chamber 70175, a clip 70136 can be advanced by the firing member 70160 into a crimping chamber in the distal end of the first and second jaws 70170a and 70170b. A clip 70136 positioned in the crimping chamber can then be crimped when the first jaw 70170a and the second jaw 70170b are moved towards each other.

FIG. 40 depicts a different clip cartridge 70130' positioned in the clip applier 70150. The clip cartridge 70130' is similar to clip cartridge 70130 discussed above, except for the differences discussed below. The clip cartridge 70130' is configured to store clips 70136' which are smaller than clips 70136. Other embodiments are envisioned where the clip cartridge 70130' is configured to store clips that are larger than clips 70136. In any event, clip cartridge 70136' comprises, one, a clip housing 70134' which stores the clips 70136' and, two, biasing members, such as springs 70138' for example, which bias the stored clips 70136' into a receiving chamber 70175'. Further, the clip cartridge 70130' comprises a cartridge body 70132', a first cartridge jaw 70132a', and a second cartridge jaw 70132b' opposing the first cartridge jaw 70132a'. The first cartridge jaw 70132a' and the second cartridge jaw 70132b' extend further inward toward each other as compared to the first cartridge jaw 70132a and the second cartridge jaw 70132b of the clip cartridge 70130. Stated another way, the gap between the first cartridge jaw 70132a' and the second cartridge jaw 70132b' is smaller than the gap between the first cartridge jaw 70132a and the second cartridge jaw 70132b. When the clip cartridge 70130' is attached to the clip applier 70150, the receiving chamber 70175' defined between the first jaw 70170a and the second jaw 70170b will be smaller than the receiving chamber 70175. By changing the distance between the first cartridge jaw and the second cartridge jaw of the clip cartridges 70130 and 70130', various sizes of receiving chambers can be created. The clip cartridges 70130 and 70130' can therefore be modified to approximate the first jaw 70170a and the second jaw 70170b of the clip applier 70150 to receive any suitable clip size.

Figure 41:
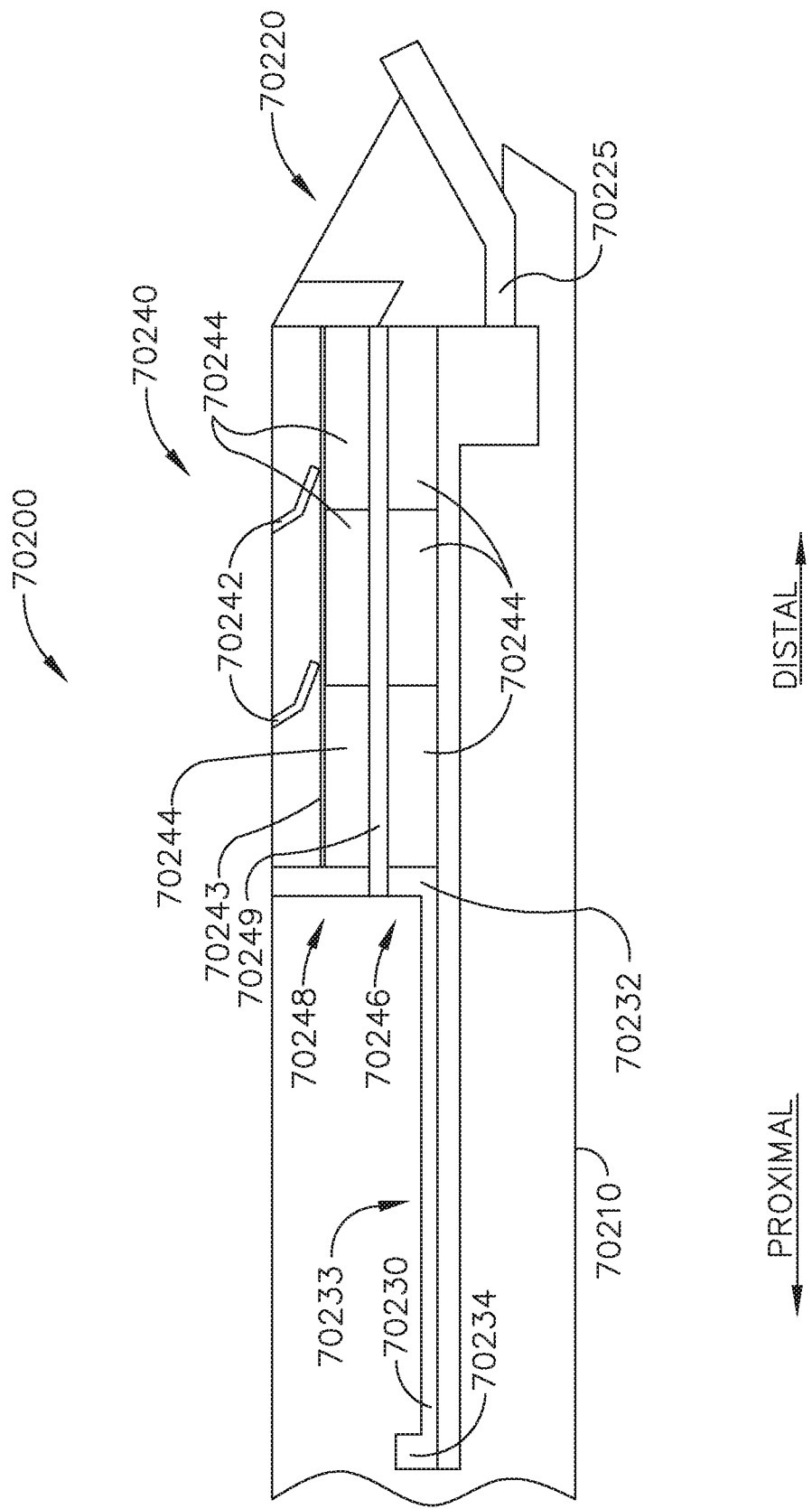
FIG. 41 is a partial cross-sectional view of a multi-level clip stack arrangement.

FIG. 41 depicts a clip applier 70200 in accordance with at least one embodiment. The clip applier comprises a shaft 70210 extending from a housing, an end effector 70220 extending from the shaft 70210, a feeder member 70230 configured to move through the clip applier 70200 in response to rotary motions generated in the housing, and a clip magazine 70240. The end effector comprises a pair of jaws 70225 configured to move relative to each other between open and closed positions. The clip magazine 70240 is not removable from the clip applier 70200; however, other embodiments are envisioned where the clip magazine 70240 is removable and/or replaceable. The clip magazine 70240 comprises a first layer 70246 of clips 70244 and a second layer 70248 of clips 70244 stored within the clip magazine 70240. The first layer 70246 of clips 70244 are in a feeding position from which they can be ejected from the clip magazine 70240. The second layer 70248 of clips 70244 are stored above the first layer 70246 of clips 70244 in a storage position from which they cannot be ejected from the clip magazine 70240. Each of the first layer 70246 and second layer 70248 comprises three clips 70244, however, other embodiments are envisioned with more or less than three clips. The first and second layers 70246 and 70248 are separated by a divider member, such as a divider plate 70249. The clip magazine 70240 further comprises a top plate 70243 and biasing members 70242. The top plate 70243 rests on top of the second layer 70248 of clips 70244. The biasing members 70242 bias the top plate 70243 toward the top of the second layer 70248 of clips 70244 and, thus, bias the second layer 70248 of clips 70244 toward the divider plate 70249. The divider plate 70249 rests on top of the first layer 70246 of clips 70244 and a distal protrusion 70232 of the feeder member 70230. The distal protrusion 70232 extends above the feeder member 70230. Operation of the clip applier 70200 is discussed in further detail below.

In use, the feeder member 70230 is translated distally to push the first layer 70246 of clips 70244 toward the end effector 70220 and out of the clip magazine 70240. As the first layer 70246 of clips 70244 is being advanced from the clip magazine 70240, the divider plate 70249 is supported by the distal protrusion 70232 of the feeder member 70230 and any of the clips 70244 which haven't been fully ejected from the clip magazine 70240. Once the feeder member 70230 has advance all of the clips 70244 in the first layer 70246 out of the clip magazine 70240, the divider plate 70249 is biased by the biasing members 70242 into a recess 70233 in the feeder member 70230. The recess 70233 is defined between the distal protrusion 70232 of the feeder member 70230 and a proximal protrusion 70234 of the feeder member 70230 extending upward from the proximal end of the feeder member 70230. Once the divider plate 70249 is seated in the recess 70233, the feeder member 70230 and divider plate 70249 can be retracted together proximally out of the clip magazine 70240. After the feeder member 70230 and divider plate 70249 are completely retracted out of the clip magazine 70240, the second layer 70248 of clips 70244 is biased by the biasing members 70242 into the feeding position (i.e., where the first layer 70246 of clips 70244 used to be). The feeder member 70230 and divider plate 70249 can be advanced together toward the end effector to eject the second layer 70248 of clips 70244 from the clip magazine 70240. The reader will appreciate that all of the clips 70244 in the first layer 70246 and/or second layer 70248 are not ejected at the same time, rather, they are ejected one at a time to allow each clip 70244 to be sequentially crimped by the pair of jaws 70255 of the end effector 70220. The above being said, other embodiments are envisioned in which more than one clip 70244 can be ejected at a time.

FIG. 42A depicts a clip applier 70250 in accordance with at least one embodiment. The clip applier 70250 comprises an elongate shaft 70260 extending from a housing, a clip cartridge 70270 extending from the elongate shaft 70260, and an end effector 70280 extending from the clip cartridge 70270. The elongate shaft 70260 and the clip cartridge 70270 define a shaft axis SA. The elongate shaft 70260 comprises a first inwardly extending detent 70264a and a second inwardly extending detent 70264b opposing the first inwardly extending detent 70264a. The first and second inwardly extending detents 70264a and 70264b extend inwardly toward the shaft axis SA and can flex outwardly away from the shaft axis SA when a force is applied thereto. The elongate shaft 70260 further comprises a top notch 70262a and a bottom notch 70262b opposing the top notch 70262a. The top notch 70262a and the bottom notch 70262b are located in the distal end of the elongate shaft 70260. The clip cartridge 70270 is releasably attachable to the distal end of the elongate shaft 70260 as discussed in further detail below.

The clip cartridge 70270 comprises a top protrusion 70272a and a bottom protrusion 70272b opposite the top protrusion 70272a. The top protrusion 70272a and the bottom protrusion 70272b extend from the clip cartridge 70270 away from the shaft axis SA. The clip cartridge 70270 further comprises a first slot and a second slot 70274b in the proximal end of the clip cartridge 70270. The first slot and the second slot 70274b oppose one another. The clip cartridge 70270 is configured to slide into the inner diameter of the elongate shaft 70260 such that the top protrusion 70272a slides into the top notch 70262a, the bottom protrusion 70272b slides into the bottom notch 70262b, the first inwardly extending detent 70264a engages the first slot of the clip cartridge 70270, and the second inwardly extending detent 70264b engages the second slot 70274b of the clip cartridge 70270 to attach the clip cartridge 70220 to the elongate shaft 70260. After the clip cartridge 70270 is attached to the elongate shaft 70260, the elongate shaft 70260 and clip cartridge 70270 are fixedly coupled such that they can rotate together about the shaft axis SA. Further, the clip cartridge 70270 can be detached from the elongate shaft 70260 by a clinician when the clinician applies a distal force to the clip cartridge 70270 to disengage the first and second inwardly extending detents 70264a and 70264b of the elongate shaft 70260 from the first slot and the second slot 70274b of the clip cartridge 70270.

Referring primarily to FIGS. 42A and 42B, the end effector 70280 comprises a first jaw 70280a and a second jaw 70280b configured to move relative to each other between an open position (FIG. 42A) and a closed position (FIG. 42B). To this end, the first jaw 70280a and the second jaw 70280b comprise openings at the proximal end thereof which are configured to receive a pin 70290. The pin 70290 is rotatably captured within an opening 70276 in the clip cartridge 70270. The pin 70290 defines a pin axis PA which is orthogonal to the shaft axis SA. The first jaw 70280a and the second jaw 70280b are rotatable relative to each other about the pin axis PA. When the first jaw 70280a and the second jaw 70280b are in the open position (FIG. 42A) a clip can be positioned between the first jaw 70280a and the second jaw 70280b. As the first jaw 70280a and the second jaw 70280b are r towards the closed position (FIG. 42B) the clip is crimped between the first jaw 70280a and the second jaw 70280b. The first jaw 70280a and the second jaw 70280b are moved from the open position to the closed position by a closure tube which cammingly engages the outer surfaces of the first jaw 70280a and the second jaw 70280b as the closure tube moves distally. When the closure tube is retracted, the first jaw 70280a and the second jaw 70280b are returned to the open position by a biasing member, or spring, which biases the first jaw 70280a and the second jaw 70280b into the open position. Other embodiments are envisioned where the first jaw 70280a and the second jaw 70280b are movable from the closed position to the open position by jaw cams on the first jaw 70280a and the second jaw 70280b interacting with the closure tube, similar to jaw cams 70124a and 70124b depicted in FIGS. 36-38, for example.

Figure 43B:
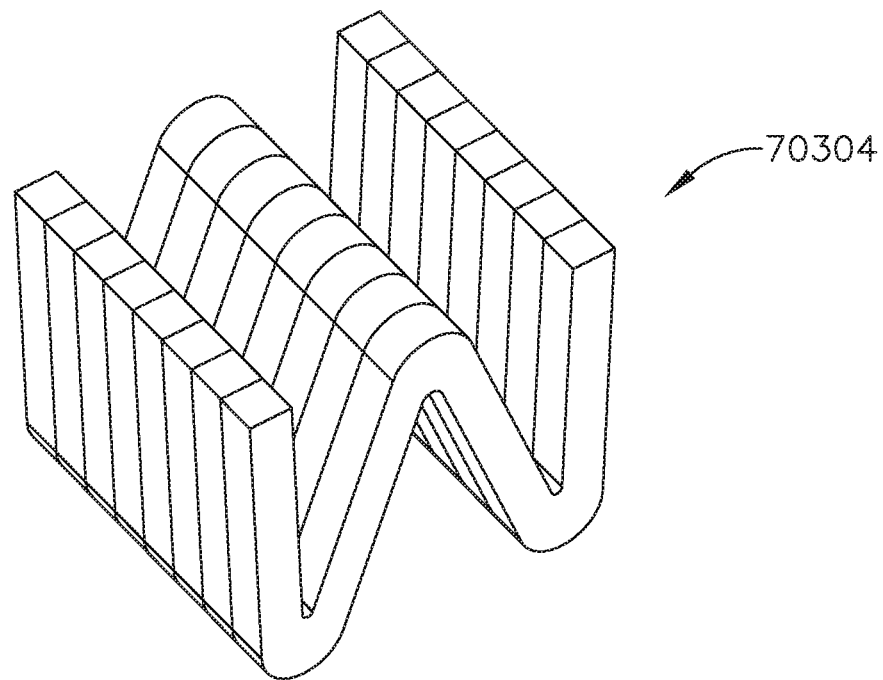
FIG. 43B is a perspective view of clips for use with the clip applier of FIG. 43A.
Figure 43A:
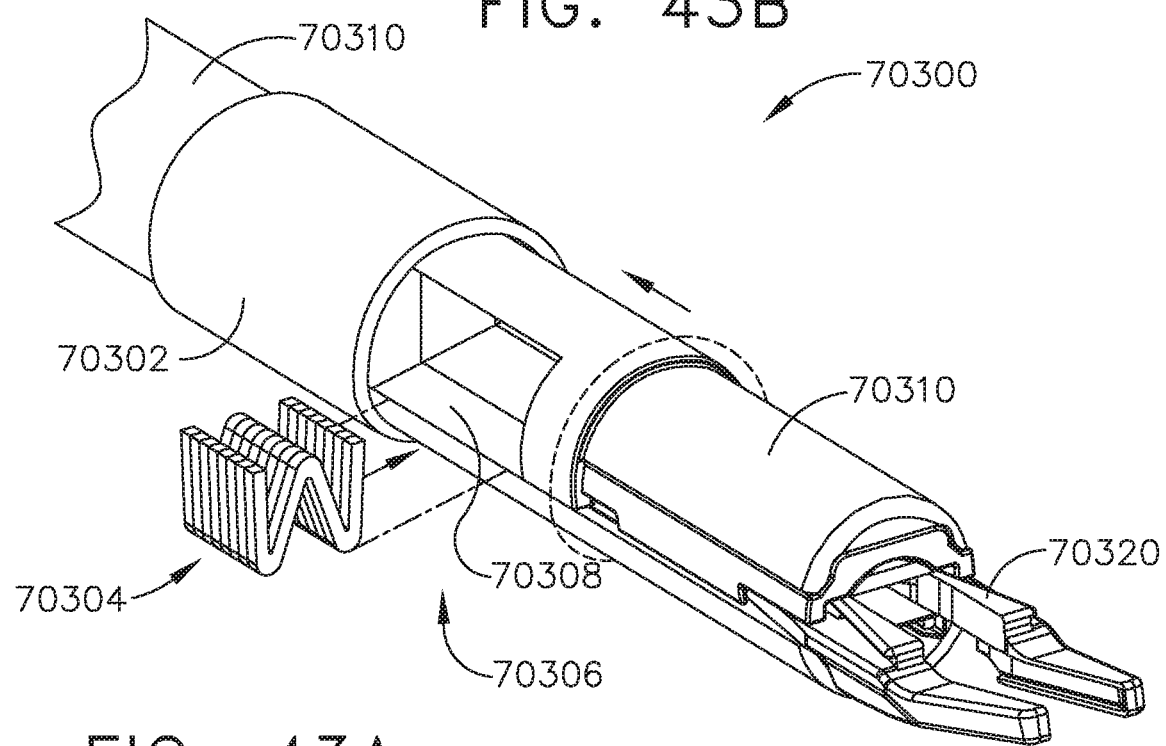
FIG. 43A is a perspective view of a clip applier comprising a clip magazine.

FIG. 43A depicts a clip applier 70300 in accordance with at least one embodiment. The clip applier 70300 comprises a shaft 70310, an end effector 70320 extending from the shaft 70310, a firing drive, and a clip magazine 70306. The clip magazine 70306 is built into the shaft 70310 of the clip applier 70300 as depicted in FIG. 43A. However, other embodiments are envisioned where the clip magazine 70306 is releasably attachable to the clip applier 70300. The shaft 70310 comprises openings 70308 on either side of the shaft 70310 which allow a user of the clip applier 70300 to access the clip magazine 70306. Other embodiments are envisioned with only one opening in the shaft 70310 of the clip applier. The clip applier 70300 further comprises an outer tube 70302 that is slidable along the shaft 70310 of the clip applier 70300. The outer tube 70302 is configured to slide along the shaft 70310 to cover the openings 70308 in the shaft 70310. The clip magazine 70306 is configured to store a plurality of clips, such as clips 70304 therein. The clips 70304 are insertable into the clip magazine 70306 through the openings 70308 when the outer tube 70302 is not obstructing the openings 70308, as depicted in FIG. 43A. Once positioned in the clip magazine 70306, the clips 70304 can be advanced out of the clip magazine 70306 into the end effector 70320 by the firing member. In at least one embodiment, the clips 70304 can be sequentially advanced out of the clip magazine 70306 into the end effector 70320.

When the outer tube 70302 is covering the openings 70308, access to the clip magazine 70306 is prevented, and, if clips 70304 have already been inserted into the clip magazine 70306, the outer tube 70302 prevents the clips 70304 from exiting the clip magazine 70306 through the openings 70308. Once all of the clips 70304 inside the clip magazine 70306 have been advanced into the end effector 70320, the outer tube 70302 can be retracted to allow a new set of clips to be inserted into the clip magazine 70306. Further to the above, the outer tube 70302 can be operably engaged with the firing member of the clip applier 70300, such that, when the outer tube 70302 is retracted as depicted in FIG. 43A, or at least partially retracted, the firing member cannot be actuated.

Figure 44:
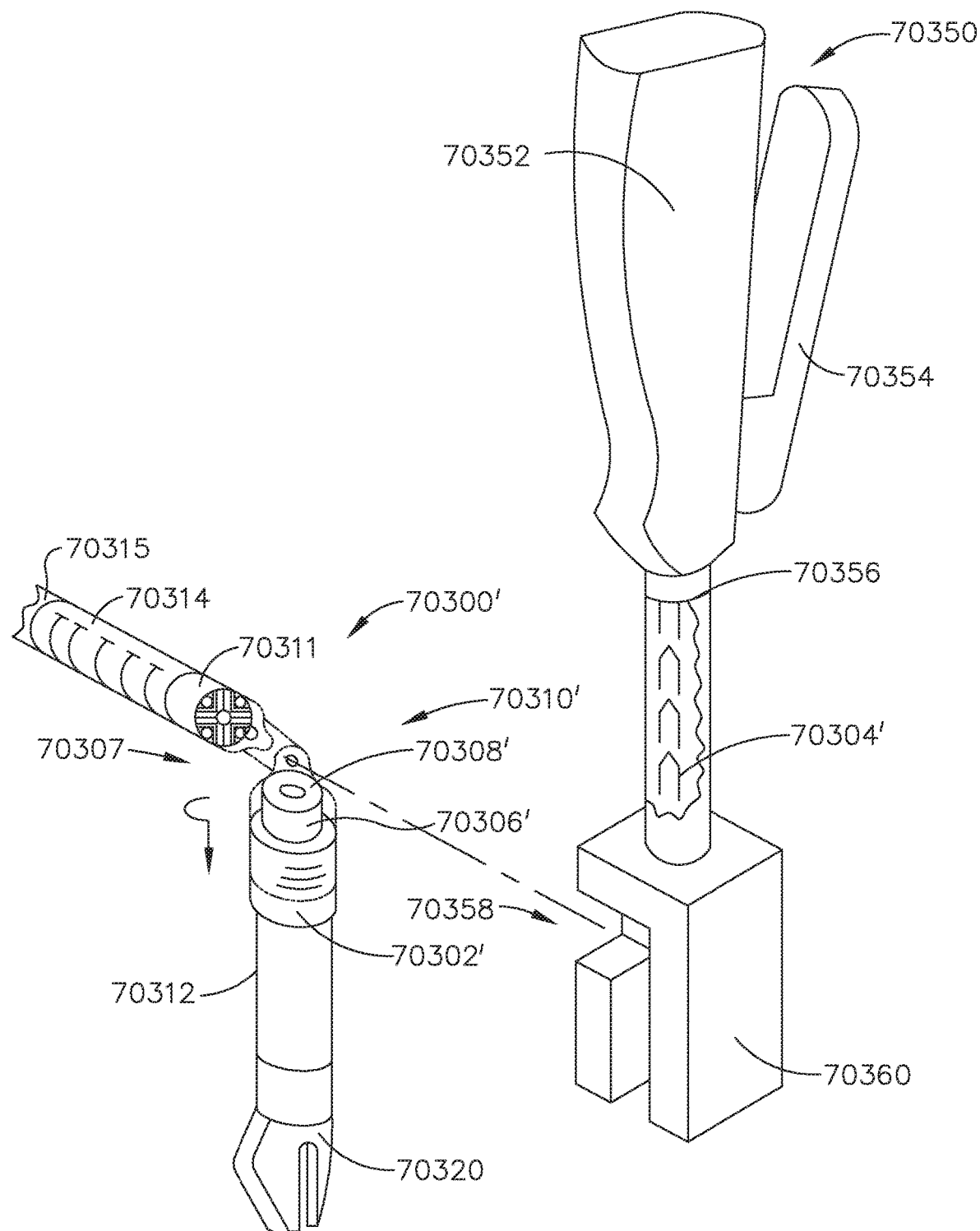
FIG. 44 is a perspective view of a clip reloader for use with a clip applier comprising a clip magazine.

FIG. 44 depicts a clip applier 70300'. Clip applier 70300' is similar to clip applier 70300 in many respects. The clip applier 70300' comprises an elongate shaft 70315 extending from a housing, an articulation joint 70314 extending from the elongate shaft 70315, a shaft assembly 70310' extending from the articulation joint 70314, an end effector 70320 extending from the shaft assembly 70310', and an outer tube 70302' positioned around the shaft assembly 70310'. The articulation joint 70314 connects the elongate shaft 70315 to the shaft assembly 70310' so that the shaft assembly 70310' can be articulated relative to the elongate shaft 70315. The shaft assembly 70310' comprises a proximal shaft portion 70311 extending from the articulation joint 70314, a distal shaft portion 70312 extending from the proximal shaft portion 70311, and a hinge 70307. The distal shaft portion 70312 further comprises a clip magazine 70306'. Other embodiments are envisioned where the proximal shaft portion 70311 comprises the clip magazine 70306'. The hinge 70307 allows the distal shaft portion 70312 to rotate away from the proximal shaft portion 70311. The outer tube 70302' is configured to slide along the shaft assembly 70310' between a locked position and an unlocked position when the proximal shaft portion 70311 and distal shaft portion 70312 are aligned. More specifically, when the proximal shaft portion 70311 and distal shaft portion 70312 are aligned and the outer tube 70302' is in the locked position, the distal shaft portion 70312 is prevented from rotating away from the proximal shaft portion 70311 about the hinge 70307. When the outer tube 70302' is in the unlocked position, the distal shaft portion 70312 is capable of rotating away from the proximal shaft portion 70311 about the hinge 70307. Further to the above, when the distal shaft portion 70312 is rotated away from the proximal shaft portion 70311, an opening 70308' in the clip magazine 70306' is exposed. The opening 70308' allows clips 70304' to be inserted into the clip magazine 70306'.

Further to the above, a clip reloader 70350 can be utilized to insert the clips 70304' into the clip applier 70300' as depicted in FIG. 44. The clip reloader comprises a housing 70352, a trigger 70354 movable relative to the housing 70352, a feeder bar operably engaged with the trigger 70354, an elongate shaft 70356 extending from the housing 70352, and a docking station 70360 extending from the elongate shaft 70356. A plurality of clips 70304' are removably stored in the elongate shaft 70356. In one embodiment, the elongate shaft 70356 stores 20 clips within a six inch span of the elongate shaft 70356. Other embodiments are envisioned with different numbers of clips and spans, for example. The clips 70304' are advanced from the elongate shaft 70356 into the docking station 70360 by the feeder bar when the trigger 70354 is moved towards the housing 70352. The docking station 70360 comprises a cavity 70358 configured to dock with the shaft assembly 70310' of the clip applier 70300' when the distal shaft portion 70312 is rotated away from the proximal shaft portion 70311. When the docking station 70360 is docked with the shaft assembly 70310' of the clip applier 70300', the clips 70304' can be advanced form the elongate shaft 70356 into the clip magazine 70306' of the clip applier.

FIGS. 45-47 depict a different clip reloader 70400. The clip reloader 70400 is similar to the clip reloader 70350 in many respects. The clip reloader 70400 comprises a housing 70410, a plurality of clips 70404 stored inside the housing 70410, and a plunger 70402. The plunger 70402 extends into and is movable relative to the housing 70410. The clips 70404 are stacked vertically in the embodiment illustrated in FIGS. 45 and 46; however, other embodiments are envisioned where the clips are stacked horizontally. A feeder block 70406 extends from the plunger 70402 and is slidably engaged with the inside of the housing 70410. The feeder block 70406 comprises angled portions that support the backside of the top-most clip in the clip stack as depicted in FIG. 45. The housing 70410 comprises a boss 70408 extending from the bottom of the housing 70410, and a flexible ramp 70409 extending from the bottom of the boss 70408. The housing 70410 further comprises a cutout region 70411. Docking the clip reloader 70400 with a clip applier is discussed in further detail below.

In various circumstances, the clip reloader 70400 is configured to insert the clips 70404 into a clip applier, such as clip applier 70450, for example. The clip applier 70450 comprises a shaft 70460, an end effector 70480 extending distally from the shaft 70460, and an articulation joint 70470 extending proximally from the shaft 70460. To align the clip reloader 70400 with the clip applier 70450, the boss 70408 docks with an opening 70464 in the shaft 70460 of the clip applier 70450, the cutout region 70411 mates with the exterior of the shaft 70460, and the flexible ramp 70409 extends into a clip slot 70462 of the clip applier 70450 as depicted in FIG. 47. The opening 70464 leads to the clip slot 70462 which comprises an angled portion that receives the boss 70408 and flexible ramp 70409 of the clip reloader 70400. The clip slot 70462 further comprises a flat portion that facilitates the advancement of the clips 70404 into the end effector 70480 of the clip applier 70450. The operation of the clip reloader 70400 in conjunction with the clip applier 70450 is discussed in further detail below.

In use, after the clip reloader 70400 is docked with the clip applier 70450, the plunger 70402 is moved towards the clip applier 70450 to advance the clips 70404 from the housing 70410 into the angled portion of the clip slot 70462. The ramp 70409 supports and guides the clips 70404 from the angled portion of the clip slot 70462 into the flat portion of the clip slot 70462. As illustrated in FIG. 47, the housing 70410 of the clip reloader 70400 is positioned at an angle relative to the longitudinal axis of the clip applier 70450 when the clip reloader 70400 is docked with the clip applier 70450. Other embodiments are envisioned where the housing 70410 is orthogonal, or at least substantially orthogonal, to the clip applier 70450 when docked. Referring primarily to FIG. 47, the clip applier 70450 further comprises a flexible firing member 70465 positioned within a firing slot 70466 located proximal to the clip slot 70462. After the clip reloader 70400 is un-docked with the clip applier 70450, the flexible firing member 70465 can move from the firing slot 70466 into the clip slot 70462 to advance the clips 70404 into the end effector 70480. Once at least one, or all, of the clips 70404 have been advanced into the end effector 70480, the flexible firing member 70465 can be retracted from the clip slot 70462 into the firing slot 70466 and additional clips 70404 can be loaded into the clip slot 70462 by the clip reloader 70400.

Figure 50:
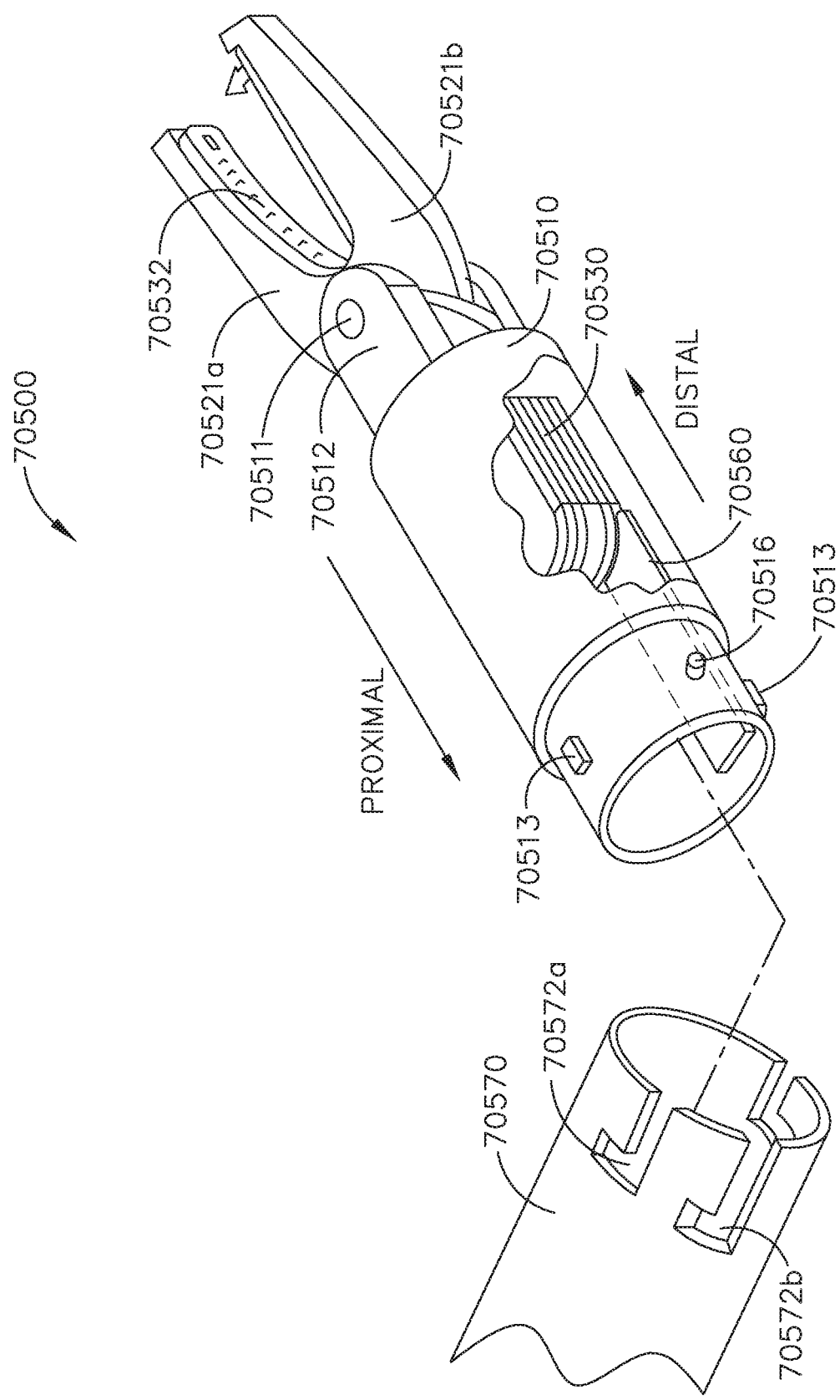
FIG. 50 is a perspective view of the clip applier of FIG. 48.

FIGS. 48-50 depict a clip applier 70500. The clip applier 70500 comprises an elongate shaft 70570 (see FIG. 50) extending from a housing, a shaft 70510 attachable to the elongate shaft 70570, an end effector 70520 extending from the shaft 70510, and a clip magazine 70530. The attachable shaft 70510 comprises an upper pivot link 70512 and a lower pivot link 70514 extending distally therefrom. The end effector 70520 comprises a first jaw 70521*a* and a second jaw 70521*b* movable relative to each other between an open position and a closed position about a pivot pin 70511. The pivot pin 70511 is constrained within openings in the upper pivot link 70512 and the lower pivot link 70514 of the shaft 70510. The clip magazine 70530 is removably positioned within the attachable shaft 70510 and comprises a plurality of clips 70532. The clip applier 70500 further comprises a closure system 70540 and a firing system 70550. The closure system 70540 and the firing system 70550 are discussed in greater detail below.

The closure system 70540 comprises a proximal closure driver 70542 comprising a threaded portion 70543, a distal closure driver 70566 comprising a closure nut 70544, an upper closure hinge 70545*a*, and a lower closure hinge 70545*b*. The proximal closure drive 70542 is configured to rotate in response to rotary motions generated inside the housing of the clip applier. The closure drive 70542 transmits rotational motion to the threaded portion 70543 which is threadably received in the closure nut 70544. The closure drive 70542 can comprise a flexible portion to facilitate the transfer of rotational motion to the closure nut 70544. The closure nut 70544 is rotatably constrained within the shaft 70510 such that rotation of the threaded portion 70543 in a first direction will result in translation of the nut 70544 distally, and rotation of the threaded portion 70543 in a second direction—opposite the first direction—will result in translation of the nut 70544 proximally. The distal closure driver 70566 extends from the closure nut 70544 and attaches to the upper closure hinge 70545*a* and the lower closure hinge 70545*b* via a closure pin 70547. The closure pin 70547 allows the upper and lower closure hinges 70545*a* and 70545*b* to translate distally and proximally with the distal closure driver 70566 while still being rotatable about the closure pin 70547. Further to the above, the upper closure hinge 70545*a* is rotatably engaged with a proximal portion 70523*a* of the first jaw 70521*a*, and the lower closure hinge 70545*b* is rotatably engaged with a proximal portion 70523*b* of the second jaw 70521*b*. As illustrated in FIG. 48, the first jaw 70521*a* and the second jaw 70521*b* cross over each other about the pivot pin 70511 in a scissor like formation. Such an arrangement allows the first jaw 70521*a* and the second jaw 70521*b* to move toward the open position when the upper and lower closure hinges 70545*a* and 70545*b* are translated distally by the closure system 70540, and allows the first jaw 70521*a* and the second jaw 70521*b* to move toward the closed position when the upper and lower closure hinges 70545*a* and 70545*b* are translated proximally by the closure system 70540.

The clip applier 70500 further comprises a firing system 70550 comprising a firing member 70560. The firing member 70560 is translatable through the end effector between an unfired position and a fired position in response to the rotary motions that drive the closure system 70540. Other embodiments are envisioned where the closure system 70540 and the firing system 70550 are operated by two separate motors within the housing of the clip applier, for instance. The firing member 70560 is configured to advance a clip 70532 from the clip magazine 70530 into the first and second jaws 70521*a* and 70521*b* of the clip applier 70500. As illustrated in FIG. 49, the clip magazine 70530 is at least partially supported by the closure system 70540. More specifically, a biasing member, such as leaf spring 70546, for example, biases the clips 70532 toward the firing member 70560 and holds the clip magazine 70530 in position. Other embodiments are envisioned where the closure system 70540 can align, and/or guide, and/or lock the clip magazine 70530 into place within the shaft 70510. The embodiment depicted in FIGS. 48 and 49 illustrates the closure system 70540 arranged around the clip magazine 70530 to allow a larger space inside the shaft 70510 for the clip magazine 70530 and clips 70532; however, a closure system can have any suitable arrangement. The closure system 70540 is discussed in further detail below.

The threaded portion 70543 and closure nut 70544 of the closure system 70540 allows for a more precise actuation of the first and second jaws 70521*a* and 70521*b* when moving between the open position and the closed position as compared to previous clip applier arrangements that utilize a translating closure tube or cam member. Rotary encoders and/or other sensors can be used in combination with the closure system 70540 to provide even greater accuracy in determining the position of the first and second jaws 70521*a* and 70521*b*.

Turning now to FIG. 50, the clip applier 70500 further comprise protrusions 70513 and 70516 extending from the proximal end of the shaft 70510. The protrusions 70513 and 70516 may be the same shape or different shapes. The protrusions 70513 and 70516 are configured to lockingly engage slots 70572*a* and 70572*b* in the elongate shaft 70570 of the clip applier 70500 to form a bayonet connection therebetween. The slots 70572*a* and 70572*b* comprise L-shaped portions that lock the protrusions 70513 and 70516 into place when the shaft 70510 is inserted into and then rotated relative to the elongate shaft 70570. FIG. 50 further depicts a clip 70532 located within the first jaw 70521*a* and the second jaw 70521*b*. The clip 70532 and other embodiments of clips for use with a clip applier, such as clip applier 70500, are discussed in further detail below.

Figure 51A:
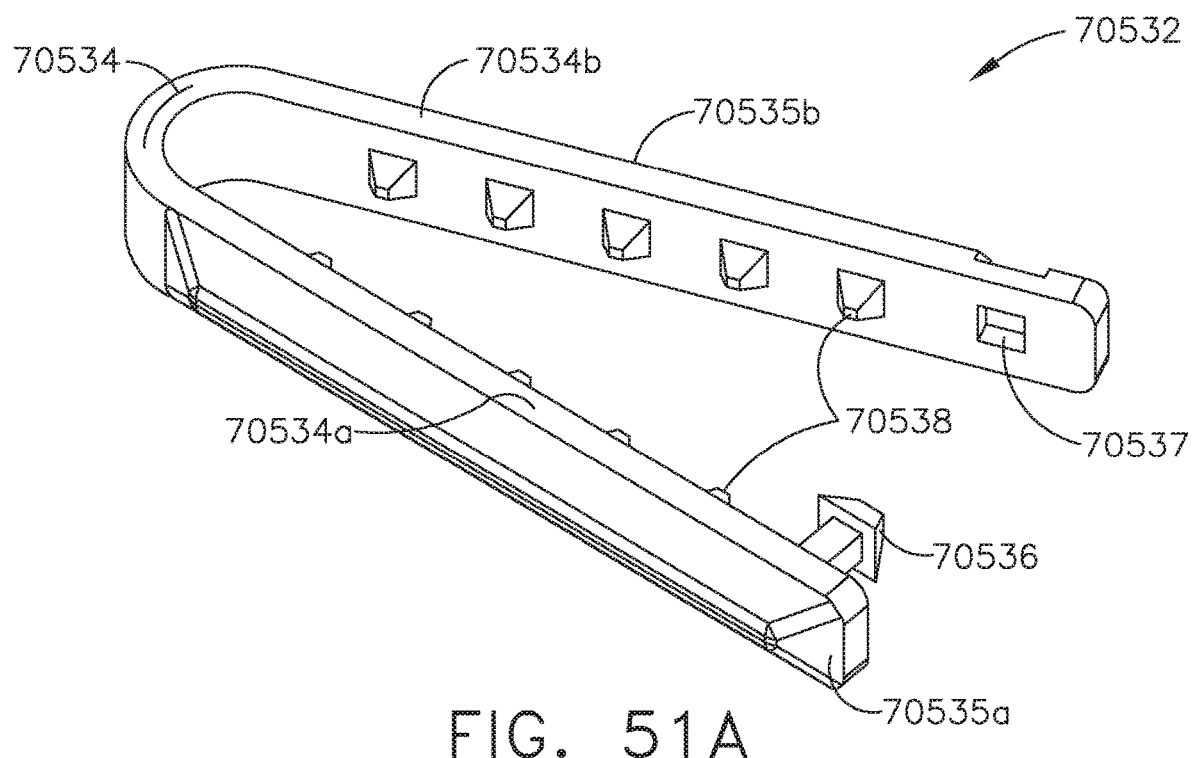
FIG. 51A is a perspective view of a clip including a flexible base.
Figure 51B:
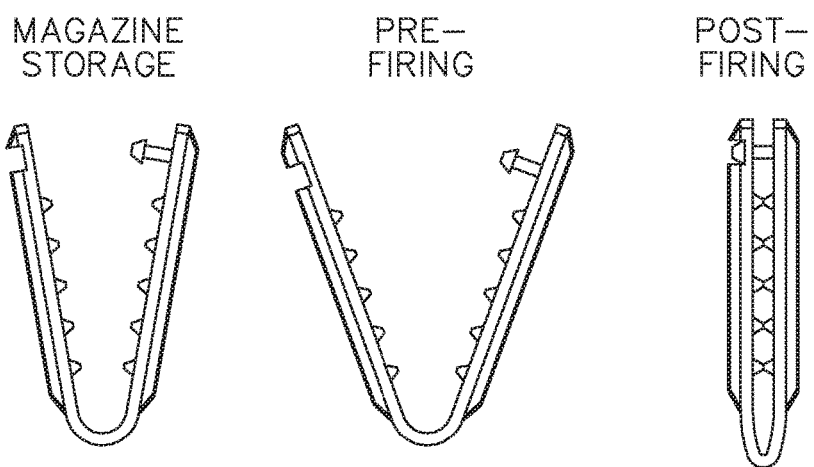
FIG. 51B is a side view of the clip of FIG. 51A in various configurations.
Figure 51C:
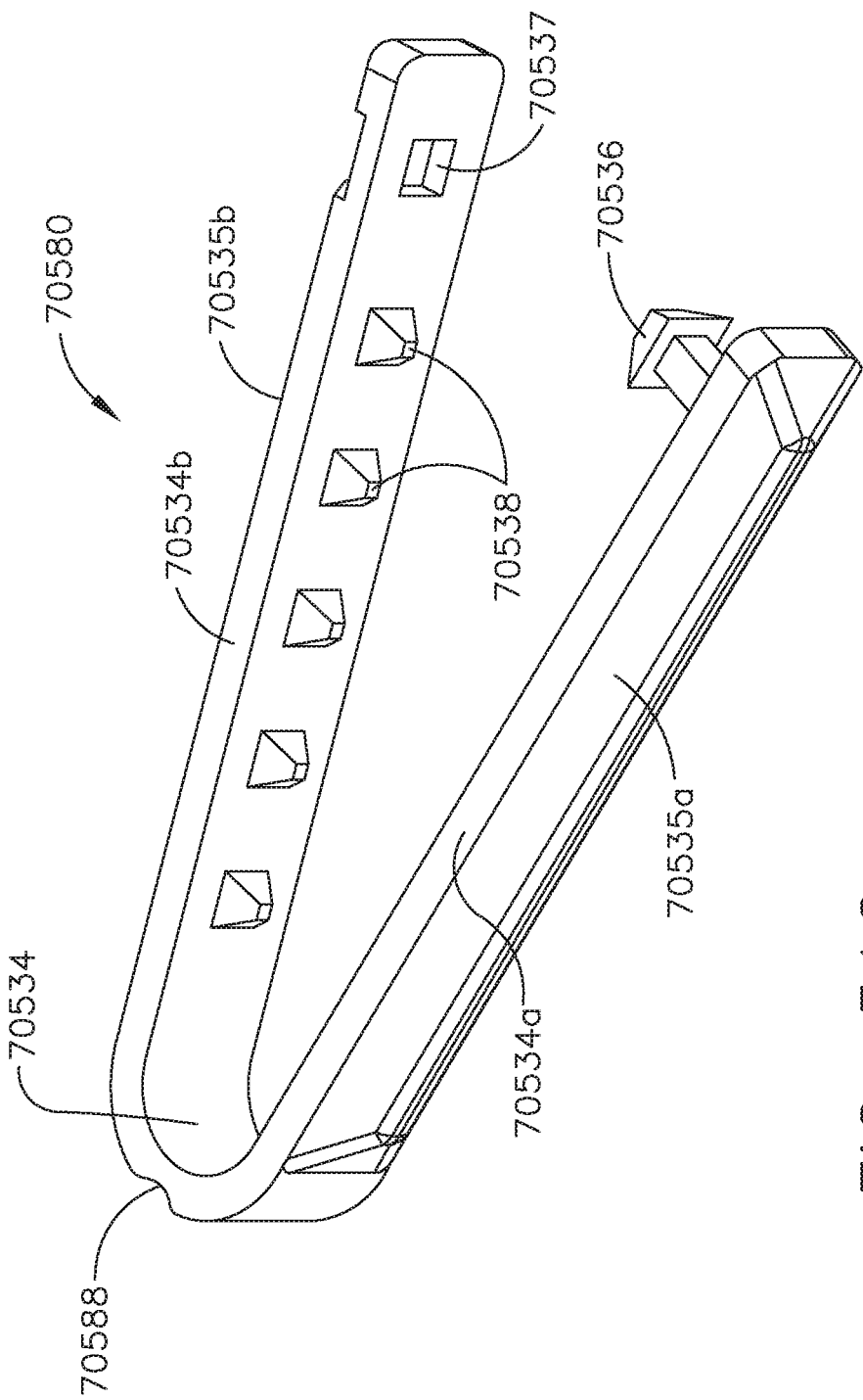
FIG. 51C is a perspective view of a clip for use with a clip applier.

Turning now to FIGS. 51A and 51B, the clip 70532 comprises a base portion 70534, a first leg 70534*a* extending from the base portion 70534, and a second leg 70534*b* extending from the base portion 70534 and opposing the first leg 70534*a*. The base portion 70534 can comprise a flexible material, such as plastic and/or any other suitable flexible material, to allow the clip 70532 to flex between multiple positions without breaking or becoming plastically deformed in an unsuitable manner. For example, the clip 70532 can be moved between a magazine storage configuration, a pre-firing configuration, and a post-firing configuration as depicted in FIG. 51B. The first leg 70534*a* comprises a reinforced region comprising a ridge 70535*a*, and the second leg 70534*b* comprises a reinforced region comprising a ridge 70535*b*. The ridges 70535*a* and 70535*b* extend along at least a portion of the first leg 70534*a* and the second leg 70534*b*, respectively. The ridges 70535*a* and 70535*b* act as a rigid backbone to prevent, or at least substantially reduce, the deformation of the first leg 70534*a* and the second leg 70534*b* during crimping. Other embodiments are envisioned where only one of the first leg 70534*a* and the second leg 70534*b* comprises a ridge. The ridges 70535*a* and/or 70535*b* may be comprised of a rigid material, such as a fiberglass-filled and/or particle-filled plastic, for example, to prevent, or at least reduce, deflection of the first leg 70534*a* and/or the second leg 70534*b* when the clip 70532 is crimped. The clip 70532 further comprises a locking portion, such as tooth 70536, for example, extending from a portion of the first leg 70534*a*. The tooth 70536 lockingly engages the edges of an opening, or window, 70537 in the second leg 70534*b* when the clip 70532 is crimped (see the post-firing configuration in FIG. 51B). Such an arrangement allows the clip 70532 to stay in a crimped state after the clip 70532 has been released from the jaws of a clip applier. Further, the clip 70532 includes grip features, such as protrusions 70538, extending from the inside surfaces of the first and second legs 70534*a* and 70534*b*. The protrusions 70538 engage tissue clamped between the first and second legs 70534*a* and 70534*b* when the clip 70532 is crimped. The protrusions 70538 prevent, or at least substantially reduce, the movement of the tissue relative to the clip 70532 after the clip 70532 is crimped around the tissue. The protrusions 70538 may be any number of shapes and sizes, such as pyramidal shapes, conical shapes, frustoconical shapes, for example, and/or any other suitable shape.

Turning now to FIGS. 51C-51F, a different clip 70580 for use with a clip applier is depicted. The clip 70580 is similar to clip 70532 in many respects. That said, the base 70534 of the clip 70580 comprises a stress relief notch 70588 on the side of the base 70534 opposite the first and second legs 70534a and 70534b. In use, the stress relief notch 70588 allows the first and second legs 70534a and 70534b to flex inwardly and then outwardly a number of times without being plastically deformed in an unsuitable manner. However, in various circumstances, the clip 70580 can be configured to yield, or deform plastically, when the clip 70580 is sufficiently compressed. Such designed or controlled yielding, in various instances, can help the clip 70580 fold into the desired shape.

Figure 52:
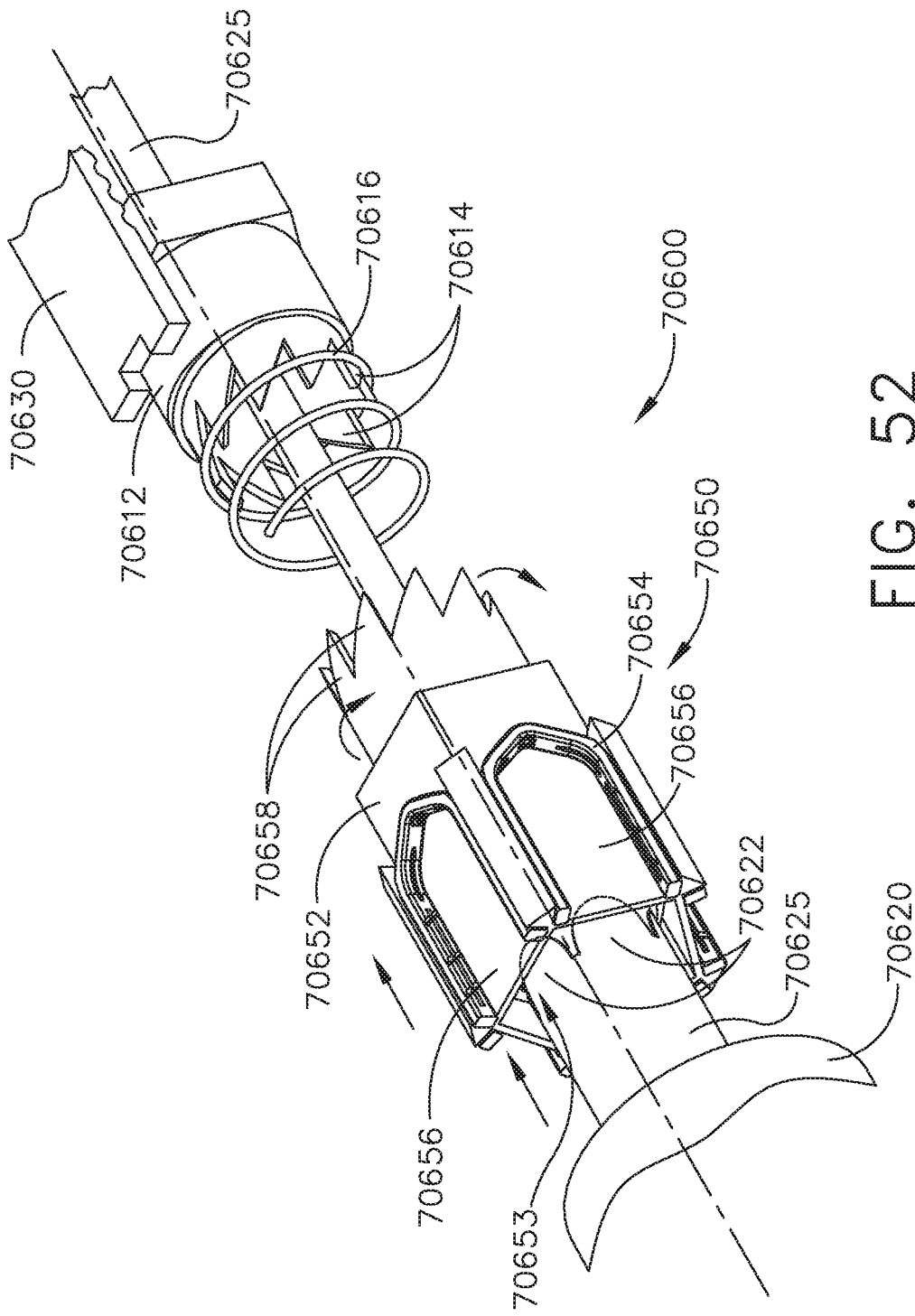
FIG. 52 is a perspective view of a clip applier including a rotatable clip magazine.
Figure 53:
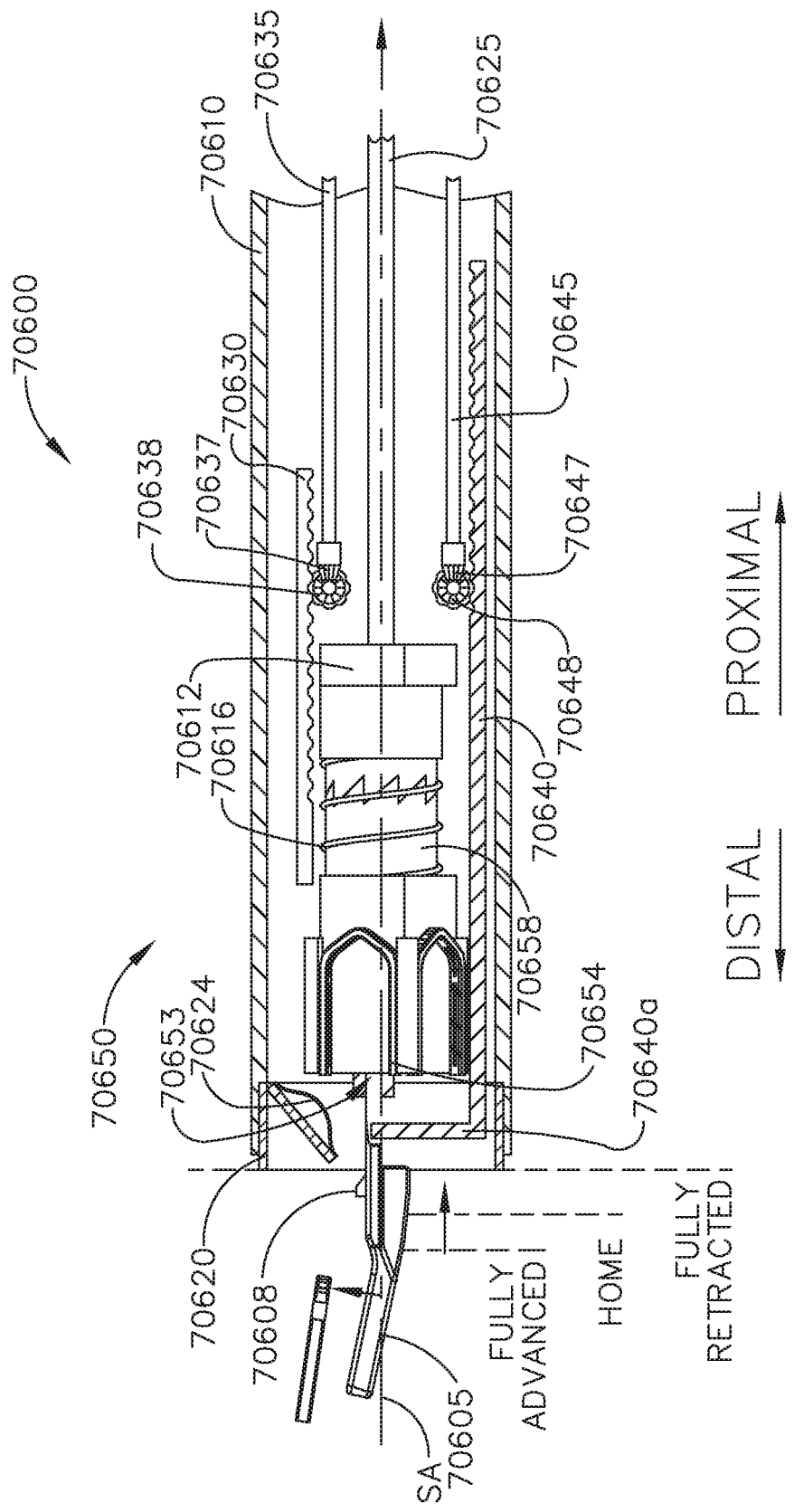
FIG. 53 is a partial cross-sectional view of the clip applier of FIG. 52 illustrating a closure tube of the clip applier in a fully retracted position.

FIGS. 52-60 depict a clip applier 70600. Turning now to FIG. 53, the clip applier 70600 comprises a shaft 70610 extending from a housing, an end effector 70605 extending from the shaft 70610, and a rotatable clip magazine 70650. The end effector 70605 comprises a first jaw and a second jaw that are movable relative to each other between an open position and a closed position, similar to the first jaw 70123a and the second jaw 70123b of the clip applier 70100 discussed above. The rotatable clip magazine 70650 is rotatably and slidably supported within the clip applier 70600. More specifically, the rotatable clip magazine 70650 is rotatable about shaft axis SA and translatable along shaft axis SA. The shaft axis SA is defined by the shaft 70610. Further detail regarding how the clip magazine 70650 is supported within the clip applier 70600 is provided below.

Referring to FIG. 52, the rotatable clip magazine 70650 comprises a body portion 70652 including five sides, each of which comprises a clip channel 70656 configured to removably store a clip 70654 therein. The body portion 70652 further comprises an opening 70653 that extends through the body portion 70652. In the illustrated embodiment, the body portion 70652 is pentagonal in shape, for example; however, other embodiments are envisioned in which the opening 70653 comprises different shapes to allow for more than or less than five clip channels 70656 and, therefore, more than or less than five clips 70654 stored in the rotatable clip magazine 70650. In at least one embodiment, the clips 70654 comprise a clip width of 0.080", a clip thickness of 0.03", and a clip length of 0.310" (for a Lig 5 Clip) or 0.315" (for an ER320 Clip), for example; however, clips having any suitable size can be used. Moreover, it is envisioned that the clips stored in the clip magazine 70650 will have the same, or at least substantially the same size; however, alternative embodiments are envisioned in which clips having different sizes may be stored in the same clip magazine. Further, in at least one embodiment, the overall diameter of the entire rotatable clip magazine 70650 is 0.996", for example; however, the clip magazine 70650 can have any suitable diameter—including diameters which can permit the clip magazine 70650 to be inserted through a trocar. The rotatable clip magazine 70650 further includes a clocking portion, such as teeth 70658, for example, extending proximally from the clip magazine 70650. The clip applier 70600 comprises several drives and drivers which define the motion and/or operating sequence of the clip applier 70600, as described in further detail below.

Referring again to FIG. 53, the clip applier 70600 further comprises a closure tube 70620, a feeder member 70630, and a firing member 70640. The closure tube 70620 comprises a closure drive 70625 extending proximally from the closure tube 70620. The closure drive 70625 extends through the opening 70653 in the clip magazine 70650 and is operably engaged with an actuator inside the housing of the clip applier 70600. The clip magazine 70650 is supported on at least a portion of the closure drive 70625. The closure tube 70620 is at least partially supported and aligned within a recess in the shaft 70610. The closure tube 70620 is movable between a plurality of positions, such as a fully retracted position, a home position, and a fully advanced position (see FIGS. 53 and 54A). Similar to the crimping drive 70180 of the clip applier 70100, the closure tube 70620 is configured to move the first jaw and the second jaw of the end effector 70605 toward and away from each other. When the closure tube 70620 moves distally, the closure tube 70620 cammingly engages the first and second jaws to move the first and second jaws to the closed position and, when the closure tube 70620 moves proximally, the closure tube 70620 engages jaw cams on each of the first and second jaws to move the first and second jaws to the open position. That said, any suitable jaw opening and closing arrangement could be used.

The feeder member 70630 is aligned with one of the clip channels 70656 of the rotatable clip cartridge 70650, and is configured to advance a clip 70654 out of the clip channel 70656 that is aligned with the feeder member 70630 toward the end effector 70605. The feeder member 70630 is translatable linearly through the clip applier 70600 by a feeder gear 70638 and a feeder drive 70635 which are operably engaged with a rack portion of the feeder member 70630. The feeder drive 70635 comprises a pinion gear 70637 at the distal end thereof which is operably engaged with the feeder gear 70638 such that, as the feeder drive 70635 is rotated, the feeder member 70630 is translated linearly through the clip applier 70600. The feeder drive 70635 is operably engaged with a first motor inside the housing of the clip applier 70600. The first motor transmits rotational motion to the feeder drive 70635. Similar to the operation of the feeder member 70630, the firing member 70640 is translatable linearly through the clip applier by a firing gear 70648 and a firing drive 70645 which are operably engaged with a rack portion of the firing member 70640. The firing drive 70645 comprises a pinion gear 70647 on the distal end thereof which is engaged with the firing gear 70648 such that, as the firing drive 70645 is rotated, the firing member 70640 is translated linearly through the clip applier 70600. Further, the firing drive 70645 is operably engaged with a second motor inside the housing of the clip applier 70600. The second motor transmits rotational motion to the firing drive 70645. Other embodiments are envisioned where the feeder drive 70635 and the firing drive 70645 are rotatable by the same motor utilizing a transmission. Further, other embodiments are envisioned, and are described further below, where the feeder member 70630 and the firing member 70640 translate together through the clip applier 70600. Operation of the feeder member 70630 and firing member 70640 are also described in greater detail below.

Referring primarily to FIG. 53, the firing member 70640 comprises a distal portion 70640a extending therefrom that is configured to advance a clip 70654 into the end effector. The shaft 70610 further includes a ground portion 70612 mounted to the shaft 70610 and aligned with the clip magazine 70650. The ground portion 70612 is mounted to the shaft 70610 such that the ground portion 70612 is not movable, translatable, and/or rotatable relative to the shaft 70610. The ground portion 70612 includes a clocking portion, such as teeth 70614, for example, extending distally therefrom as illustrated in FIG. 54B. The teeth 70614 of the ground portion 70612 are aligned, or at least substantially aligned, with the teeth 70658 of the rotatable clip magazine 70650. Further, the ground portion 70612 supports a biasing member, such as spring 70616, for example, thereon. The spring 70616 biases the clip magazine 70650 distally toward the closure tube 70620 and the end effector 70605, as illustrated in FIG. 54A. Other embodiments are envisioned where the spring comprises a leaf spring and the clip applier 70600 further comprises a track and the leaf spring can be configured to both index the clip magazine 70650 and prevent the clip magazine 70650 from counter rotation. In any event, the rotation of the clip magazine 70650 about the shaft axis SA and translation of the clip magazine 70650 along shaft axis SA is described in further detail below.

Referring primarily to FIG. 52, the closure tube 70620 includes clocking channels 70622 located radially around the closure drive 70625. The closure drive 70625 rotatably and slidably supports the rotatable clip magazine 70650 thereon as discussed above. The clocking channels 70622 are engaged with protrusions within the opening 70653 of the clip magazine 70650 to rotatingly lock the clip magazine 70650 into place relative to the closure tube 70620 when the closure tube is in the home position or the fully advanced position. When the closure tube 70620 is moved to the fully retracted position, as illustrated in FIG. 53, the spring 70616 moves/biases the clip magazine 70650 toward the closure tube 70620 resulting in the clocking channels 70622 becoming disengaged from the protrusions within the opening 70653 of the clip magazine 70650. As such, the clip magazine 70650 can rotate freely about shaft axis SA. Further, when the closure tube 70620 is moved to the fully retracted position, the teeth 70658 of the clip magazine 70650 engage the teeth 70614 of the ground portion 70612 to rotate (i.e., cycle) the clip magazine 70650. More specifically, the teeth 70658 and the teeth 70614 are structured to rotate the clip magazine 70650 about the shaft axis SA a predefined amount of degrees based on the spacing and angles of the teeth 70658 relative to the teeth 70614. The reader will appreciate that the spacing and angles of the teeth 70658 relative to the teeth 70614 can be designed to generate a suitable degree of rotation for the clip magazine 70650 about shaft axis SA. In the embodiment depicted in FIGS. 52-54A, the teeth 70658 and the teeth 70614 are spaced and aligned such that, when they are engaged, the clip magazine 70650 rotates 72 degrees to align an adjacent clip 70654 with the feeder member 70630. After the clip magazine 70650 is cycled, the closure tube 70620 can be moved distally from the fully retracted position to the home position (FIG. 54A) resulting in the clocking channels 70622 engaging the protrusions in the opening 70653 of the clip magazine 70650 to lock the rotation of the clip magazine 70650 as discussed above. Usage of the clip applier 70600 to advance, form, and fire a clip 70654 is describe in further detail below.

Figure 55:
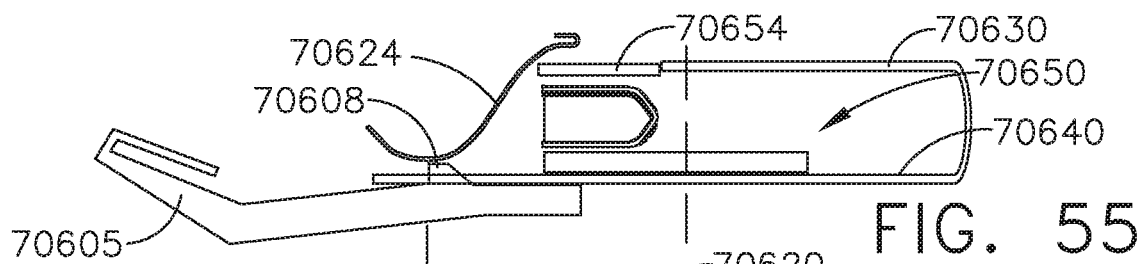
FIG. 55 is a partial cross-sectional view of the clip applier of FIG. 52 illustrating clips stored in the rotatable clip magazine prior to being advanced, illustrated with some components removed.
Figure 56:
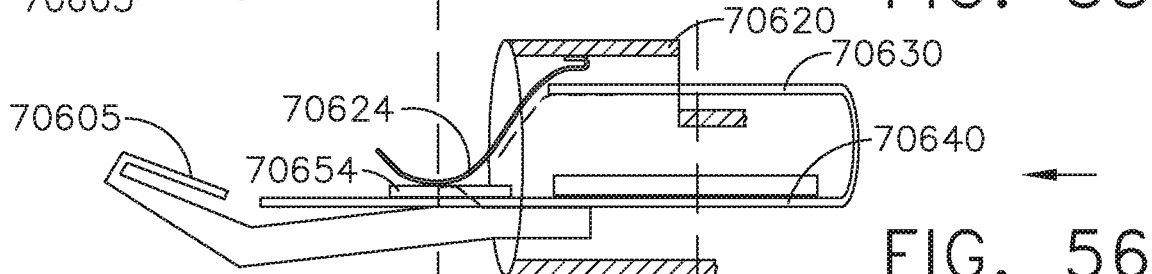
FIG. 56 is a partial cross-sectional view of the clip applier of FIG. 52 illustrating a clip being advanced from the rotatable clip magazine by a feeder member of the clip applier.
Figure 57:
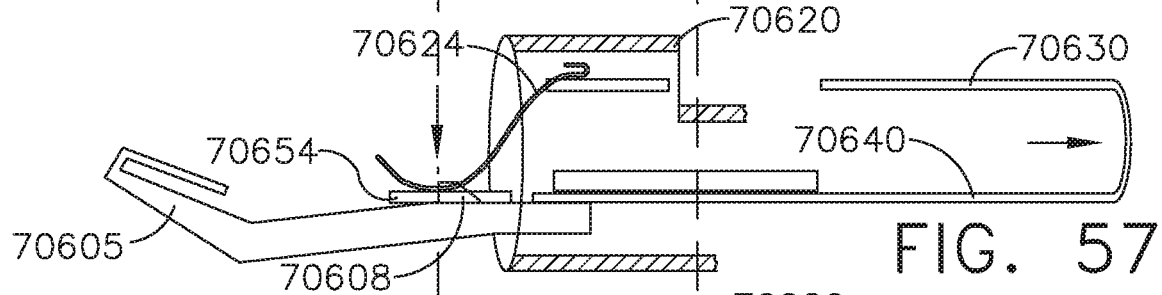
FIG. 57 is a partial cross-sectional view of the clip applier of FIG. 52 illustrating the feeder member retracted.

As mentioned above, the feeder member 70630 and firing member 70640 can be translatable together. For simplicity, FIGS. 55-60 illustrate the functions of clip applier 70600 where the feeder member 70630 and firing member 70640 move together to feed and fire a clip 70654 from the rotatable clip magazine 70650. Turning now to FIGS. 55 and 56, a clip 70654 is advanced from the rotatable clip magazine 70650 into engagement with a biasing member, such as a leaf spring 70624, for example, of the closure tube 70620 by the feeder member 70630. The leaf spring 70624 biases and guides the clip 70654 onto the top of the firing member 70640, as illustrated in FIG. 56. When the firing member 70640 and feeder member 70630 are retracted, the clip 70654 is moved further downward by the leaf spring 70624 and seated around pre-form features, such as protrusions 70608, for example, depicted in FIG. 57. Protrusions 70608 can be similar to protrusions 70126a and 70126b described above (See FIGS. 35A and 35B). One protrusion 70608 is located on one jaw of the end effector 70605, and another protrusion 70608 is located on another jaw of the end effector 70605.

Figure 58:
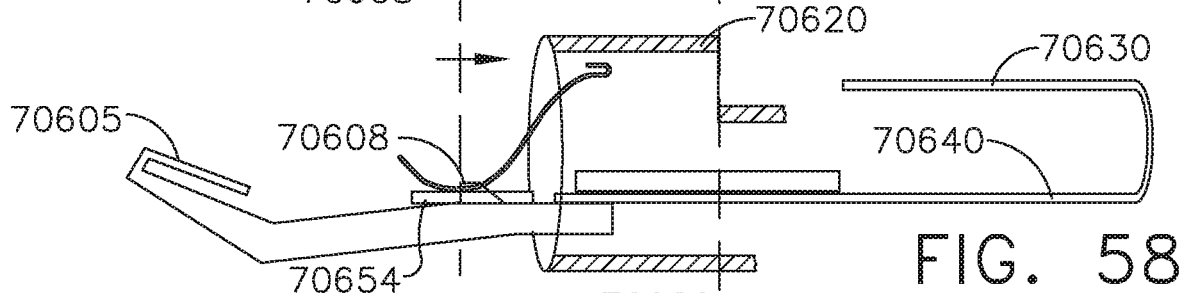
FIG. 58 is a partial cross-sectional view of the clip applier for FIG. 52 illustrating a closure tube of the clip applier in a fully retracted position.
Figure 59:
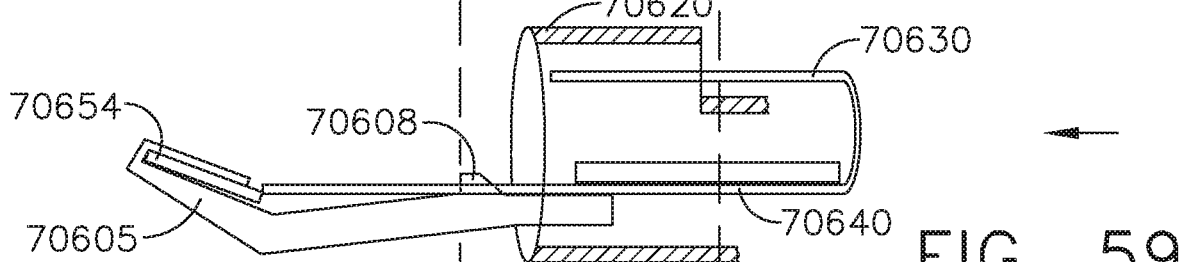
FIG. 59 is a partial cross-sectional view of the clip applier of FIG. 52 illustrating the closure tube in a home position and a firing member advancing a clip, illustrated with some components removed.
Figure 60:
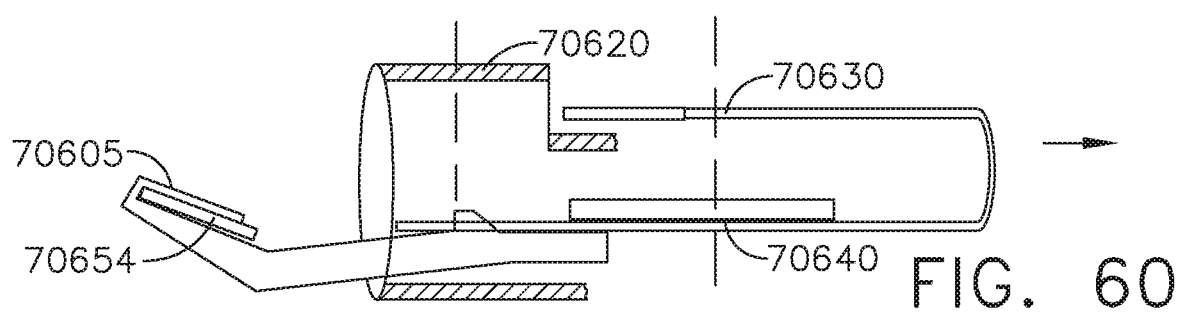
FIG. 60 is a partial cross-sectional view of the clip applier of FIG. 53 illustrating the firing member retracted and the closure tube in a fully advanced position, illustrated with some components removed.

When the closure tube 70620 is in the fully retracted position, referring to FIG. 58, the jaws of the clip applier 70600 are in the open position and the protrusions 70608 expand the clip 70654 from a storage configuration into a firing configuration—similar to the expansion of clip 70140 described above in connection with FIGS. 35A and 35B. When the closure tube 70620 is moved to the fully retracted position, as described above, the rotatable clip magazine 70650 is rotated (i.e., cycled) about the shaft axis SA to position another clip 70654 into alignment with the feeder member 70630. Turning to FIG. 59, the firing member 70640 can be moved toward the end effector 70605 to advance the clip 70654 over the protrusions 70608 and into the end effector 70605. As discussed above in connection with protrusions 70126a and 70126b, the protrusions 70608 can comprise angled portions that allow the clip 70654 to slide over the protrusions 70608 when advanced distally by the firing member 70640. Once the clip 70654 is positioned in the end effector 70605, the closure tube 70620 can be moved to the fully advanced position (FIG. 60) to move the jaws from the open position to the closed position to crimp the clip 70654 positioned between the jaws.

Because the feeder member 70630 and the firing member 70640 translate together, further to the above, the feeder member 70630 advances another clip 70654 (i.e., the clip that was rotated into position when the closure tube 70620 was fully retracted) from the clip cartridge 70650 down onto the firing member 70654 with the aid of the leaf spring 70624, as discussed above, when the firing member 70640 advances a clip 70654 into the end effector 70605. Again, the firing member 70640 and the feeder member 70630 can be retracted to allow the new clip 70654 to be biased downward by the leaf spring 70624 and seated around the protrusions 70608. The new clip 70654 can then be expanded to the firing configuration as clip magazine 70650 is cycled, and then the new clip 70654 can be advanced into the end effector 70605 for crimping as discussed above. The process discussed above can be repeated until the clip magazine 70650 has been spent. The reader will appreciate that the closure tube 70620 can be moved between the home position (FIGS. 56 and 57) and the fully advanced position (FIG. 60) to crimp and release a clip 70654 within the end effector 70605 without cycling the clip magazine 70650. This allows the jaws of the end effector 70605 to move between the open and closed positions without cycling the clip magazine 70650 and/or ejecting another clip from the clip magazine 70650.

Figure 61:
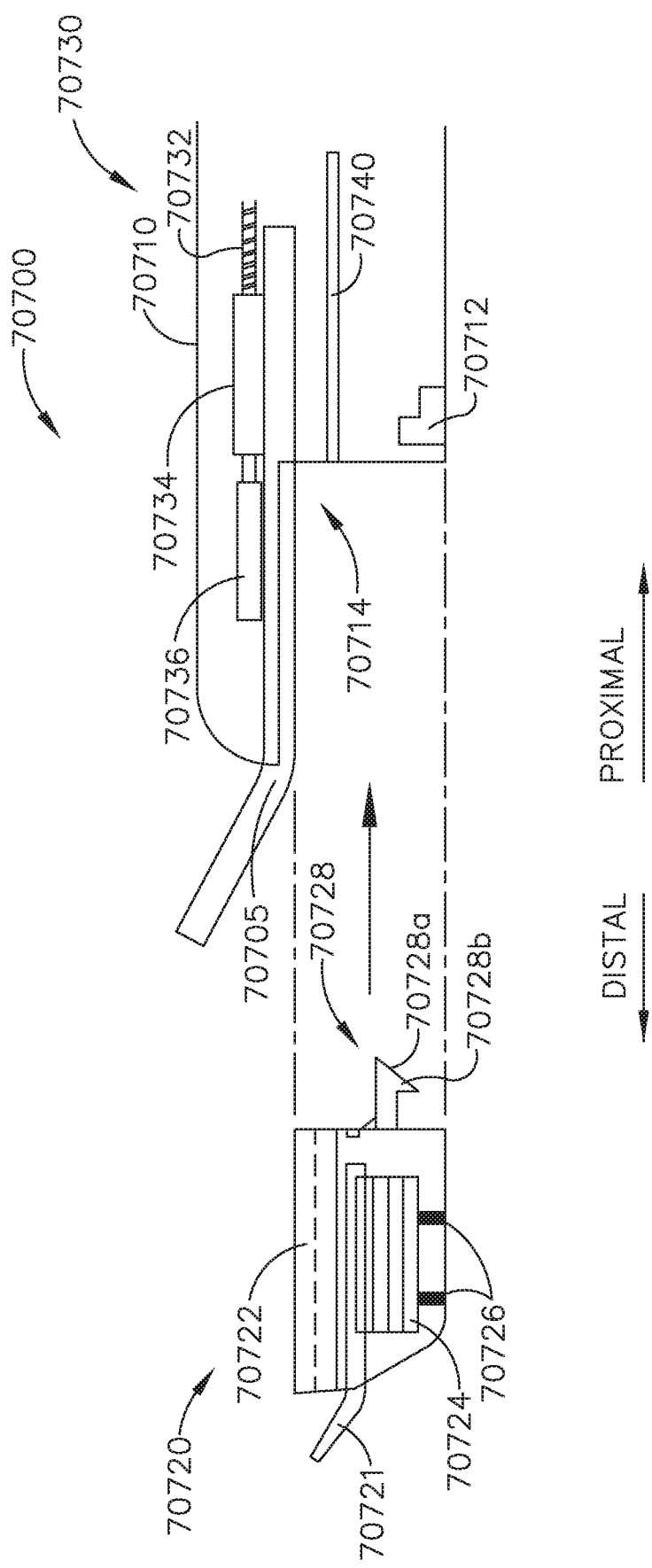
FIG. 61 is a partial cross-sectional view of a clip applier comprising a replaceable cartridge.

FIG. 61 depicts a clip applier 70700 in accordance with at least one embodiment. The clip applier 70700 comprises a shaft 70710 extending from a housing, an end effector 70705 extending from the shaft 70710, and a clip cartridge 70720 that is releasably attachable to the clip applier 70700. The end effector 70705 comprises a first jaw and a second jaw movable relative to each other, similar to the first and second jaws 70123a and 70123b discussed above. The clip applier 70700 further comprises a firing system 70730 that comprises a rotatable drive 70732 which is operably responsive to a motor inside the housing of the clip applier 70700. The rotatable drive 70732 comprises a threaded portion. The firing system 70730 further includes a firing member 70736 and a firing nut 70734. The firing nut 70734 is threadably received on the threaded portion of the rotatable drive 70732. The firing nut 70734 is rotatably constrained within the clip applier 70700 such that the rotation of the rotatable drive 70732 translates the firing nut 70734 through the clip applier 70700. The firing member 70736 is engaged with the firing nut 70734 and translates into the first and second jaws of the end effector 70705 in response to translation of the firing nut 70734 by the rotatable drive 70732. Attachment of the clip cartridge 70720 to the clip applier 70700 is described in greater detail below.

The clip applier 70700 further comprises a docking region, or recess 70714, in the distal end of the clip applier 70700, as illustrated in FIG. 61. The clip cartridge 70720 comprises a body portion 70722 that is slidably receivable in the recess 70714 of the clip applier 70700. A locking feature 70728 extends proximally from the clip cartridge 70720. The locking feature 70728 includes an angled surface 70728*a* at the proximal end thereof and a detent 70728*b* extending downwardly, although the locking feature 70728 can include any suitable arrangement. The locking feature 70728 engages a protrusion 70712 of the shaft 70710 when the clip cartridge 70720 is docked within the recess 70714. More specifically, the angled surface 70728*a* slides over the protrusion 70712 and the downwardly extending detent 70728*b* locks into place proximal to the protrusion 70712, thus locking the clip cartridge 70720 to the clip applier 70700. In such instances, the locking feature 70728 deflects as the angled surface 70728*a* slides over the protrusion 70712 and then resiliently returns to, or at least toward, its undeflected configuration, when the detent 70728*b* locks into place. A sufficient distal pulling motion can cause the locking feature 70728 to deflect and release the clip cartridge 70720 from the clip applier 70700. Operation of the clip applier 70700 is described in further detail below.

The clip cartridge 70720 further comprises a ramp portion 70721, a plurality of clips 70724 positioned in a stack, and biasing members, such as springs 70726, for example. The clips 70724 are biased toward the ramp portion 70721 by the springs 70726. In fact, the top clip 70724 in the stack of clips is biased into the ramp portion 70712 by the springs 70726. When the clip cartridge 70720 is docked with the clip applier 70700, as discussed above, the ramp portion 70721 aligns with a feeder drive 70740 of the clip applier 70700. The feeder drive 70740 is operably responsive to an actuator within the housing of the clip applier 70700. The feeder drive 70740 is configured to reciprocatingly actuate into the ramp portion 70721. To accommodate an angled portion within the ramp portion 70721 the feeder drive 70740 can be flexible. The feeder drive 70740 feeds the top clip 70724 in the stack of clips through the ramp portion 70721 and into the end effector 70720. Once in the end effector 70705, the clip 70724 can be advanced further distally into the first and second jaws of the end effector 70705 by translation of the firing member 70736, as discussed above. Once located in the first and second jaws, the clip 70724 can be crimped by a crimping drive. The feeder drive 70740 can be retracted, allowing another clip 70724 to be biased into the ramp portion 70721. The feeder drive 70740 can advance the new clip 70724 through the ramp portion 70721 and into the first and second jaws of the end effector 70705 as discussed above. The process discussed above can be repeated until all of the clips 70724 in the clip cartridge 70720 have been depleted, and/or until a suitable number of clips have been applied to the tissue.

Figure 62B:
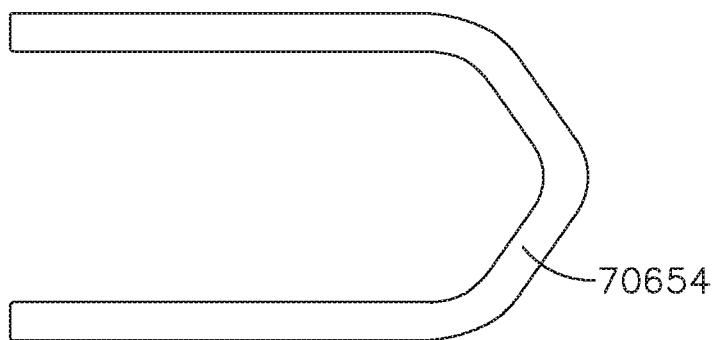
FIG. 62B is a plan view of a clip for use with the rotatable clip magazine of FIG. 62A.
Figure 62A:
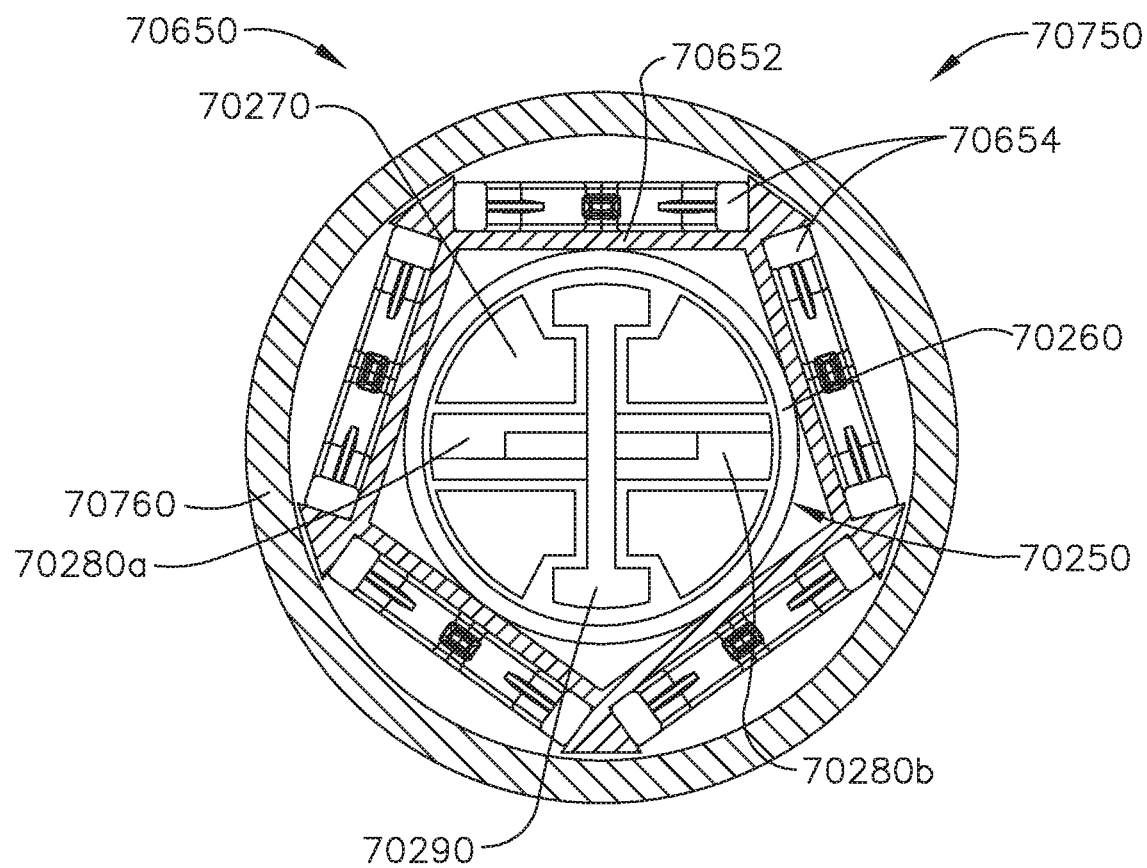
FIG. 62A is a cross-sectional end view of a rotatable clip magazine.

FIG. 62A depicts a clip applier system 70750 in accordance with at least one embodiment. The clip applier system 70750 comprises a shaft 70760 extending from a housing, the clip applier 70250 depicted in FIG. 42 positioned at least partially within the shaft 70760, and the rotatable clip magazine 70650 depicted in FIGS. 52-60 positioned within the shaft 70760. A feeder member is configured to advance the clips 70654 from the rotatable clip magazine 70650—one at a time—into the first and second jaws 70280*a* and 70280*b* of the clip applier 70250. Once located within the first and second jaws 70280*a* and 70280*b*, the clip 70654 can be crimped as discussed above in relation to FIGS. 42A and 42B. Once the clip 70654 is crimped, the rotatable clip magazine 70650 can be cycled (i.e., rotated) to position another clip 70654 for advancement into the first and second jaws 70280*a* and 70280*b* of the clip applier 70250 by the feeder member. This process can continue until all of the clips 70654 in the rotatable clip magazine 70650 have been spent. After all of the clips 70654 have been spent, the rotatable clip magazine 70650 can be replaced with another rotatable clip magazine 70650 containing a full complement of clips 70650. Other embodiments are envisioned where the spent rotatable clip magazine 70650 can be detached from the clip applier system 70750, reloaded with clips 70650, and then re-attached to the clip applier system 70750 for further use.

Figures 63A, 63B:
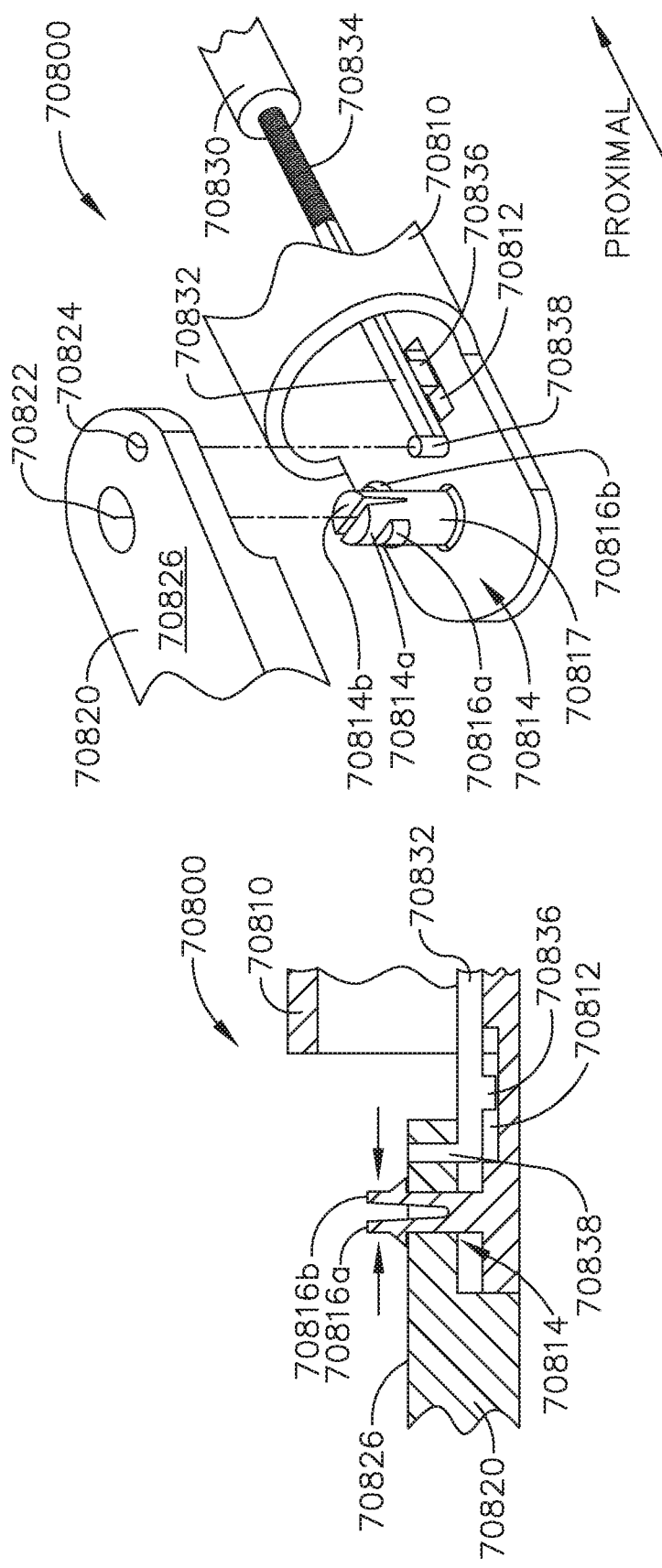
FIG. 63A is a perspective view of a releasable clip cartridge including an articulation joint.
FIG. 63B is a partial cross-sectional view of the releasable clip cartridge and articulation joint of FIG. 63A.

Turning now to FIGS. 63A and 63B, an articulation joint 70800 for use with a clip applier is illustrated. The articulation joint 70800 releasably couples a clip cartridge 70820 to a shaft 70810 of a clip applier. The shaft 70810 comprises an articulation pivot, or pivot pin 70814, extending from the inside of the shaft 70810. The pivot pin 70814 comprises a base portion 70817, a first leg 70814*a* extending from the base portion 70817, and a second leg 70814*b* extending from the base portion 70817 and opposing the first leg 70814*a*. The first and second legs 70814*a* and 70814*b* extend away from each other. The first leg 70814*a* comprises a first detent, or shoulder, 70816*a* extending outwardly from the first leg 70814*a*, and the second leg 70814*b* comprises a second detent, or shoulder, 70816*b* extending outwardly from the second leg 70814*b*. The clip cartridge 70820 comprises a first opening 70822 and, also, a second opening 70824 positioned adjacent and lateral to the first opening 70822. The first opening 70822 is centered in the clip cartridge 70820 and rotatably receives the pivot pin 70814 when the clip cartridge 70820 is attached to the shaft 70810. The first leg 70814*a* and the second leg 70814*b* flex towards each other when the first opening 70822 is slid onto the pivot pin 70814 due to angled surfaces at the end of each of the first leg 70814*a* and second leg 70814*b* (See FIG. 63B). As the first leg 70814*a* and second leg 70814*b* flex toward each other, the pivot pin 70814 can slide through the first opening 70822 until the first and second detents 70816*a* and 70816*b* clear the first opening 70822, as illustrated in FIG. 63B. Once the first and second detents 70816*a* and 70816*b* clear the first opening 70822, the first and second legs 70814*a* and 70814*b* can expand to lock the clip cartridge 70820 to the pivot pin 70814. More specifically, the bottom surfaces of the first and second detents 70816*a* and 70816*b* rest on an outer surface 70826 of the clip cartridge 70822 preventing the clip cartridge 70820 from being detached from the pivot pin 70814 unless a sufficient force is applied that exceeds a predetermined, or designed, force threshold. The reader will appreciate that, with force, a user of the clip applier can attach and detach the clip cartridge 70820 to the shaft 70810. Articulation of the clip cartridge about the pivot pin 70814 is described in further detail below.

The clip applier depicted in FIGS. 63A and 63B further comprises a rotatable output 70830 that is operably responsive to a motor located within the housing of the clip applier. The rotatable output 70830 is threadably engaged with a threaded portion 70834 of an articulation bar 70832. Rotation of the rotatably output 70830 in a first direction translates the articulation bar 70832 distally, and rotation of the rotatable output 70830 in a second, or opposite, direction translates the articulation bar 70832 proximally. The articulation bar 70832 comprises a downwardly extending protrusion 70836 that is slidably received in a slot 70812 defined in the shaft 70810. The protrusion 70836 and slot 70812 guide the articulation bar 70832 as the articulation bar 70832 translates and limit relative lateral motion between the articulation bar 70832 and the shaft 70810. The articulation bar 70832 further comprises an upwardly extending protrusion 70838 which is received in the second opening 70824 of the clip cartridge 70820 when the clip cartridge 70820 is attached to the shaft 70810. In use, the distal translation of the articulation bar 70832 will rotate the clip cartridge 70820 about the pivot pin 70814 in a first direction and the proximal translation of the articulation bar 70832 will rotate the clip cartridge 70820 about the pivot pin 70814 in a second, or opposite, direction. The articulation bar 70832 can be flexible to allow the articulation bar 70832 to flex as needed when the clip cartridge 70820 is articulated about the pivot pin 70814.

Figure 64:
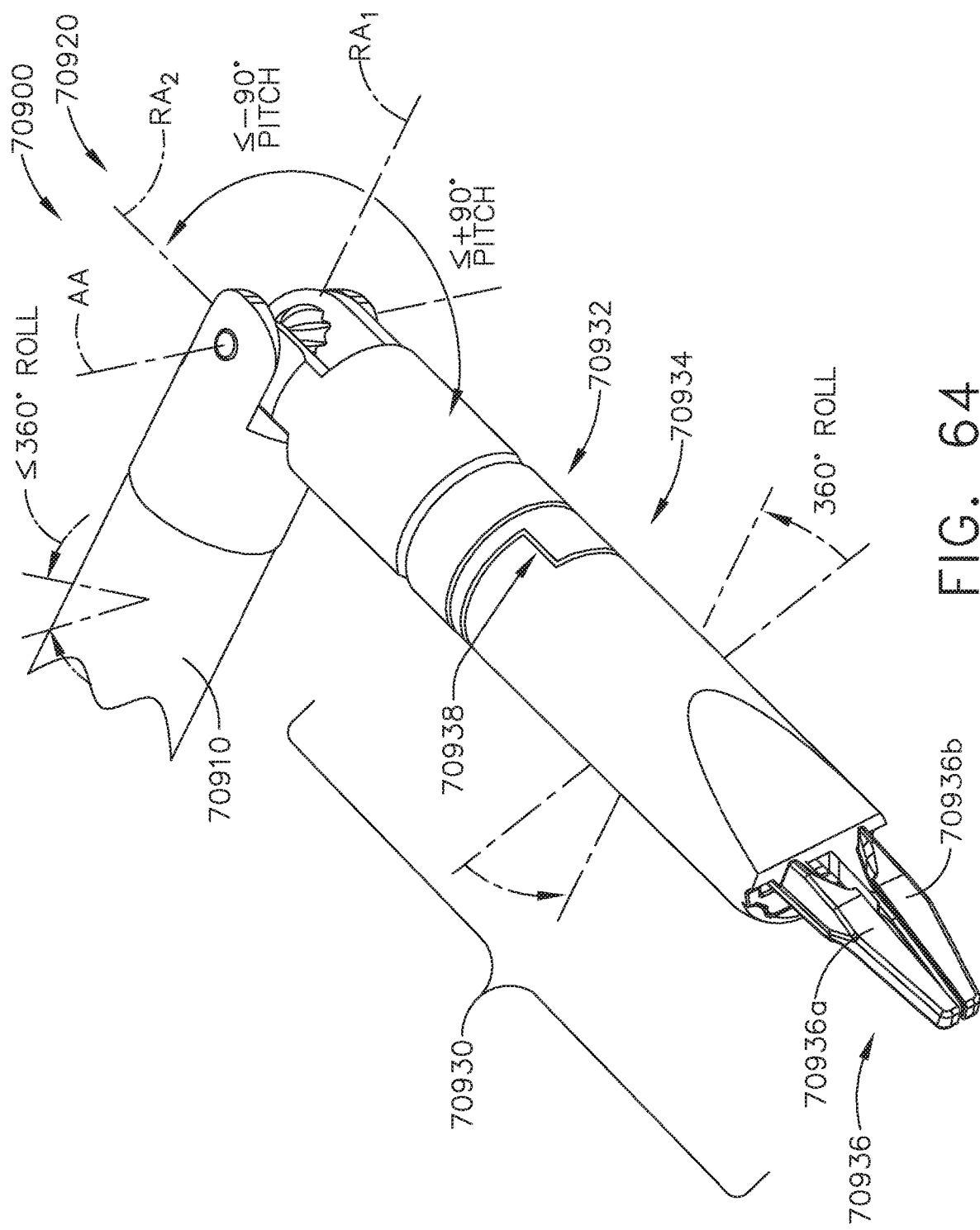
FIG. 64 is a perspective view of a clip applier including an articulation joint.

FIG. 64 depicts a clip applier 70900 in accordance with at least one embodiment. The clip applier 70900 comprises an elongate shaft 70910, an articulation joint 70920, and a distal head 70930. The articulation joint 70920 extends from the elongate shaft 70910 and the distal head 70930 extends from the articulation joint 70920. The distal head 70930 comprises a distal shaft 70932 attached to the articulation joint 70920, an end effector 70936 including a first jaw 70936a and a second jaw 70936b, and a clip cartridge 70934. The first jaw 70936a and second jaw 70936b are movable relative to each other between open and closed positions by any suitable drive system, such as the drive systems disclosed herein, for example. The clip cartridge 70934 stores a plurality of clips which can be advanced into the end effector 70936 and crimped by the first jaw 70936a and the second jaw 70936b. The clip cartridge 70934 is removably attachable to the distal shaft 70932 via a keying arrangement 70938. Other embodiments are envisioned where the clip cartridge 70934 is not removably attachable to the distal shaft 70932. The elongate shaft 70910 defines a first roll axis $RA_1$ and the distal head 70930 defines a second roll axis $RA_2$. The elongate shaft 70910 and the distal head 70930 are articulable relative to each other about articulation axis AA via the articulation joint 70920. The arrangement depicted in FIG. 64 is attachable—via the elongate shaft 70910—to a plurality of clip applier handle types, such as, a standard handle (i.e., a wand grip) and/or a pistol grip handle, for example. Depending on the type of handle that is attached to the elongate shaft 70910, different actuations of, or within, the handle may perform different actuations of the arrangement depicted in FIG. 64 about the first roll axis $RA_1$, the second roll axis $RA_2$, and the articulation axis AA. These actuations are described in further detail below.

If the elongate shaft 70910 is attached to a standard handle (i.e., a wand handle), referring still to FIG. 64, the elongate shaft 70910, the articulation joint 70920, and the distal head 70930 are all rotatable about the first roll axis $RA_1$ by the clinician rotating the wand handle. Further, a rotary knob on the wand handle is operably engaged with the elongate shaft 70910, through an electric motor and/or control system, for example, such that manually rotating the rotary knob will result in the distal head 70930 rotating about the second roll axis $RA_2$. Further, articulation of the distal head 70930 relative to the elongate shaft 70910 about articulation axis AA is driven by an articulation driver operably engaged with a motor housed within the wand handle, for example. If the elongate shaft 70910 is attached to a pistol grip handle, such as the handle 700 discussed above, for example, the elongate shaft 70910, the articulation joint 70920, and the distal head 70930 are all rotatable about the first roll axis $RA_1$ by a rotary knob, for example. Further, the distal head 70930 is rotated about the second roll axis $RA_2$ by a dedicated motor within the pistol grip handle. Further still, articulation of the distal head 70930 relative to the elongate shaft 70910 about articulation axis AA is induced by an articulation driver operably engaged with a motor housed within the pistol grip handle. The reader should appreciate that, depending on the type of handle attached to the arrangement depicted in FIG. 64, rotation of the elongate shaft 70910 about the first roll axis $RA_1$ can be accomplished by rotating the entire handle manually, rotation of a rotary knob engaged with the elongated shaft, and/or by a dedicated motor inside the handle. Further, the rotation of the distal head 70930 about the second roll axis $RA_2$ can be accomplished by rotation of a rotary knob engaged within the elongate shaft 70910 or by a dedicated motor inside the handle.

A clip applier jaw assembly 70950, or half of the jaw assembly 70950, and a clip leg 70954 of a clip are illustrated in FIG. 65. As can be seen in FIG. 65, the clip applier jaw assembly 70950 comprises a first jaw 70950a which includes a base 70952, a first leg 70952a extending from the base 70952, and a second leg 70952b extending from the base 70952. The first leg 70952a and second leg 70952b oppose one another and define a receiving area 70953 therebetween. The clip leg 70954 is received in the receiving area 70953 but, notably, part of the clip leg 70954 cross-section is not positioned within the receiving area 70953. Thus, only portions of the clip leg 70954 cross-section are supported by the first jaw 70950a. Other arrangements exist where the receiving area 70953 is substantially the same depth and width as the clip leg 70954 of the clip such that all, or at least substantially all, of the cross-section of the clip leg 70954 is positioned within the receiving area 70953 and supported by the first jaw 70950a.

A clip applier jaw assembly 70960 is depicted in FIG. 66A. The clip applier jaw assembly 70960 comprises a first jaw 70960a which includes a base 70962, a first leg 70962a, a second leg 70962b, and a receiving area 70963 which receives a first clip leg 70964 of a clip. The first leg 70962a of the first jaw 70960a extends from the base portion 70962 beyond the first clip leg 70964 when the first clip leg 70964 is seated in the receiving area 70963. The second leg 70962b of the first jaw 70960a extends from the base portion 70962 and terminates prior to the end of the first clip leg 70964 such that only a portion of the first clip leg 70964 is supported by the second leg 70962b of the first jaw 70960a.

The clip applier jaw assembly 70960 further comprises a second jaw 70960b positioned opposite, or opposing, the first jaw 70960a. The second jaw 70960b comprises a base 70962', a first leg 70962a', a second leg 70962b', and a receiving area 70963' which receives a second clip leg 70964' of the clip. The second jaw 70960b opposes the first jaw 70960a such that the first leg 70962a of the first jaw 70960a is aligned with the first leg 70962a' of the second jaw 70960b, and the second leg 70962b of the first jaw 70960a is aligned with the second leg 70962b' of the second jaw 70960*b*. The second leg 70962*b'* of the second jaw 70960*b* extends from the base portion 70962' beyond the second clip leg 70964' of the clip when the second clip leg 70964' is seated in the receiving area 70963'. Further, the first leg 70962*a'* of the second jaw 70960*b* extends from the base portion 70962' and terminates prior to the end of the second clip leg 70964' such that only a portion of the second clip leg 70964' is supported by the first leg 70962*a'* of the second jaw 70960*b*.

When the first jaw 70962*a* and the second jaw 70962*b* of the clip applier jaw assembly 70960 are in a closed configuration, as depicted in FIG. 66B, the first leg 70962*a* of the first jaw 70960*a* supports the entire first clip leg 70964 of the clip and, also, a portion of the second clip leg 70964' of the clip. Further, the second leg 70962*b'* of the second jaw 70960*b* supports the entire second clip leg 70964' of the clip and, also, a portion of the first clip leg 70964 of the clip. Because the first leg 70962*a* of the first jaw 70960*a* and the second leg 70962*b'* of the second jaw 70960*b* are opposite one another, the cross-sections of the first clip leg 70964 and the second clip leg 70964' are supported by both the first jaw 70960*a* and the second jaw 70960*b*—along at least a portion of the leg lengths. Such an arrangement prevents, or at least inhibits, the clip from twisting when the clip is crimped.

Referring to FIG. 67, the clip leg 70954 is seated within the first clip jaw 70950*a* of the clip applier jaw assembly 70950 but is not prevented from being slid longitudinally within the clip applier jaw assembly 70950. In accordance with at least one embodiment, such as the clip applier jaw assembly 70960, for example, the first jaw 70960*a* and/or the second jaw 70960*b* comprise a clip ejection prevention feature, such as distal stop 70966. The distal stop 70966 prevents the clip 70964 from sliding out of the distal end of the first jaw 70950*a* and/or the second jaw 70950*b* of the clip applier jaw assembly 70960. Other clip applier jaw shapes and guidance features configured to control the position of the clip, and/or prevent the unintentional dropping and/or ejection of the clip from the clip applier, are discussed in greater detail below.

As discussed above, the jaws of a clip applier, or "clip jaws", are used to deform the clips. As the reader should appreciate, the clip jaws themselves undergo stresses and strains and, in some instances, can be plastically deformed. Clip jaws designed to resist plastic deformation during use may comprise clip jaws which vary in thickness, width, and/or clip path depth along the clip jaw lengths in order to improve the stiffness in a lap clip applier, for example. Further, a proximal portion of one of the clip applier jaws can comprise a protruding bar (i.e., a tongue portion) and a proximal portion of the other clip applier jaw can comprise a recess (i.e., a groove portion) such that the protruding bar is seated in the recess when the clip applier jaws are closed. Such an arrangement provides for superior jaw resilience to vertical skewing and/or twisting of the clip applier jaws relative to each other during crimping of a clip. Improved clip retention structures are discussed in further detail below.

In at least one embodiment, the clip applier jaws may comprise a clip retention channel, or recess, to allow a clip to be advanced into the clip applier jaws via a feeder member from below. The feeder member includes a flexible drive plate that is retracted when the clip applier jaws are actuated (i.e., moved from an open position to a closed position) and is extended into the distal end of the clip applier jaws to hold the clip in a distal position until the clip applier jaws are actuated. Further, the feeding member prevents any further clips from inadvertently advancing into the clip applier jaws until the feeder member is retracted to retrieve and advance the next clip. Clip applier jaws including a distal retaining feature are discussed in greater detail below.

In at least one embodiment, the clip applier jaws each comprise a distal retaining feature, such as a ledge, for example, that extends above a guidance trough in the clip applier jaws. The guidance trough may comprise retention features, such as recesses, for example, on the distal end thereof which mate with protrusions on the clip to allow the clip to remain in a distal position within the clip applier jaws without needing to be held into place by a firing member and/or feeder member. The construction and manufacturing of certain clip applier jaws is discussed in greater detail below.

In various embodiments, the clip applier jaws are manufactured using a two part method where at least the distal portions of the clip applier jaws are metal injection molded (MIM) within an injection mold. In certain instances, the injection mold comprises two sides which are translatable toward and away from each other along a parting axis and the interface between the two mold halves is often planar, or at least substantially planar, and is often called a "parting plane". In at least one such instance, the parting plane is perpendicular to the axis of a clip trough of the clip applier jaws formed within the injection mold. Such an arrangement allows stiffening features, such as a rail, for example, to be designed onto the back side of the clip applier jaws, friction or holding features within the clip trough, and/or the distal holding features discussed above, for instance. Using a MIM process may often require the clip applier jaws to be machined, ground, and/or polished, for example, after being removed from the injection mold. The clip applier jaws are then either pivotally pined together and/or welded pivotally to the connection features of an end effector. By using MIM to produce certain portions of the jaws, the cost to produce the jaws can be reduced as inexpensive manufacturing methods can be utilized for the connection features, as opposed to using MIM to produce the entire clip applier jaws. Further, the clip applier jaws can be independently manufactured using MIM and then welded to a spring based interconnection clip. Moreover, independently manufactured clip applier jaws that are thereafter assembled together allows for the clip applier jaws to have a metallic clip guidance track to be built into the lateral inside facing portion of the clip applier jaws. The independently manufactured clip applier jaws using MIM may further comprise distal clip retention features, such as ledges, for example, which prevent the unintentional ejection of a clip from the distal end of the clip applier jaws. Such distal clip retention features can extend above the primary face of the clip applier jaws owing to these MIM processes.

As discussed above, and as described in greater detail below, certain clip appliers are configured to be inserted into a patient through a passage defined in a trocar. That said, the clip jaws of many clip appliers are wider than the trocar passage when they are in their open configuration. Described below are various systems that can be incorporated into a clip applier to facilitate the insertion of the clip applier through the trocar passage.

Figure 69:
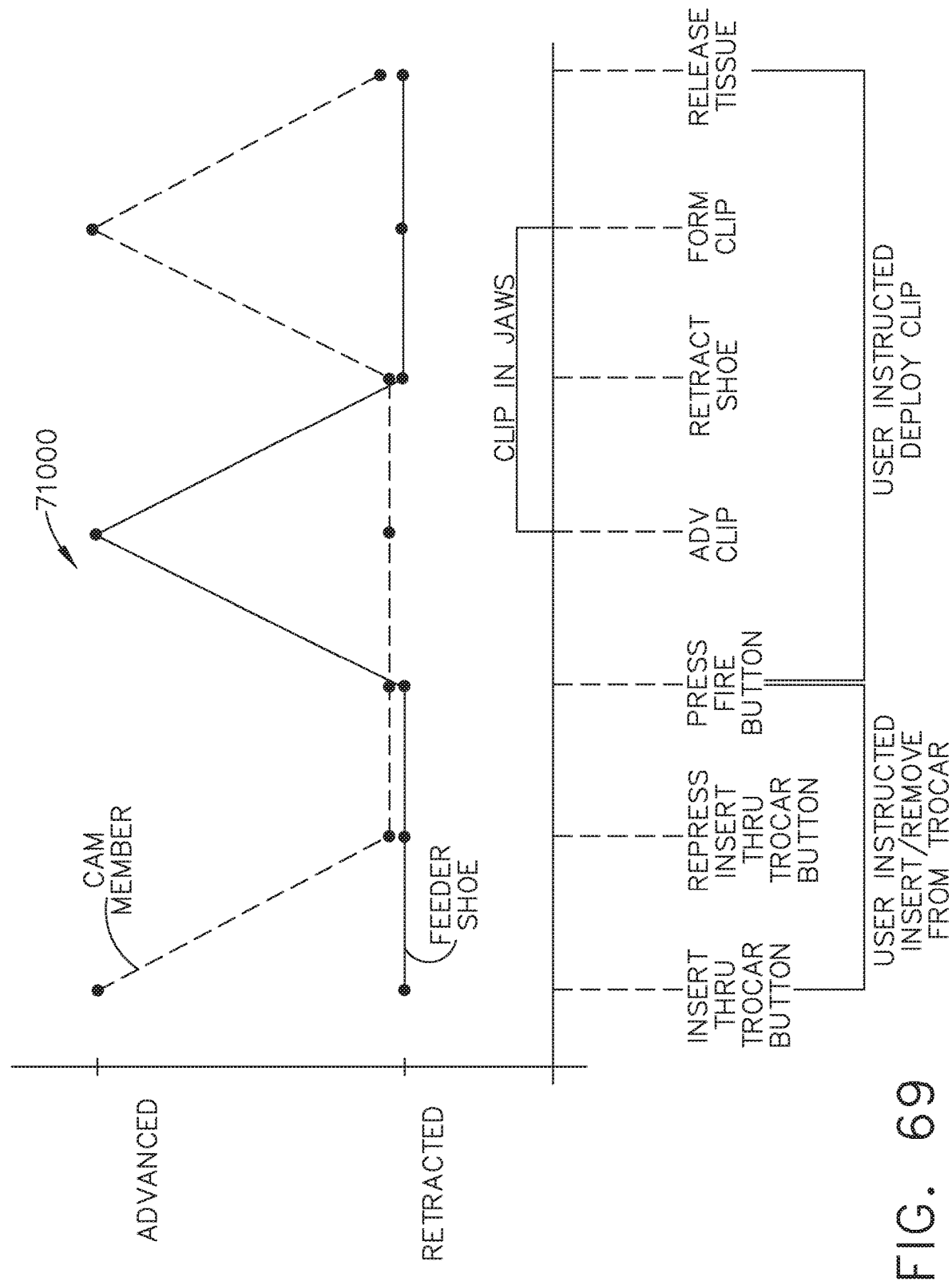
FIG. 69 is a graphical depiction of the movements of a cam member and a feeder shoe of a clip applier throughout the operation of the clip applier.

Referring to FIG. 69, a graph 71000 depicts the movements of a cam member and a feeder/firing member of a clip applier, such as the clip applier 70100, for example. The cam member is similar to cam member 70180 and the feeder shoe is similar to firing member 70165 illustrated in FIGS. 35A-38, for example. In order to configure the clip applier 70100 in a trocar-insertion configuration, the cam member is moved to a fully advanced position to close the jaws of the clip applier and the feeder shoe is moved to a fully retracted position. In various instances, the clip applier comprises a control system including a button which, when depressed, places the clip applier in its trocar-insertion configuration. In at least one instance, the control system operates the one or more electric motors of the clip applier to configure the drive systems as described above. At such point, the clip applier is ready to be inserted into the patient through the trocar. Once inserted into the patient, the button can be pressed again and, in response thereto, the control system will retract the cam member to a fully retracted position and open the jaws of the clip applier. This button can be pressed repeatedly to toggle the configuration of the clip applier as needed. Such an arrangement is also useful to remove the clip applier from the patient through the trocar. The reader should appreciate that the opening and closing of the jaws via the button will not affect the other functions of the clip applier such as advancing a clip, forming a clip, and/or ejecting a clip from the clip magazine.

Once the clip applier has been inserted through the trocar and the button has been actuated a second time (i.e., the jaws are open), further to the above, a firing button can be pressed resulting in the feeder shoe advancing to a fully advanced position. A clip will be advanced with the feeder shoe as described above in relation to clip applier 70100 (FIGS. 35A-38), for instance. The feeder shoe can then be retracted to a fully retracted position and the cam member can be advanced to the fully advanced position to form the clip around tissue of the patient, as also described above. The cam member can then be retracted to the fully retracted position to release the clip and the tissue. Once all of the clips have been applied, or at least a sufficient number of clips have been applied, the button could be actuated again to close the jaws to allow the clip applier to be removed through the trocar. Such an arrangement enables the user of the clip applier to close the jaws without releasing a loose clip into the patient.

Further to the above, embodiments are envisioned where a clip applier comprises a motor and a motor controller. The motor controller can be configured to control the motor via a processor and a memory. The motor controller can implement motor control algorithms to configure the jaws to open and close as well as advance a clip into the jaws. For example, a motor control algorithm can be implemented to allow the jaws to advance a clip into a crimping and/or forming position, as described above, after the jaws have been inserted through the trocar. By not feeding a clip into the jaws until after the clip applier has been introduced into the patient, the jaws can be moved into a very compact arrangement when being inserted through the trocar as discussed above.

Figure 70:
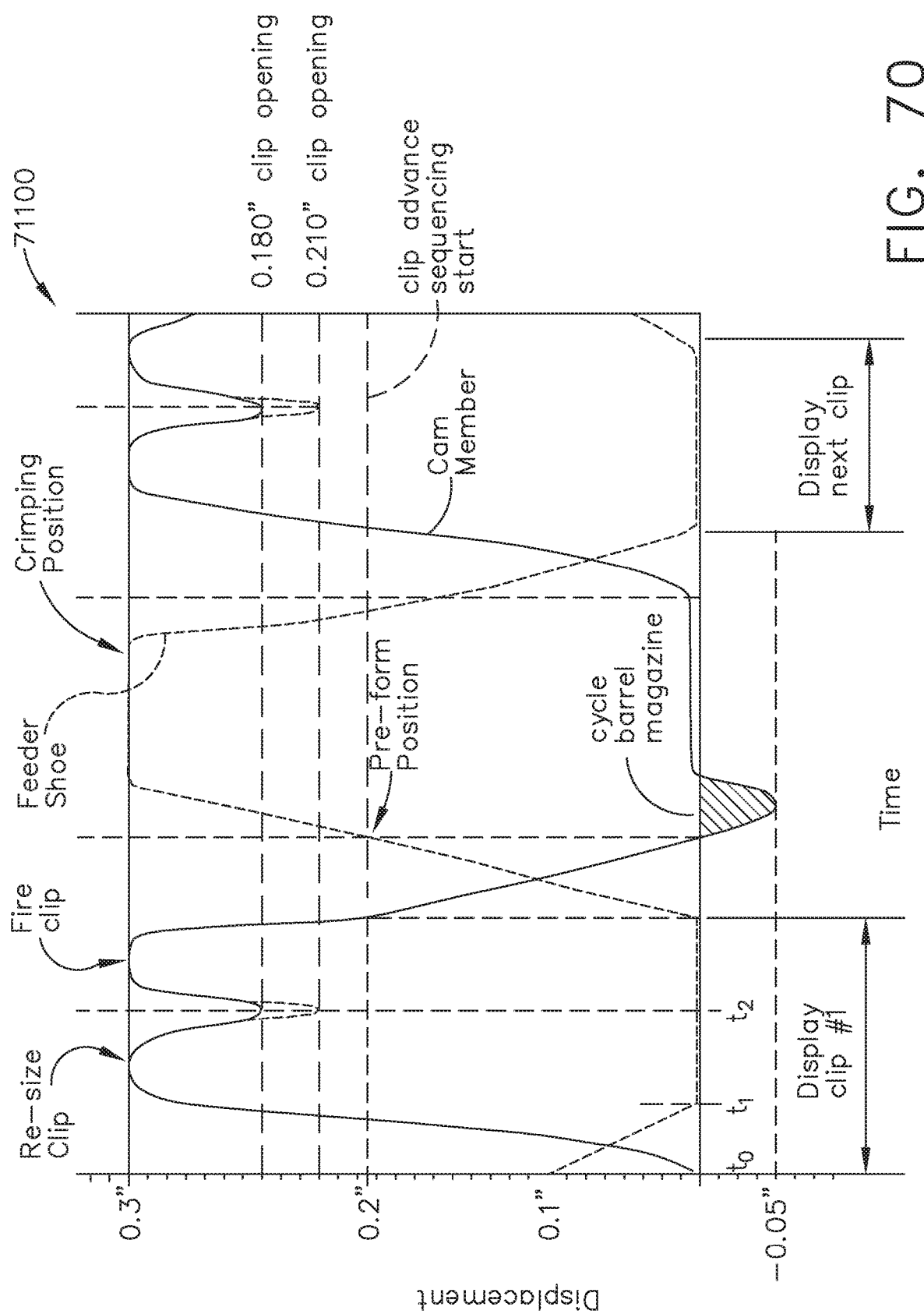
FIG. 70 is a graph depicting the displacement of a cam member and feeder shoe of the clip applier of FIG. 52 as a function of time.

Turning now to FIG. 70, a graph 71100 depicts the movements of a cam member and a feeder shoe of a clip applier comprising a rotating clip magazine (i.e., a barrel magazine), such as the clip applier 70600, for example. The operation of the clip applier depicted in FIG. 70 is similar to that of clip applier 70600 in many respects. For example, the cam member is similar to closure tube 70620, the feeder shoe is similar to feeder member 70630, and the barrel magazine is similar to rotatable clip magazine 70650 illustrated in FIGS. 52-60, for example. The clip applier is placed into the patient through a trocar with the jaws closed and a clip positioned in the jaws and another clip aligned with the feeder shoe for deployment out of the barrel magazine. With the feeder shoe in the home position (i.e., zero displacement) the cam member can be advanced to a fully advanced position from the home position to crimp the clip already placed within the jaws. In at least one instance, the distance between the home position and the fully advanced position is 0.3", for example. The cam member is then retracted to a partially advanced position just proximal to the fully advanced position to reduce the force applied to the clip by the jaws. The cam member is advanced again to the fully advanced position to crimp the clip again. By applying a force, reducing that force, and then applying the same, or another, force again, the elasticity within the clip can be reduced such that full plastic deformation can occur to properly crimp the clip onto the patient tissue. The partially advanced position is dependent on the type of clip being utilized with the clip applier. For example, the partially advanced position is preferably 0.2" distal from the home position for a clip with a clip opening of 0.210" and is preferably 0.23" distal from the home position for a clip with a clip opening of 0.180", for example. Suitable thresholds can be set by the user depending on the type of clips in the barrel magazine being utilized with the clip applier. Other embodiments are envisioned with different clip sizes and position arrangements for the partially retracted and fully advanced positions.

In any event, after the clip has been properly crimped, the cam member is then retracted proximally toward the home position as the feeder shoe distally advances a clip out of the barrel magazine toward the jaws of the clip applier into a pre-form position when the feeder shoe is 0.08" distal from the home position, for example. When the clip is in the pre-form position, the jaws can be partially opened by retracting the cam member slightly beyond the home position, i.e., the cam member interacts with the jaws of the clip applier to open the jaws when the cam member is retracted proximal to the home position, as discussed above. Such an arrangement allows the clip to be expanded by the pre-form features on each of the jaws (i.e., protrusions 70608) as discussed above. The feeder shoe then distally advances the clip further into a crimping position—0.3" distal to the home position, for example. Once the feeder shoe is advanced beyond the barrel magazine (i.e., to the pre-form position) the barrel magazine can be cycled (i.e., rotated) to position another clip for advancement into the jaws. The barrel magazine is cycled by retracting the cam member to a fully retracted position—0.05" proximal to the home position, for example. The cycled clip will be biased against the feeder shoe which prevents the clip from being completely ejected from the barrel magazine. Once the feeder shoe is retracted to the home position the cycled clip can be displayed (i.e., the biasing member in the barrel magazine can now position the cycled clip into alignment with the feeder shoe because the feeder shoe has been retracted and is no longer blocking such movement). At this point a clip that has been pre-formed is positioned in the jaws and another clip is aligned with the feeder shoe for deployment out of the barrel magazine into the clip applier jaws, just as when the clip applier was first inserted into the patient. The same operations discussed above can be performed until all of the clips in the barrel magazine are spent.

Figure 71:
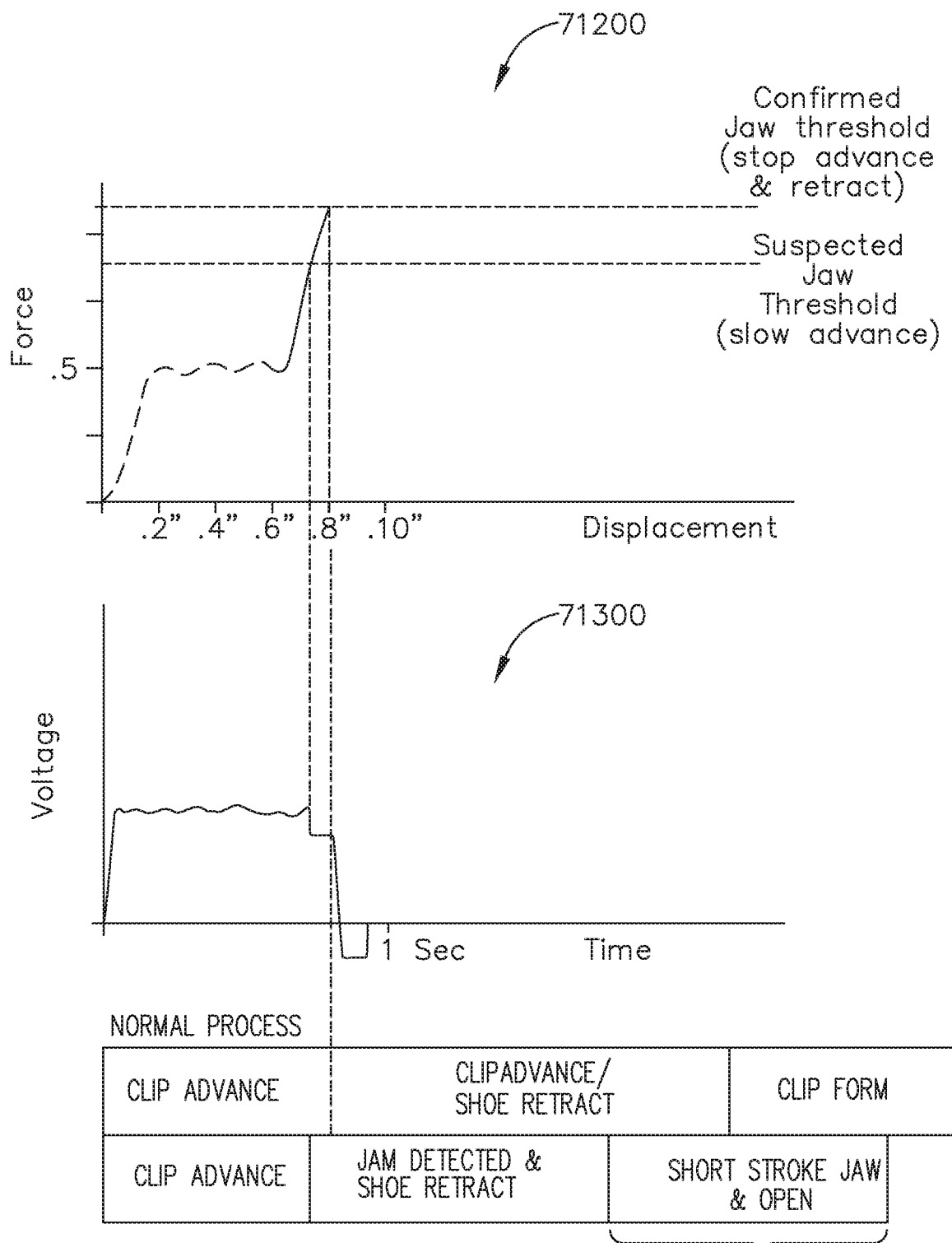
FIG. 71 depicts a first graph illustrating the force to advance a clip of a clip applier as a function of displacement and a second graph illustrating the voltage of a motor of the clip applier as a function of time.

A graph 71200 of a firing member of a clip applier, such as any of the clip appliers described herein, for example, is illustrated in FIG. 71. The graph 71200 shows the relationship between the force required to advance a clip within the clip applier (i.e., via the firing member) versus displacement. With further reference to FIG. 71, a graph 71300 of the same clip applier is illustrated showing the relationship between the voltage applied to the motor driving the firing member of the clip applier versus time. The motor controller of the clip applier can monitor the current being drawn by the motor and/or the force being applied to the firing member by the motor to detect a clip feed jam, or an irregular force within the clip applier, and then prevent further advancement of the firing member by implementing changes to the voltage applied to electric motor, as seen in graph 71300. In other words, if the monitored force exceeds a threshold value, and/or the monitored motor current exceeds a threshold value, during the clip feed step, the motor controller can, one, reduce the magnitude of the voltage potential being applied to the motor for a period of time and, two, further assess the force within the firing system and/or further assess the electrical current being drawn by the motor. If the force and/or motor current continue to increase with the continued application of voltage to the motor, the motor control system can stop the motor and/or reverse the direction of the motor shaft to retract the firing member through a short stroke distance to clear the jammed clip. Once the jammed clip is cleared, the clip applier can return to its normal operation and prepare the next clip to be advanced in accord with the normal operating sequence of the clip applier.

Other embodiments are envisioned where clearing the jammed clip is accomplished by interrupting the normal sequence of the end effector jaw operations. More specifically, once the clip jam is detected the control system of the clip applier (i.e., motor controller, processor, and memory) could request the clinician initiate a jam removal actuation. The jam removal actuation results in the jaws of the clip applier being opened further than normal prior to another attempt to re-advance the clip. During the attempt to re-advance the clip, the acceptable load threshold, i.e., the current threshold and/or the force threshold, could be elevated above the normal thresholds previously discussed to insure the clip is ejected from the jaws. Once the jammed clip has been ejected, the clip applier could return to its normal operation and prepare the next clip to be advanced in accord with the normal operating sequence of the clip applier.

As mentioned above, certain clip appliers can be loaded with clips having a first size and/or a second size. The relative size of the clips can be measured using any suitable dimension, such as the leg-to-leg width of the clips, for example. First clips having a first width can be wider than second clips having a second width. In various instances, the clip applier can be loaded with only first clips, only second clips, or both first and second clips at the same time. In any event, clips having different sizes may deform differently for a given closure stroke of the clip jaws. Thus, for instance, a first closure stroke of the clip jaws may be more preferable for the first clips while a second closure stroke of the clip jaws may be more preferable for the second clips. Many of the clip appliers disclosed herein are capable of selectively applying more than one closure stroke to the clip jaws; however, in order to apply the correct closure stroke to a clip, the clip applier needs to be able to assess which size of clip is positioned within the clip jaws. In certain instances, such information can be manually entered into the control system of the clip applier by the clinician. Such an arrangement is convenient when the clips in the clip applier all have the same size. In various instances, the clip cartridge attached to the clip applier comprises a marker, such as a microchip, for example, which can be evaluated by the control system and/or a sensor circuit in communication with the control system, for example. Such an arrangement is convenient when the clips in the clip cartridge all have the same size.

In various instances, further to the above, the clip applier can be configured to assess the clip positioned between the clip jaws of the clip applier to assess the size of the clip. Once a clip is loaded between the clip jaws, the control system can partially operate the jaw closure drive and observe the force within the jaw closure drive and/or the current drawn by the electric motor of the jaw closure drive. The control system is configured to compare the measured data to data stored in a memory device, for example, to assess whether the clip between the clip jaws is a first clip or a second clip, or any other clip. For instance, if the measured force and/or motor current follows a first profile, then the control system will determine that the clip is a first clip and then apply the first closure stroke. Similarly, the control system will apply the second closure stroke if the measured force and/or motor current follows a second profile for the second clip. As such, the control system can use the jaw closure drive to apply a short evaluation closure stroke to assess the clip size and then complete the full closure stroke as appropriate. In at least one instance, the control system can reset the jaw closure drive after performing the short evaluation closure stroke and then complete a full closure stroke as appropriate. In various instances, it is envisioned that the short evaluation closure stroke does not plastically deform, or at least substantially plastically deform, the clip.

Referring to FIG. 72, a graph 71400 of the force applied to a pair of jaws of a clip applier versus time is illustrated. The control system of the clip applier can monitor the force within the crimping drive and/or the electric current drawn by the motor to determine the amount of force needed to crimp a clip positioned within the jaws of the clip applier. This feedback force is initially dependent on the size and/or type of clip that is within the jaws for a first portion of the closure stroke of the jaws. Once the size/type of clip is determined, the force applied to the jaws of the clip applier can be adjusted for the remainder of the jaw closure stroke to crimp the clip with the proper amount of force. Such an arrangement is convenient when more than one size of clip has been loaded into the clip applier. Other embodiments are envisioned where an adaptive control program change is initiated by the cartridge identifying itself to the clip applier upon insertion into the clip applier. This allows the clip applier to update to the alternative control program and thresholds (i.e., the forces applied to the jaws) for the size/type of clip loaded into the clip applier. Further, an alternative to the identification of the cartridge could be the detection of the loads needed to accomplish the first job of the clip applier, which could be the advancement of a clip from the cartridge or pre-forming a clip within the jaws as discussed above. The first job of the clip applier may have a significantly higher load threshold needed to complete the operation and exceeding that threshold, or not, will then determine the subsequent operations the clip applier and the threshold limits of each operation.

Many of the clip appliers discussed herein have been discussed in the context that the clip jaws of the clip appliers are squeezed to crush a clip into its proper size. Other embodiments are envisioned in which a clip is elastically or resiliently stretched and then released once the targeted tissue has been positioned within the stretched clip. Such an arrangement can be particularly useful when clamping or clipping blood vessels, for example. In such instances, a clip can be released to resiliently return to, or at least toward, its unstretched position and clamp the blood vessel in an atraumatic, or a nearly atraumatic, manner. All of the clip appliers disclosed herein can be adapted to apply such stretch-and-release clips. Moreover, further to the above, the clip appliers disclosed herein can be configured to apply both the clamp-to-crush clips and the stretch-and-release clips. Similar to the above, the clip appliers would need to be able to identify the type of clips contained therein in order to apply them properly to the patient tissue. Identification chips in the clip cartridges could be used for such purposes, for example.

Figure 75:
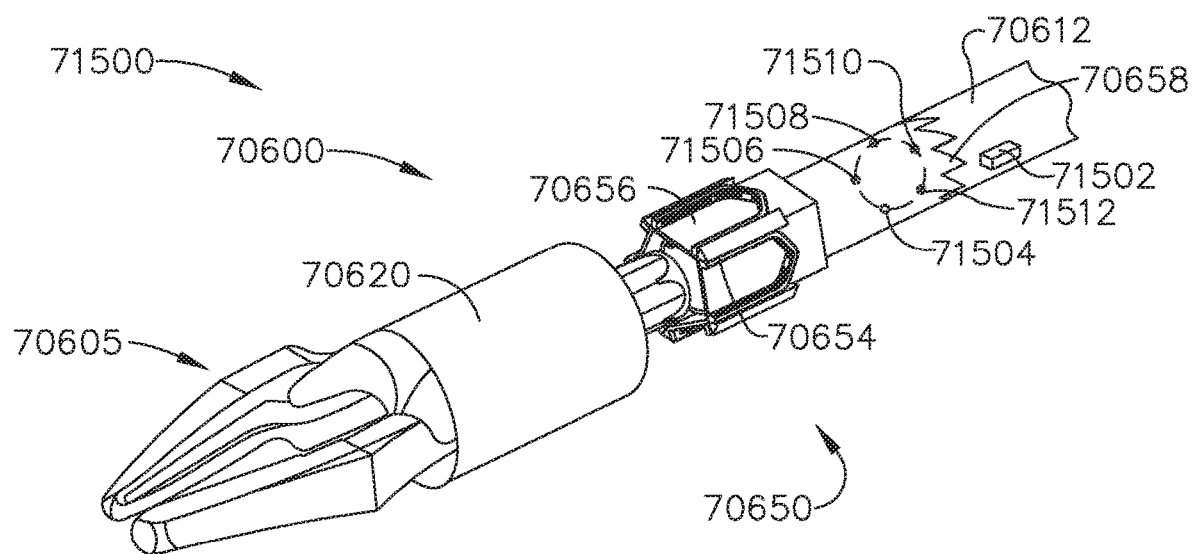
FIG. 75 is a perspective view of a clip applier including a rotating clip magazine, a magnet, and a Hall Effect sensor.
Figure 76:
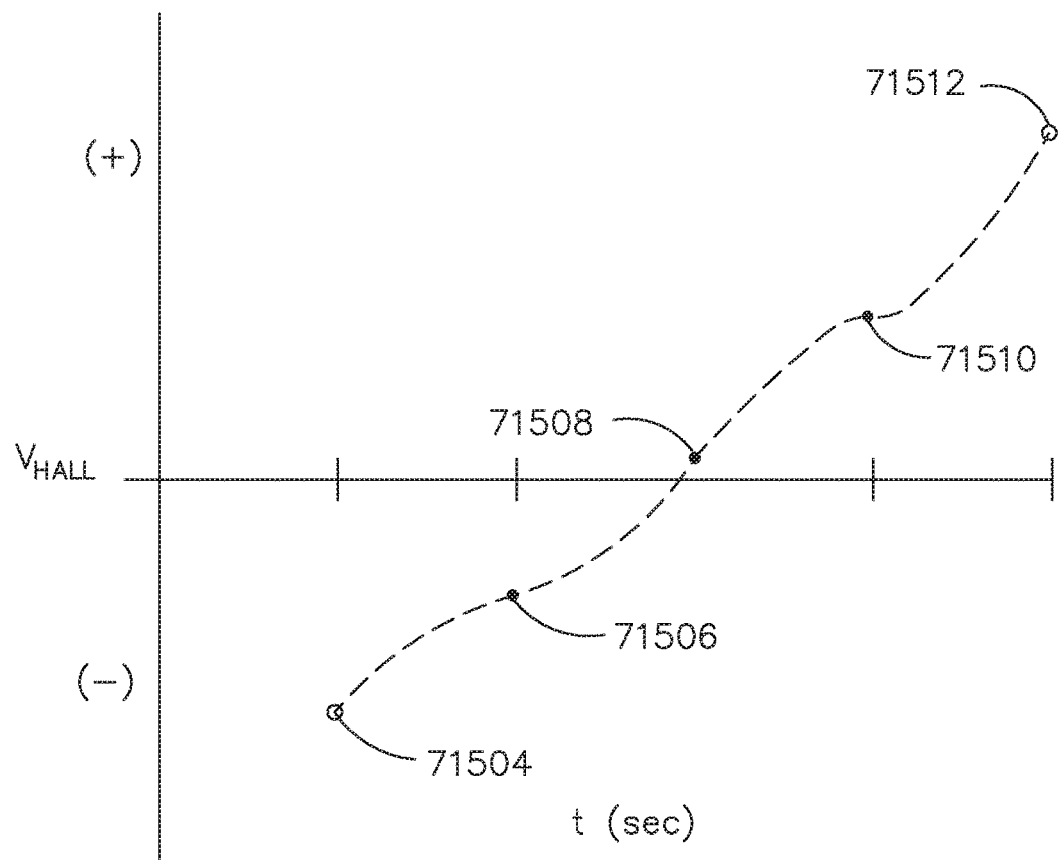
FIG. 76 is a graphical depiction of the clip applier of FIG. 75 illustrating the voltage of the Hall Effect sensor as a function of the position of the magnet over time.

FIG. 75 depicts a clip applier system 71500 in accordance with at least one embodiment. The clip applier system 71500 comprises the clip applier 70600 discussed above. The clip applier system 71500 further comprises a magnet aligned with one of the clips 70654 of the rotatable clip magazine 70650. The clip applier system 71500 further comprises a sensor, such as a Hall Effect sensor 71502, for example, fixedly positioned within the ground portion 70612 of the clip applier 70600. The magnet can be sensed by the Hall Effect sensor 71502 and, based on the voltage potential created by the Hall Effect sensor, the control system of the clip applier 71500 can determine the radial location and orientation of the magnet and, thus, the radial location and orientation of the clip magazine 70650. When the magnet is in a first position 71504, referring to FIG. 76, the rotatable clip magazine 70650 is loaded with a full compliment of clips 70654 and one of the clips 70654 can be advanced out of the rotatable clip magazine 70650 into the end effector 70605. The rotatable clip magazine 70650 can then be cycled (e.g., rotated) as discussed above, causing the magnet to move between the first position 71504 and a second position 71506. Another clip 70654 can be advanced out of the rotatable clip magazine 70650 and the rotatable clip magazine 70650 can be cycled again, causing the magnet to move to a third position 71508. Another clip 70654 can be advanced out of the rotatable clip magazine 70650 and the rotatable clip magazine 70650 can be cycled again, causing the magnet to move to a fourth position 71510. Further, another clip 70654 can be advanced out of the rotatable clip magazine 70650 and the rotatable clip magazine 70650 can be cycled again, causing the magnet to move to a fifth position 71512. In the fifth position 71512, the last clip 70654 in the rotatable clip magazine 70650 can be advanced out of the rotatable clip magazine 70650. Thus, the clip applier system 71500 can determine the status of the clip magazine 70650 (i.e., the number of clips remaining) depending on the position of the magnet relative to the Hall Effect sensor 71502. Further to the above, FIG. 76 depicts the voltage potential generated by the Hall Effect sensor 71502 depending on the position of the magnet.

In at least one alternative embodiment of the clip applier system 71500, the clip magazine 70650 further comprises an extension member, or bar, that extends proximally from the clip magazine 70650 once all of the clips 70654 have been ejected from the clip magazine 70650. The extension member is sensed by the Hall Effect sensor 71502 and/or another electrical sensor within the clip applier 70600. When the extension member is detected by the clip applier system 71500, the mechanical systems (i.e., the feeder member 70630, firing member 70640, and drive tube 70620) of the clip applier 70600 can be locked out to prevent further actuation.

Figure 77:
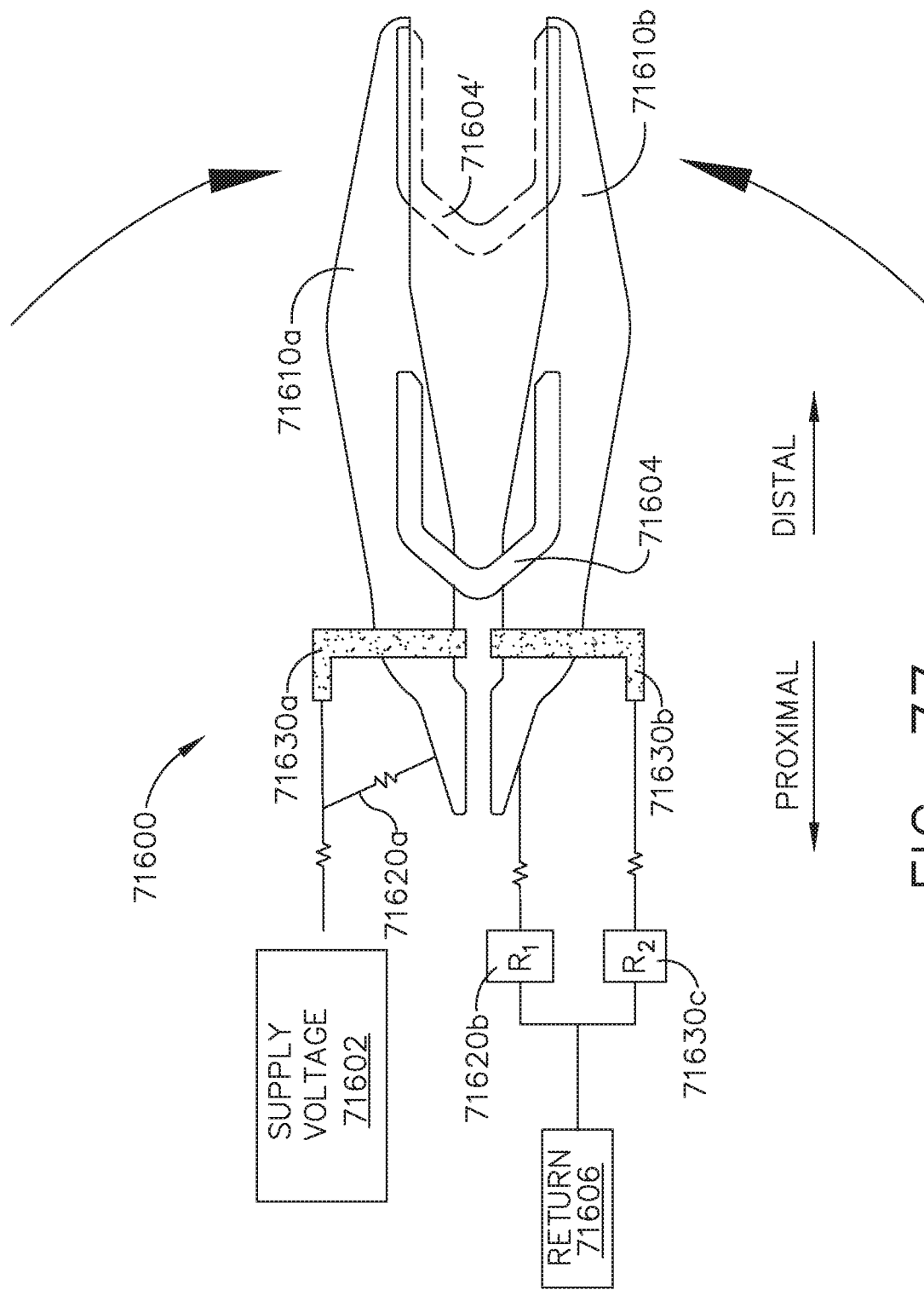
FIG. 77 is a partial cross-sectional view of a clip applier including resistive sensing circuits.

FIG. 77 depicts a clip applier 71600. The clip applier 71600 comprises a first jaw 71610*a* and a second jaw 71610*b* moveable relative to each other between open and closed positions. The clip applier 71600 is configured to receive a clip 71604 which is crimped by the first jaw 71610*a* and the second jaw 71610*b* when the first jaw 71610*a* and the second jaw 71610*b* are moved toward the closed position. The clip applier 71600 comprises a resistive sensing circuit configured to determine the position of the clip 71604 within the clip applier 71600. The resistive sensing circuit comprises a supply voltage source 71602 which supplies current through a first lead 71620*a*, the first jaw 71610*a*, the clip 71604, the second jaw 71610*b*, and a Resistor 71620*b* and back to a return 71606 where the current can be measured. When the clip 71604 is moved distally though the clip applier, such as to the position shown by clip 71604', for example, the path through which the current flows is larger (i.e., larger than the path for clip 71604) and the resistance within the path is greater and, as a result, the current measured at the return 71606 will be smaller. Thus, the current measured at the return 71606 is directly proportional to the position of the clip 71604 within the clip applier 71600. The control system of the clip applier is configured to use the magnitude of the current in this sensing circuit to assess the position of the clip 71604' within the jaws 71610*a* and 71610*b*. Higher current magnitudes indicate that the clip 71604' is more proximal and lower current magnitudes indicate that the clip 71604's is more distal, while intermediate current magnitudes indicate that the clip 71604' is positioned in the middle of the jaws 71610*a* and 71610*b*.

Referring still to FIG. 77, the clip applier 71600 further comprises a second resistive sensing circuit configured to determine when the first jaw 71610*a* and the second jaw 71610*b* are in the closed position. More specifically, the supply voltage supplies current which flows through a first lead 71630*a* connected to the first jaw 71610*a*. The first lead 71630*a* is insulated from the first jaw 71610*a*, i.e., it does not allow current to flow into the first jaw 71610*a*. When the first jaw 71610*a* and the second jaw 71610*b* are in the closed position, the first lead 71630*a* contacts a second lead 71630*b* connected to the second jaw 71610*b* which allows current to flow into a resistor 71630*c* and into the return 71606 where the current can be measured. The second lead 71630*b* is also insulated from the second jaw 71610*b*. Thus, when the first jaw 71610*a* and the second jaw 71610*b* are in the closed position, the control system, via the return, will sense a current determined by a second resistance through the resistor 71630*c* which indicates that the first and second jaws 71610*a*, 71610*b* are in the closed position. The control system may, at the same time, also sense the resistance through resistor 71620*b* which indicates the position of the clip 71604 within the clip applier 71600. Other embodiments are envisioned where only one of the resistive sensing circuits discussed above are utilized with the clip applier 71600.

Figure 78A:
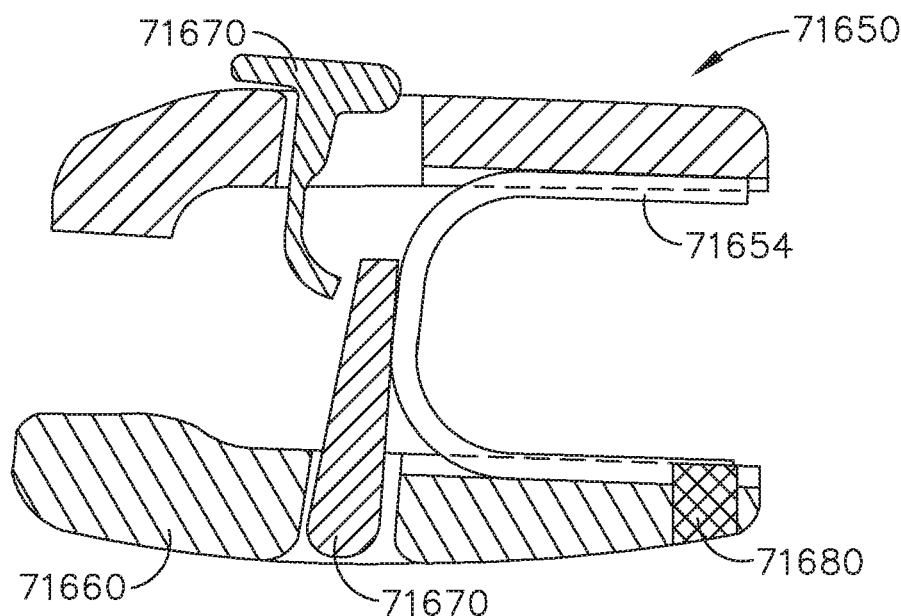
FIG. 78A is a partial cross-sectional view of a clip applier including a variable resistance meter.
Figure 78B:
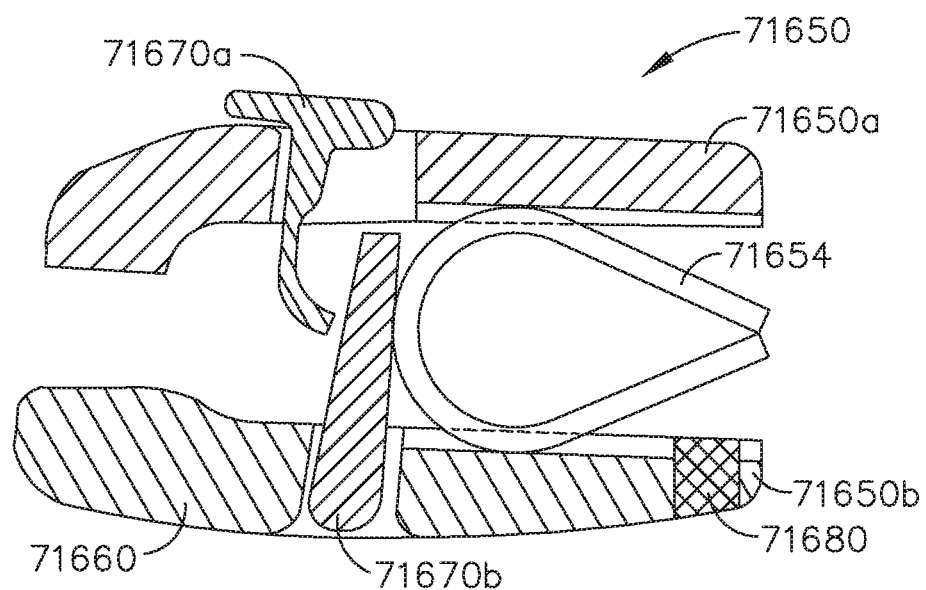
FIG. 78B is a partial cross-sectional view of the clip applier of FIG. 78A in a partially crimped configuration.

FIGS. 78A and 78B depict a variable resistance system for use with a clip applier 71650 configured to gather information (i.e., data) on the position of the clip jaws and the formation of the clip during a crimping stroke. The clip applier 71650 is similar to clip applier 71600, for example, in many respects. The clip applier 71650 comprises a first jaw 71650*a* and a second jaw 71650*b* moveable relative to each other between an open position (FIG. 78A), a partially closed position (FIG. 78B) and a closed position. The clip applier 71650 is configured to receive a clip 71654 which is crimped by the first and second jaws 71650*a*, 71650*b* when the first and second jaws 71650*a*, 71650*b* are moved toward the closed position. The legs of the clip 71654 positioned within the first and second jaws 71650*a*, 71650*b* extend outwardly into engagement with the first and second jaws 71650*a*, 71650*b* to ensure the clip 71654 is properly seated therebetween (i.e., so there is no slop or play between the clip 71654 and the first and second jaws 71650*a*, 71650*b*). In various instances, the legs of the clip are slightly deflected inwardly when the clip is fed into the first and second jaws

71650a, 71650b. The variable resistance system of the clip applier 71650 is described in further detail below.

The variable resistance system comprises three return paths through which an electrical current can flow and be sensed by the control system of the clip applier in order to determine the position of the first and second jaws 71650a, 71650b relative to each other, and to sense the formation of the clip 71654. The first return path 71660 comprises the second jaw 71650b. The second return path 71670 comprises a variable resistor configured to determine the position of the first jaw 71650a and the second jaw 71650b relative to each other. More specifically, as the first jaw 71650a and the second jaw 71650b are moved from the open position (FIG. 78A) toward the closed position the resistance in the variable resistor will change. The third return path 71680 comprises another variable resistor at the distal end of the second jaw 71650b which is insulated from the second jaw 71650b. When the first jaw 71650a and the second jaw 71650b are in the open position (FIG. 78A), the clip 71654 is in contact with the first return path 71660 and the third return path 71680. When the first jaw 71650a and the second jaw 71650n are in the partially closed position (FIG. 78B), the clip 71654 is only in contact with the first return path 71660. When the first jaw 71650a and the second jaw 71650b are in the closed position the clip 71654 has been fully crimped and is once again in contact with the first return path 71660 and the third path 71680. Throughout the movement of the first jaw 71650a and the second jaw 71650b between the open position, the partially closed position, and the closed position, the second return path 71670 determines the position of the first jaw 71650a relative to the second jaw 71650b. Thus, the variable resistance system can determine jaw position and sense clip formation throughout the clip formation process by determining the resistance through each of the three paths.

Figure 79:
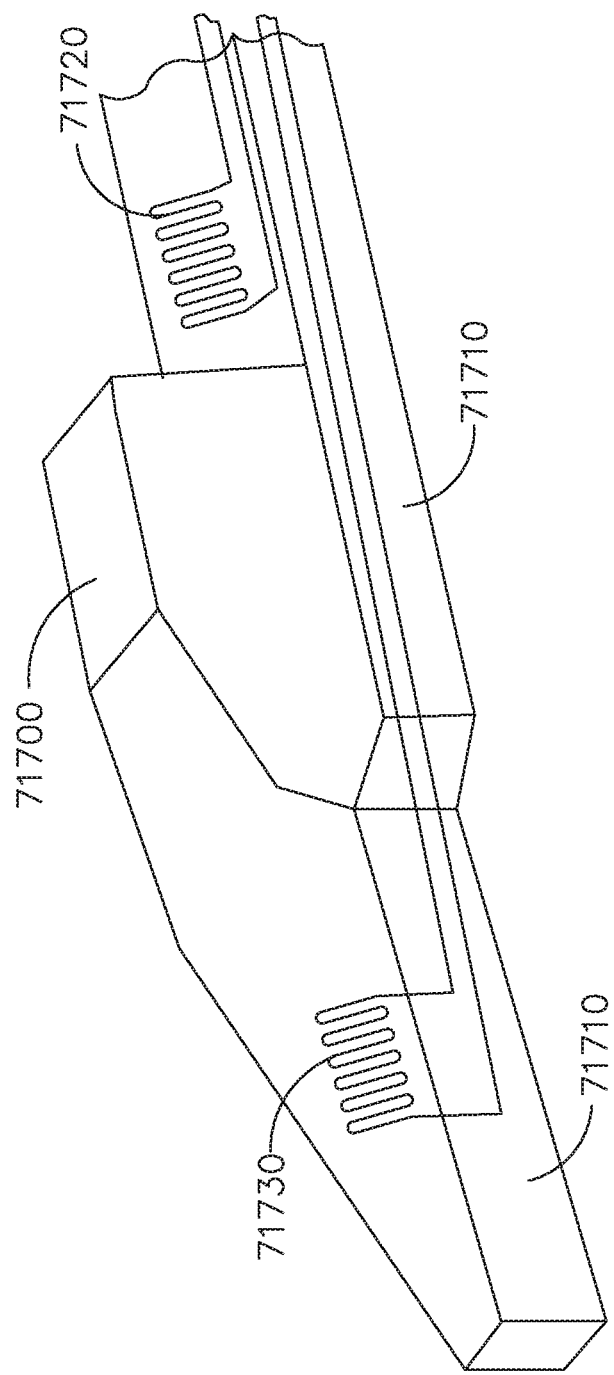
FIG. 79 is a perspective view of a clip applier jaw including strain gauges.

FIG. 79 depicts a clip applier jaw 71700 in accordance with at least one embodiment. The clip applier jaw 71700 is configured to move toward and away from another clip applier jaw and is further configured to crimp a clip as discussed above in relation to various embodiments disclosed herein. The clip applier comprises a proximal strain gauge 71720 and a distal strain gauge 71730, and/or any number of suitable strain gauges. The proximal strain gauge 71720 and the distal strain gauge 71730 are positioned on a face 71710 of the clip applier jaw 71700. Other embodiments are envisioned with more than two strain gauges spaced along any suitable face of the clip applier jaw 71700 and/or built into the clip applier jaw 71710 itself. The proximal strain gauge 71720 is part of a proximal strain gauge circuit and generates a voltage signal indicative of the strain within the clip applier jaw 71700 in a first location and the distal strain gauge 71730 is part of a distal strain gauge circuit and generates a voltage signal indicative of the strain within the clip applier jaw 71700 in a second location. The proximal and distal strain gauge circuits are in communication with the control system of the clip applier and, as a clip is formed between the clip applier jaw 71700 and another clip applier jaw, different levels of strain will be detected by the control system at the first location and the second location.

Figure 80:
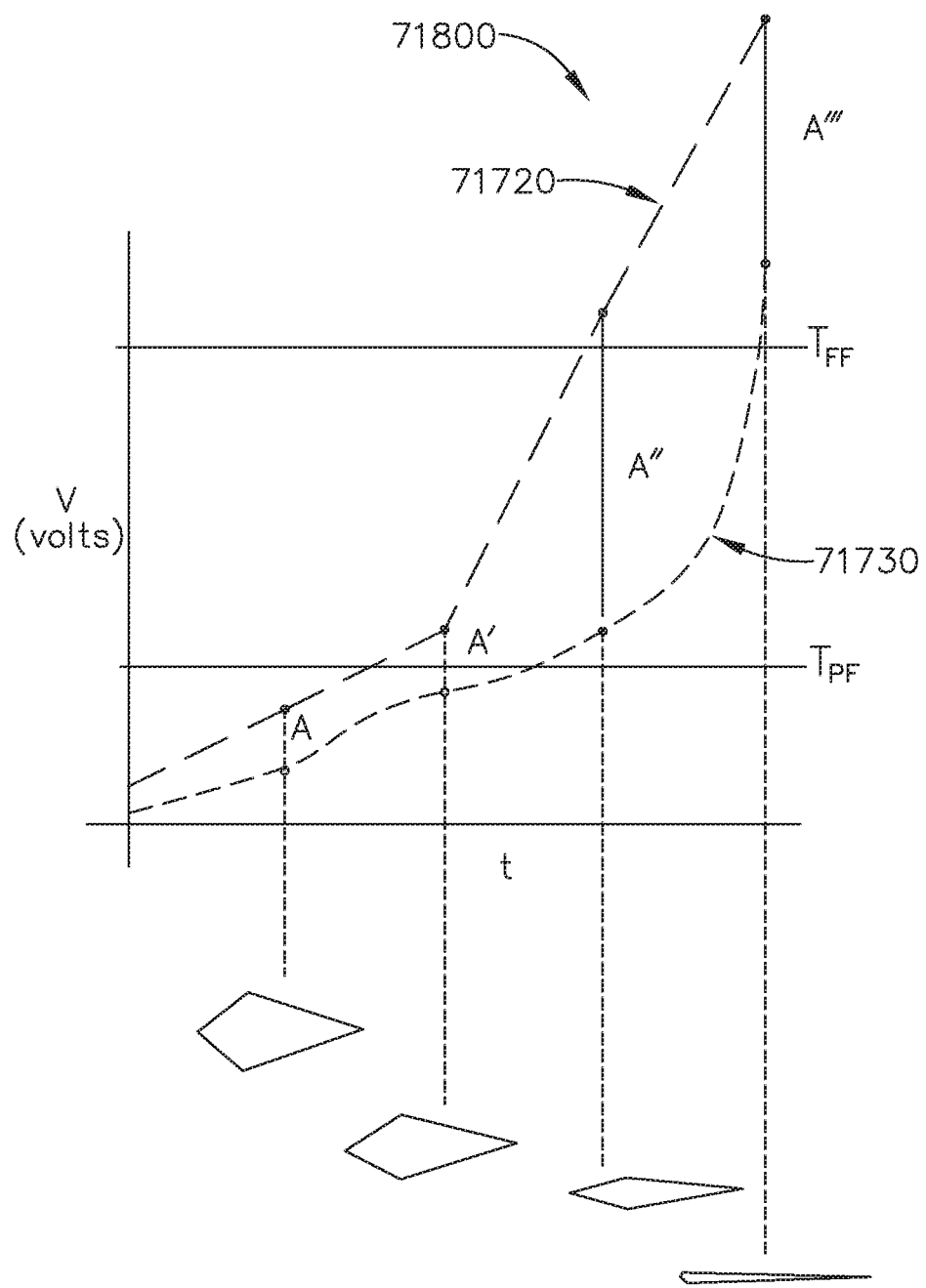
FIG. 80 is a graphical depiction of the clip applier jaw of FIG. 79 illustrating the voltage of the strain gauges as a function of time.

Referring to FIG. 80, a graph 71800 of the strain (measured in Volts, but could be more conveniently illustrated in mV) within the proximal strain gauge 71720 and the distal strain gauge 71730 at various stages of clip formation is depicted. Upon the initial placement of a clip between the clip applier jaws, the clip legs of certain clips are biased outwardly into engagement with the jaws, as discussed above. In such instances, a larger strain may be measured in the proximal strain gauge 71720 as compared to the distal strain gauge 71730. The difference in the voltages within the strain gauges 71720, 71730 at this stage is voltage A as depicted in FIG. 80. As the jaws of the clip applier begin to form the clip, the reading from the proximal strain gauge 71720 will exceed a pre-formed strain threshold $T_{PF}$ while the reading from the distal strain gauge 71730 remains below the pre-formed strain threshold $T_{PF}$. This can indicate that the clip has only been formed at or near the proximal strain gauge 71720. The difference in the voltages between the readings of the strain gauges 71720, 71730, at this stage, is measured to be A'. As the jaws of the clip applier form the clip further, the reading from the distal strain gauge 71730 will eventually exceed the pre-formed strain threshold $T_{PF}$ and the reading from the proximal strain gauge 71720 will eventually exceed a full-formed strain threshold $T_{FF}$. This can indicate that the clip has been fully formed at or near the proximal strain gauge 71720 and has begun to be deformed at or near the distal strain gauge 71730. When the readings from the proximal strain gauge 71720 and the distal strain gauge 71730 are both measured to be beyond the full-formed threshold $T_{FF}$ and the pre-formed threshold $T_{PF}$, respectively, the difference in the strain gauge readings is measured as A" as depicted in FIG. 80. Further, as the jaws of the clip applier form the clip further, the reading from the distal strain gauge 71730 will eventually exceed the full-formed strain threshold $T_{FF}$ and the reading from the proximal strain gauge 71720 will continue to increase above the full-formed strain threshold $T_{FF}$. When the reading from the proximal strain gauge 71720 and the distal strain gauge 71730 are measured to both be beyond the full-formed threshold $T_{FF}$, the difference in the strain gauge readings is measured as A''' as depicted in FIG. 80.

Further to the above, the state of the clip can be determined by measuring the differences between the readings of the proximal strain gauge 71720 and the distal strain gauge 71730 throughout the formation of a clip. More specifically, a difference in voltage measuring A indicates that the clip has yet to be deformed. A difference in voltage measuring A' indicates that only a proximal portion of the clip has been deformed. A difference in voltage measuring A" indicates that the proximal portion of the clip has been fully formed and the distal portion of the clip has begun to be deformed. And lastly, a difference in the voltage measuring A''' indicates that both the proximal and distal portions of the clip have been fully formed.

As discussed above, a clip applier is often inserted into a patient through a trocar. As a result, the diameter of the passageway through the trocar dictates a lot of the design considerations of the clip applier—especially of the portions of the clip applier that are inserted through and/or into the trocar passageway. That said, there is often motivation to make trocars as narrow as possible to reduce the size of the incisions in the patient, among other reasons. As such, narrow trocars, and narrow trocar passageways, present significant design constraints and often limit the widths of the clips that can be used. With this in mind, clip appliers are disclosed herein which are configured to store the clips in a small configuration and then enlarge the clips once they are on the other side of the trocar. Such an arrangement can allow clips to be used which, in their enlarged state, exceed the diameter of the trocar that they were inserted through.

Figure 81A:
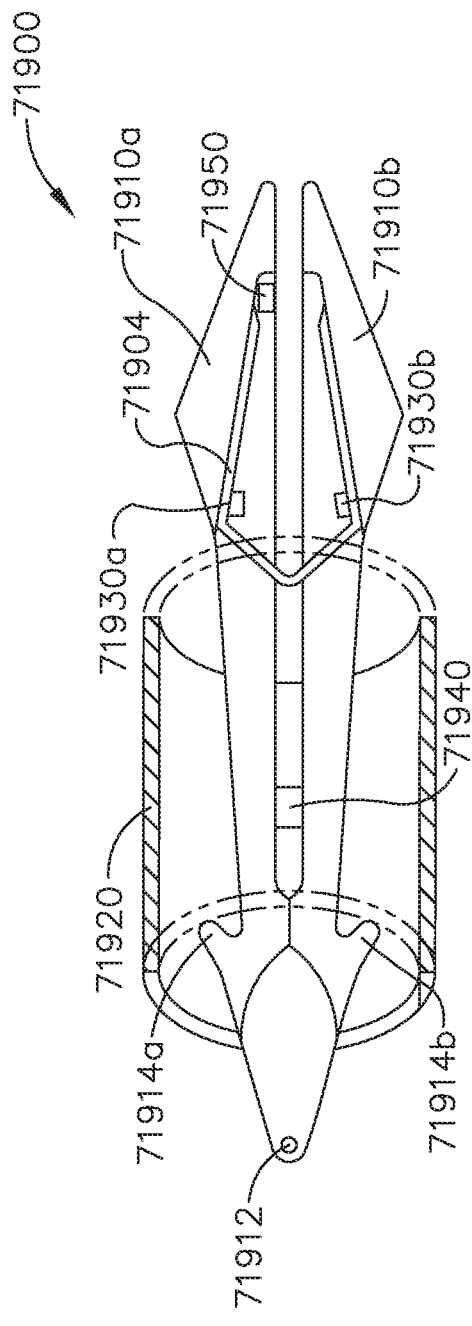
FIG. 81A is a partial cross-sectional view of a clip applier including a sensor array and a magnet.
Figure 81B:
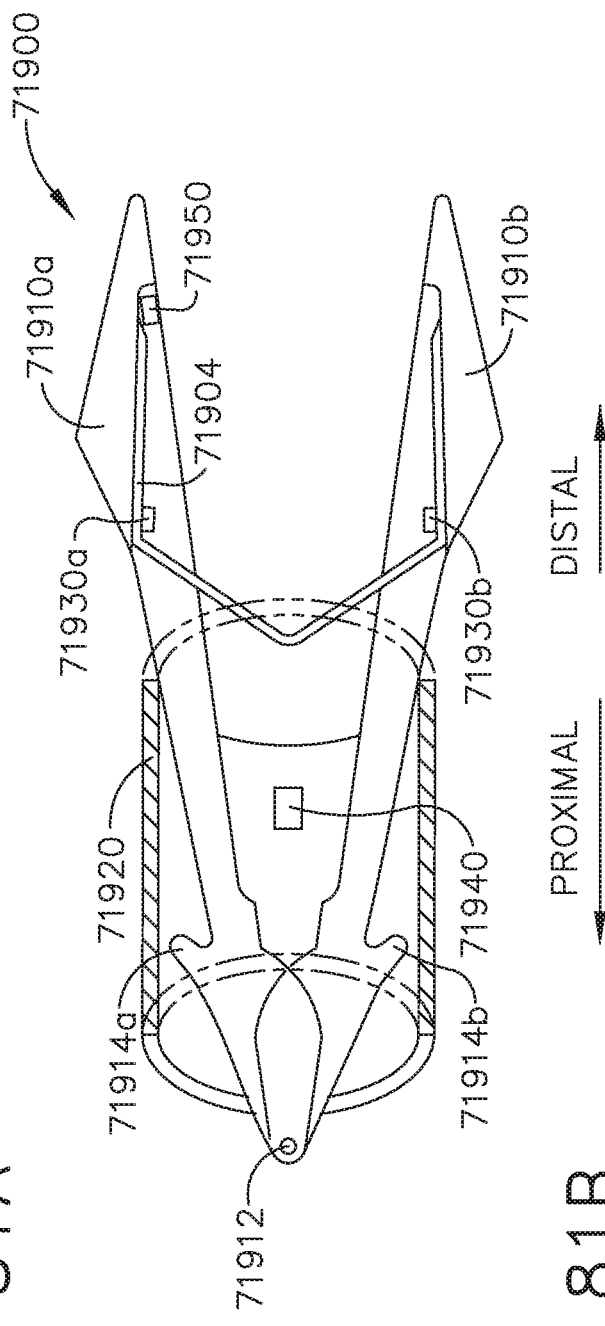
FIG. 81B is a partial cross-sectional view of the clip applier of FIG. 81A.

FIGS. 81A and 81B depict a clip applier 71900 in accordance with at least one embodiment. The clip applier 71900 comprises a first jaw 71910a and a second jaw 71910b moveable relative to each other about a pivot pin 71912 between a closed position, a home position (FIG. 81A), and an open position (FIG. 81B). The clip applier 71900 further comprises a cam member 71920 configured to move the first jaw 71910a and the second jaw 71910b between the closed position, the home position, and the open position. More specifically, the first jaw 71910a and the second jaw 71910b are moved to the open position by the cam member 71920 when the cam member 71920 is moved to a fully retracted position (FIG. 81B) due to the cam member 71920 engaging a first jaw cam 71914a on the first jaw 71910a and a second jaw cam 71914b on the second jaw 71910b. Furthermore, the first jaw 71910a and the second jaw 71910b are moved to the home position by the cam member 71920 when the cam member 71920 is moved distally to a home position depicted in FIG. 81A (i.e., the cam member 71920 is no longer engaging the first jaw cam 71914a and the second jaw cam 71914b allowing the first jaw 71910a and the second jaw 71910b to assume the home position). Further still, the first jaw 71910a and the second jaw 71910b are moved to the closed position by the cam member 71920 when the cam member 71920 is moved distally to a fully advanced position due to the cam member 71920 cammingly engaging the outer surfaces of the first jaw 71910a and the second jaw 71910b. The first jaw 71910a and the second jaw 71910b are configured to receive a clip 71904 therein to be expanded during a pre-form operation and crimped during a crimping operation. FIG. 81A depicts the clip 71904 in a storage configuration when the first jaw 71910a and the second jaw 71910b are in the home position. The clip 71904 can be a 5 mm clip in the storage configuration, for example. Expansion of the clip 71904 during the pre-form operation and crimping of the clip 71904 during the crimping operation are described in further detail below.

The first jaw 71910a and the second jaw 71910b comprise pre-forming features, or protrusions 71930a and 71930b, similar to protrusions 70126a and 70126b discussed above. The protrusions 71930a and 71930b engage the inner surfaces of the clip 71904 and expand the clip 71904 from the storage configuration (FIG. 81A) to a firing configuration (FIG. 81B) when the first jaw 71910a and the second jaw 71910b are moved to the open position. For example, the clip 71904 is expanded from the storage configuration where the clip 71904 has an approximately 5 mm width to a firing configuration where the clip 71904 has an approximately 10 mm width. That said, a clip can have any suitable stored width and any suitable expanded width. After the clip 71904 has been expanded to the firing configuration, a firing member advances the clip over the protrusions 71930a, 71930b into a crimping position within the first jaw 71910a and the second jaw 71910b. The protrusions 71930a and 71930b comprise angled portions which allow the clip 71904 to slide over the protrusions 71930a and 71930b when advanced by the firing member. Once a clip is in the crimping position, the cam member 71920 is advanced distally to the fully advanced position during a crimping stroke to move the first jaw 71910a and the second jaw 71910b to the closed position, and, thus, crimp the clip 71904 within the crimping chamber.

Further to the above, the clip applier 71900 further comprises a sensor array 71940 that detects a magnet 71950 included in one of the first jaw 71910a and the second jaw 71910b. The sensor array 71940 detects the location of the magnet 71950 relative to the sensor array 71940 in order to determine the position of the first jaw 71910a and the second jaw 71910b relative to each other during the operation of the clip applier 71900.

As discussed herein, clip appliers are loaded with clips in a variety of manners. For instance, clips can be loaded into a clip applier by way of a clip cartridge. Such clip cartridges can comprise clips stacked along a longitudinal axis, for example. Such clip cartridges can also comprise clips stacked along an axis which is transverse to the longitudinal axis of the clip applier. Certain cartridges are stored in a circumferential configuration, as described above. That being said, some clip appliers may be configured to hold only one clip at a time. The teachings provided herein are adaptable to such clip appliers. In at least one instance, a one-clip clip applier, for example, can be used with a docking station comprising a plurality of clips stored therein. In such instances, the clinician can use the docking station to re-supply a clip to the one-clip clip applier after each use of the clip applier. In certain instances, the docking station can be positioned in the patient which prevents the need to remove the clip applier from the patient such that the clip applier can be reloaded. In at least one instance, as discussed below, the docking station can be attached to a trocar inserted into the patient, for example. The above being said, the idea of a docking station positioned within a patient can also be used with a multi-clip clip applier. In such instances, one or more clips from the docking station can be loaded into the multi-clip clip applier without having to remove the clip applier from the patient.

Figure 82:
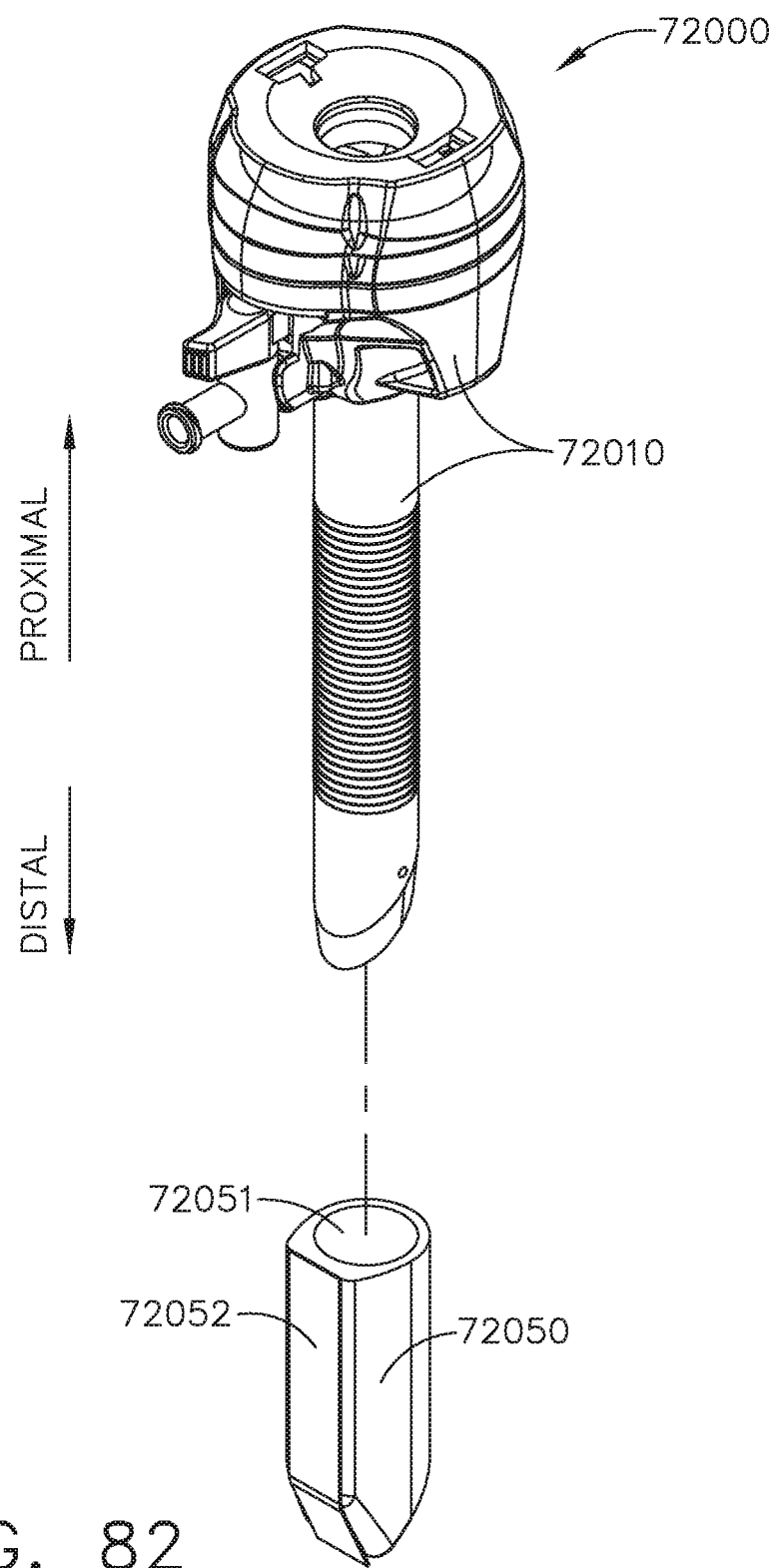
FIG. 82 is a perspective view of a clip applier system utilizing a trocar.
Figure 83:
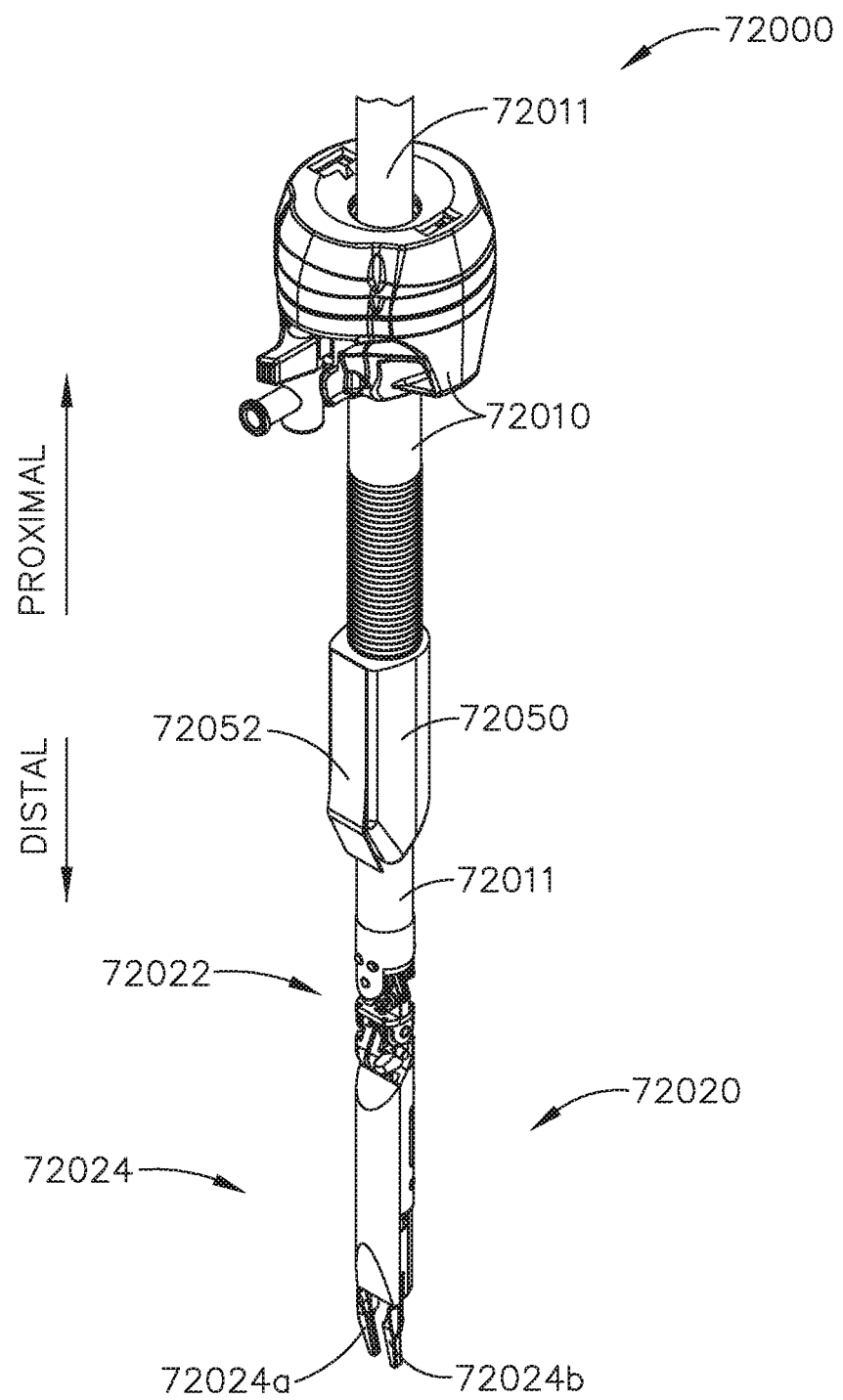
FIG. 83 is a perspective view of the clip applier system of FIG. 82.

Turning to FIGS. 82 and 83, a clip applier system 72000 is depicted. The clip applier system comprises a trocar 72010, a clip magazine 72050, and a clip applier 72020. The clip applier 72020 comprises an elongate shaft 72011 extending from a housing, an articulation joint 72022 extending from the elongate shaft 72011, and an end effector 72024 extending from the articulation joint 72022. The end effector 72024 comprises a first jaw 72024a and a second jaw 72024b moveable relative to each other between an open position and a closed position. The end effector 72024 is articulable relative to the elongate shaft 72011 about the articulation joint 72022. The clip magazine 72050 comprises an opening 72051 (see FIG. 82) through the clip magazine 72050. Prior to insertion of the clip applier 72020 through the trocar 72010, the clip magazine 72050 is positioned within the patient and attached to the distal end of the trocar 72010. The opening 72051 allows the clip magazine 72050 to be received and attached to the distal end of the trocar 72010 as depicted in FIG. 83. The clip magazine 72050 can be threadably attached to the distal end of the trocar 72010, for example. The clip applier 72020 is then inserted through the trocar 72010 and the opening 72051 of the clip magazine 72050 until the end effector 72024 of the clip applier 72020 is positioned distal to the clip magazine 72050. As the clip applier 72020 is retracted toward the clip magazine 72050, the clip applier 72020 engages the clip magazine 72050 to eject a clip from the clip magazine 72050 into the end effector of the clip applier 72020, as discussed in greater detail below.

Figure 84A:
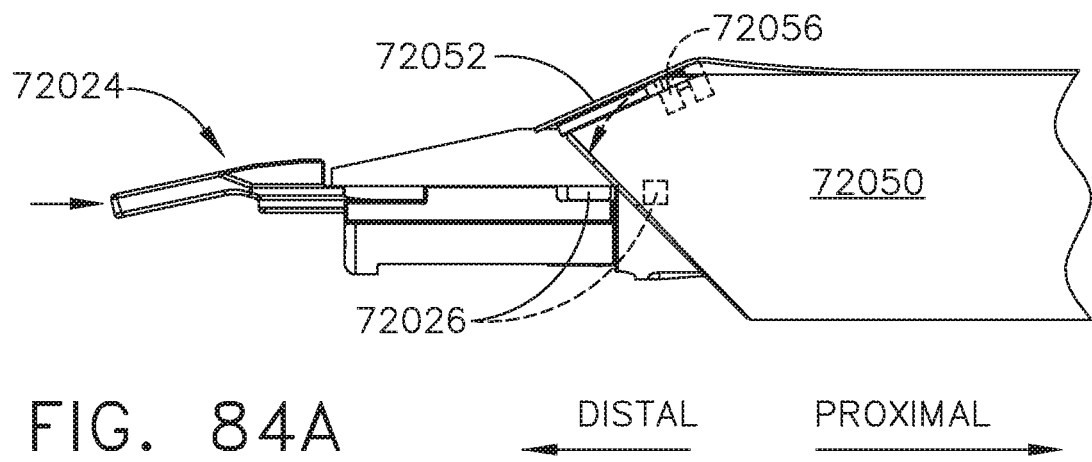
FIG. 84A is a partial side elevation view of the clip applier system of FIG. 82 depicting a jaw wing of a clip applier of the clip applier system positioned distal to a loading arm of a clip magazine of the clip applier system.
Figure 84B:
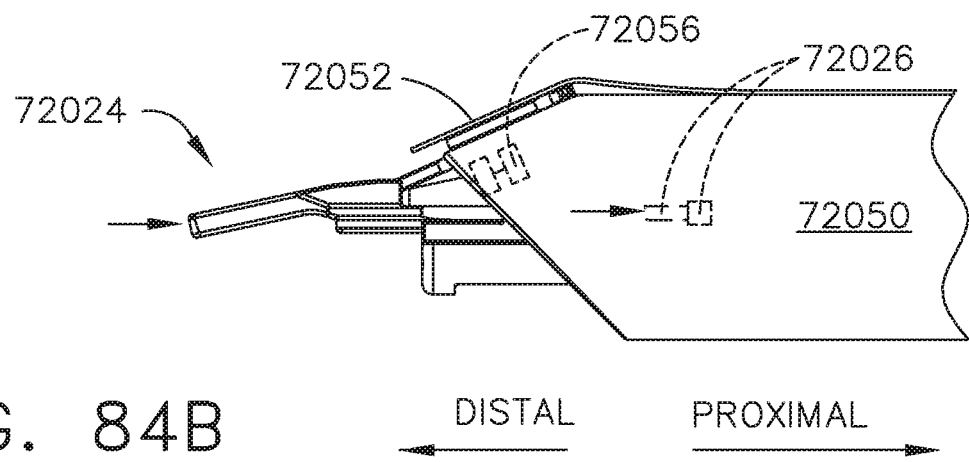
FIG. 84B is a partial side elevation view of the clip applier system of FIG. 82 depicting the jaw wing of the clip applier positioned proximal to the loading arm of the clip magazine.
Figure 84C:
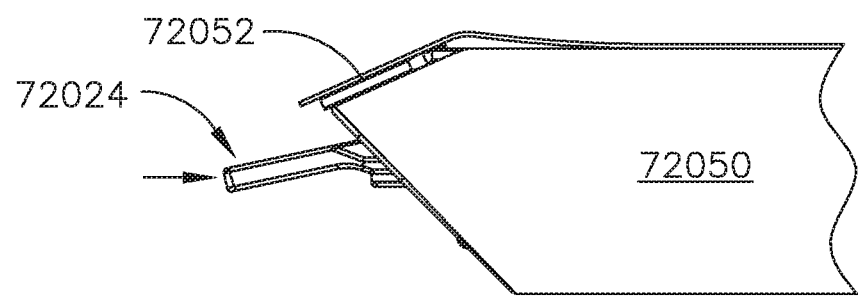
FIG. 84C is a partial side elevation view of the clip applier system of FIG. 82 depicting the jaw wing of the clip applier positioned proximal to the loading arm of the clip magazine.
Figure 85B:
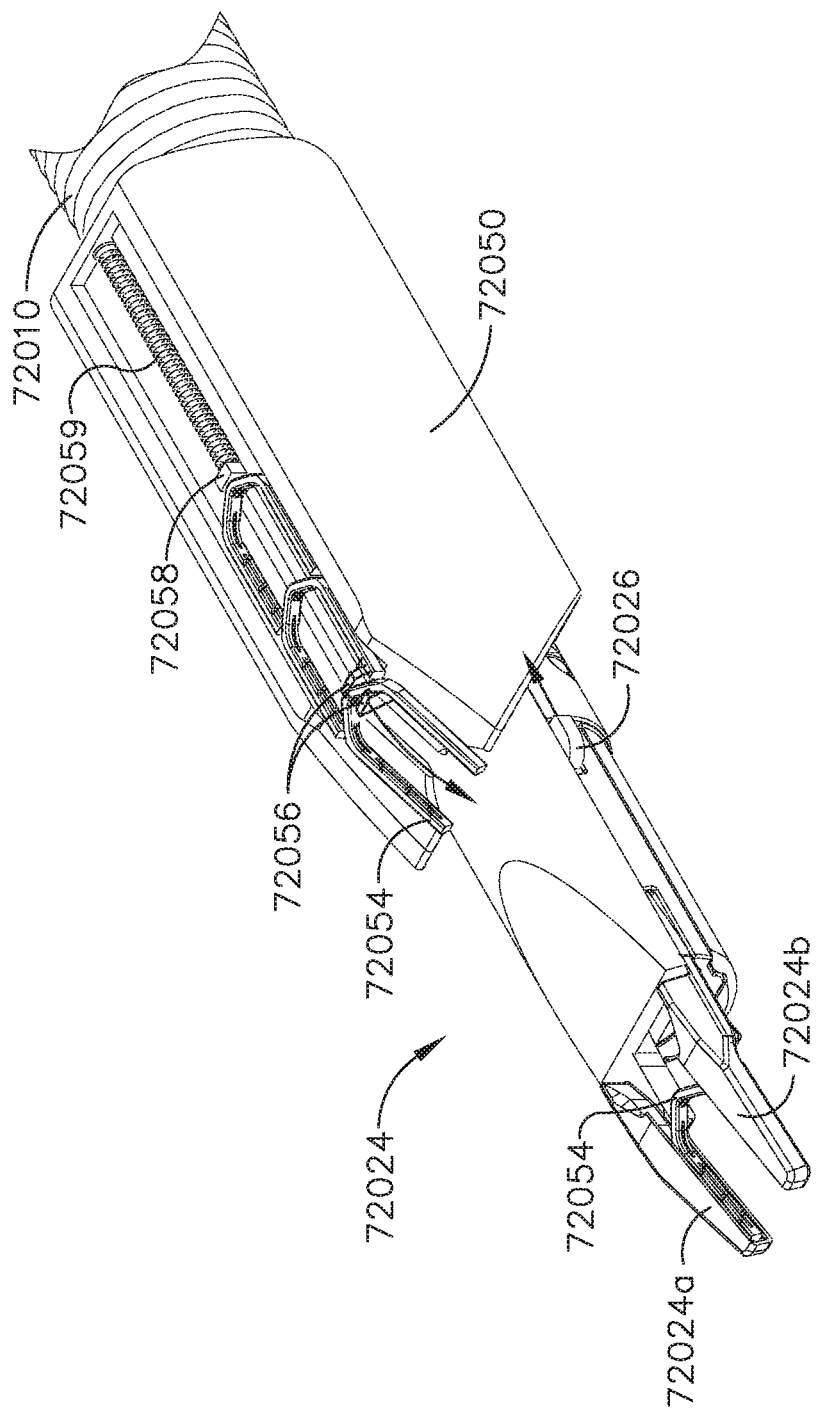
FIG. 85B is a cross-sectional perspective view of the clip applier system of FIG. 82.

Turning to FIGS. 85A and 85B, the clip magazine 72050 further comprises, a leaf spring 72052, a plurality of clips 72054 removably stored in the clip magazine 72050, a spring 72059, a sled 72058, and a loading arm 72056. The leaf spring 72052 prevents the clips 72054 from falling out of the clip magazine 72050 inadvertently. The spring 72059 biases the sled 72058 distally to bias the clips 72054 toward the loading arm 72056. The loading arm 72056 grasps and holds a clip 72054 in place until acted upon by the clip applier 72020. To this end, the loading arm 72056 engages a jaw wing 72026 of the clip applier 72020 as the clip applier 72020 is retracted towards the clip magazine 72050 (i.e., proximally). When the jaw wing 72026 is engaged by the loading arm 72056, the jaw wing 72026 moves proximally and the loading arm 72056 rotates toward the end effector 72024 to load a clip 72054 from the clip magazine 72050 into the end effector 72024 of the clip applier 72020. FIGS. 84A-84C depict the movements of the jaw wing 72024 and the loading arm 72056 as the clip applier 72020 is retracted towards the clip magazine 72050. After a clip 72054 has been loaded into the end effector 72024, the clip applier 72024 can be moved distally to a desired location within the patient to crimp the clip 72054 around patient tissue. After the clip 72054 is crimped and released, the clip applier 72020 can be retracted toward the clip magazine 72050 (i.e., proximally) to engage the jaw wing 72026 with the loading arm 72056 of the clip magazine 72050 to load another clip into the clip applier 72020. This process can be repeated until all of the clips 72054 have been depleted from the clip magazine 72050, and/or until a suitable number of clips have been applied.

Figure 86A:
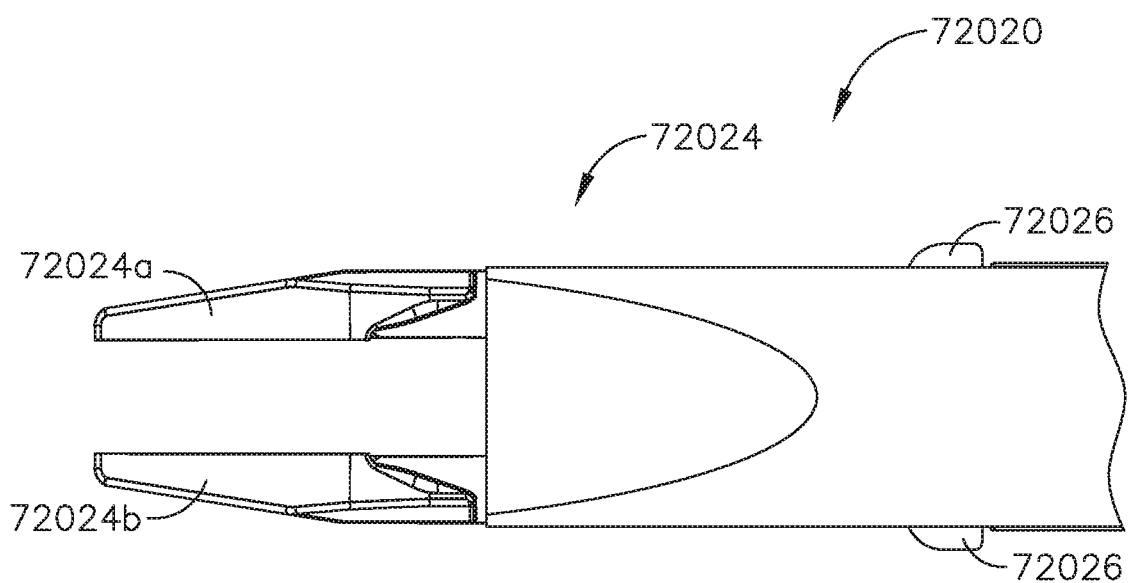
FIG. 86A is a plan view of the clip applier system of FIG. 82 depicting a jaw wing of the clip applier in an expanded configuration.
Figure 86B:
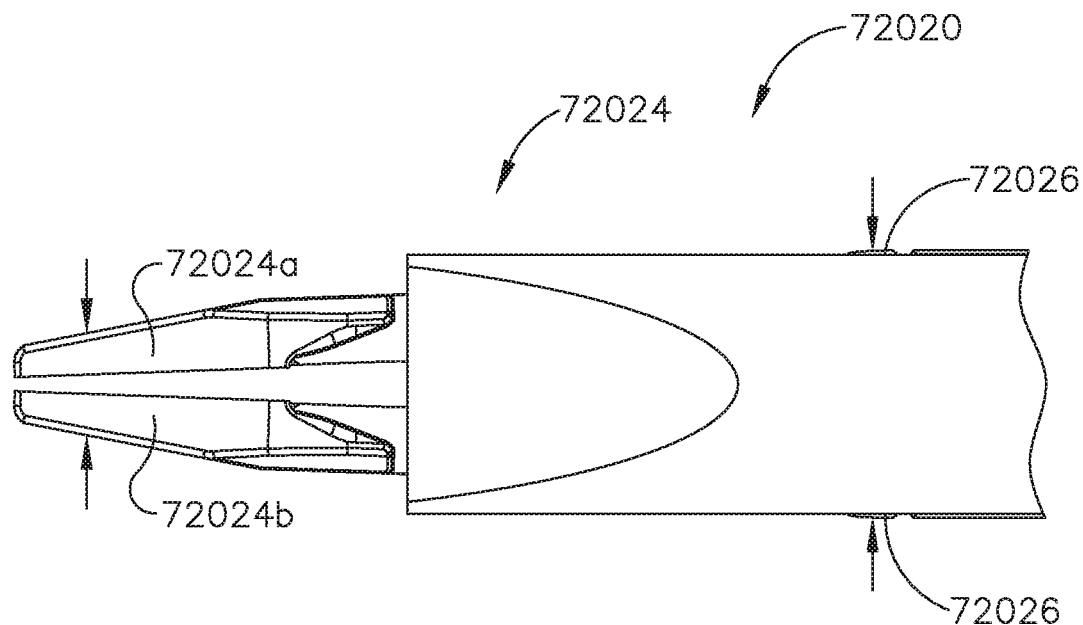
FIG. 86B is a plan view of the clip applier system of FIG. 82 depicting the jaw wing of the clip applier in a retracted configuration.

Turning now to FIGS. 86A and 86B, the relationship between the jaw wing 72026 and the first and second jaws 72024a and 72024b of the clip applier 72020 is depicted. The jaw wing 72026 is operably engaged with the first and second jaws 72024a and 72024b such that, when the first and second jaws 72024a and 72024b are in the closed position (FIG. 86B), the jaw wing 72026 is retracted. To this end, the clip applier 72020 can be inserted through the clip magazine 72050 without the jaw wing 72026 engaging the loading arm 72056 of the clip magazine 72050. Other embodiments are envisioned where the clip applier 72020 engages the clip magazine 72050 to load a clip 72054 into the end effector 72024 when the clip applier 72020 is moved from a proximal position behind the clip magazine 72050 to a distal position beyond the clip magazine 72050.

A clip applier 73000 is depicted in FIGS. 87A-87D. The clip applier 73000 comprises an elongate shaft 73010 extending from a housing, an articulation joint 73020 extending from the elongate shaft 73010, a magazine housing 73030 extending from the articulation joint 73020, and an end effector 73040 extending from the magazine housing 73030. The end effector 73040 comprises a first jaw 73040a and a second jaw 73040b moveable relative to each other between an open position and a closed position. The magazine housing 73030 comprises a bottom housing 73030b and a top housing 73030a. The top housing 73030a is movable relative to the bottom housing 73030b between an open position (FIG. 87A) and a closed position (FIG. 87C) about a pivot pin 73032 attached to the articulation joint 73020. The magazine housing 73030 can receive a clip magazine 73050 comprising a plurality of clips 73054 stored therein. The clips 73054 are loaded into the clip magazine 73030 and are locked in place by a biasing member, or leaf spring 73056. The leaf spring 73056 prevents the clips 73054 from being ejected form the clip magazine 73050 until the clip magazine 73050 is seated in the magazine housing 73030, as discussed in greater detail below.

Figure 87A:
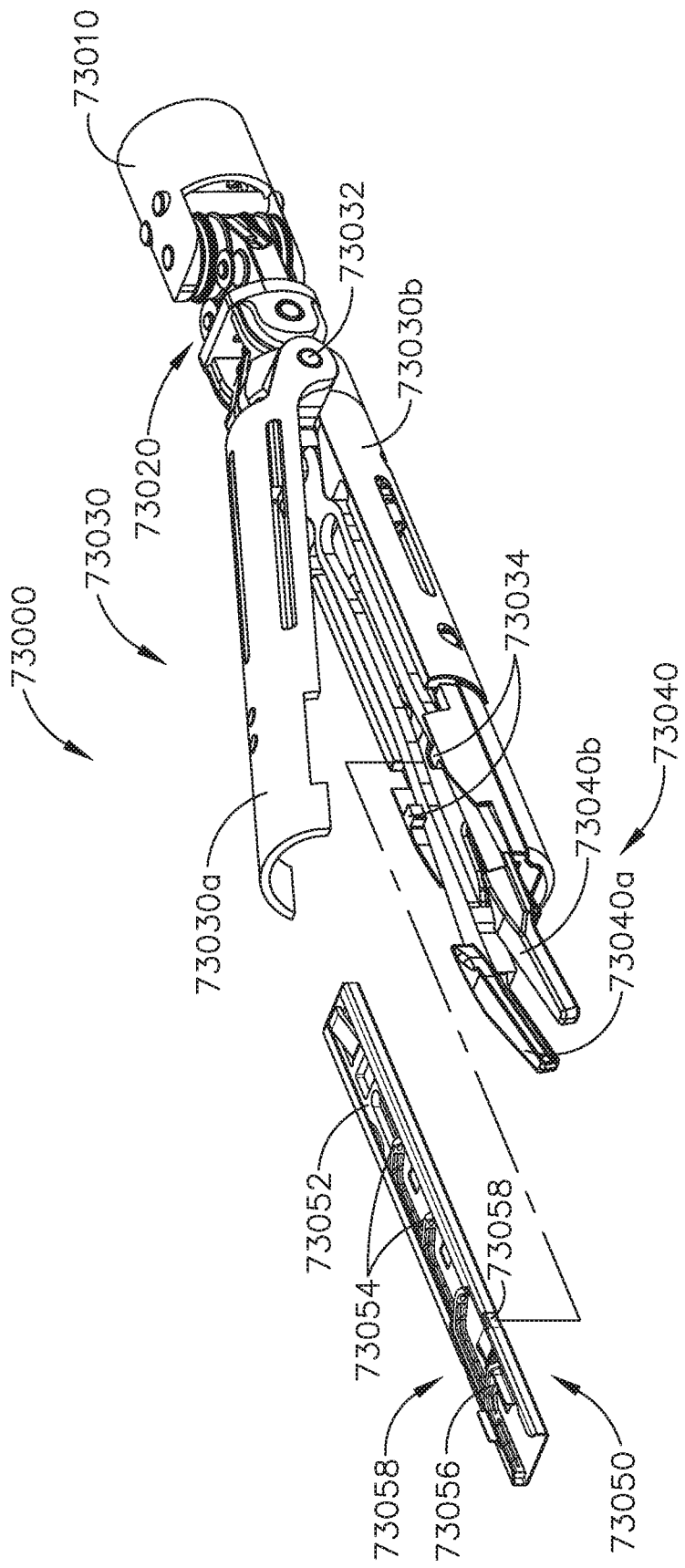
FIG. 87A is a perspective view of a clip applier and a clip magazine for use with the clip applier.
Figure 87B:
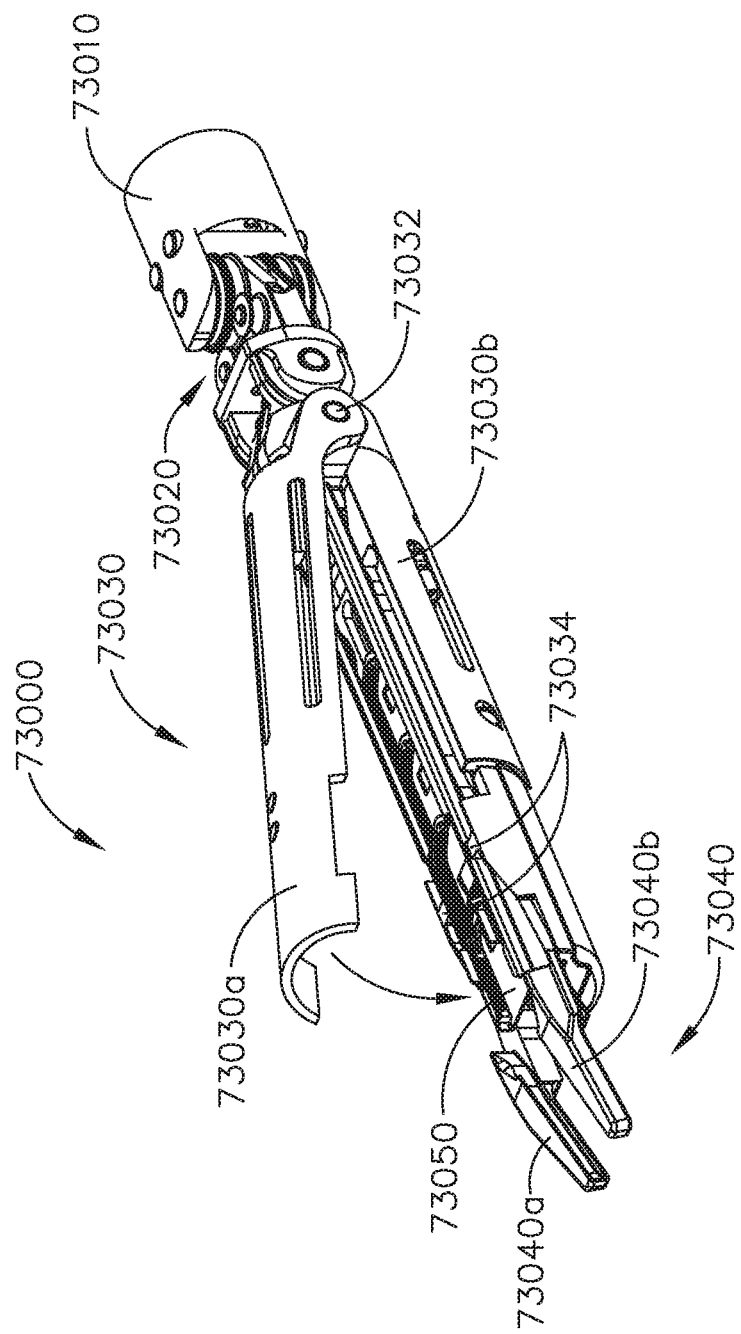
FIG. 87B is a perspective view of the clip magazine seated into the clip applier of FIG. 87A.
Figure 87C:
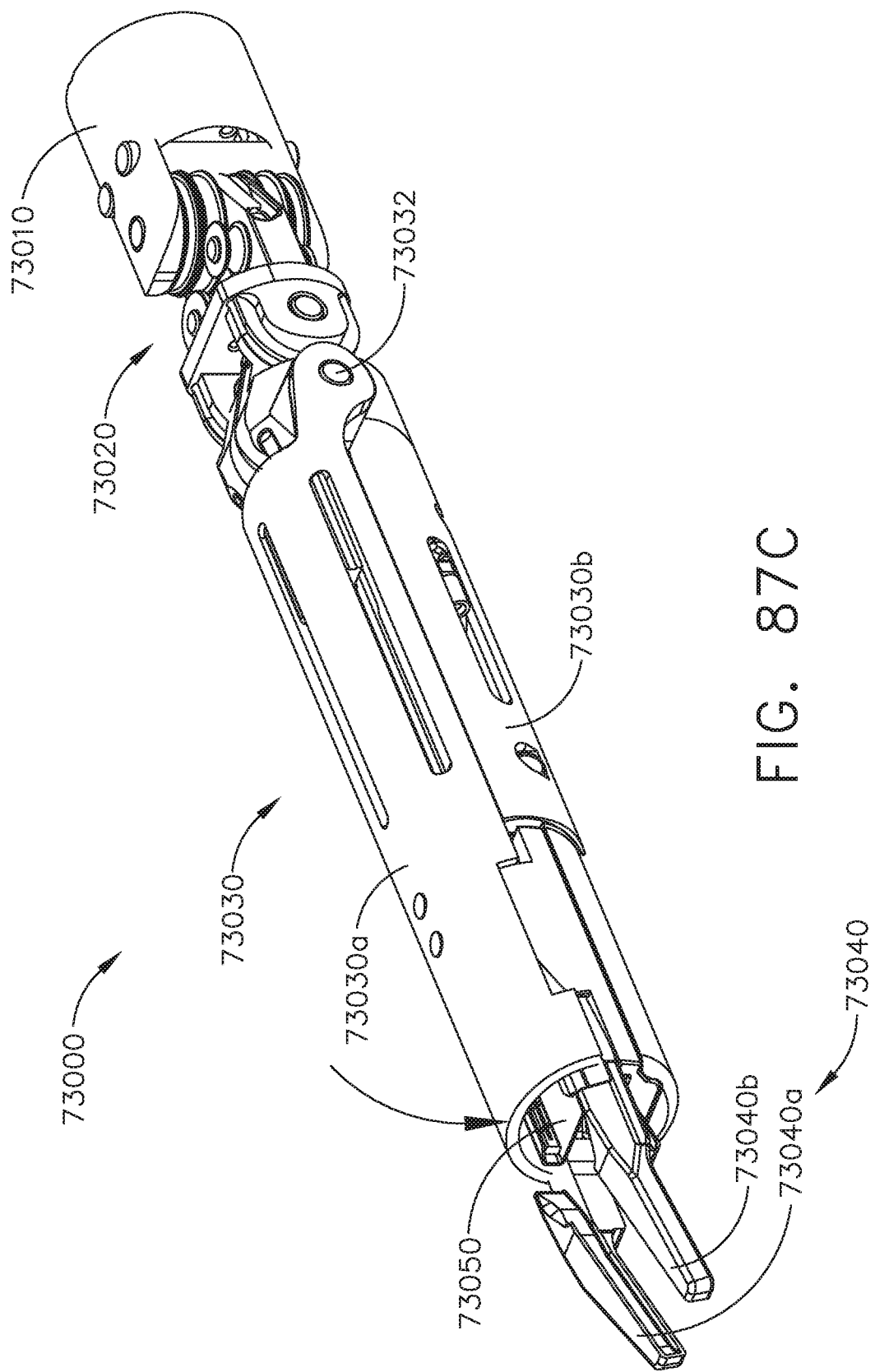
FIG. 87C is a perspective view of the clip applier and the clip magazine of FIG. 87A in a loaded configuration.
Figure 87D:
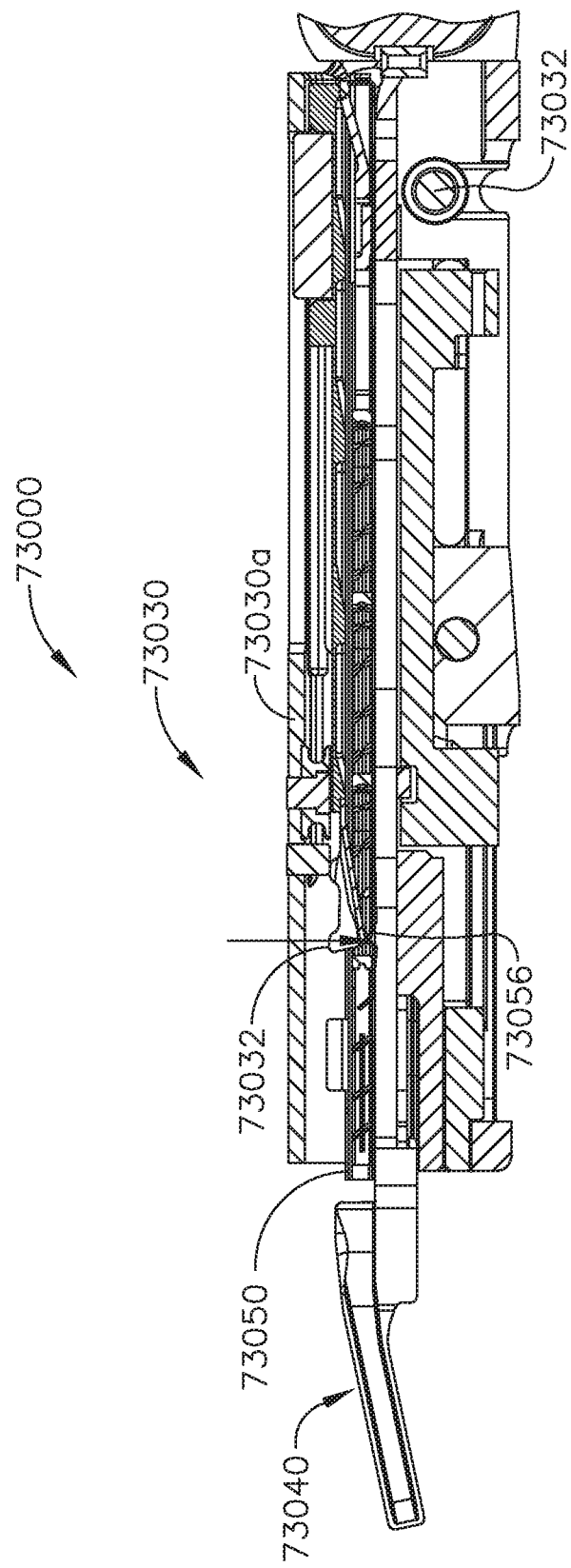
FIG. 87D is a cross-sectional view of the clip applier and the clip magazine of FIG. 87A in the loaded configuration of FIG. 87C.

The clip magazine 73050 further comprises notches 73058 on either side of the clip magazine 73050. To properly seat the clip magazine 73050 in the magazine housing 73030, the notches 73058 of the clip magazine 73050 are aligned with protrusions 73034 of the magazine housing 73030 to seat and align the clip magazine 73050 in the magazine housing 73030 as depicted in FIG. 87B. Once the clip magazine 73050 is installed into the magazine housing 73030, the top housing 73030a can be moved to the closed position as depicted in FIG. 87C. The top housing 73030a comprises a lockout release, or protrusion 73032, that engages the leaf spring 73056 of the clip magazine 73050 when the clip magazine 73050 is installed in the magazine housing 73030 and the top housing 73030a is in the closed position as depicted in FIG. 87D. When the leaf spring 73056 is depressed by the protrusion 73032, the clips 73054 are no longer locked into position within the clip magazine 73050 and can be ejected from the clip magazine 73050 into the end effector 73040 by a firing member.

Figure 88A:
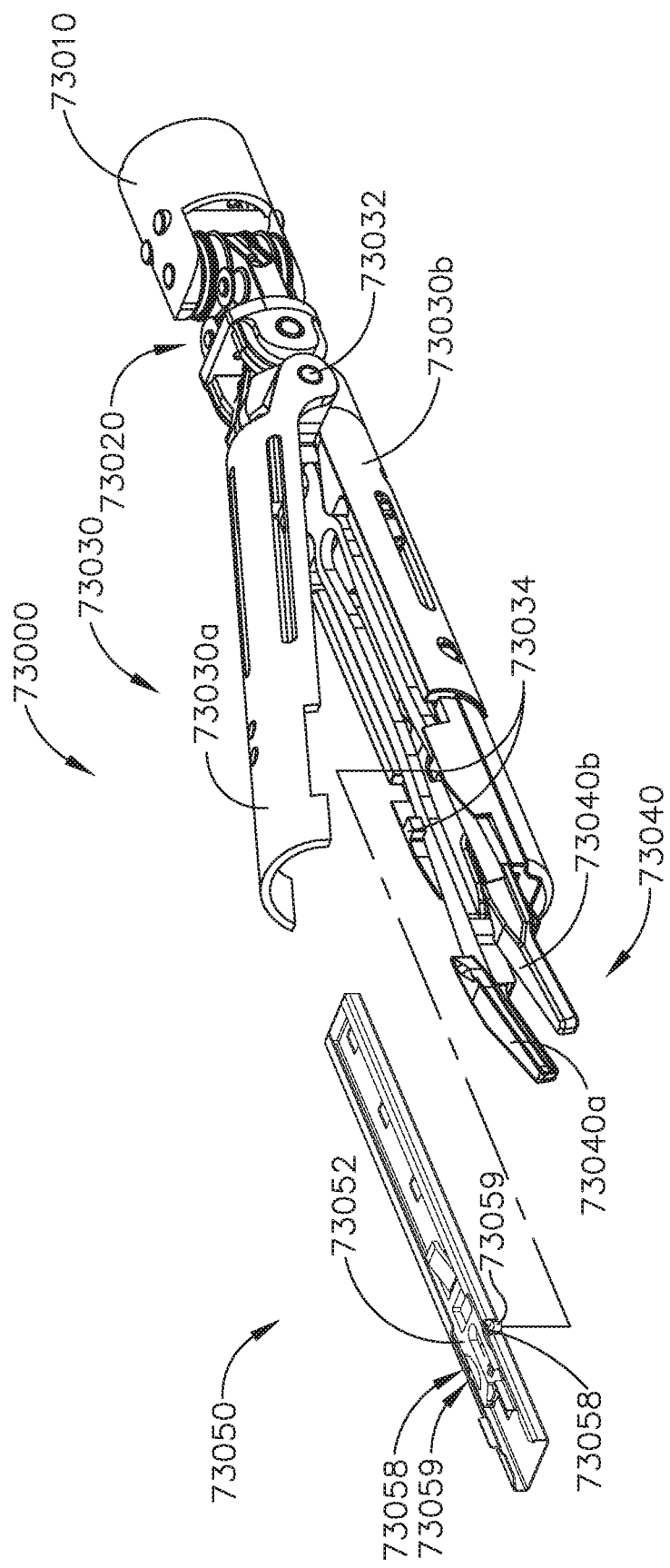
FIG. 88A is a perspective view the spent clip magazine removed from the clip applier of FIG. 87A.
Figure 88B:
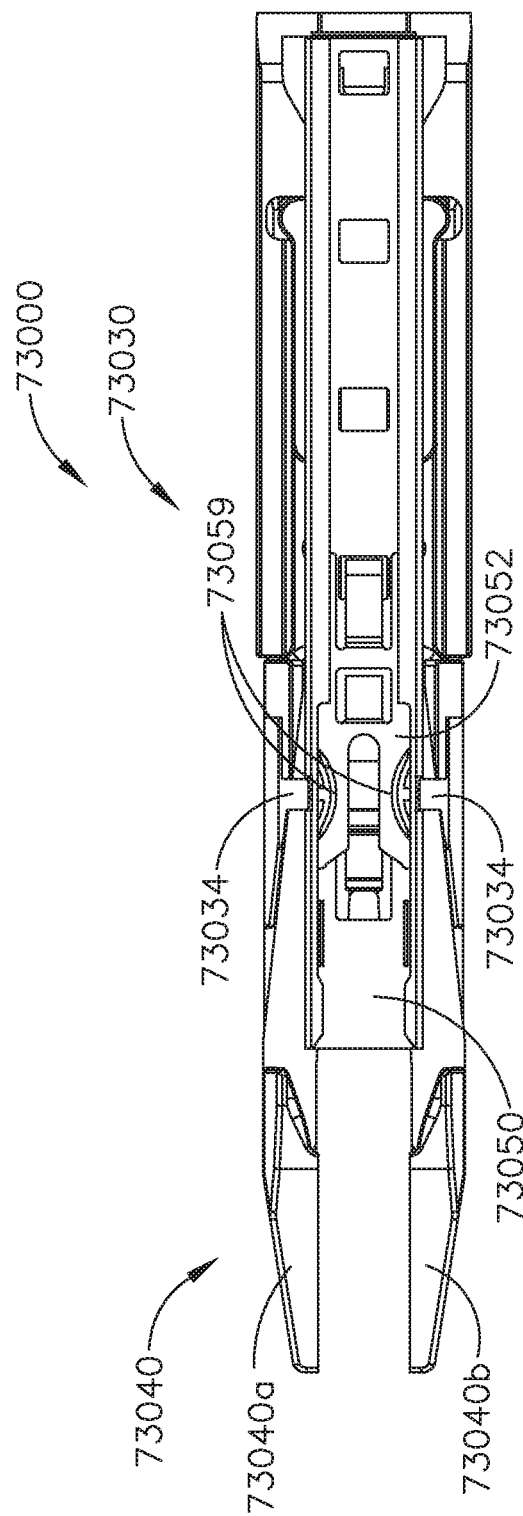
FIG. 88B is a plan view of the spent clip magazine seated into the clip applier of FIG. 87A.

Turning now to FIGS. 88A-88D, after all of the clips 73054 have been ejected from the clip magazine 73050, the clip magazine 73050 can be locked out when removed from the magazine housing 73030 to prevent the clip magazine 73050 from being re-installed into the magazine housing 73030 until reloaded with at least one new clip 73054. More specifically, the clip magazine 73030 comprises a sled 73052 that moves through the clip magazine 73030 as the clips 73054 are ejected. The sled 73052 comprises spring loaded detents 73059 which align with the notches 73058 in the clip magazine 73050 when the last clip 73054 has been ejected form the clip magazine 73050. When the clip magazine 73050 is installed in the magazine housing 73030 and the clip magazine 73050 has been spent, the spring loaded detents 73059 are biased against the protrusions 73034 as depicted in FIGS. 88B and 88D. After the clip magazine 73050 is removed from the magazine housing 73030, the spring loaded detents 73059 protrude through the notches 73058 to lock the sled 73052 into place as depicted in FIG. 88A. The spent clip magazine 73050 cannot be re-installed into the magazine housing 73030 unless at least one clip 73054 is loaded into the clip magazine 73050. More specifically, until the sled 73052 is retracted to disengage the spring loaded detents 73059 from the notches 73058 (i.e., at least one clip 73054 is installed) the clip magazine 73050 cannot be installed into the magazine housing 73030 because the spring loaded detents 73059 occupy the notches 73058 and will not allow the notches 73058 to properly align and seat with the protrusions 73034 of the magazine housing 73030.

Other embodiments are envisioned where a clip applier system comprises a clip applier, a trocar, and a sensing system. The clip applier of the clip applier system is similar to clip applier 72020 in many respects and the trocar is similar to the trocar 72010 in many respects. The trocar can comprise a sensor, such as a Hall Effect sensor, for example, attached to, or near, the distal end of the trocar. The clip applier further comprises a detectable element, such as a magnet, for example, positioned in the end effector of the clip applier. The magnet in the end effector of the clip applier and the Hall Effect sensor on the distal end of the trocar are included in the sensing system. The sensing system is in signal communication with the control system of the clip applier via a wireless signal transmitter in the trocar and a wireless signal receiver in the clip applier. The control system of the clip applier is configured to automatically control the opening and closing of the jaws of the end effector depending on the position of the magnet relative to the Hall Effect sensor. More specifically, when the magnet in the jaws is positioned a predetermined distance distal to the Hall Effect sensor of the trocar—which indicates that the jaws have passed through the trocar, the clip jaws are automatically moved to an open position by the control system of the clip applier. Moreover, the control system of the clip applier can also automatically load a clip into the open jaws. Such an arrangement reduces the time needed to load the clip applier after being inserted into a patient. Further, when the magnet in the jaws is approaching the Hall Effect sensor of the trocar from a distal position (i.e., the clip applier is being retracted proximally toward the trocar) the control system automatically moves the jaws to a closed position to allow the clip applier to be retracted through the trocar.

Figure 89:
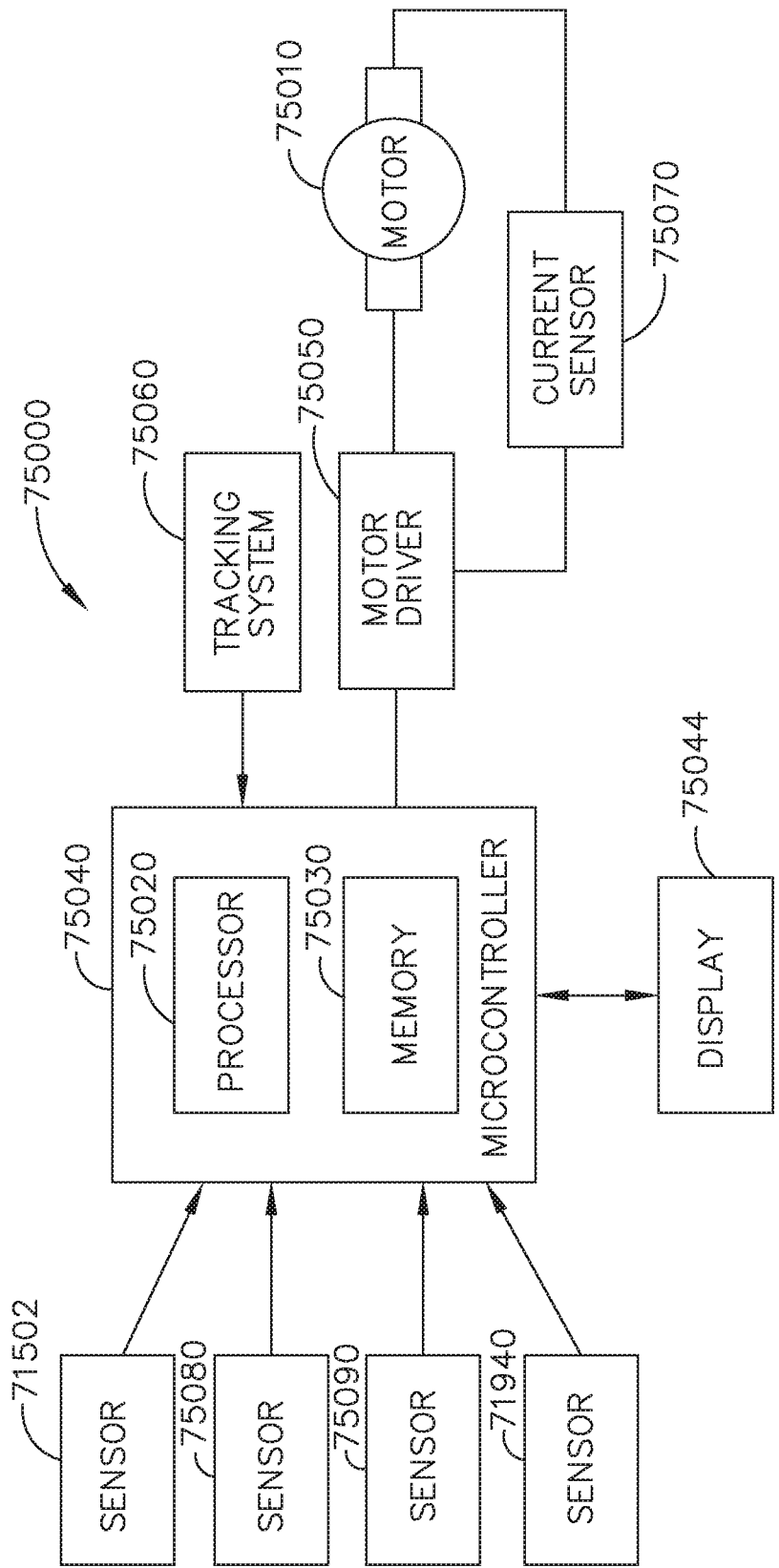
FIG. 89 is a schematic of a control system for use with any of the surgical instruments disclosed herein.

FIG. 89 is a logic diagram of a control system 75000 for use with any of the various clip appliers described herein. The control system 75000 comprises a control circuit. The control circuit includes a microcontroller 75040 comprising a processor 75020 and a memory 75030. One or more sensors, such as sensor 75080, sensor 75090, sensor 71502, and sensor array 71940, for example, provide real time feedback to the processor 75020. The control system 75000 further comprises a motor driver 75050 configured to control an electric motor 75010 and a tracking system 75060 configured to determine the position of one or more longitudinally movable components in the clip applier, such as firing member 70165 (FIG. 35A), crimping drive 70180 (FIG. 36), feeder member 70630 (FIG. 53), firing member 70640 (FIG. 53), and closure tube 70620 (FIG. 53), for example. The tracking system 75060 is also configured to determine the position of one or more rotational components in the clip applier, such as the rotatable clip magazine 70650 (FIG. 52), for example. The tracking system 75060 provides position information to the processor 75020, which can be programmed or configured to, among other things, determine the position of the rotatable clip magazine 70650 (FIG. 52), determine the position of the firing member, feeder member, closure tube and/or crimping drive, as well as determine the orientation of the jaws of the clip applier. The motor driver 75050 may be an A3941 available from Allegro Microsystems, Inc., for example; however, other motor drivers may be readily substituted for use in the tracking system 75060. A detailed description of an absolute positioning system is described in U.S. Patent Application Publication No. 2017/0296213, entitled SYSTEMS AND METHODS FOR CONTROLLING A SURGICAL STAPLING AND CUTTING INSTRUMENT, the entire disclosure of which is hereby incorporated herein by reference.

The microcontroller 75040 may be any single core or multicore processor such as those known under the trade name ARM Cortex by Texas Instruments, for example. In at least one instance, the microcontroller 75040 is a LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules and/or frequency modulation (FM) modules, one or more quadrature encoder inputs (QEI) analog, one or more 12-bit Analog-to-Digital Converters (ADC) with 12 analog input channels, for example, details of which are available from the product datasheet.

In various instances, the microcontroller 75040 comprises a safety controller comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 75040 is programmed to perform various functions such as precisely controlling the speed and/or position of the firing member, feeder member, crimping drive or closure tube of any of the clip appliers disclosed herein, for example. The microcontroller 75040 is also programmed to precisely control the rotational speed and position of the end effector of the clip applier and the articulation speed and position of the end effector of the clip applier. In various instances, the microcontroller 75040 computes a response in the software of the microcontroller 75040. The computed response is compared to a measured response of the actual system to obtain an "observed" response, which is used for actual feedback decisions. The observed response is a favorable, tuned, value that balances the smooth, continuous nature of the simulated response with the measured response, which can detect outside influences on the system.

The motor 75010 is controlled by the motor driver 75050. In various forms, the motor 75010 is a DC brushed driving motor having a maximum rotational speed of approximately 25,000 RPM, for example. In other arrangements, the motor 75010 includes a brushless motor, a cordless motor, a synchronous motor, a stepper motor, or any other suitable electric motor. The motor driver 75050 may comprise an H-bridge driver comprising field-effect transistors (FETs), for example. The motor driver 75050 may be an A3941 available from Allegro Microsystems, Inc., for example. The A3941 motor driver 75050 is a full-bridge controller for use with external N-channel power metal oxide semiconductor field effect transistors (MOSFETs) specifically designed for inductive loads, such as brush DC motors. In various instances, the motor driver 75050 comprises a unique charge pump regulator provides full (>10 V) gate drive for battery voltages down to 7 V and allows the A3941 motor driver 75050 to operate with a reduced gate drive, down to 5.5 V. A bootstrap capacitor may be employed to provide the above-battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the lowside FETs. The power FETs are protected from shoot-through by resistor adjustable dead time. Integrated diagnostics provide indication of undervoltage, overtemperature, and power bridge faults, and can be configured to protect the power MOSFETs under most short circuit conditions. Other motor drivers may be readily substituted.

The tracking system 75060 comprises a controlled motor drive circuit arrangement comprising one or more position sensors, such as the sensor 75080, sensor 75090, sensor 71502, and sensory array 71940, for example. The position sensors for an absolute positioning system provide a unique position signal corresponding to the location of a displacement member. As used herein, the term displacement member is used generically to refer to any movable member of any of the clip appliers disclosed herein. In various instances, the displacement member may be coupled to any position sensor suitable for measuring linear displacement or rotational displacement. Linear displacement sensors may include contact or non-contact displacement sensors. The displacement sensors may comprise linear variable differential transformers (LVDT), differential variable reluctance transducers (DVRT), a slide potentiometer, a magnetic sensing system comprising a movable magnet and a series of linearly arranged Hall Effect sensors similar to the arrangement illustrated in FIG. 75, a magnetic sensing system comprising a fixed magnet and a series of movable linearly arranged Hall Effect sensors similar to the arrangement illustrated in FIGS. 81A and 81B, an optical sensing system comprising a movable light source and a series of linearly arranged photo diodes or photo detectors, or an optical sensing system comprising a fixed light source and a series of movable linearly arranged photo diodes or photo detectors, or any combination thereof.

The position sensors 75080, 75090, 71502, and 71940 for example, may comprise any number of magnetic sensing elements, such as, for example, magnetic sensors classified according to whether they measure the total magnetic field or the vector components of the magnetic field. The techniques used to produce both types of magnetic sensors encompass many aspects of physics and electronics. The technologies used for magnetic field sensing include search coil, fluxgate, optically pumped, nuclear precession, SQUID, Hall-Effect, anisotropic magnetoresistance, giant magnetoresistance, magnetic tunnel junctions, giant magnetoimpedance, magnetostrictive/piezoelectric composites, magnetodiode, magnetotransistor, fiber optic, magnetooptic, and microelectromechanical systems-based magnetic sensors, among others.

In various instances, one or more of the position sensors of the tracking system 75060 comprise a magnetic rotary absolute positioning system. Such position sensors may be implemented as an AS5055EQFT single-chip magnetic rotary position sensor available from Austria Microsystems, AG and can be interfaced with the controller 75040 to provide an absolute positioning system. In certain instances, a position sensor comprises a low-voltage and low-power component and includes four Hall-Effect elements in an area of the position sensor that is located adjacent a magnet. A high resolution ADC and a smart power management controller are also provided on the chip. A CORDIC processor (for Coordinate Rotation Digital Computer), also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface such as an SPI interface to the controller 75040. The position sensors can provide 12 or 14 bits of resolution, for example. The position sensors can be an AS5055 chip provided in a small QFN 16-pin 4×4×0.85 mm package, for example.

The tracking system 75060 may comprise and/or be programmed to implement a feedback controller, such as a PID, state feedback, and adaptive controller. A power source converts the signal from the feedback controller into a physical input to the system, in this case voltage. Other examples include pulse width modulation (PWM) and/or frequency modulation (FM) of the voltage, current, and force. Other sensor(s) may be provided to measure physical parameters of the physical system in addition to position. In various instances, the other sensor(s) can include sensor arrangements such as those described in U.S. Pat. No. 9,345,481, entitled STAPLE CARTRIDGE TISSUE THICKNESS SENSOR SYSTEM, which is hereby incorporated herein by reference in its entirety; U.S. Patent Application Publication No. 2014/0263552, entitled STAPLE CARTRIDGE TISSUE THICKNESS SENSOR SYSTEM, which is hereby incorporated herein by reference in its entirety; and U.S. patent application Ser. No. 15/628,175, entitled TECHNIQUES FOR ADAPTIVE CONTROL OF MOTOR VELOCITY OF A SURGICAL STAPLING AND CUTTING INSTRUMENT, which is hereby incorporated herein by reference in its entirety. In a digital signal processing system, absolute positioning system is coupled to a digital data acquisition system where the output of the absolute positioning system will have finite resolution and sampling frequency. The absolute positioning system may comprise a compare and combine circuit to combine a computed response with a measured response using algorithms such as weighted average and theoretical control loop that drives the computed response towards the measured response. The computed response of the physical system takes into account properties like mass, inertial, viscous friction, inductance resistance, etc., to predict what the states and outputs of the physical system will be by knowing the input.

The absolute positioning system provides an absolute position of the displacement member upon power up of the instrument without retracting or advancing the displacement member to a reset (zero or home) position as may be required with conventional rotary encoders that merely count the number of steps forwards or backwards that the motor 75010 has taken to infer the position of a device actuator, a firing member, a feeder drive, a crimping drive, a closure tube, and the like.

A sensor 75080 comprising a strain gauge or a microstrain gauge, for example, is configured to measure one or more parameters of the end effector of the clip applier, such as, for example, the strain experienced by the jaws during a crimping operation. In one embodiment, the sensor 75080 can comprise the strain gauges 71720 and 71730 (FIG. 79) discussed in greater detail above, for example. The measured strain is converted to a digital signal and provided to the processor 75020. In addition to or in lieu of the sensor 75080, a sensor 75090 comprising a load sensor, for example, can measure the closure force applied by the closure drive system to the jaws of the clip applier. In various instances, a current sensor 75070 can be employed to measure the current drawn by the motor 75010. The force required to clamp the first and second jaws to crimp a clip can correspond to the current drawn by the motor 75010, for example. The measured force is converted to a digital signal and provided to the processor 75020. A magnetic field sensor can be employed to measure the thickness of the captured tissue. The measurement of the magnetic field sensor can also be converted to a digital signal and provided to the processor 75020.

The measurements of the tissue compression, the tissue thickness, and/or the force required to close the end effector and crimp a clip around tissue as measured by the sensors can be used by the controller 75040 to characterize the position and/or speed of the movable member being tracked. In at least one instance, the memory 75030 may store a technique, an equation, and/or a look-up table which can be employed by the controller 75040 in the assessment. In various instances, the controller 75040 can provide the user of the clip applier with a choice as to the manner in which the clip applier should be operated. To this end, a display 75044 can display a variety of operating conditions of the clip applier and can include touch screen functionality for data input. Moreover, information displayed on the display 75044 may be overlaid with images acquired via the imaging modules of one or more endoscopes and/or one or more additional surgical instruments used during the surgical procedure.

As discussed above, the clip appliers disclosed herein may comprise control systems. Each of the control systems can comprise a circuit board having one or more processors and/or memory devices. Among other things, the control systems are configured to store sensor data, for example.

They are also configured to store data which identifies the type of clip applier attached to a handle or housing, such as handle 700 (FIG. 29), for example. More specifically, the type of clip applier can be identified when attached to the handle or housing by the sensors and the sensor data can be stored in the control system. Moreover, they are also configured to store data including whether or not the clip applier has been previously used and/or how many clips have been ejected from the clip magazine or clip cartridge of the clip applier during operation. This information can be obtained by the control system to assess whether or not the clip applier is suitable for use and/or has been used less than a predetermined number of times, for example.

The surgical instrument systems described herein are motivated by an electric motor; however, the surgical instrument systems described herein can be motivated in any suitable manner. In certain instances, the motors disclosed herein may comprise a portion or portions of a robotically controlled system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail, the entire disclosure of which is incorporated by reference herein.

EXAMPLES

Example 1—A surgical device for clipping tissue comprising a housing comprising a motor, a shaft extending from the housing, an end effector extending from the shaft, and a first clip magazine releasably attached to the surgical device. The first clip magazine comprises a plurality of first clips and is replaceable with a second clip magazine comprising a plurality of second clips. The surgical device further comprises a firing drive operably responsive to the motor. The firing drive is configured to move a first clip from the first clip magazine into the end effector when the first clip magazine is attached to the surgical device. The firing drive is further configured to move a second clip from the second clip magazine into the end effector when the second clip magazine is attached to the surgical device. The surgical device further comprises a crimping drive operably responsive to the motor. The crimping drive is configured to crimp the first clip positioned in the end effector during a first crimping stroke when the first clip magazine is attached to the surgical device. The crimping drive is further configured to crimp the second clip positioned in the end effector during a second crimping stroke when the second clip magazine is attached to the surgical device. The surgical device further comprises a strain gauge configured to measure the strain within the end effector during the first crimping stroke. The surgical device further comprises a motor controller in signal communication with the motor and the strain gauge. The motor controller is configured to modify the second crimping stroke based on the measured strain in the end effector during the first crimping stroke.

Example 2—The surgical device of Example 1, wherein the housing comprises a handle.

Example 3—The surgical device of Example 1, wherein the housing is couplable to a robotic system.

Example 4—The surgical device of Examples 1, 2, or 3, further comprising the second clip magazine.

Example 5—A surgical device for clipping tissue comprising a housing comprising a motor, a shaft extending from the housing, an end effector extending from the shaft, and a first clip magazine comprising a first plurality of clips. The first clip magazine is replaceable with a second clip magazine comprising a second plurality of clips. The surgical device further comprises a firing drive configured to move a first clip from the first clip magazine into the end effector when the first clip magazine is attached to the surgical device. The firing drive is further configured to move a second clip from the second clip magazine into the end effector when the second clip magazine is attached to the surgical device. The surgical device further comprises a crimping drive configured to perform a first crimping stroke when the first clip magazine is attached to the surgical device. The crimping drive is further configured to perform a second crimping stroke when the second clip magazine is attached to the surgical device. The surgical device further comprises a strain gauge configured to measure the strain within the end effector during the first crimping stroke. The surgical device further comprises a motor controller in signal communication with the motor and the strain gauge. The motor controller is configured to move the crimping drive through a first crimping stroke with a first force. The motor controller is further configured to move the crimping drive through a second crimping stroke with a second force different than the first force. The second force is at least partially determined by the strain measured during the first crimping stroke.

Example 6—The surgical device of Example 5, wherein the housing comprises a handle.

Example 7—The surgical device of Example 5, wherein the housing is couplable to a robotic system.

Example 8—The surgical device of Examples 5, 6, or 7, further comprising the second clip magazine.

Example 9—A surgical device for clipping tissue comprising a housing comprising a motor, a shaft extending from the housing, and an end effector extending from the shaft. The end effector comprises a first jaw and a second jaw. The first jaw and the second jaw are movable relative to each other between an open position and a closed position. The surgical device further comprises a first clip cartridge comprising a plurality of clips. The first clip cartridge is removably attached to the surgical device. The surgical device further comprises a second clip cartridge comprising a plurality of clips. The second clip cartridge is removably attachable to the surgical device when the first clip cartridge is not attached to the surgical device. The surgical device further comprises a feeder member configured to move each clip in the first clip cartridge and each clip in the second clip cartridge into the end effector during separate firing strokes. The surgical device further comprises a crimping drive configured to move the first jaw and the second jaw toward the closed position during a crimping stroke for each clip in the first clip cartridge and each clip in the second clip cartridge. The surgical device further comprises a strain gauge positioned in the end effector. The strain gauge is configured to measure the strain within the end effector during the crimping stroke for each clip from the first clip cartridge. The surgical device further comprises a motor controller comprising a memory configured to store the strains measured during the crimping stroke for each clip from the first clip cartridge. The motor controller further comprises a processor in signal communication with the memory and the strain gauge. The processor is configured to modify the crimping stroke for each clip from the second clip cartridge based on the strains stored in the memory.

Example 10—The surgical device of Example 9, wherein the housing comprises a handle.

Example 11—The surgical device of Example 9, wherein the housing is couplable to a robotic system.

Example 12—A surgical device for applying clips comprising a shaft extending from a housing, and an end effector extending from the shaft. The end effector comprises a first jaw comprising a first protrusion extending therefrom, and a second jaw comprising a second protrusion extending therefrom. The first jaw and the second jaw are movable relative to each other between an open position and a closed position. The first jaw and the second jaw at least partially define a receiving chamber. The surgical device further comprises a cartridge comprising a storage chamber and a plurality of clips removably positioned within the storage chamber, wherein each clip is in a storage configuration. The surgical device further comprises a firing drive configured to advance a clip positioned in the storage chamber onto the first protrusion and the second protrusion. The surgical device further comprises a crimping drive configured to move the first jaw and the second jaw to the open position during a retraction stroke. The clip positioned on the first protrusion and the second protrusion is transitioned from the storage configuration to a deployment configuration during the retraction stroke. The deployment configuration is larger than the storage configuration.

Example 13—The surgical device of Example 12, wherein the firing drive is further configured to advance the clip in the deployment configuration into the receiving chamber, wherein the crimping drive is further configured to move the first jaw and the second jaw to the closed position during a crimping stroke, and wherein the clip is crimped around the tissue of a patient during the crimping stroke.

Example 14—The surgical device of Example 13, wherein the crimped clip is released from the receiving chamber when the first jaw and the second jaw are moved to the open position during another retraction stroke of the crimping drive, and wherein another clip is transitioned from the storage configuration to the deployment configuration during the another retraction stroke.

Example 15—The surgical device of Examples 12, 13, or 14, wherein the firing drive comprises a support portion configured to support a proximal portion of a clip during the transition of the clip from the storage configuration to the deployment configuration.

Example 16—The surgical device of Examples 12, 13, 14, or 15, wherein the first jaw comprises a first cam member, wherein the second jaw comprises a second cam member, and wherein the first cam member and the second cam member interact with the crimping drive to move the first jaw and the second jaw to the open position during the retraction stroke.

Example 17—The surgical device of Examples 12, 13, 14, 15, or 16, wherein the first protrusion comprises a first angled surface, wherein the second protrusion comprises a second angled surface, and wherein the first angled surface and the second angled surface allow a clip to slide past the first protrusion and the second protrusion as the clip is advanced towards the receiving chamber.

Example 18—The surgical device of Examples 12, 13, 14, 15, 16, or 17, wherein the cartridge is releasably attachable to the surgical device.

Example 19—A surgical device for applying clips comprising a shaft extending from a housing and an end effector extending from the shaft. The end effector comprises a receiving chamber. The surgical device further comprises a plurality of clips removably positioned within a clip cartridge. The clip cartridge is releasably attachable to the surgical device. Each clip is configured to assume a plurality of states during the operation of the surgical device. The plurality of states comprises a storage state, wherein each clip comprises a first size when in the storage state. The plurality of states further comprises a deployment state, wherein each the clip comprises a second size larger than the first size when in the deployment state. The surgical device further comprises pre-form features configured to transition a clip from the storage state to the deployment state. The surgical device further comprises a firing drive configured to advance a clip from the clip cartridge into the receiving chamber of the end effector.

Example 20—The surgical device of Example 19, further comprising a crimping drive configured to crimp a clip in the receiving chamber around the tissue of a patient during a crimping stroke.

Example 21—The surgical device of Example 20, wherein the crimped clip is released from the receiving chamber during a retraction stroke of the crimping drive, and wherein another clip is transitioned from the storage state to the deployment state during the retraction stroke.

Example 22—The surgical device of Examples 19, 20, or 21, wherein the firing drive comprises a support portion configured to support a proximal portion of a clip during the transition of the clip from the storage state to the deployment state.

Example 23—The surgical device of Example 22, wherein the support portion is further configured to support the proximal portion of the clip when the clip is advanced into the receiving chamber.

Example 24—The surgical device of Examples 19, 20, 21, 22, or 23, wherein the end effector further comprises a first jaw and a second jaw which at least partially define the receiving chamber, wherein the first jaw and the second jaw are movable relative to each other between an open position and a closed position, and wherein the pre-form features comprise a first protrusion on the first jaw and a second protrusion on the second jaw.

Example 25—The surgical device of Example 24, wherein the first protrusion comprises a first angled surface and the second protrusion comprises a second angled surface, and wherein the first angled surface and the second angled surface facilitate travel of a clip over the pre-form features as the clip is moved towards the receiving chamber.

Example 26—A surgical device for applying clips comprising a shaft extending from a housing and an end effector extending from the shaft. The end effector comprises a receiving chamber. The surgical device further comprises a plurality of clips removably positioned within the surgical device. Each clip comprises a storage configuration and a deployment configuration during the operation of the surgical device. The deployment configuration is larger than the storage configuration. The surgical device further comprises a reciprocating firing drive configured to advance a first clip in the deployment configuration into the receiving chamber. The surgical device further comprises a crimping drive movable between a fully retracted position and a fully advanced position. The crimping drive is configured to crimp the first clip in the deployment configuration when the crimping drive is moved toward the fully advanced position. The first clip is released from the receiving chamber and a second clip is transitioned to the deployment configuration when the crimping drive is moved toward the fully retracted position.

Example 27—The surgical device of Example 26, further comprising a clip magazine releasably attachable to the surgical device, wherein the clip magazine stores the plurality of clips in the storage configuration.

Example 28—The surgical device of Example 27, wherein the reciprocating firing drive is further configured to advance a clip from the clip magazine into a deployment position, wherein the clip is transitioned to the deployment configuration in the deployment position.

Example 29—The surgical device of Example 28, wherein the end effector further comprises pre-form features configured to transition the clip from the storage configuration to the deployment configuration when the crimping drive is moved toward the fully retracted position.

Example 30—The surgical device of Examples 26, 27, 28, or 29, wherein the reciprocating firing drive comprises a support portion configured to support a proximal portion of a first clip during the transition of the first clip from the storage configuration to the deployment configuration.

Example 31—The surgical device of Example 30, wherein the support portion is further configured to support the proximal portion of the first clip during the advancement of the first clip into the receiving chamber.

Example 32—A surgical device for clipping tissue comprising a shaft comprising a longitudinal axis. The surgical device further comprises a magazine housing extending from the shaft, an end effector extending from the magazine housing, and a reloadable clip magazine releasably attachable to the magazine housing. The reloadable clip magazine is rotatable about the longitudinal axis. The reloadable clip magazine comprises a plurality of clips removably positioned within the clip magazine, a notch, and a biasing member configured to protrude into the notch when the plurality of clips have been ejected from the reloadable clip magazine into the end effector and the reloadable clip magazine has been detached from the magazine housing. The biasing member prevents the reloadable clip magazine from being re-attached to the magazine housing when the reloadable clip magazine is empty.

Example 33—The surgical device of Example 32, wherein the biasing member is moved out of engagement with the notch when at least one clip is loaded into the clip magazine.

Example 34—The surgical device of Examples 32 or 33, wherein the magazine housing comprises a protrusion configured to extend into the notch when the clip magazine is not empty and is attached to the magazine housing.

Example 35—The surgical device of Examples 32, 33, or 34, further comprising a firing member configured to eject the clips from the clip magazine into the end effector when the clip magazine is attached to the magazine housing.

Example 36—The surgical device of Example 35, wherein the end effector comprises a first jaw and a second jaw, wherein one of the first jaw and the second jaw is movable relative to the other of the first jaw and the second jaw between an open position and a closed position, and wherein the first jaw and the second jaw are configured to crimp a clip positioned in the end effector when the first jaw and the second jaw are moved toward the closed position.

Example 37—The surgical device of Examples 32, 33, 34, 35, or 36, further comprising an articulation joint rotatably connecting the magazine housing to the shaft, wherein the magazine housing is movable relative to the shaft between an un-articulated position and an articulated position.

Example 38—A surgical device for clipping tissue comprising a shaft extending from a housing and a magazine housing extending from the shaft. The magazine housing comprises a lockout release. The surgical device further comprises an end effector extending from the magazine housing and a reloadable clip magazine releasably attachable to the magazine housing. The reloadable clip magazine comprises a plurality of clips removably positioned within the clip magazine and a lockout configured to prevent the plurality of clips from being ejected from the clip magazine when the clip magazine is not attached to the magazine housing, wherein, when the clip magazine is attached to the magazine housing, the lockout of the clip magazine is defeated by the lockout release of the magazine housing to allow the clips to be ejected from the clip magazine.

Example 39—The surgical device of Example 38, wherein the clips are ejected from the clip magazine by a firing member after the lockout is defeated.

Example 40—The surgical device of Examples 38 or 39, wherein the magazine housing further comprises a bottom portion and a top portion movable relative to the bottom portion between an open position and a closed position. The lockout release extends from the top portion.

Example 41—The surgical device of Example 40, wherein the lockout release is defeated by the lockout when the clip magazine is attached to the magazine housing and the top portion of the magazine housing is in the closed position.

Example 42—The surgical device of Examples 40 or 41, wherein the lockout release of the magazine housing comprises a protrusion extending from the top portion of the magazine housing.

Example 43—The surgical device of Example 42, wherein the lockout of the clip magazine comprises a biasing member.

Example 44—The surgical device of Example 43, wherein the protrusion of the top portion of the magazine housing engages the biasing member of the clip magazine to defeat the lockout of the clip magazine when the clip magazine is attached to the magazine housing and the top portion of the magazine housing is in the closed position.

Example 45—The surgical device of Examples 38, 39, 40, 41, 42, 43, or 44, further comprising an articulation joint rotatably connecting the magazine housing to the shaft, wherein the magazine housing is movable relative to the shaft between an un-articulated position and an articulated position.

Example 46—A surgical device for clipping tissue comprising a shaft extending from a housing, an end effector extending from the shaft, and a replaceable clip magazine operably attachable to the end effector. The end effector comprises a receiver. The replaceable clip magazine comprises a plurality of clips removably positioned therein, and a biasing member configured to prevent the plurality of clips from being ejected form the clip magazine when the clip magazine is not attached to the end effector.

Example 47—The surgical device of Example 46, wherein the clip magazine further comprises a notch, and wherein the biasing member extends into the notch when the clip magazine is empty.

Example 48—The surgical device of Example 47, wherein the end effector further comprises a protrusion configured to extend into the notch when the clip magazine is attached to the end effector, wherein the protrusion prevents the biasing member from extending into the notch.

Example 49—The surgical device of Examples 46, 47, or 48, further comprising a firing member configured to eject the clips from the clip magazine into the receiver of the end effector when the clip magazine is attached to the end effector.

Example 50—The surgical device of Example 49, wherein the end effector comprises a first jaw and a second jaw that at least partially define the receiver, wherein one of the first jaw and the second jaw is movable relative to the other of the first jaw and the second jaw between an open position and a closed position, and wherein the first jaw and the second jaw are configured to crimp a clip positioned in the receiver when the first jaw and the second jaw are moved toward the closed position.

Example 51—The surgical device of Examples 46, 47, 48, 49, or 50, further comprising an articulation joint rotatably connecting the end effector to the shaft, wherein the end effector is movable relative to the shaft between an un-articulated position and an articulated position.

Example 52—A surgical device for clipping tissue comprising a housing comprising a motor configured to output rotary motions. The surgical device further comprises a shaft extending from the housing, and an end effector extending from the shaft. The end effector comprises a first jaw rotatably coupled to the shaft, a second jaw rotatably coupled to the shaft, and a receiving chamber. The surgical device further comprises a crimping drive configured to move the first jaw and the second jaw toward each other during a crimping stroke. The crimping drive is operably responsive to the rotary motions. The surgical device further comprises a clip magazine comprising a plurality of clips. The plurality of clips are in a storage configuration when in the clip magazine. The surgical device further comprises a reciprocating firing drive configured to move a clip from the clip magazine to a forming position in the end effector during a clip feed stroke in response to the rotary motions, wherein a clip in the forming position is in a forming configuration, and wherein the forming configuration is the same as the storage configuration. The surgical device further comprises a motor controller configured to control the reciprocating firing drive independent of the crimping drive. The motor controller is configured to actuate the motor to perform the clip feed stroke after the surgical device has been inserted into a treatment area.

Example 53—The surgical device of Example 52, further comprising a processor and a memory, wherein the motor controller is configured to control the motor via the processor and the memory.

Example 54—The surgical device of Example 53, wherein the processor is configured to execute a motor control algorithm stored in the memory to move the crimping drive through the crimping stroke independent of the clip feed stroke.

Example 55—The surgical device of Example 53, wherein the processor is configured to execute a motor control algorithm stored in the memory to advance the reciprocating firing drive through the clip feed stroke independent of the crimping stroke.

Example 56—The surgical device of Examples 52, 53, 54, or 55, wherein the clip magazine is replaceable.

Example 57—A surgical device for clipping tissue comprising a shaft extending from a housing, and an end effector extending from the shaft. The end effector comprises a first jaw, a second jaw, and a crimping drive. The first jaw and the second jaw are movable relative to each other between an open configuration and a closed configuration. The crimping drive is configured to transition the first jaw and the second jaw between the open configuration and the closed configuration. The surgical device further comprises a clip magazine comprising a plurality of clips, a feeder drive configured to move a clip from the clip magazine to a forming position in the end effector, and a control system configured to operate the surgical device in a plurality of modes. The plurality of modes comprises a first mode wherein the first jaw and the second jaw are moved toward the open configuration and the feeder drive does not move a clip from the clip magazine into the forming position, and a second mode wherein the first jaw and the second jaw are moved toward the open configuration and the feeder drive moves a clip from the magazine into the forming position.

Example 58—The surgical device of Example 57, further comprising a motor configured to output rotary motions, wherein the crimping drive is operably responsive to the rotary motions, and wherein the feeder drive is operably responsive to the rotary motions.

Example 59—The surgical device of Examples 57 or 58, wherein the crimping drive and the feeder drive are operably independent to one another.

Example 60—The surgical device of Examples 57, 58, or 59, wherein the control system comprises a motor controller comprising a processor and a memory, wherein the motor controller is configured to control the motor based on instructions stored in the memory and executed by the processor.

Example 61—The surgical device of Example 60, wherein the processor is configured to execute a motor control algorithm stored in the memory to transition the first jaw and the second jaw towards the open configuration.

Example 62—The surgical device of Example 60, wherein the processor is configured to execute a motor control algorithm stored in the memory to move a the clip from the clip magazine to the forming position in the end effector.

Example 63—The surgical device of Examples 57, 58, 59, 60, 61, or 62, wherein the clip magazine is replaceable.

Example 64—The surgical device of Examples 57, 58, 59, 60, 61, 62, or 63, wherein the clip magazine is reloadable with another plurality of clips.

Example 65—A surgical device for clipping tissue comprising a housing comprising a motor configured to output rotary motions, a shaft extending from the housing, and an end effector extending from the shaft. The end effector comprises a first jaw rotatably coupled to the shaft, and a second jaw rotatably coupled to the shaft. The surgical device further comprises a crimping drive configured to move the first jaw and the second jaw toward each other during a crimping stroke in response to the rotary motions. The surgical device further comprises a clip cartridge comprising a plurality of clips. The surgical device further comprises a firing member configured to move a clip from the clip cartridge into the end effector during a clip feed stroke in response to the rotary motions. The surgical device further comprises a motor controller configured to control the firing member independent of the crimping drive. The motor controller is configured to actuate the motor to perform the clip feed stroke after the surgical device has been inserted into a treatment area.

Example 66—The surgical device of Example 65, further comprising a processor and a memory, wherein the motor controller is configured to control the motor via the processor and the memory.

Example 67—The surgical device of Examples 65 or 66, wherein the crimping drive and the firing member are operably independent to one another.

Example 68—The surgical device of Example 66, wherein the motor controller is configured to execute a motor control algorithm stored in the memory to move the first jaw and the second jaw toward each other during the crimping stroke independent of the clip feed stroke.

Example 69—The surgical device of Example 66, wherein the motor controller is further configured to execute a motor control algorithm stored in the memory to advance the firing member through the clip feed stroke independent of the crimping stroke.

Example 70—The surgical device of Examples 65, 66, 67, 68, or 69, wherein the clip cartridge is replaceable with another clip cartridge comprising another plurality of clips.

Example 71—The surgical device of Examples 65, 66, 67, 68, 69, or 70, wherein the clip cartridge is reloadable with another plurality of clips.

Example 72—A surgical device for clipping tissue comprising a housing comprising a motor configured to output rotary motions, a power source configured to supply power to the motor, a current meter configured to measure the current draw of the motor, a shaft extending from the housing, and an end effector extending from the shaft. The end effector comprises a first jaw rotatably coupled to the shaft, a second jaw rotatably coupled to the shaft, and a receiver. The surgical device further comprises a crimping drive configured to move the first jaw and the second jaw towards each other during a crimping stroke. The crimping drive is operably responsive to the rotary motions. The surgical device further comprises a clip magazine comprising a plurality of clips, and a reciprocating firing drive configured to advance a clip from the clip magazine into the receiver of the end effector during a firing stroke. The reciprocating firing drive is operably responsive to the rotary motions. The surgical device further comprises a motor controller connected to the current meter. The motor controller is configured to adjust the speed of the firing stroke when the current draw of the motor reaches a threshold value.

Example 73—The surgical device of Example 72, wherein after the speed of the firing stroke is adjusted and the current draw of the motor still exceeds the threshold value, the motor controller is configured to stop the motor.

Example 74—The surgical device of Example 72, wherein after the speed of the firing stroke is adjusted and the current draw of the motor still exceeds the threshold value, the motor controller is configured to reverse the direction of the motor to retract the firing member through a short stroke distance.

Example 75—The surgical device of Example 74, wherein the crimping drive is further configured to move the first jaw and the second jaw away from each other during a retraction stroke.

Example 76—The surgical device of Example 75, wherein after the firing member is retracted through the short stroke distance the motor controller is further configured to move the crimping drive through the retraction stroke.

Example 77—The surgical device of Examples 72, 73, 74, 75, or 76, wherein the clip magazine is removably attachable to the surgical device.

Example 78—The surgical device of Examples 72, 73, 74, 75, 76, or 77, wherein the clip magazine is configured to be reloaded with another plurality of clips when the clip magazine has been spent.

Example 79—A surgical device for clipping tissue comprising a housing comprising a motor configured to output rotary motions, a power source configured to supply power to the motor, a motor controller configured to control the motor, a current meter configured to measure the current draw of the motor, a shaft extending from the housing, and an end effector extending from the shaft. The end effector comprises a first jaw and a second jaw. The first jaw and the second jaw are movable between a fully open position, an open position, and a closed position relative to each other. The surgical device further comprises a crimping drive configured to move the first jaw and the second jaw relative to each other between the fully open position, the open position, and the closed position. The surgical device further comprises a clip magazine comprising a plurality of clips. The surgical device further comprises a reciprocating firing drive configured to advance a clip from the clip magazine into the end effector during a firing stroke. The reciprocating firing drive is operably responsive to the rotary motions, wherein when a clip is jammed in the end effector the current meter is configured to detect the jammed clip and the crimping drive is configured to move the first jaw and the second jaw to the fully open position.

Example 80—The surgical device of Example 79, wherein the crimping drive is operably responsive to the rotary motions.

Example 81—The surgical device of Examples 79 or 80, wherein the motor controller is in signal communication with the motor and the current meter.

Example 82—The surgical device of Examples 79, 80, or 81, wherein the current meter is configured to measuring the current draw of the motor, and wherein the current meter detects the jammed clip when the current draw of the motor exceeds a threshold value.

Example 83—The surgical device of Examples 79, 80, 81, or 82, wherein the first jaw and the second jaw comprise protrusions, and wherein the protrusions are operably engaged by the crimping drive to move the first jaw and the second jaw to the fully open position when the current meter detects the jammed clip.

Example 84—The surgical device of Examples 79, 80, 81, 82, or 83, wherein the motor controller is configured to retract the reciprocating firing drive a short stroke distance when the current meter detects the jammed clip.

Example 85—The surgical device of Examples 79, 80, 81, 82, 83, or 84, wherein the clip magazine is removably attachable to the surgical device.

Example 86—The surgical device of Examples 79, 80, 81, 82, 83, 84, or 85, wherein the clip magazine is configured to be reloaded with another plurality of clips when the clip magazine has been spent.

Example 87—A surgical device for clipping tissue comprising a housing comprising a motor. The surgical device further comprises a shaft extending from the housing, a current sensor configured to measure the current draw of the motor, and an end effector extending from the shaft. The end effector comprises a first jaw and a second jaw. The first jaw and the second jaw are movable relative to each other between an open position and a closed position. The surgical device further comprises a clip cartridge configured to store a plurality of clips. The surgical device further comprises a feeder member configured to advance a clip from the clip cartridge during a firing stroke. The feeder member is further configured to retract during a retraction stroke. The feeder member is operably responsive to the rotary motions. The surgical device further comprises a closure tube configured to move the first jaw and the second jaw toward the open position during a retraction stroke. The closure tube is operably responsive to the rotary motions. The surgical device further comprises a motor controller in signal communication with the current sensor and the motor. The motor controller is configured to move the feeder member through the retraction stroke and move the closure tube through the retraction stroke when the current sensor detects a current draw that exceeds a threshold value.

Example 88—The surgical device of Example 87, wherein the threshold value is indicative of a clip which has been jammed in the end effector.

Example 89—The surgical device of Examples 87 or 88, wherein the first jaw and the second jaw comprise protrusions, and wherein the protrusions are operably engaged by the closure tube during the retraction stroke of the closure tube.

Example 90—The surgical device of Examples 87, 88, or 89, wherein the clip cartridge is removably attachable to the surgical device.

Example 91—The surgical device of Examples 87, 88, 89, or 90, wherein the clip cartridge is configured to be reloaded with another plurality of clips when the clip cartridge has been spent.

Example 92—A surgical device for clipping tissue comprising a housing. The housing comprising a motor configured to output rotary motions. The surgical device further comprises a shaft extending from the housing and an end effector extending from the shaft. The end effector comprises a first jaw rotatably coupled to the shaft, a second jaw rotatably coupled to the shaft, and a receiver. The surgical device further comprises a clip magazine comprising a plurality of clips. The surgical device further comprises a reciprocating firing drive operably responsive to the rotary motions. The firing drive is configured to move a clip from the clip magazine into the receiver. The surgical device further comprises a crimping drive operably responsive to the rotary motions. The crimping drive is configured to move the first jaw and the second jaw towards each other during a crimping stroke, wherein a clip positioned in the receiver is crimped during the crimping stroke. The surgical device further comprises a strain gauge positioned in at least one of the first jaw and the second jaw. The strain gauge is configured to measure the strain within the end effector during the crimping stroke. The surgical device further comprises a motor controller in communication with the motor and the strain gauge, wherein the motor controller is configured to adjust the output torque of the motor based on the measured strain in the strain gauge during the crimping stroke.

Example 93—The surgical device of Example 92, wherein the strain gauge comprises a proximal strain gauge, and where the surgical device further comprises a distal strain gauge positioned in at least one of the first jaw and the second jaw.

Example 94—The surgical device of Example 93, wherein the proximal strain gauge is configured to measure a first strain in the end effector during the crimping stroke, and wherein the distal strain gauge is configured to measure a second strain in the end effector during the crimping stroke.

Example 95—The surgical device of Example 94, wherein the motor controller is configured to adjust the output torque of the motor based on the difference between the first strain and the second strain during the crimping stroke.

Example 96—The surgical device of Examples 92, 93, 94, or 95, wherein the clip magazine is removable attachable to the surgical device.

Example 97—A surgical device for clipping tissue comprising a housing. The housing comprising a motor configured to output rotary motions. The surgical device further comprises a shaft extending from the housing and an end effector extending from the shaft. The end effector comprises a first jaw and a second jaw. The first jaw and the second jaw are movable relative to each other between an open position and a closed position. The surgical device further comprises a crimping drive configured to move the first jaw and the second jaw to a closed position during a crimping stroke. The crimping drive is operably responsive to the rotary motions. The surgical device further comprises a clip magazine comprising a plurality of metal clips, a firing drive configured to move a metal clip from the clip magazine into the end effector, a first resistive sensing circuit configured to detect the position of the metal clip in the end effector, and a second resistive sensing circuit configure to determine whether the first jaw and the second jaw are in the open position or the closed position.

Example 98—The surgical device of Example 97, further comprising a power source, wherein the first resistive sensing circuit comprises the power source, the first jaw, a metal clip positioned in the end effector, the second jaw, a resistor, and a current meter.

Example 99—The surgical device of Example 98, wherein the power source is configured to supply a current to the first resistive sensing circuit, wherein the current meter is configured to measure an output current of the first resistive sensing circuit.

Example 100—The surgical device of Example 99, wherein the output current measured at the current meter is indicative of the position of the clip in the end effector.

Example 101—The surgical device of Example 97, further comprising a power source, wherein the second resistive sensing circuit comprises the power source, a first lead in the first jaw, a second lead in the second jaw, a resistor, and a current meter.

Example 102—The surgical device of Example 101, wherein the first lead is insulated from the first jaw, and wherein the second lead is insulated form the second jaw.

Example 103—The surgical device of Examples 101 or 102, wherein the power source is configured to supply a current to the second resistive sensing circuit, and wherein the current meter is configured to measure an output current of the second resistive sensing circuit.

Example 104—The surgical device of Example 103, wherein the output current measured at the current meter is indicative of the position of the first jaw relative to the second jaw.

Example 105—The surgical device of Examples 97, 98, 99, 100, 101, 102, 103, or 104, wherein the clip magazine is removably attachable to the surgical device.

Example 106—A surgical device for clipping tissue comprising a housing. The housing comprises a motor configured to output rotary motions. The surgical device further comprises a shaft extending from the housing and an end effector extending from the shaft. The end effector comprises a first jaw rotatably coupled to the shaft, a second jaw rotatably coupled to the shaft, and a receiver. The surgical device further comprises a crimping drive configured to move the first jaw and the second jaw towards each other during a crimping stroke. The crimping drive is operably responsive to the rotary motions. The surgical device further comprises a clip magazine comprising a plurality of clips. Each clip is stored in the clip magazine in a stored configuration. The surgical device further comprises a reciprocating firing drive configured to move a clip from the magazine to a forming position in the end effector during a clip feed stroke. The clip in the forming position is in a forming configuration that is the same as the stored configuration. The surgical device further comprises a resistive sensing circuit configured to detect when a clip is in the forming position. The crimping drive is further configured to expand the clip in the forming configuration to a deployable configuration that is larger than the forming configuration after the resistive sensing circuit detects the clip in the forming position.

Example 107—The surgical device of Example 106, wherein the resistive sensing circuit comprises a power supply configured to supply a voltage to the end effector, a current meter, and a resistor, and wherein the current meter is configured to measure the current at the resistor.

Example 108—The surgical device of Example 107, wherein the current measured at the resistor is indicative of the position of a clip in the end effector.

Example 109—The surgical device of Examples 107 or 108, wherein when a clip is in the forming position the current measured by the current meter is a first current, wherein when a clip is in the deployable configuration the current measured by the current meter is a second current, and wherein the second current is smaller than the first current.

Example 110—The surgical device of Examples 106, 107, 108, or 109, wherein the clip magazine is removably attachable to the surgical device.

Example 111—The surgical device of Examples 106, 107, 108, 109, or 110, wherein the clip magazine is configured to be reloaded with another plurality of clips when the plurality of clips have been spent.

The devices, systems, and methods disclosed in the Subject Application can be used with the devices, systems, and methods disclosed in U.S. Provisional Patent Application Ser. No. 62/659,900, entitled METHOD OF HUB COMMUNICATION, filed Apr. 19, 2018; U.S. Provisional Patent Application Ser. No. 62/611,341, entitled INTERACTIVE SURGICAL PLATFORM, filed Dec. 28, 2017; U.S. Provisional Patent Application Ser. No. 62/611,340, entitled CLOUD-BASED MEDICAL ANALYTICS, filed Dec. 28, 2017; and U.S. Provisional Patent Application Ser. No. 62/611,339, entitled ROBOT ASSISTED SURGICAL PLATFORM, filed Dec. 28, 2017.

The devices, systems, and methods disclosed in the Subject Application can also be used with the devices, systems, and methods disclosed in U.S. patent application Ser. No. 15/908,021, entitled SURGICAL INSTRUMENT WITH REMOTE RELEASE, filed Feb. 28, 2018; U.S. patent application Ser. No. 15/908,012, entitled SURGICAL INSTRUMENT HAVING DUAL ROTATABLE MEMBERS TO EFFECT DIFFERENT TYPES OF END EFFECTOR MOVEMENT, filed Feb. 28, 2018; U.S. patent application Ser. No. 15/908,040, entitled SURGICAL INSTRUMENT WITH ROTARY DRIVE SELECTIVELY ACTUATING MULTIPLE END EFFECTOR FUNCTIONS, filed Feb. 28, 2018; U.S. patent application Ser. No. 15/908,057, entitled SURGICAL INSTRUMENT WITH ROTARY DRIVE SELECTIVELY ACTUATING MULTIPLE END EFFECTOR FUNCTIONS, filed Feb. 28, 2018; U.S. patent application Ser. No. 15/908,058, entitled SURGICAL INSTRUMENT WITH MODULAR POWER SOURCES, filed Feb. 28, 2018; and U.S. patent application Ser. No. 15/908,143, entitled SURGICAL INSTRUMENT WITH SENSOR AND/OR CONTROL SYSTEMS, filed Feb. 28, 2018.

The surgical instrument systems described herein can be used in connection with the deployment and deformation of staples. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue. In addition, various embodiments are envisioned which utilize a suitable cutting means to cut the tissue.

The entire disclosures of:
U.S. Pat. No. 8,075,571, entitled SURGICAL CLIP APPLIER METHODS, which issued on Dec. 13, 2011;
U.S. Pat. No. 8,038,686, entitled CLIP APPLIER CONFIGURED TO PREVENT CLIP FALLOUT, which issued on Oct. 18, 2011;
U.S. Pat. No. 7,699,860, entitled SURGICAL CLIP, which issued on Apr. 20, 2010;
U.S. patent application Ser. No. 11/013,924, entitled TROCAR SEAL ASSEMBLY, now U.S. Pat. No. 7,371,227;
U.S. patent application Ser. No. 11/162,991, entitled ELECTROACTIVE POLYMER-BASED ARTICULATION MECHANISM FOR GRASPER, now U.S. Pat. No. 7,862,579;
U.S. patent application Ser. No. 12/364,256, entitled SURGICAL DISSECTOR, now U.S. Patent Application Publication No. 2010/0198248;
U.S. patent application Ser. No. 13/536,386, entitled EMPTY CLIP CARTRIDGE LOCKOUT, now U.S. Pat. No. 9,282,974;
U.S. patent application Ser. No. 13/832,786, entitled CIRCULAR NEEDLE APPLIER WITH OFFSET NEEDLE AND CARRIER TRACKS, now U.S. Pat. No. 9,398,905;
U.S. patent application Ser. No. 12/592,174, entitled APPARATUS AND METHOD FOR MINIMALLY INVASIVE SUTURING, now U.S. Pat. No. 8,123,764;
U.S. patent application Ser. No. 12/482,049, entitled ENDOSCOPIC STITCHING DEVICES, now U.S. Pat. No. 8,628,545;
U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;
U.S. patent application Ser. No. 11/343,803, entitled SURGICAL INSTRUMENT HAVING RECORDING CAPABILITIES, now U.S. Pat. No. 7,845,537;
U.S. patent application Ser. No. 14/200,111, entitled CONTROL SYSTEMS FOR SURGICAL INSTRUMENTS, now U.S. Pat. No. 9,629,629;
U.S. patent application Ser. No. 14/248,590, entitled MOTOR DRIVEN SURGICAL INSTRUMENTS WITH LOCKABLE DUAL DRIVE SHAFTS, now U.S. Pat. No. 9,826,976;
U.S. patent application Ser. No. 14/813,242, entitled SURGICAL INSTRUMENT COMPRISING SYSTEMS FOR ASSURING THE PROPER SEQUENTIAL OPERATION OF THE SURGICAL INSTRUMENT, now U.S. Patent Application Publication No. 2017/0027571;
U.S. patent application Ser. No. 14/248,587, entitled POWERED SURGICAL STAPLER, now U.S. Pat. No. 9,867,612;
U.S. patent application Ser. No. 12/945,748, entitled SURGICAL TOOL WITH A TWO DEGREE OF FREEDOM WRIST, now U.S. Pat. No. 8,852,174;
U.S. patent application Ser. No. 13/297,158, entitled METHOD FOR PASSIVELY DECOUPLING TORQUE APPLIED BY A REMOTE ACTUATOR INTO AN INDEPENDENTLY ROTATING MEMBER, now U.S. Pat. No. 9,095,362;
International Application No. PCT/US2015/023636, entitled SURGICAL INSTRUMENT WITH SHIFTABLE TRANSMISSION, now International Patent Publication No. WO 2015/153642 A1;

International Application No. PCT/US2015/051837, entitled HANDHELD ELECTROMECHANICAL SURGICAL SYSTEM, now International Patent Publication No. WO 2016/057225 A1;

U.S. patent application Ser. No. 14/657,876, entitled SURGICAL GENERATOR FOR ULTRASONIC AND ELECTROSURGICAL DEVICES, U.S. Patent Application Publication No. 2015/0182277;

U.S. patent application Ser. No. 15/382,515, entitled MODULAR BATTERY POWERED HANDHELD SURGICAL INSTRUMENT AND METHODS THEREFOR, U.S. Patent Application Publication No. 2017/0202605;

U.S. patent application Ser. No. 14/683,358, entitled SURGICAL GENERATOR SYSTEMS AND RELATED METHODS, U.S. Patent Application Publication No. 2016/0296271;

U.S. patent application Ser. No. 14/149,294, entitled HARVESTING ENERGY FROM A SURGICAL GENERATOR, U.S. Pat. No. 9,795,436;

U.S. patent application Ser. No. 15/265,293, entitled TECHNIQUES FOR CIRCUIT TOPOLOGIES FOR COMBINED GENERATOR, U.S. Patent Application Publication No. 2017/0086910; and U.S. patent application Ser. No. 15/265,279, entitled TECHNIQUES FOR OPERATING GENERATOR FOR DIGITALLY GENERATING ELECTRICAL SIGNAL WAVEFORMS AND SURGICAL INSTRUMENTS, U.S. Patent Application Publication No. 2017/0086914, are hereby incorporated by reference herein.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical device for clipping tissue, comprising:
   a shaft comprising a longitudinal axis;
   a magazine housing extending from said shaft;
   an end effector extending from said magazine housing; and
   a reloadable clip magazine releasably attachable to said magazine housing, wherein said reloadable clip magazine is rotatable about said longitudinal axis, and wherein said reloadable clip magazine comprises:
      a plurality of clips removably positioned within said clip magazine;
      a notch; and
      a biasing member configured to protrude into said notch when said plurality of clips have been ejected from said reloadable clip magazine into said end effector and said reloadable clip magazine has been detached from said magazine housing, wherein said biasing member prevents said reloadable clip magazine from being re-attached to said magazine housing when said reloadable clip magazine is empty.

2. The surgical device of claim 1, wherein said biasing member is moved out of engagement with said notch when at least one clip is loaded into said clip magazine.

3. The surgical device of claim 1, further comprising an articulation joint rotatably connecting said magazine housing to said shaft, wherein said magazine housing is movable relative to said shaft between an un-articulated position and an articulated position.

4. A surgical device for clipping tissue, comprising:
   a shaft comprising a longitudinal axis;
   a magazine housing extending from said shaft;
   an end effector extending from said magazine housing; and
   a reloadable clip magazine releasably attachable to said magazine housing, wherein said reloadable clip magazine is rotatable about said longitudinal axis, and wherein said reloadable clip magazine comprises:
      a plurality of clips removably positioned within said clip magazine;
      a notch; and
      a biasing member configured to protrude into said notch when said plurality of clips have been ejected from said reloadable clip magazine into said end effector and said reloadable clip magazine has been detached from said magazine housing, wherein said biasing member prevents said reloadable clip magazine from being re-attached to said magazine housing when said reloadable clip magazine is empty, wherein said biasing member is moved out of engagement with said notch when at least one clip is loaded into said clip magazine, and wherein said magazine housing comprises a protrusion configured to extend into said notch when said clip magazine is not empty and is attached to said magazine housing.

5. The surgical device of claim 4, further comprising a firing member configured to eject said plurality of clips from said clip magazine into said end effector when said clip magazine is attached to said magazine housing.

6. The surgical device of claim 5, wherein said end effector comprises a first jaw and a second jaw, wherein one of said first jaw and said second jaw is movable relative to the other of said first jaw and said second jaw between an open position and a closed position, and wherein said first jaw and said second jaw are configured to crimp a said clip positioned in said end effector when said first jaw and said second jaw are moved toward said closed position.

7. A surgical device for clipping tissue, comprising:
a shaft extending from a housing;
a magazine housing extending from said shaft, wherein said magazine housing comprises a lockout release;
an end effector extending from said magazine housing; and
a reloadable clip magazine releasably attachable to said magazine housing, wherein said reloadable clip magazine comprises:
a plurality of clips removably positioned within said clip magazine; and
a lockout configured to prevent said plurality of clips from being ejected from said clip magazine when said clip magazine is not attached to said magazine housing, wherein, when said clip magazine is attached to said magazine housing, said lockout of said clip magazine is defeated by said lockout release of said magazine housing to allow said plurality of clips to be ejected from said clip magazine.

8. The surgical device of claim 7, wherein said plurality of clips are ejected from said clip magazine by a firing member after said lockout is defeated.

9. The surgical device of claim 7, further comprising an articulation joint rotatably connecting said magazine housing to said shaft, wherein said magazine housing is movable relative to said shaft between an un-articulated position and an articulated position.

10. A surgical device for clipping tissue, comprising:
a shaft extending from a housing;
a magazine housing extending from said shaft, wherein said magazine housing comprises a lockout release;
an end effector extending from said magazine housing; and
a reloadable clip magazine releasably attachable to said magazine housing, wherein said reloadable clip magazine comprises:
a plurality of clips removably positioned within said clip magazine; and
a lockout configured to prevent said plurality of clips from being ejected from said clip magazine when said clip magazine is not attached to said magazine housing, wherein, when said clip magazine is attached to said magazine housing, said lockout of said clip magazine is defeated by said lockout release of said magazine housing to allow said plurality of clips to be ejected from said clip magazine, wherein said plurality of clips are ejected from said clip magazine by a firing member after said lockout is defeated, and wherein said magazine housing further comprises:
a bottom portion; and
a top portion movable relative to said bottom portion between an open position and a closed position, wherein said lockout release extends from said top portion.

11. The surgical device of claim 10, wherein said lockout release is defeated by said lockout when said clip magazine is attached to said magazine housing and said top portion of said magazine housing is in said closed position.

12. The surgical device of claim 11, wherein said lockout release of said magazine housing comprises a protrusion extending from said top portion of said magazine housing.

13. The surgical device of claim 12, wherein said lockout of said clip magazine comprises a biasing member.

14. The surgical device of claim 13, wherein said protrusion of said top portion of said magazine housing engages said biasing member of said clip magazine to defeat said lockout of said clip magazine when said clip magazine is attached to said magazine housing and said top portion of said magazine housing is in said closed position.

15. A surgical device for clipping tissue, comprising:
a shaft extending from a housing;
an end effector extending from said shaft, wherein said end effector comprises a receiver; and
a replaceable clip magazine operably attachable to said end effector, wherein said replaceable clip magazine comprises:
a plurality of clips removably positioned therein; and
a biasing member configured to prevent said plurality of clips from being ejected form said clip magazine when said clip magazine is not attached to said end effector, wherein said biasing member prevents said replaceable clip magazine from being re-attached to said end effector when said replaceable clip magazine is empty.

16. The surgical device of claim 15, wherein said clip magazine further comprises a notch, and wherein said biasing member extends into said notch when said clip magazine is empty.

17. The surgical device of claim 15, further comprising an articulation joint rotatably connecting said end effector to said shaft, wherein said end effector is movable relative to said shaft between an un-articulated position and an articulated position.

18. A surgical device for clipping tissue, comprising:
a shaft extending from a housing;
an end effector extending from said shaft, wherein said end effector comprises a receiver; and
a replaceable clip magazine operably attachable to said end effector, wherein said replaceable clip magazine comprises:
a plurality of clips removably positioned therein; and
a biasing member configured to prevent said plurality of clips from being ejected form said clip magazine when said clip magazine is not attached to said end effector, wherein said clip magazine further comprises a notch, wherein said biasing member extends into said notch when said clip magazine is empty, wherein said end effector further comprises a protrusion configured to extend into said notch when said clip magazine is attached to said end effector, and wherein said protrusion prevents said biasing member from extending into said notch.

19. The surgical device of claim 18, further comprising a firing member configured to eject said plurality of clips from said clip magazine into said receiver of said end effector when said clip magazine is attached to said end effector.

20. The surgical device of claim 19, wherein said end effector comprises a first jaw and a second jaw that at least partially define said receiver, wherein one of said first jaw and said second jaw is movable relative to the other of said first jaw and said second jaw between an open position and a closed position, and wherein said first jaw and said second jaw are configured to crimp a said clip positioned in said receiver when said first jaw and said second jaw are moved toward said closed position.

\* \* \* \* \*